(12) United States Patent
Dunn et al.

(10) Patent No.: US 11,439,539 B2
(45) Date of Patent: Sep. 13, 2022

(54) NEGATIVE PRESSURE WOUND CLOSURE DEVICE

(71) Applicants: Smith & Nephew Inc., Memphis, TN (US); University of Massachusetts, Boston, MA (US)

(72) Inventors: Raymond M. Dunn, Shrewsbury, MA (US); Victoria Jody Hammond, Hull (GB); Edward Yerbury Hartwell, Hull (GB); Marcus Damian Phillips, Wakefield (GB); Mark Richardson, Grimsby (GB); Carl Dean Saxby, Brough (GB); Michael Sugrue, Donegal (IE)

(73) Assignees: University of Massachusetts, Boston, MA (US); Smith & Nephew Inc., Memphis, TN (US)

( * ) Notice: Subject to any disclaimer, the term of this patent is extended or adjusted under 35 U.S.C. 154(b) by 828 days.

(21) Appl. No.: 15/570,268

(22) PCT Filed: Apr. 28, 2016

(86) PCT No.: PCT/US2016/029888
§ 371 (c)(1),
(2) Date: Oct. 27, 2017

(87) PCT Pub. No.: WO2016/176513
PCT Pub. Date: Nov. 3, 2016

(65) Prior Publication Data
US 2018/0140465 A1 May 24, 2018

Related U.S. Application Data

(60) Provisional application No. 62/154,609, filed on Apr. 29, 2015.

(51) Int. Cl.
| | | |
|---|---|---|
| A61F 13/00 | (2006.01) | |
| A61M 1/00 | (2006.01) | |
| A61F 13/02 | (2006.01) | |

(52) U.S. Cl.
CPC ......... *A61F 13/00068* (2013.01); *A61M 1/90* (2021.05); *A61F 13/0216* (2013.01);
(Continued)

(58) Field of Classification Search
CPC ...... A61F 13/00068; A61F 2013/00178; A61F 2013/00174; A61F 13/0216; A61M 1/0086; A61M 1/0088
See application file for complete search history.

(56) References Cited

U.S. PATENT DOCUMENTS

| | | |
|---|---|---|
| 1,006,716 A | 10/1911 | Bloomer |
| 3,014,483 A | 12/1961 | Frank et al. |

(Continued)

FOREIGN PATENT DOCUMENTS

| | | |
|---|---|---|
| AU | 2012261793 B2 | 11/2014 |
| AU | 2013206230 B2 | 5/2016 |

(Continued)

OTHER PUBLICATIONS

International Search Report and Written Opinion for International Application No. PCT/US2016/029888 dated Aug. 17, 2016 in 11 pages.

(Continued)

*Primary Examiner* — Jessica R Arble
(74) *Attorney, Agent, or Firm* — McCarter & English, LLP; Thomas O. Hoover; Nathan D. Harrison

(57) ABSTRACT

The present invention relates to wound closure devices, systems and methods. Embodiments of the invention facilitate closure of the wound by preferentially contracting under negative pressure to provide for movement of the surround- (Continued)

ing tissues. Some embodiments may utilize tissue securing portions that aid in securing the invention within a wound.

17 Claims, 126 Drawing Sheets

(52) U.S. Cl.
CPC ............... *A61F 2013/00174* (2013.01); *A61F 2013/00178* (2013.01); *A61M 1/86* (2021.05)

(56) References Cited

U.S. PATENT DOCUMENTS

| | | | |
|---|---|---|---|
| 3,194,239 A | 7/1965 | Sullivan | |
| 3,578,003 A | 5/1971 | Everett | |
| 3,789,851 A | 2/1974 | LeVeen | |
| 3,812,616 A | 5/1974 | Koziol | |
| 3,952,633 A | 4/1976 | Nakai | |
| 4,000,845 A | 1/1977 | Zeller | |
| 4,467,805 A | 8/1984 | Fukuda | |
| 4,608,041 A | 8/1986 | Nielsen | |
| 4,637,819 A * | 1/1987 | Ouellette | A61F 13/5123 |
| | | | 604/369 |
| 4,699,134 A | 10/1987 | Samuelsen | |
| 4,771,482 A | 9/1988 | Shlenker | |
| 4,815,468 A | 3/1989 | Annand | |
| 5,176,663 A | 1/1993 | Svedman et al. | |
| 5,264,218 A | 11/1993 | Rogozinski | |
| 5,332,149 A | 7/1994 | Gepfer | |
| 5,368,910 A * | 11/1994 | Langdon | A61F 13/512 |
| | | | 428/137 |
| 5,368,930 A | 11/1994 | Samples | |
| 5,376,067 A | 12/1994 | Daneshvar | |
| 5,409,472 A | 4/1995 | Rawlings et al. | |
| 5,415,715 A | 5/1995 | Delage et al. | |
| 5,423,857 A | 6/1995 | Rosenman et al. | |
| 5,512,041 A | 4/1996 | Bogart | |
| 5,514,105 A * | 5/1996 | Goodman, Jr. | B29C 51/00 |
| | | | 428/137 |
| 5,562,107 A | 10/1996 | Lavendar et al. | |
| 5,584,859 A | 12/1996 | Brotz | |
| 5,636,643 A | 6/1997 | Argenta et al. | |
| 5,695,777 A | 12/1997 | Donovan et al. | |
| 5,853,863 A | 12/1998 | Kim | |
| 5,928,210 A * | 7/1999 | Ouellette | A61F 13/15731 |
| | | | 604/383 |
| 5,960,497 A | 10/1999 | Castellino et al. | |
| 6,000,403 A | 12/1999 | Cantwell | |
| 6,080,168 A | 6/2000 | Levin et al. | |
| 6,086,591 A | 7/2000 | Bojarski | |
| 6,142,982 A | 11/2000 | Hunt et al. | |
| 6,176,868 B1 | 1/2001 | Detour | |
| 6,291,050 B1 * | 9/2001 | Cree | A61F 13/512 |
| | | | 428/131 |
| 6,398,767 B1 | 6/2002 | Fleischmann | |
| 6,471,715 B1 | 10/2002 | Weiss | |
| 6,500,112 B1 | 12/2002 | Khouri | |
| 6,503,208 B1 | 1/2003 | Skovlund | |
| 6,530,941 B1 | 3/2003 | Muller et al. | |
| 6,548,727 B1 | 4/2003 | Swenson | |
| 6,553,998 B2 | 4/2003 | Heaton et al. | |
| 6,566,575 B1 | 5/2003 | Stickels et al. | |
| 6,641,575 B1 | 11/2003 | Lonky | |
| 6,685,681 B2 | 2/2004 | Lockwood et al. | |
| 6,695,823 B1 | 2/2004 | Lina et al. | |
| 6,712,830 B2 | 3/2004 | Esplin | |
| 6,712,839 B1 | 3/2004 | Lonne | |
| 6,767,334 B1 | 7/2004 | Randolph | |
| 6,770,794 B2 | 8/2004 | Fleischmann | |
| 6,776,769 B2 | 8/2004 | Smith | |
| 6,787,682 B2 | 9/2004 | Gilman | |
| 6,814,079 B2 | 11/2004 | Heaton et al. | |
| 6,883,531 B1 | 4/2005 | Perttu | |
| 6,893,452 B2 | 5/2005 | Jacobs | |
| 6,936,037 B2 | 8/2005 | Bubb et al. | |
| 6,951,553 B2 | 10/2005 | Bubb et al. | |
| 6,977,323 B1 | 12/2005 | Swenson | |
| 6,994,702 B1 | 2/2006 | Johnson | |
| 7,004,915 B2 | 2/2006 | Boynton et al. | |
| 7,025,755 B2 | 4/2006 | Epstein | |
| 7,070,584 B2 | 7/2006 | Johnson et al. | |
| 7,117,869 B2 | 10/2006 | Heaton et al. | |
| 7,128,735 B2 | 10/2006 | Weston | |
| 7,144,390 B1 | 12/2006 | Hannigan et al. | |
| 7,153,312 B1 | 12/2006 | Torrie et al. | |
| 7,156,862 B2 | 1/2007 | Jacobs et al. | |
| 7,172,615 B2 | 2/2007 | Morriss et al. | |
| 7,189,238 B2 | 3/2007 | Lombardo et al. | |
| 7,196,054 B1 | 3/2007 | Drohan et al. | |
| 7,198,046 B1 | 4/2007 | Argenta et al. | |
| 7,216,651 B2 | 5/2007 | Argenta et al. | |
| D544,092 S | 6/2007 | Lewis | |
| 7,262,174 B2 | 8/2007 | Jiang et al. | |
| 7,279,612 B1 | 10/2007 | Heaton et al. | |
| 7,315,183 B2 | 1/2008 | Interscher | |
| 7,351,250 B2 | 4/2008 | Zamierowski | |
| 7,361,184 B2 | 4/2008 | Joshi | |
| 7,367,342 B2 | 5/2008 | Butler | |
| 7,381,211 B2 | 6/2008 | Zamierowski | |
| 7,381,859 B2 | 6/2008 | Hunt et al. | |
| 7,413,571 B2 | 8/2008 | Zamierowski | |
| 7,438,705 B2 * | 10/2008 | Karpowicz | A61M 1/0031 |
| | | | 604/313 |
| 7,494,482 B2 | 2/2009 | Orgill et al. | |
| 7,524,315 B2 | 4/2009 | Blott et al. | |
| 7,534,240 B1 | 5/2009 | Johnson | |
| 7,540,848 B2 | 6/2009 | Hannigan et al. | |
| 7,553,306 B1 | 6/2009 | Hunt et al. | |
| 7,553,923 B2 | 6/2009 | Williams et al. | |
| 7,569,742 B2 | 8/2009 | Haggstrom et al. | |
| 7,578,532 B2 | 8/2009 | Schiebler | |
| D602,583 S | 10/2009 | Pidgeon et al. | |
| 7,611,500 B1 | 11/2009 | Lina et al. | |
| 7,612,248 B2 | 11/2009 | Burton et al. | |
| 7,615,036 B2 | 11/2009 | Joshi et al. | |
| 7,617,762 B1 | 11/2009 | Ragner | |
| 7,618,382 B2 | 11/2009 | Vogel et al. | |
| 7,622,629 B2 | 11/2009 | Aali | |
| 7,625,362 B2 | 12/2009 | Boehringer et al. | |
| 7,645,269 B2 | 1/2010 | Zamierowski | |
| 7,651,484 B2 | 1/2010 | Heaton et al. | |
| 7,670,323 B2 | 3/2010 | Hunt et al. | |
| 7,678,102 B1 | 3/2010 | Heaton | |
| 7,683,667 B2 | 3/2010 | Kim | |
| 7,699,823 B2 | 4/2010 | Haggstrom et al. | |
| 7,699,830 B2 | 4/2010 | Martin | |
| 7,699,831 B2 | 4/2010 | Bengtson et al. | |
| 7,700,819 B2 | 4/2010 | Ambrosio et al. | |
| 7,708,724 B2 | 5/2010 | Weston | |
| 7,713,743 B2 | 5/2010 | Villanueva et al. | |
| 7,722,528 B2 | 5/2010 | Arnal et al. | |
| 7,723,560 B2 | 5/2010 | Lockwood et al. | |
| 7,753,894 B2 | 7/2010 | Blott et al. | |
| 7,754,937 B2 | 7/2010 | Boehringer et al. | |
| 7,776,028 B2 | 8/2010 | Miller et al. | |
| 7,777,522 B2 | 8/2010 | Yang et al. | |
| 7,779,625 B2 | 8/2010 | Joshi et al. | |
| D625,801 S | 10/2010 | Pidgeon et al. | |
| 7,811,269 B2 | 10/2010 | Boynton et al. | |
| 7,815,616 B2 | 10/2010 | Boehringer et al. | |
| 7,820,453 B2 | 10/2010 | Heylen et al. | |
| 7,846,141 B2 | 12/2010 | Weston | |
| 7,857,806 B2 | 12/2010 | Karpowicz et al. | |
| 7,863,495 B2 | 1/2011 | Aali | |
| 7,892,181 B2 | 2/2011 | Christensen et al. | |
| 7,896,856 B2 | 3/2011 | Petrosenko et al. | |
| 7,909,805 B2 | 3/2011 | Weston | |
| 7,910,789 B2 | 3/2011 | Sinyagin | |
| 7,931,774 B2 | 4/2011 | Hall et al. | |
| 7,942,866 B2 | 5/2011 | Radl et al. | |
| 7,951,124 B2 | 5/2011 | Boehringer et al. | |
| 7,964,766 B2 | 6/2011 | Blott et al. | |
| 7,976,519 B2 | 7/2011 | Bubb et al. | |

(56) References Cited

U.S. PATENT DOCUMENTS

| | | |
|---|---|---|
| 7,976,524 B2 | 7/2011 | Kudo et al. |
| 7,981,098 B2 | 7/2011 | Boehringer et al. |
| 8,030,534 B2 | 10/2011 | Radl et al. |
| 8,057,447 B2 | 11/2011 | Olson et al. |
| 8,062,272 B2 | 11/2011 | Weston |
| 8,062,295 B2 | 11/2011 | McDevitt et al. |
| 8,062,331 B2 | 11/2011 | Zamierowski |
| 8,067,662 B2 | 11/2011 | Aali et al. |
| 8,070,773 B2 | 12/2011 | Zamierowski |
| 8,080,702 B2 | 12/2011 | Blott et al. |
| 8,100,887 B2 | 1/2012 | Weston et al. |
| 8,114,126 B2 | 2/2012 | Heaton et al. |
| 8,123,781 B2 | 2/2012 | Zamierowski |
| 8,128,615 B2 | 3/2012 | Blott et al. |
| 8,129,580 B2 | 3/2012 | Wilkes et al. |
| 8,142,419 B2 | 3/2012 | Heaton et al. |
| 8,162,909 B2 | 4/2012 | Blott et al. |
| 8,172,816 B2 | 5/2012 | Kazala, Jr. et al. |
| 8,182,413 B2 | 5/2012 | Browning |
| 8,187,237 B2 | 5/2012 | Seegert |
| 8,188,331 B2 | 5/2012 | Barta et al. |
| 8,192,409 B2 | 6/2012 | Hardman et al. |
| 8,197,467 B2 | 6/2012 | Heaton et al. |
| 8,207,392 B2 | 6/2012 | Haggstrom et al. |
| 8,215,929 B2 | 7/2012 | Shen et al. |
| 8,235,955 B2 | 8/2012 | Blott et al. |
| 8,235,972 B2 | 8/2012 | Adahan |
| 8,246,590 B2 | 8/2012 | Hu et al. |
| 8,246,606 B2 | 8/2012 | Stevenson et al. |
| 8,246,607 B2 * | 8/2012 | Karpowicz ......... A61M 1/0031 604/543 |
| 8,257,328 B2 | 9/2012 | Augustine et al. |
| 8,273,105 B2 | 9/2012 | Cohen et al. |
| 8,298,200 B2 | 10/2012 | Vess et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,362,315 B2 | 1/2013 | Aali |
| 8,376,972 B2 | 2/2013 | Fleischmann |
| 8,399,730 B2 | 3/2013 | Kazala, Jr. et al. |
| 8,430,867 B2 | 4/2013 | Robinson et al. |
| 8,439,882 B2 | 5/2013 | Kelch |
| 8,444,392 B2 | 5/2013 | Turner et al. |
| 8,444,611 B2 | 5/2013 | Wilkes et al. |
| 8,447,375 B2 | 5/2013 | Shuler |
| 8,454,990 B2 | 6/2013 | Canada et al. |
| 8,460,255 B2 | 6/2013 | Joshi et al. |
| 8,460,257 B2 * | 6/2013 | Locke ............ A61F 13/00068 604/319 |
| 8,481,804 B2 | 7/2013 | Timothy |
| 8,486,032 B2 | 7/2013 | Seegert et al. |
| 8,500,704 B2 * | 8/2013 | Boehringer ............ A61F 13/36 604/313 |
| 8,500,776 B2 | 8/2013 | Ebner |
| 8,523,832 B2 | 9/2013 | Seegert |
| 8,535,296 B2 | 9/2013 | Blott et al. |
| 8,562,576 B2 | 10/2013 | Hu et al. |
| 8,608,776 B2 | 12/2013 | Coward et al. |
| 8,622,981 B2 | 1/2014 | Hartwell et al. |
| 8,628,505 B2 | 1/2014 | Weston |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 * | 4/2014 | Robinson ............ A61F 13/0203 604/319 |
| 8,715,256 B2 | 5/2014 | Greener |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,784,392 B2 * | 7/2014 | Vess ............ A61M 1/0023 604/304 |
| 8,791,315 B2 | 7/2014 | Lattimore et al. |
| 8,791,316 B2 * | 7/2014 | Greener ............ A61F 13/00987 602/46 |
| 8,801,685 B2 * | 8/2014 | Armstrong ............ A61F 13/022 604/319 |
| 8,802,916 B2 | 8/2014 | Griffey et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,853,486 B2 | 10/2014 | Wild et al. |
| 8,882,730 B2 | 11/2014 | Zimnitsky et al. |
| 8,936,618 B2 | 1/2015 | Sealy et al. |
| 8,945,030 B2 | 2/2015 | Weston |
| 8,951,235 B2 | 2/2015 | Allen et al. |
| 8,956,336 B2 * | 2/2015 | Haggstrom ......... A61M 1/0088 604/313 |
| 9,044,579 B2 | 6/2015 | Blott et al. |
| 9,050,398 B2 | 6/2015 | Armstrong et al. |
| 9,061,095 B2 | 6/2015 | Adie et al. |
| 9,084,845 B2 | 7/2015 | Adie et al. |
| 9,180,132 B2 | 11/2015 | Fein et al. |
| 9,180,231 B2 | 11/2015 | Greener |
| 9,204,801 B2 | 12/2015 | Locke et al. |
| 9,220,822 B2 | 12/2015 | Hartwell |
| 9,226,737 B2 | 1/2016 | Dunn |
| 9,301,742 B2 | 4/2016 | Dunn |
| 9,339,248 B2 | 5/2016 | Tout et al. |
| 9,352,076 B2 | 5/2016 | Boynton et al. |
| 9,408,755 B2 | 8/2016 | Larsson et al. |
| 9,421,132 B2 | 8/2016 | Dunn |
| 9,555,170 B2 | 1/2017 | Fleischmann |
| 9,597,484 B2 | 3/2017 | Dunn |
| 9,655,807 B2 | 5/2017 | Locke et al. |
| 9,737,649 B2 | 8/2017 | Begin et al. |
| 9,757,500 B2 | 9/2017 | Locke et al. |
| 9,770,368 B2 | 9/2017 | Robinson et al. |
| 9,801,986 B2 | 10/2017 | Greener |
| 9,820,888 B2 * | 11/2017 | Greener ............ A61F 13/00038 |
| D805,039 S | 12/2017 | Dejanovic et al. |
| 9,844,472 B2 | 12/2017 | Hammond et al. |
| 9,849,023 B2 | 12/2017 | Hall et al. |
| 9,895,270 B2 | 2/2018 | Coward et al. |
| 9,962,295 B2 | 5/2018 | Dunn et al. |
| 10,070,994 B2 | 9/2018 | Dodd et al. |
| 10,117,782 B2 | 11/2018 | Dagger et al. |
| 10,124,098 B2 | 11/2018 | Dunn et al. |
| 10,130,520 B2 * | 11/2018 | Dunn ............ A61F 13/00068 |
| 10,143,485 B2 | 12/2018 | Locke et al. |
| 10,166,148 B2 | 1/2019 | Dunn |
| 10,179,073 B2 | 1/2019 | Hartwell et al. |
| 10,201,642 B2 | 2/2019 | Hartwell et al. |
| 10,245,185 B2 | 4/2019 | Hicks et al. |
| 10,405,861 B2 | 9/2019 | Dunn |
| 10,537,657 B2 | 1/2020 | Phillips et al. |
| 10,575,991 B2 | 3/2020 | Dunn |
| 10,660,992 B2 | 5/2020 | Canner et al. |
| 10,729,590 B2 | 8/2020 | Simmons et al. |
| 10,814,049 B2 | 10/2020 | Dunn |
| 11,083,631 B2 | 8/2021 | Dunn et al. |
| 2001/0029956 A1 | 10/2001 | Argenta |
| 2001/0034499 A1 * | 10/2001 | Sessions ............ A61F 13/00021 602/46 |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0065360 A1 | 4/2003 | Jacobs et al. |
| 2003/0108587 A1 | 6/2003 | Orgill et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0178274 A1 | 9/2003 | Chi |
| 2003/0220660 A1 | 11/2003 | Kortenbach et al. |
| 2004/0006319 A1 | 1/2004 | Lina et al. |
| 2004/0010275 A1 | 1/2004 | Jacobs et al. |
| 2004/0030304 A1 | 2/2004 | Hunt et al. |

(56) References Cited

U.S. PATENT DOCUMENTS

| | | |
|---|---|---|
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0243073 A1 | 12/2004 | Lockwood et al. |
| 2004/0267312 A1 | 12/2004 | Kanner et al. |
| 2005/0107731 A1* | 5/2005 | Sessions ............... A61F 13/12 602/41 |
| 2005/0119694 A1 | 6/2005 | Jacobs et al. |
| 2005/0131414 A1 | 6/2005 | Chana |
| 2005/0142331 A1 | 6/2005 | Anderson et al. |
| 2005/0182445 A1 | 8/2005 | Zamierowski |
| 2005/0209574 A1 | 9/2005 | Boehringer et al. |
| 2005/0222544 A1 | 10/2005 | Weston |
| 2005/0222613 A1 | 10/2005 | Ryan |
| 2005/0240220 A1 | 10/2005 | Zamierowski |
| 2005/0258887 A1 | 11/2005 | Ito et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur |
| 2006/0135921 A1 | 6/2006 | Wiercinski et al. |
| 2006/0213527 A1 | 9/2006 | Argenta et al. |
| 2006/0217795 A1 | 9/2006 | Besselink et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0027414 A1 | 2/2007 | Hoffman et al. |
| 2007/0027475 A1 | 2/2007 | Pagedas |
| 2007/0032755 A1 | 2/2007 | Walsh |
| 2007/0032763 A1 | 2/2007 | Vogel |
| 2007/0038172 A1 | 2/2007 | Zamierowski |
| 2007/0052144 A1 | 3/2007 | Knirck et al. |
| 2007/0055209 A1 | 3/2007 | Patel et al. |
| 2007/0104941 A1 | 5/2007 | Kameda et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1* | 6/2007 | McLeod ............... A61M 1/0084 602/41 |
| 2007/0149910 A1 | 6/2007 | Zocher |
| 2007/0161937 A1 | 7/2007 | Aali |
| 2007/0179421 A1* | 8/2007 | Farrow ................. A61H 9/005 602/75 |
| 2007/0185463 A1 | 8/2007 | Mulligan |
| 2007/0213597 A1 | 9/2007 | Wooster |
| 2007/0219513 A1 | 9/2007 | Lina et al. |
| 2007/0265585 A1 | 11/2007 | Joshi et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0103462 A1 | 5/2008 | Wenzel et al. |
| 2008/0108977 A1 | 5/2008 | Heaton et al. |
| 2008/0167593 A1 | 7/2008 | Fleischmann |
| 2008/0177253 A1 | 7/2008 | Boehringer et al. |
| 2008/0243096 A1 | 10/2008 | Svedman |
| 2008/0275409 A1 | 11/2008 | Kane et al. |
| 2008/0287973 A1 | 11/2008 | Aster et al. |
| 2008/0306456 A1 | 12/2008 | Riesinger |
| 2009/0005716 A1 | 1/2009 | Abuzaina et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0204423 A1 | 8/2009 | DeGheest et al. |
| 2009/0227938 A1 | 9/2009 | Fasching et al. |
| 2009/0227969 A1 | 9/2009 | Jaeb et al. |
| 2009/0246238 A1 | 10/2009 | Gorman et al. |
| 2009/0259203 A1 | 10/2009 | Hu et al. |
| 2009/0293887 A1 | 12/2009 | Wilkes et al. |
| 2009/0299255 A1 | 12/2009 | Kazala, Jr. et al. |
| 2009/0299256 A1 | 12/2009 | Barta et al. |
| 2009/0299303 A1 | 12/2009 | Seegert |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2009/0312685 A1 | 12/2009 | Olsen et al. |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0047324 A1 | 2/2010 | Fritz et al. |
| 2010/0081983 A1 | 4/2010 | Zocher et al. |
| 2010/0087854 A1 | 4/2010 | Stopek et al. |
| 2010/0100022 A1 | 4/2010 | Greener et al. |
| 2010/0100063 A1 | 4/2010 | Joshi et al. |
| 2010/0106106 A1 | 4/2010 | Heaton et al. |
| 2010/0106184 A1* | 4/2010 | Coward ............ A61F 13/00987 606/213 |
| 2010/0106188 A1* | 4/2010 | Heaton ............. A61F 13/00025 606/216 |
| 2010/0121286 A1 | 5/2010 | Locke et al. |
| 2010/0121287 A1 | 5/2010 | Smith et al. |
| 2010/0125233 A1 | 5/2010 | Edward et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0160876 A1 | 6/2010 | Robinson et al. |
| 2010/0160901 A1 | 6/2010 | Hu et al. |
| 2010/0179515 A1 | 7/2010 | Swain et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262092 A1 | 10/2010 | Hartwell |
| 2010/0262106 A1 | 10/2010 | Hartwell |
| 2010/0262126 A1 | 10/2010 | Hu et al. |
| 2010/0280468 A1 | 11/2010 | Haggstrom et al. |
| 2010/0292717 A1 | 11/2010 | Petter-Puchner et al. |
| 2010/0298866 A1 | 11/2010 | Fischvogt |
| 2010/0305490 A1 | 12/2010 | Coulthard et al. |
| 2010/0312159 A1 | 12/2010 | Aali et al. |
| 2010/0318046 A1 | 12/2010 | Boehringer et al. |
| 2011/0004173 A1 | 1/2011 | Hu et al. |
| 2011/0009838 A1 | 1/2011 | Greener |
| 2011/0015594 A1 | 1/2011 | Hu et al. |
| 2011/0015595 A1 | 1/2011 | Robinson et al. |
| 2011/0021965 A1 | 1/2011 | Karp et al. |
| 2011/0022082 A1 | 1/2011 | Burke et al. |
| 2011/0054283 A1 | 3/2011 | Shuler |
| 2011/0054365 A1 | 3/2011 | Greener |
| 2011/0059291 A1 | 3/2011 | Boyce et al. |
| 2011/0060204 A1 | 3/2011 | Weston |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0105963 A1 | 5/2011 | Hu et al. |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0113559 A1 | 5/2011 | Dodd |
| 2011/0130774 A1 | 6/2011 | Criscuolo et al. |
| 2011/0152800 A1 | 6/2011 | Eckstein et al. |
| 2011/0172760 A1 | 7/2011 | Anderson |
| 2011/0178451 A1 | 7/2011 | Robinson et al. |
| 2011/0196420 A1 | 8/2011 | Ebner |
| 2011/0213287 A1 | 9/2011 | Lattimore et al. |
| 2011/0213319 A1* | 9/2011 | Blott ................... A61M 1/0092 604/291 |
| 2011/0224631 A1* | 9/2011 | Simmons ......... A61F 13/00995 604/319 |
| 2011/0224632 A1* | 9/2011 | Zimnitsky ............. A61F 13/02 604/319 |

(56) References Cited

U.S. PATENT DOCUMENTS

| | | |
|---|---|---|
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |
| 2011/0245788 A1 | 10/2011 | Marquez Canada |
| 2011/0264138 A1 | 10/2011 | Avelar et al. |
| 2011/0270201 A1 | 11/2011 | Bubb et al. |
| 2011/0270301 A1 | 11/2011 | Cornet et al. |
| 2011/0275964 A1 | 11/2011 | Greener |
| 2011/0282136 A1 | 11/2011 | Browning |
| 2011/0282309 A1 | 11/2011 | Adie et al. |
| 2011/0282310 A1 | 11/2011 | Boehringer et al. |
| 2011/0305736 A1 | 12/2011 | Wieland et al. |
| 2011/0313374 A1 | 12/2011 | Lockwood et al. |
| 2011/0319804 A1 | 12/2011 | Greener |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Coulthard et al. |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0041402 A1* | 2/2012 | Greener .............. A61F 13/00068 604/319 |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0073736 A1 | 3/2012 | O'Connor et al. |
| 2012/0083755 A1 | 4/2012 | Lina et al. |
| 2012/0095426 A1 | 4/2012 | Visscher et al. |
| 2012/0109188 A1 | 5/2012 | Viola |
| 2012/0121556 A1 | 5/2012 | Fraser et al. |
| 2012/0123358 A1 | 5/2012 | Hall et al. |
| 2012/0130327 A1 | 5/2012 | Marquez Canada |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0144989 A1 | 6/2012 | Du Plessis et al. |
| 2012/0150078 A1 | 6/2012 | Chen et al. |
| 2012/0150133 A1 | 6/2012 | Heaton et al. |
| 2012/0157942 A1 | 6/2012 | Weston |
| 2012/0165764 A1 | 6/2012 | Allen et al. |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0203189 A1 | 8/2012 | Barta et al. |
| 2012/0209226 A1 | 8/2012 | Simmons et al. |
| 2012/0209227 A1* | 8/2012 | Dunn .................... A61B 17/08 604/319 |
| 2012/0220968 A1 | 8/2012 | Confalone et al. |
| 2012/0222687 A1 | 9/2012 | Czajka, Jr. et al. |
| 2012/0238931 A1 | 9/2012 | Rastegar et al. |
| 2012/0253302 A1 | 10/2012 | Corley |
| 2012/0277773 A1 | 11/2012 | Sargeant et al. |
| 2012/0302440 A1 | 11/2012 | Theliander et al. |
| 2013/0012891 A1 | 1/2013 | Gross et al. |
| 2013/0023842 A1 | 1/2013 | Song |
| 2013/0066365 A1 | 3/2013 | Belson et al. |
| 2013/0096518 A1 | 4/2013 | Hall et al. |
| 2013/0110058 A1 | 5/2013 | Adie et al. |
| 2013/0110066 A1 | 5/2013 | Sharma et al. |
| 2013/0131564 A1 | 5/2013 | Locke et al. |
| 2013/0138054 A1 | 5/2013 | Fleischmann |
| 2013/0150813 A1 | 6/2013 | Gordon et al. |
| 2013/0150814 A1 | 6/2013 | Buan |
| 2013/0190705 A1 | 7/2013 | Vess et al. |
| 2013/0197457 A1 | 8/2013 | Kazala et al. |
| 2013/0204213 A1 | 8/2013 | Heagle et al. |
| 2013/0245527 A1 | 9/2013 | Croizat et al. |
| 2013/0253401 A1 | 9/2013 | Locke et al. |
| 2013/0274717 A1 | 10/2013 | Dunn |
| 2013/0310781 A1 | 11/2013 | Phillips et al. |
| 2013/0317465 A1 | 11/2013 | Seegert |
| 2013/0325142 A1 | 12/2013 | Hunter et al. |
| 2013/0331757 A1 | 12/2013 | Belson |
| 2014/0066868 A1 | 3/2014 | Freedman et al. |
| 2014/0068914 A1 | 3/2014 | Coward et al. |
| 2014/0088455 A1 | 3/2014 | Christensen et al. |
| 2014/0094730 A1 | 4/2014 | Greener |
| 2014/0109560 A1 | 4/2014 | Ilievski et al. |
| 2014/0163415 A1 | 6/2014 | Zaiken et al. |
| 2014/0180225 A1* | 6/2014 | Dunn ................... A61M 1/0088 604/319 |
| 2014/0180229 A1* | 6/2014 | Fuller .................... A61L 15/22 604/360 |
| 2014/0194836 A1 | 7/2014 | Kazala, Jr. et al. |
| 2014/0194837 A1 | 7/2014 | Robinson et al. |
| 2014/0195004 A9* | 7/2014 | Engqvist ............. A61B 17/8085 623/23.61 |
| 2014/0213994 A1 | 7/2014 | Hardman et al. |
| 2014/0228789 A1 | 8/2014 | Wilkes et al. |
| 2014/0249495 A1* | 9/2014 | Mumby .............. A61F 13/0253 604/359 |
| 2014/0316359 A1* | 10/2014 | Collinson ......... A61F 13/00068 604/319 |
| 2014/0336602 A1 | 11/2014 | Karpowicz et al. |
| 2014/0343517 A1 | 11/2014 | Jameson |
| 2014/0343518 A1* | 11/2014 | Riesinger ............ A61M 1/0088 604/319 |
| 2015/0000018 A1 | 1/2015 | Brandt |
| 2015/0005722 A1 | 1/2015 | Hu et al. |
| 2015/0025484 A1 | 1/2015 | Simmons et al. |
| 2015/0030806 A1* | 1/2015 | Fink ........................ B32B 3/12 428/116 |
| 2015/0057762 A1* | 2/2015 | Harms ................. A61L 31/148 623/23.74 |
| 2015/0065805 A1* | 3/2015 | Edmondson ....... A61B 17/0218 600/204 |
| 2015/0065968 A1 | 3/2015 | Sealy et al. |
| 2015/0075697 A1 | 3/2015 | Gildersleeve |
| 2015/0080947 A1 | 3/2015 | Greener |
| 2015/0100008 A1* | 4/2015 | Chatterjee ........... A61F 13/0206 602/46 |
| 2015/0112290 A1 | 4/2015 | Dunn |
| 2015/0112311 A1 | 4/2015 | Hammond et al. |
| 2015/0119837 A1 | 4/2015 | Thompson, Jr. et al. |
| 2015/0119865 A1 | 4/2015 | Barta et al. |
| 2015/0148760 A1 | 5/2015 | Dodd et al. |
| 2015/0150729 A1 | 6/2015 | Dagger et al. |
| 2015/0157758 A1 | 6/2015 | Blucher et al. |
| 2015/0159066 A1 | 6/2015 | Hartwell et al. |
| 2015/0164174 A1 | 6/2015 | West |
| 2015/0174304 A1 | 6/2015 | Askem et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320434 A1 | 11/2015 | Ingram et al. |
| 2015/0320602 A1 | 11/2015 | Locke et al. |
| 2015/0374561 A1 | 12/2015 | Hubbard, Jr. et al. |
| 2016/0022885 A1 | 1/2016 | Dunn et al. |
| 2016/0030646 A1 | 2/2016 | Hartwell et al. |
| 2016/0067939 A1 | 3/2016 | Liebe et al. |
| 2016/0144085 A1 | 5/2016 | Melin et al. |
| 2016/0166744 A1 | 6/2016 | Hartwell |
| 2016/0184496 A1 | 6/2016 | Jaecklein et al. |
| 2016/0235897 A1 | 8/2016 | Boynton et al. |
| 2016/0354086 A1 | 12/2016 | Dunn |
| 2017/0007462 A1 | 1/2017 | Hartwell et al. |
| 2017/0007751 A1 | 1/2017 | Hartwell et al. |
| 2017/0065751 A1 | 3/2017 | Toth |
| 2017/0156611 A1 | 6/2017 | Burnett et al. |
| 2017/0281838 A1 | 10/2017 | Dunn |
| 2019/0105202 A1 | 4/2019 | Dunn et al. |
| 2019/0231599 A1 | 8/2019 | Dagger et al. |
| 2019/0231944 A1 | 8/2019 | Dunn et al. |
| 2019/0262182 A1 | 8/2019 | Collinson et al. |
| 2019/0290495 A1 | 9/2019 | Dunn et al. |

(56) References Cited

U.S. PATENT DOCUMENTS

| | | |
|---|---|---|
| 2020/0038023 A1 | 2/2020 | Dunn |
| 2020/0188564 A1 | 6/2020 | Dunn |
| 2020/0268562 A1 | 8/2020 | Dunn |
| 2020/0330661 A1 | 10/2020 | Canner et al. |

FOREIGN PATENT DOCUMENTS

| | | |
|---|---|---|
| CA | 2747743 A1 | 7/2010 |
| CA | 2701233 A1 | 11/2010 |
| CN | 1438904 A | 8/2003 |
| CN | 101112326 A | 1/2008 |
| CN | 101123930 A | 2/2008 |
| CN | 101208115 A | 6/2008 |
| CN | 101257938 A | 9/2008 |
| CN | 101588836 A | 11/2009 |
| CN | 101744688 A | 6/2010 |
| CN | 201519362 U | 7/2010 |
| CN | 102038575 A | 5/2011 |
| CN | 102046117 A | 5/2011 |
| CN | 102196830 A | 9/2011 |
| CN | 102256637 A | 11/2011 |
| CN | 102781380 A | 11/2012 |
| CN | 202568632 U | 12/2012 |
| CN | 103071197 A | 5/2013 |
| CN | 103405846 A | 11/2013 |
| CN | 103501709 A | 1/2014 |
| CN | 203408163 | 1/2014 |
| CN | 104736110 A | 6/2015 |
| CN | 104768474 A | 7/2015 |
| CN | 104812343 A | 7/2015 |
| DE | 2 949 920 | 3/1981 |
| DE | 102005007016 A1 | 8/2006 |
| DE | 102012001752 A1 | 8/2013 |
| EP | 1 320 342 | 6/2003 |
| EP | 2094211 A1 | 9/2009 |
| EP | 2 279 016 | 2/2011 |
| EP | 2366721 A1 | 9/2011 |
| EP | 2368523 A1 | 9/2011 |
| EP | 2404571 A1 | 1/2012 |
| EP | 2404626 A2 | 1/2012 |
| EP | 2 341 955 | 12/2012 |
| EP | 2529767 A2 | 12/2012 |
| EP | 2547375 A1 | 1/2013 |
| EP | 2 567 717 | 3/2013 |
| EP | 2563421 A1 | 3/2013 |
| EP | 2567682 A1 | 3/2013 |
| EP | 2 594 299 | 5/2013 |
| EP | 2 601 984 A2 | 6/2013 |
| EP | 2 623 137 | 8/2013 |
| EP | 2 367 517 | 9/2013 |
| EP | 2759265 A2 | 7/2014 |
| EP | 2829287 A1 | 1/2015 |
| EP | 2852419 A2 | 4/2015 |
| EP | 2872085 A1 | 5/2015 |
| EP | 3 225 261 | 10/2017 |
| GB | 2378392 A | 2/2003 |
| GB | 2389794 | 12/2003 |
| GB | 2423019 | 8/2006 |
| GB | 2489947 | 10/2012 |
| GB | 2496310 | 5/2013 |
| GB | 2524510 A | 9/2015 |
| IE | 20140129 A1 | 3/2016 |
| JP | S62-57560 A | 3/1987 |
| JP | H0341952 A | 2/1991 |
| JP | H09-503923 A | 4/1997 |
| JP | 2006-528038 A | 12/2006 |
| JP | 2007-505678 A | 3/2007 |
| JP | 2007-531567 A | 11/2007 |
| JP | 2008-529618 A | 8/2008 |
| JP | 2009-525087 A | 7/2009 |
| JP | 2009-536851 A | 10/2009 |
| JP | 2010-526597 A | 8/2010 |
| JP | 2011-500170 A | 1/2011 |
| JP | 2011521740 A | 7/2011 |
| JP | 2011-523575 A | 8/2011 |
| JP | 2011-526798 A | 10/2011 |
| JP | 2012-504460 A | 2/2012 |
| JP | 2012-105840 A | 6/2012 |
| JP | 2012-513826 A | 6/2012 |
| JP | 2012529974 A | 11/2012 |
| JP | 2013-526938 A | 6/2013 |
| JP | 2014168573 A | 9/2014 |
| JP | 2018-519864 A | 7/2018 |
| RU | 1818103 | 5/1993 |
| RU | 62504 | 4/2007 |
| WO | 1994/20041 A1 | 9/1994 |
| WO | 2000/59424 A1 | 10/2000 |
| WO | 2001/34223 A1 | 5/2001 |
| WO | WO 2001/085248 | 11/2001 |
| WO | WO 2001/089392 | 11/2001 |
| WO | WO 2002/05737 | 1/2002 |
| WO | WO 2003/003948 | 1/2003 |
| WO | WO 03/049598 A2 | 6/2003 |
| WO | WO 2004/018020 | 3/2004 |
| WO | WO 2004/037334 | 5/2004 |
| WO | WO 2005/046761 | 5/2005 |
| WO | WO 2005/105174 | 11/2005 |
| WO | 2006/041496 A1 | 4/2006 |
| WO | WO 2006/046060 | 5/2006 |
| WO | 2006/087021 A1 | 8/2006 |
| WO | 2006/100053 A2 | 9/2006 |
| WO | WO 2007/030601 | 3/2007 |
| WO | 2007/120138 A2 | 10/2007 |
| WO | WO 2007/133618 | 11/2007 |
| WO | 2008/005532 A2 | 1/2008 |
| WO | WO 2008/027449 A2 | 3/2008 |
| WO | WO 2008/039223 | 4/2008 |
| WO | WO-2008039839 A2 * | 4/2008 ........... A61B 17/083 |
| WO | WO 2008/064502 | 6/2008 |
| WO | WO 2008/091521 | 7/2008 |
| WO | WO 2008/104609 | 9/2008 |
| WO | 2009/019495 A1 | 2/2009 |
| WO | 2009/071926 A1 | 6/2009 |
| WO | 2009/071933 A2 | 6/2009 |
| WO | 2009/093116 A1 | 7/2009 |
| WO | WO 2009/112062 | 9/2009 |
| WO | WO 2009/112848 | 9/2009 |
| WO | WO 2009/114624 | 9/2009 |
| WO | 2009/156709 A1 | 12/2009 |
| WO | 2009/158125 A1 | 12/2009 |
| WO | 2009/158126 A1 | 12/2009 |
| WO | WO 2009/158132 | 12/2009 |
| WO | WO 2010/033725 | 3/2010 |
| WO | WO 2010/051073 | 5/2010 |
| WO | WO 2010/059612 | 5/2010 |
| WO | 2010/075178 A2 | 7/2010 |
| WO | 2010/078349 A2 | 7/2010 |
| WO | 2010/079359 A1 | 7/2010 |
| WO | WO 2010/075180 | 7/2010 |
| WO | WO 2010/092334 | 8/2010 |
| WO | WO 2010/097570 | 9/2010 |
| WO | WO-2010097570 A1 * | 9/2010 ....... A61F 13/00068 |
| WO | 2010/147535 A1 | 12/2010 |
| WO | WO 2011/023384 | 3/2011 |
| WO | 2011/087871 A2 | 7/2011 |
| WO | 2011/091169 A1 | 7/2011 |
| WO | 2011/115908 A1 | 9/2011 |
| WO | 2011/116691 A1 | 9/2011 |
| WO | WO 2011/106722 | 9/2011 |
| WO | 2011/135286 A1 | 11/2011 |
| WO | 2011/135287 A1 | 11/2011 |
| WO | WO 2011/135284 | 11/2011 |
| WO | WO 2011/137230 | 11/2011 |
| WO | WO 2011/144888 | 11/2011 |
| WO | WO 2012/021553 | 2/2012 |
| WO | 2012/038727 A2 | 3/2012 |
| WO | 2012/069793 A1 | 5/2012 |
| WO | 2012/069794 A1 | 5/2012 |
| WO | 2012/087376 A1 | 6/2012 |
| WO | WO 2012/082716 | 6/2012 |
| WO | WO 2012/082876 | 6/2012 |
| WO | WO 2012/106590 | 8/2012 |
| WO | WO 2012/112204 | 8/2012 |
| WO | WO-2012106590 A2 * | 8/2012 ............. A61B 17/08 |

(56) References Cited

FOREIGN PATENT DOCUMENTS

| WO | WO 2012/136707 | | 10/2012 | | |
|----|----|----|----|----|----|
| WO | WO 2012/142473 | | 10/2012 | | |
| WO | 2012/156655 | A1 | 11/2012 | | |
| WO | 2012/168678 | A1 | 12/2012 | | |
| WO | WO 2013/007973 | | 1/2013 | | |
| WO | WO 2013/012381 | | 1/2013 | | |
| WO | WO 2013/043258 | | 3/2013 | | |
| WO | 2013/074829 | A1 | 5/2013 | | |
| WO | WO 2013/071243 | | 5/2013 | | |
| WO | WO 2013/076450 | A1 | 5/2013 | | |
| WO | WO 2013/079947 | | 6/2013 | | |
| WO | WO-2013079447 | A1 | 6/2013 | | |
| WO | 2013/136181 | A2 | 9/2013 | | |
| WO | WO 2013/175309 | | 11/2013 | | |
| WO | WO 2013/175310 | | 11/2013 | | |
| WO | WO 2014/013348 | | 1/2014 | | |
| WO | WO 2014/014842 | | 1/2014 | | |
| WO | WO 2014/014871 | | 1/2014 | | |
| WO | WO 2014/014922 | | 1/2014 | | |
| WO | WO-2014014871 | A1 * | 1/2014 | ....... | A61F 13/00068 |
| WO | WO 2014/024048 | | 2/2014 | | |
| WO | WO 2014/140578 | | 9/2014 | | |
| WO | WO 2014/158526 | | 10/2014 | | |
| WO | WO 2014/165275 | | 10/2014 | | |
| WO | WO 2014/178945 | A1 | 11/2014 | | |
| WO | WO 2014/194786 | | 12/2014 | | |
| WO | WO 2015/008054 | | 1/2015 | | |
| WO | WO 2015/061352 | | 4/2015 | | |
| WO | WO 2015/109359 | | 7/2015 | | |
| WO | WO 2015/110409 | | 7/2015 | | |
| WO | WO 2015/110410 | | 7/2015 | | |
| WO | WO 2015/169637 | | 11/2015 | | |
| WO | WO 2015/172108 | | 11/2015 | | |
| WO | WO 2015/193257 | A1 | 12/2015 | | |
| WO | WO 2016/018448 | A1 | 2/2016 | | |
| WO | 2016/184913 | A1 | 11/2016 | | |
| WO | WO 2016/176513 | | 11/2016 | | |
| WO | WO 2016/179245 | A1 | 11/2016 | | |
| WO | 2017/063036 | A1 | 4/2017 | | |
| WO | WO 2017/106576 | A1 | 6/2017 | | |
| WO | 2018/038665 | A1 | 3/2018 | | |
| WO | 2018/041805 | A1 | 3/2018 | | |
| WO | 2018/044944 | A1 | 3/2018 | | |
| WO | 2018/044949 | A1 | 3/2018 | | |
| WO | 2018/237206 | A2 | 12/2018 | | |

OTHER PUBLICATIONS

Definition of "Adhere", The Free Dictionary, accessed Mar. 23, 2017, in 6 pages. URL: http://www.thefreedictionary.com/adhere.
Definition of "Oculiform", Webster's Revised Unabridged Dictionary, 1913, accessed from The Free Dictionary on May 30, 2018, in 1 page. URL: https://www.thefreedictionary.com/Oculiform.
Definition of "Throughout", Merriam-Webster Dictionary, accessed Aug. 29, 2017, in 11 pages. URL: https://www.merriam-webster.com/dictionary/throughout.
Hougaard, et al., "The open abdomen: temporary closure with a modified negative pressure therapy technique", International Wound Journal, (2014), ISSN 1742-4801, pp. 13-16.
International Preliminary Reporton Patentability, re PCT Application No. PCT/US2016/029888, dated Nov. 9, 2017.
Kapischke, et al., "Self-fixating mesh for the Lichtenstein procedure-a prestudy", Langenbecks Arch Surg (2010), 395 pp. 317-322.
"Definition of 3D Printer," American Heritage Dictionary of the English Language, Fifth Edition, accessed on Feb. 22, 2018 from URL: https://www.thefreedictionary.com, 2016, 1 page.
Bengezi et al., Elevation as a treatment for fasciotomy wound closure. Can J Plast Surg. 2013 Fall;21(3):192-4.
Epstein et al., Lipoabdominoplasty Without Drains or Progressive Tension Sutures: An Analysis of 100 Consecutive Patients. Aesthetic Surgery Journal. Apr. 2015;35(4):434-440.
Jauregui et al., Fasciotomy closure techniques. J Orthop Surg (Hong Kong). Jan. 2017;25(1):2309499016684724. 8 pages.
Macias et al., Decrease in Seroma Rate After Adopting Progressive Tension Sutures Without Drains: A Single Surgery Center Experience of 451 Abdominoplasties over 7 Years. Aesthetic Surgery Journal. Mar. 2016;36(9):1029-1035.
Pollock et al.. Progressive Tension Sutures in Abdominoplasty: A Review of 597 Consecutive Cases. Aesthetic Surgery Journal. Aug. 2012;32(6):729-742.
Quaba et al., The no-drain, no quilt abdominoplasty: a single-surgeon series of 271 patients. Plast Reconstr Surg. Mar. 2015;135(3):751-60.
Rothenberg et al., Emerging Insights on Closed Incision NPWT and Transmetatarsal Amputations. http://www.podiatrytoday.com/emerging-insights-closed-incision-npwt-and-transmetatarsal-amputations. Apr. 2015;28(4):1-5.
Argenta et al., Vacuum-assisted closure: a new method for wound control and treatment: clinical experience. Ann PlastSurg. Jun. 1997;38(6):563-76.
Armstrong et al., Negative pressure wound therapy after partial diabetic foot amputation: a multicentre, randomised controlled trial. Lancet. Nov. 12, 2005;366(9498):1704-10.
Atkins et al., Does negative pressure wound therapy have a role in preventing poststernotomy wound complications? Surg Innov. Jun. 2009;16(2):140-6.
Blume et al., Comparison of negative pressure wound therapy using vacuum-assisted closure with advanced moist wound therapy in the treatment of diabetic foot ulcers: a multicenter randomized controlled trial. Diabetes Care. Apr. 2008;31(4):631-6.
Easterlin et al., A Novel Technique of Vacuum-assisted Wound Closure That Functions as a Delayed Primary Closure. Wounds. Dec. 2007;19(12):331-3.
Gomoll et al., Incisional vacuum-assisted closure therapy. J Orthop Trauma. Nov.-Dec. 2006;20(10):705-9.
Grauhan et al., Prevention of poststernotomy wound infections in obese patients by negative pressure wound therapy. J Thorac Cardiovasc Surg. May 2013;145(5):1387-92.
Kaplan et al., Early intervention of negative pressure wound therapy using Vacuum-Assisted Closure in trauma patients: impact on hospital length of stay and cost. Adv Skin Wound Care. Mar. 2009;22(3):128-32.
Masden et al.. Negative pressure wound therapy for at-risk surgical closures in patients with multiple comorbidities: a prospective randomized controlled study. Ann Surg. Jun. 2012;255(6):1043-7.
Pachowsky et al., Negative pressure wound therapy to prevent seromas and treat surgical incisions after total hip arthroplasty. Int Orthop. Apr. 2012;36(4):719-22.
Reddix et al., Incisional vacuum-assisted wound closure in morbidly obese patients undergoing acetabular fracture surgery. Am J Orthop (Belle Mead NJ). Sep. 2009;38(9):446-9.
Reddix et al., The effect of incisional negative pressure therapy on wound complications after acetabular fracture surgery. J Surg Orthop Adv. 2010 Summer;19(2):91-7.
Stannard et al., Incisional negative pressure wound therapy after high-risk lower extremity fractures. J Orthop Trauma. Jan. 2012;26(1):37-42.
Stannard et al., Negative pressure wound therapy to treat hematomas and surgical incisions following high-energy trauma. J Trauma. Jun. 2006;60(6):1301-6.

* cited by examiner

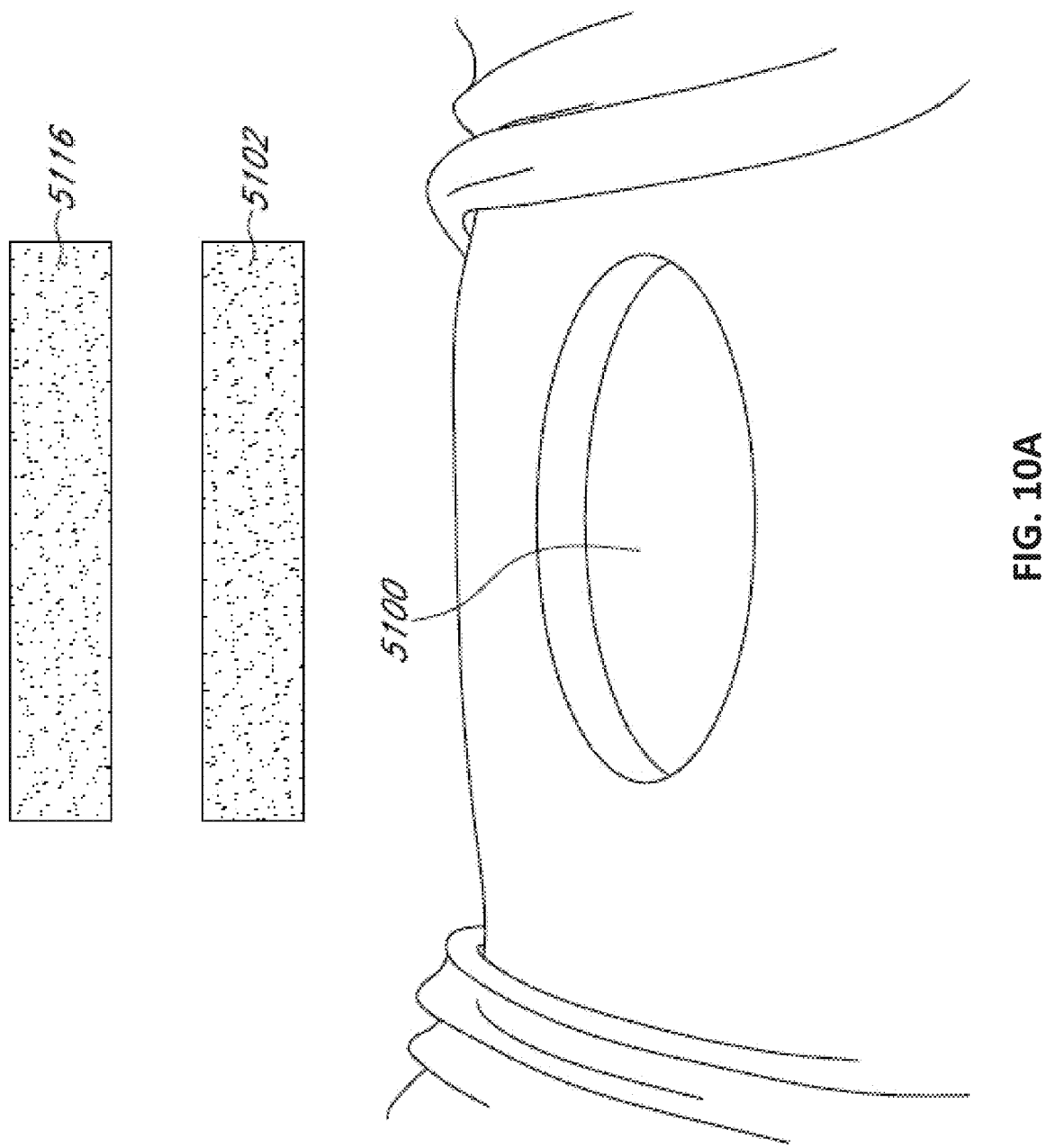

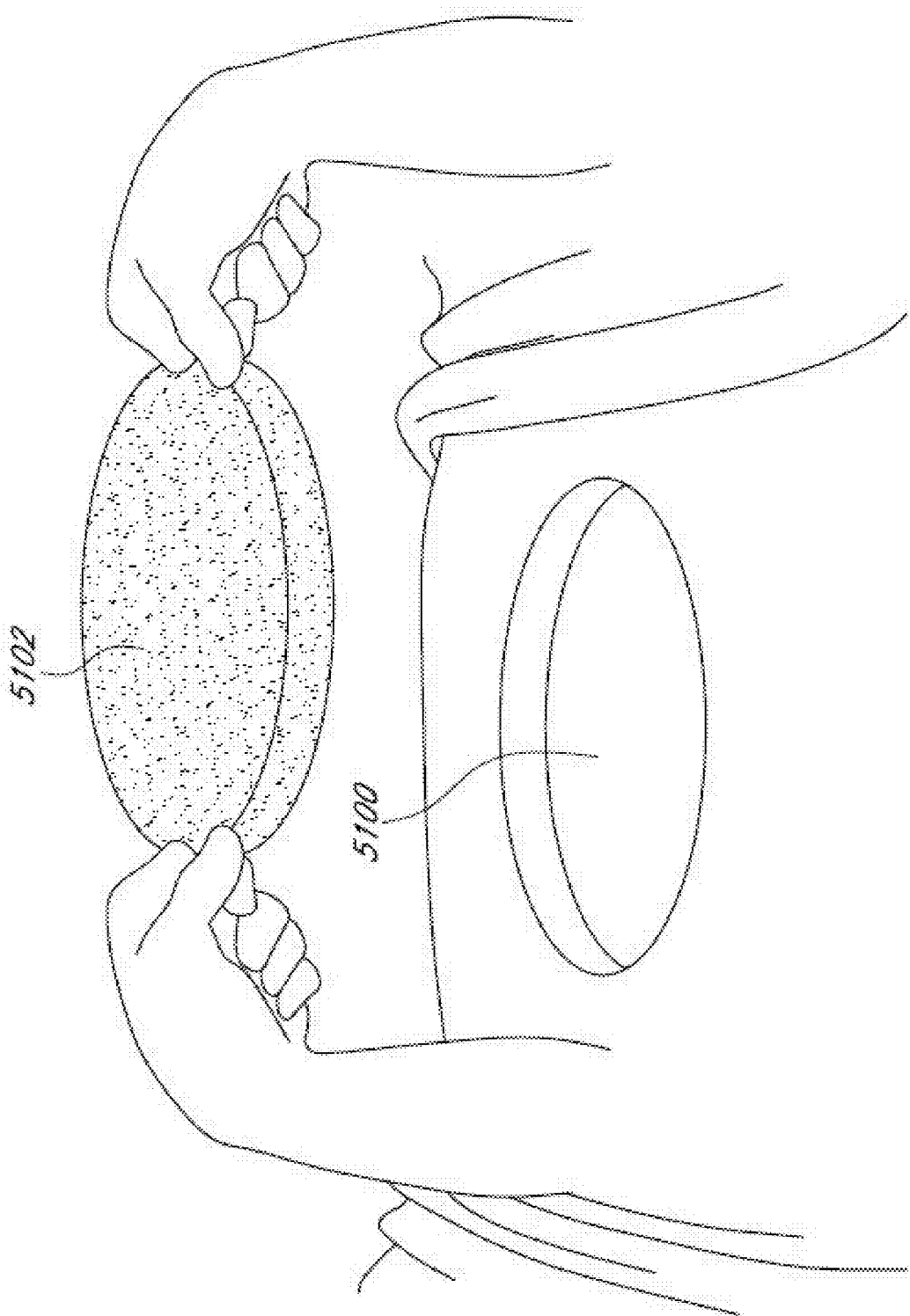

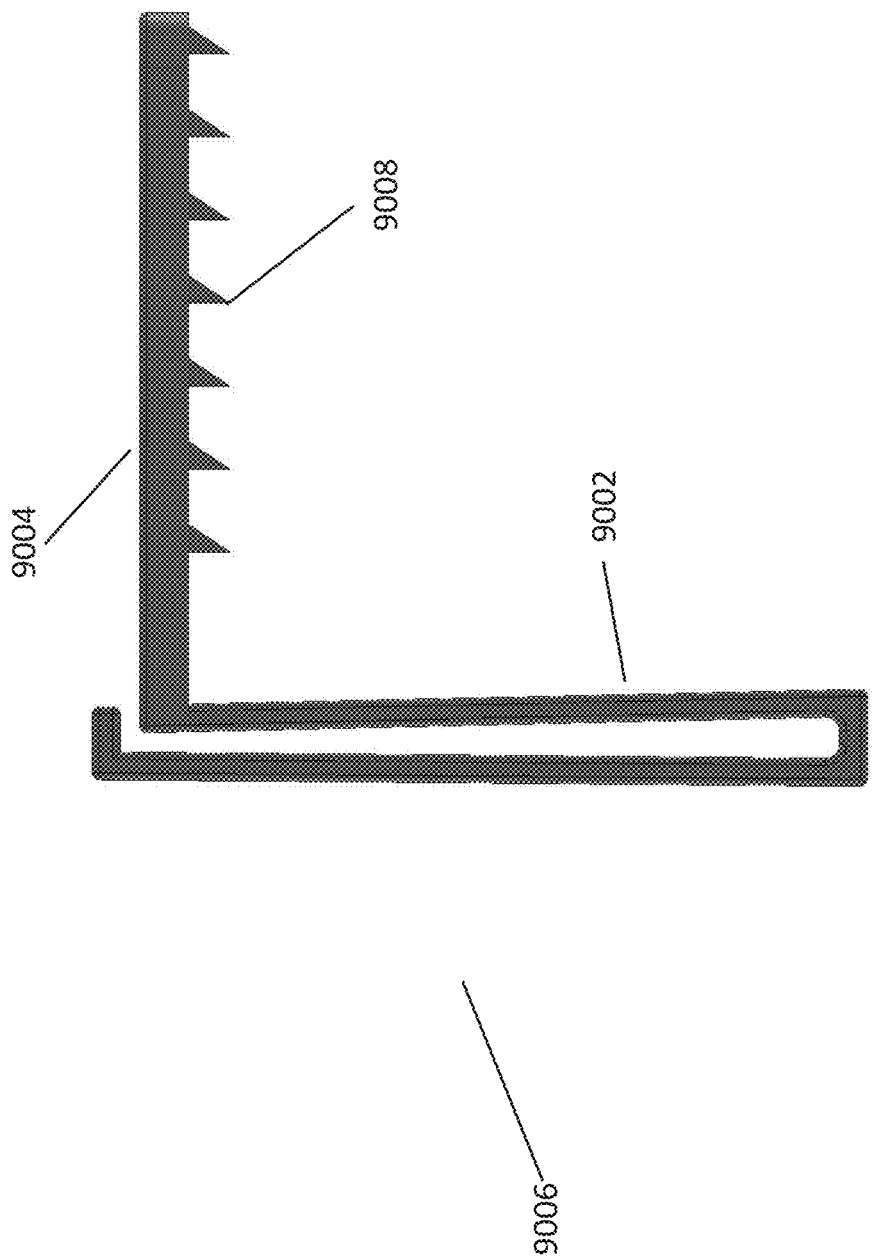

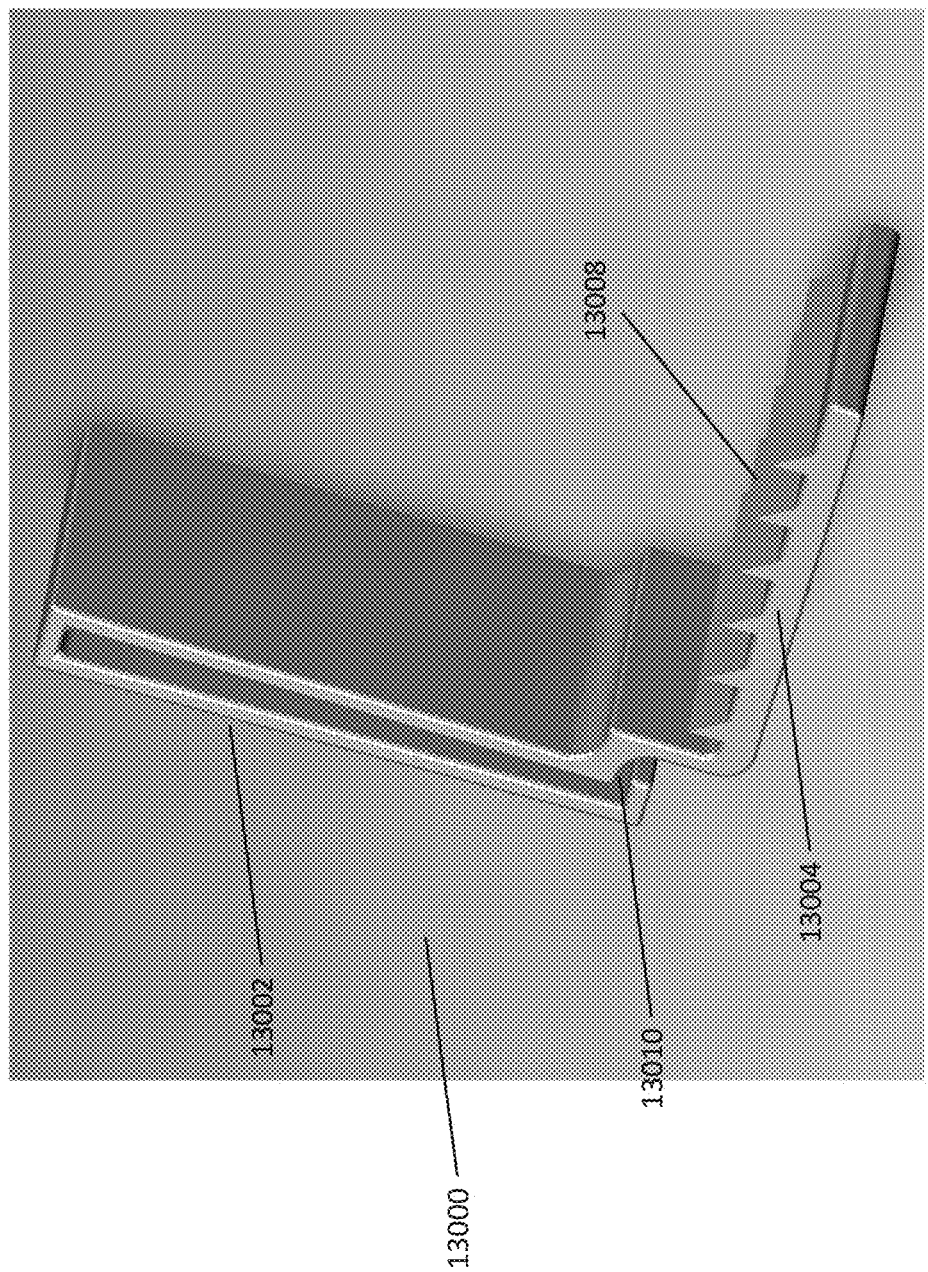

Updated matrix X12_Feb15_03 (15mm Foam Attached to top and bottom, bottom foam under facia) incremental vacuum increase [2]

| Width mm - Pre Vacuum | Width mm - (xx) mmHg | % Change | Actual Change mm |
|---|---|---|---|
| Single Measurement | Single Measurement | | |
| 123.4 | 83.4 (40) | 32.41% | 40.0 |
| 123.4 | 83.4 (50) | 34.85% | 43.0 |
| 123.4 | 83.4 (60) | 36.06% | 44.5 |
| 123.4 | 83.4 (70) | 38.41% | 47.4 |
| 123.4 | 83.4 (80) | 38.82% | 47.9 |
| 123.4 | 83.4 (100) | 42.79% | 52.8 |
| 123.4 | 83.4 (120) | 44.65% | 55.1 |
| 123.4 | 83.4 (140) | 46.76% | 57.7 |
| 123.4 | 83.4 (160) | 48.87% | 60.3 |
| 123.4 | 83.4 (180) | 50.41% | 62.2 |
| 123.4 | 83.4 (200) | 50.89% | 62.8 |
| 123.4 | 83.4 (200) Relax | 52.11% | 64.3 |

FIG. 32A

NEGATIVE PRESSURE WOUND CLOSURE DEVICE

CROSS-REFERENCE TO RELATED APPLICATIONS

This application is a national stage application of International Patent Application No. PCT/US2016/029888, filed on Apr. 28, 2016, which claims the benefit of U.S. Provisional Application No. 62/154,609, filed Apr. 29, 2015, entitled NEGATIVE PRESSURE WOUND CLOSURE DEVICE. The content of the aforementioned applications is hereby incorporated by reference in its entirety as if fully set forth herein. The benefit of priority to the foregoing applications is claimed under the appropriate legal basis, including, without limitation, under 35 U.S.C. § 119(e).

BACKGROUND OF THE INVENTION

Field of the Invention

This application describes embodiments of apparatuses, methods, and systems for the treatment of wounds, specifically to aid in the closure of large wounds, in conjunction with the administration of negative pressure.

Description of the Related Art

Negative pressure wound therapy has been used in the treatment of wounds, and in many cases can improve the rate of healing while also removing exudates and other deleterious substances from the wound site.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created onto the patient. Closure of this wound, while minimizing the risk of secondary infections and other complications, and after the underlying edema has subsided, then becomes a priority. However, acute open abdominal conditions may be caused by other reasons in addition to compartment syndrome, as described further below.

Other large or incisional wounds, either as a result of surgery, trauma, or other conditions, may also require closure. For example, wounds resulting from sterniotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds.

SUMMARY OF THE INVENTION

Embodiments of the present invention relate to negative pressure wound closure devices, methods, and systems that facilitate closure of a wound. It will be understood by one of skill in the art that the wounds described herein this specification may encompass any wound, and are not limited to a particular location or type of wound. The devices, methods, and systems may operate to reduce the need for repetitive replacement of wound filler material currently employed and can advance the rate of healing. The devices, methods, and systems may be simultaneously used with negative pressure to remove wound fluids.

In embodiments, an apparatus for treating a wound with negative pressure wound therapy, comprises:
a stabilizing structure having an oculiform shape for insertion into a wound, the stabilizing structure configured to collapse more in a horizontal plane parallel to a length and a width of the stabilizing structure than in a vertical plane perpendicular to the horizontal plane.

The stabilizing structure may comprise two extended sections extending in opposite directions along a longitudinal axis of the stabilizing structure. The extended sections can comprise a stepped shaped. In some embodiments, the stabilizing structure comprises a plurality of cells. The extended sections may comprise a plurality of rows of cells. In particular embodiments, the extended sections comprise a first row comprising four cells, a second row comprising two cells, and a third row comprising two cells. In some embodiments, the apparatus may comprise a plurality of tabs extending outward from the outer wall. The tabs may comprise a surgical adhesive and/or the tabs may comprise anchors configured to grip foam. In certain embodiments, the apparatus comprises a first bottom layer of foam attached to a bottom of the stabilizing structure. The first bottom layer of foam may comprise a lip that extends outward to extend into surrounding tissue. In certain embodiments, the apparatus further comprises a top layer of foam attached to a top of the stabilizing structure. The apparatus may comprise a second bottom layer of foam attached to the bottom layer of foam. The second bottom layer of foam can comprise a lip that extends outward from the stabilizing structure for positioning beneath a fascia layer. In embodiments, the foam layers are attached to a plurality of tabs extending from the outer wall of the stabilizing structure. In certain embodiments, at least one of the foam layers comprise printed symbols, the symbols comprising arrows indicating the proper positioning of the foam layer within the wound.

In some embodiments, a wound closure device comprises:
a stabilizing structure for insertion into a wound; and
a plurality of stabilizing clips connected by a plurality of linkers, the plurality of stabilizing clips attachable to an outer wall of the stabilizing structure, the stabilizing clips configured to extend outward into surrounding tissue and prevent the stabilizing structure from lifting upwards in a direction out of the wound.

The stabilizing structure may be configured to collapse more in a horizontal plane parallel to a length and a width of the stabilizing structure than in a vertical plane perpendicular to the horizontal plane. In certain embodiments, the stabilizing clips comprise an attachment portion configured to clip to a wall of the stabilizing structure and a securing portion that extends outward from the attachment portion in a horizontal direction. The securing portions may comprise a plurality of grippers. In embodiments, the stabilizing clips can comprise a recess where the securing portion extends from the attachment portion. The attachment portion may be configured to loop over the outer wall of the stabilizing structure, wherein the attachment portion comprises a foot at an end of the loop of the attachment portion. In some embodiments, the securing portion may comprise grippers configured to extend into the surrounding tissue. The linkers may comprise string. In certain embodiments, the stabilizing structure may have an oculiform shape and/or an elliptical shape and/or a diamond shape.

In embodiments, a wound closure device may comprise:
a stabilizing structure for insertion into a wound;
a top layer of foam attached to a top of the stabilizing structure, the top layer of foam conforming to the shape of the stabilizing structure;
a middle layer of foam attached to a bottom of the stabilizing structure, the middle layer of foam conforming to the shape of the stabilizing structure; and
a bottom layer of foam, the bottom layer of foam attached to the middle layer of foam, the bottom layer of foam comprising a lip that extends outward into the surrounding tissue of the wound. In certain embodiments, the stabilizing structure may have an oculiform shape.

In some embodiments, a method of treating a wound comprises:
providing a stabilizing structure;
attaching a top layer of foam to the stabilizing structure;
attaching a bottom layer of foam to the stabilizing structure, the bottom layer of foam comprising a lip extending outward into the surrounding tissue; and
inserting the stabilizing structure into the wound, wherein after insertion the lip engages tissue to prevent the stabilizing structure from lifting upwards in a direction out of the wound.

The method may further comprise:
covering the stabilizing structure with at least one drape sealed to skin surrounding the wound; and
applying negative pressure through the at least one drape to the wound via a source of negative pressure, wherein the application of negative pressure causes the stabilizing structure to horizontally collapse.

The method can also further comprise inserting a tissue protection layer over the wound before inserting the stabilizing structure. The bottom layer of foam may be wider than the top layer of foam. The stabilizing structure may have an oculiform shape.

Other embodiments of wound closure devices, stabilizing structures and associated apparatuses are described below.

BRIEF DESCRIPTION OF THE DRAWINGS

Other features and advantages of the present invention will be apparent from the following detailed description of the invention, taken in conjunction with the accompanying drawings of which:

FIGS. 10A-C illustrate an embodiment of steps of a method of treating a wound.

FIGS. 20A-G illustrate embodiments of stabilizing structures and foam layers.

FIGS. 25A-G illustrate embodiments of stabilizing clips with grippers.

FIGS. 28A-E illustrate embodiments of a stabilizing device for attachment to a stabilizing structure.

FIGS. 32A-B present experimental data collected using embodiments of stabilizing structures and wound closure devices.

DETAILED DESCRIPTION OF THE PREFERRED EMBODIMENTS

Figure 1:
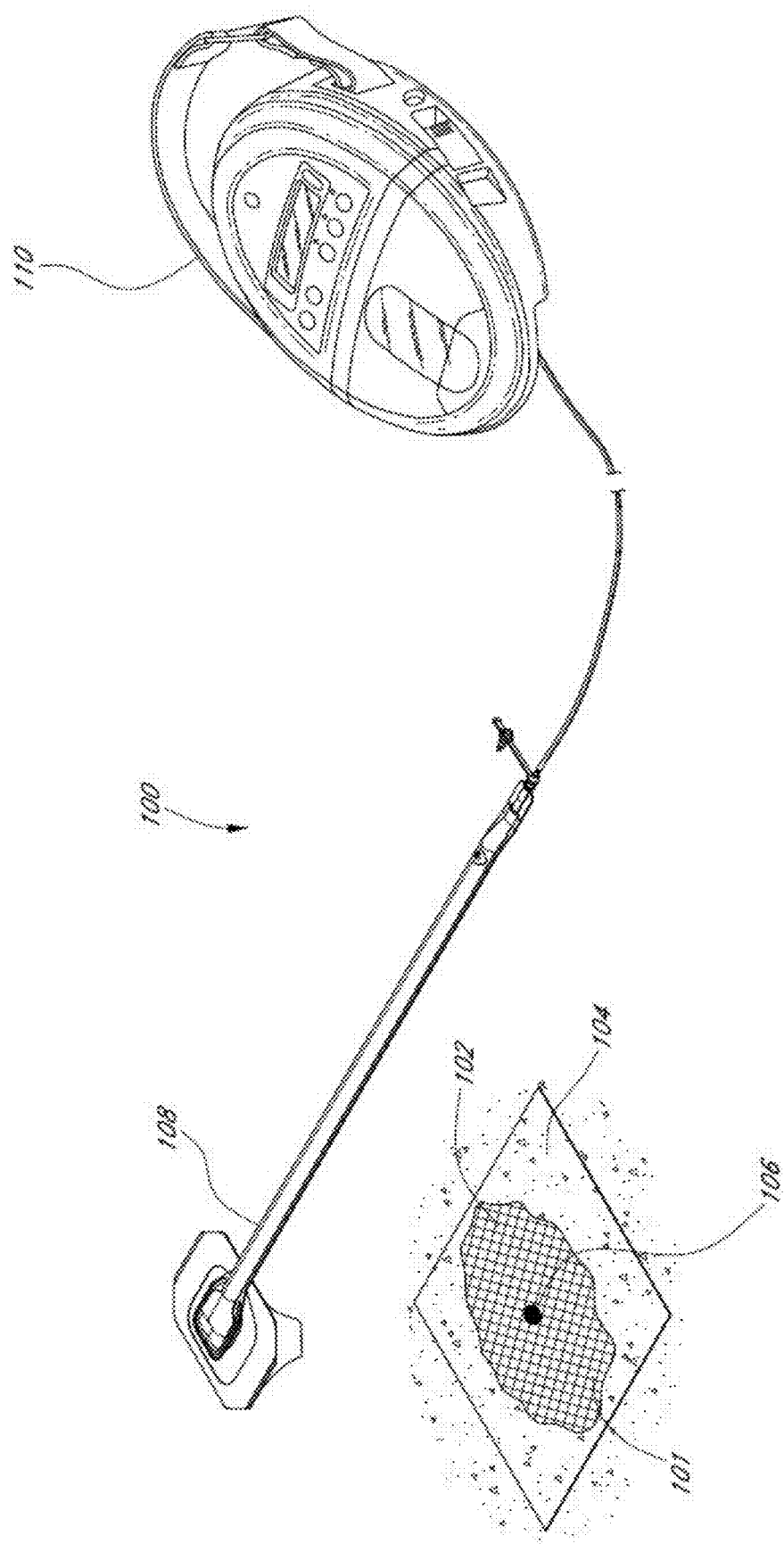
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for some embodiments of the present disclosure can be approximately −80 mmHg, or between about −10 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively, a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments, the negative pressure range can be as small as about −20 mmHg or about −25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Examples of such applications where additional disclosure relating to the preceding descriptions may be found include U.S. Pat. No. 8,235,955, titled "Wound treatment apparatus and method," issued Aug. 7, 2012 and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227, the entireties of each of which are hereby incorporated by reference. Still more applications that may contain teachings relevant for use with the embodiments described in this specification are application Ser. No. 13/942,493, titled "Negative Pressure Wound Closure Device," filed Jul. 15, 2013, published as US 2014/0180225; PCT App. No. PCT/US2013/050619, filed Jul. 16, 2013 titled "Negative Pressure Wound Closure Device," published as WO 2014/014871 A1; PCT App. No. PCT/US2013/050698, filed Jul. 16, 2013 titled "Negative Pressure Wound Closure Device," published as WO 2014/014922 A1; PCT App. No. PCT/M2013/01555, titled "Devices and Methods for Treating and Closing Wounds with Negative Pressure," filed May 5, 2013, published as WO 2013/175309 A1; PCT App. No. PCT/US2014/025059, titled "Negative Pressure Wound Closure Device and Systems and Methods of Use in Treating Wounds with Negative Pressure," filed Mar. 12, 2014, published as WO 2014/165275 A1; and PCT App. No. PCT/GB2014/050746, "Compressible Wound Fillers and Systems and Methods of Use In Treating Wounds With Negative Pressure," filed Mar. 13, 2014, published as WO 2014/140578 A1, and "Negative Pressure Wound Closure Device," filed Oct. 21, 2014, and published as PCT/US2014/061627. The entireties of the aforementioned applications are each hereby incorporated by reference and should be considered part of the present specification.

It will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 time, 10 times, 12 times or more greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound packer 102 inserted into a wound 101. The wound packer 102 may comprise porous materials such as foam, and in some embodiments may comprise one or more embodiments of wound closure devices described in further detail in this section or elsewhere in this specification. In some embodiments, the perimeter or top of any wound closure device inserted into the wound 101 may also be covered with foam or other porous materials. A single drape 104 or multiple drapes may be placed over the wound 101, and is preferably adhered or sealed to the skin on the periphery of the wound 101 so as to create a fluid-tight seal. An aperture 106 may be made through the drape 104 which can be manually made or preformed into the drape 104 so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922, 118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

Any structure or component disclosed herein this section or elsewhere in the specification may comprise a radiopaque material. A radiopaque material advantageously allows a clinician to more easily find pieces of the wound closure device that may have come loose from the structure and become lost in the wound. Some examples of radiopaque materials include barium sulfate, bismuth trioxide, bismuth subcarbonate, bismuth oxychloride, and tungsten.

Stabilizing Structures and Wound Closure Devices of FIG. 2A-3E

Figure 2A:
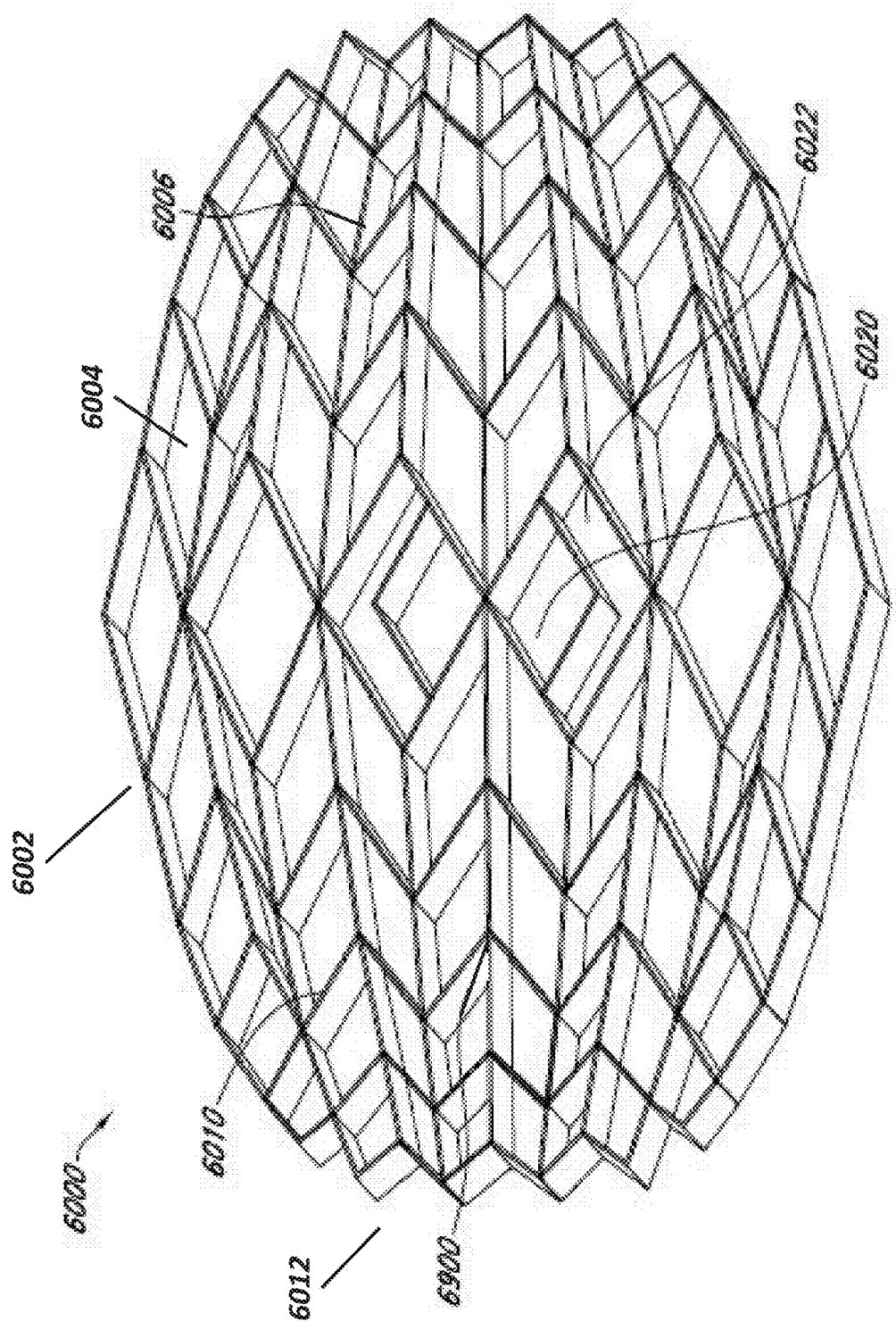
FIGS. 2A-C illustrate multiple views of an embodiment of a stabilizing structure.

FIG. 2A is a drawing of an embodiment of a stabilizing structure 6000 comprising a plurality of elongate strips 6006 arranged in parallel or semi-parallel, whose longitudinal length can be aligned with the longitudinal axis of a wound. In embodiments, the elongate strips 6006 may also be arranged in a non-parallel fashion. The various cells within this stabilizing structure 6000 may have a variety of shapes and sizes. As will be described in greater detail below, the length and shape of the elongate strips 6006, intervening members 6010, and cells 6004 may be designed so as to facilitate greater closure of the stabilizing structure. In certain embodiments, the junctions 6900 between the elongate strips and intervening members may be thinned to better facilitate rotation and closure of the stabilizing structures. In some embodiments, the stabilizing structure is tearable, such that the structure may be shaped into the shape of a wound. As described elsewhere in the specification, tears may be completed at the intersections between intervening members and elongate strips or at any suitable location along the elongate strip or intervening member.

All stabilizing structures described herein this section or elsewhere in the specification may be fashioned to accommodate any size of wound. However, to better accommodate the needs of the clinical environment, in certain embodiments, the stabilizing structures described herein may be provided in a pack of two sizes, one smaller stabilizing structure and one larger stabilizing structure about 1.25 times as larger, about 1.5 times as large, about 1.75 times as large, about 2 times as larger, about 2.5 times as larger, about 3 times as large, about 4 times as large, about 5 times as large, or more than about 5 times as large. In some embodiments, the pack may comprise more than two sizes, such as three sizes, four sizes, five sizes, or more than five sizes. The stabilizing structures within the pack may be of a variety of sizes in relation to one another such as the ratios described above.

In certain embodiments, the stabilizing structure 6000 can collapse in any manner described in this section or elsewhere in this specification with or without the application of negative pressure. For example, the stabilizing structure may collapse significantly more in one plane than in another plane upon application of negative pressure. In some embodiments, the stabilizing structure is configured to collapse more in a horizontal plane parallel to the length and width of the stabilizing structure than in a vertical plane perpendicular to the horizontal plane. In embodiments, particular rows may collapse in a first direction, while another row may collapse in the same or an opposing direction. In certain embodiments, the stabilizing structure may collapse along the width of the stabilizing structure while remaining relatively rigid along the length of the stabilizing structure and in the vertical direction.

The stabilizing structure may be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam. In certain embodiments, the stabilizing structure may comprise a radio opaque material, to more readily allow a clinician to find pieces of the stabilizing structure within the wound.

Returning to FIG. 2A, stabilizing structure 6000 may have an outer perimeter that defines an at least partially elliptical shape. As described above, stabilizing structure 6000 may comprise a plurality of cells 6004 provided side-by-side, each cell defined by one or more walls, each cell having a top end and a bottom end with an opening extending through the top and bottom ends. As with the other stabilizing structures described herein this section and elsewhere in the specification, the stabilizing structure 6000 is configured to collapse by collapsing one or more cells 6004. In some embodiments, the cells are all of the same approximate shape and size; however, in other embodiments, the cells are of different shapes and sizes. In some embodiments, the stabilizing structures as described herein this section or elsewhere in the specification may be domed, such that the central portion of the stabilizing structure bulges upward. For example, a lower portion of the stabilizing structure may be concave, while an upper portion of the stabilizing structure is convex.

The elongate strips 6006 may be made from one single material, such as those described elsewhere in the specification, or the elongate strips may be made from multiple materials. For example, elongate strips 6006 may comprise sections of more rigid material and sections of more flexible material. The elongate strips 6006 may be curved along their length so as to facilitate the curved outer perimeter of the stabilizing structure 6000. The elongate strips may be curved along their lengths outward away from a center of the stabilizing structure 6000. The arch of the curves of the elongate strips 6006 may vary considerably, with some strips 6006 being highly curved while other are minimally curved or even straight.

Similarly, the stabilizing structure 6000 can further comprise a plurality of intervening members 6010 connected to the elongate strips 6006. The intervening members 6010 may all be of a similar shape and size or they may be of a variety of shapes and sizes. The intervening members may be constructed from any material disclosed herein this section or elsewhere in the specification. Further, the intervening members may be constructed from multiple materials.

Advantageously, the elliptical shape of stabilizing structure 6000 may allow the structure to better accommodate the shape of the wound. Most wounds are in shapes that are rounded, thus, an elliptically shaped stabilizing structure 6000 may better fit into a wound.

In embodiments, the outer perimeter 6002 may have a reduced edge 6012 so as to facilitate collapse of the stabilizing structure. By removing mass of the stabilizing structure at reduced edge 6012, the stabilizing structure can collapse more freely at reduced edge 6012, thus allowing for a better fit within the wound. Further, by reduced the mass at reduced edge 6012, there may be less pinching of the surrounding tissue during and after collapse of the stabilizing structure 6000.

The stabilizing structure 6000 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can be placed into a wound for a period of time and then removed or replaced with another stabilizing structure. For example, a stabilizing structure could be inserted into a wound for a period of time, promoting closure of the wound by drawing the edges closer together. After a period of time has passed, the stabilizing structure can be replaced by a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue. In certain embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate. In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Returning to FIG. 2A, in some embodiments, the pattern of the stabilizing structure 6000 is designed in such a way as to facilitate maximum closure of the stabilizing structure. Preferably, maximum closure is in a direction perpendicular to the length of the elongate members and within the horizontal plane. As will be described in greater detail below, greater closure may be achieved by varying the length of the elongate strips 6006, the length of the intervening members 6010, and the shape of the cells 6004. The shape of the cells 6004 may comprise any shape described herein this section or elsewhere in the specification. For example, as depicted in FIG. 2A, the cells 6004 may be diamond-shaped or parallelepiped with smaller diamond-like shapes 6020 located within larger diamonds 6022. Such a construction may provide greater overall closure of the stabilizing device 6000 to provide for maximum closure of the wound. Additionally, the smaller diamond-like shapes 6020 located within larger diamonds 6022 can spread the load over a greater area reducing the chance of damage to the tissue structures below the matrix. This construction can also reduce the likelihood of the foam or the drape being pulled into the matrix and preventing closure of the wound.

Figure 2B:
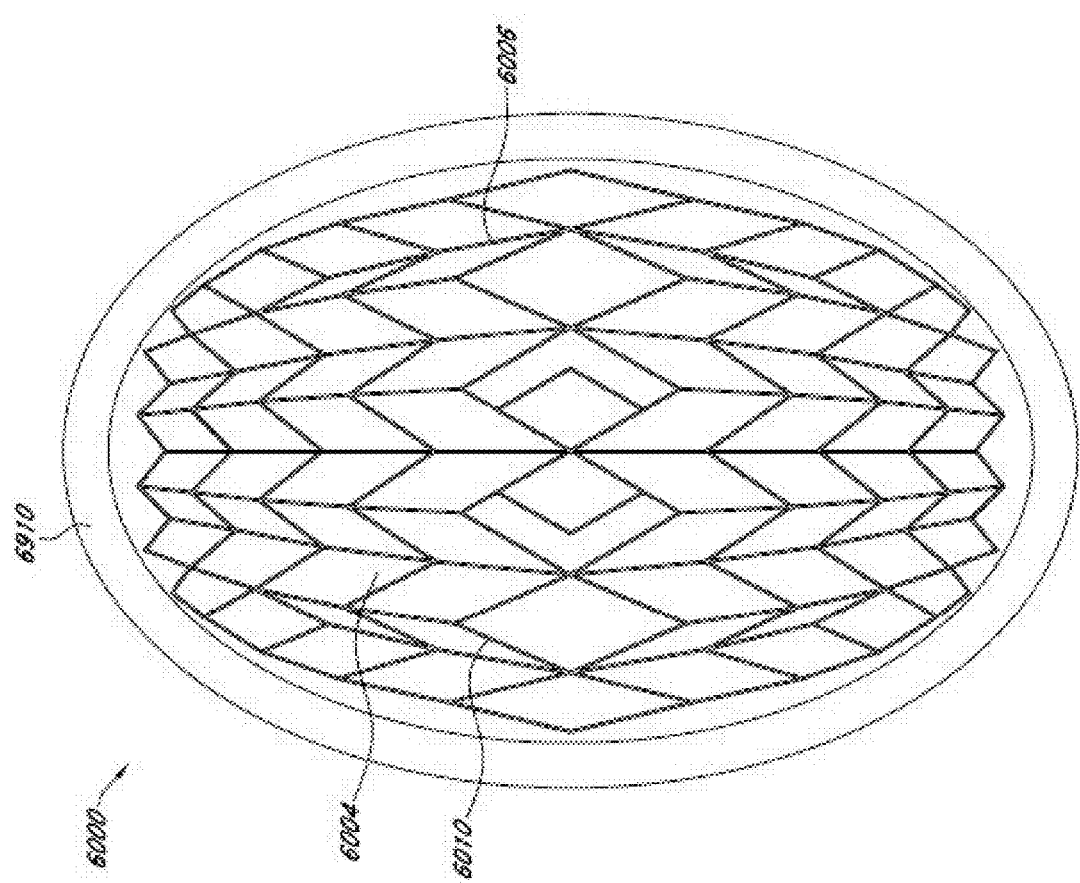
Figure 2C:
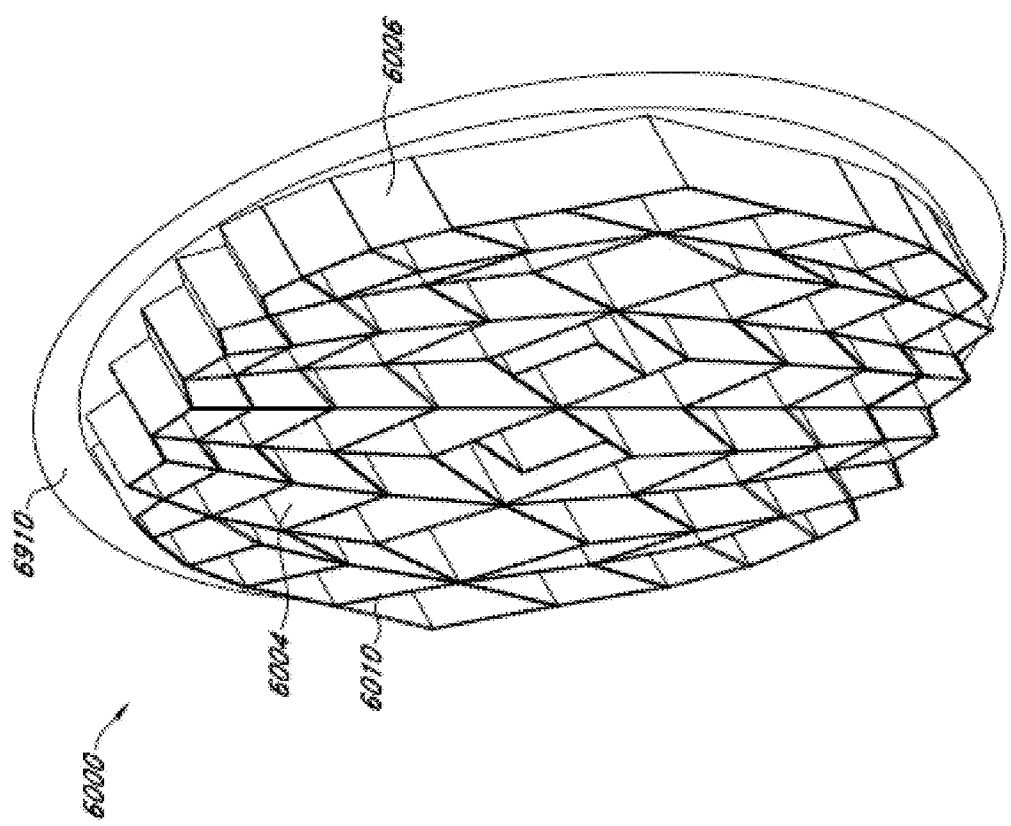

FIGS. 2B-C are illustrations of different views of the stabilizing structure embodiment of FIG. 2A. As described above in relation to FIG. 2A, the stabilizing structure comprises cells 6004, intervening members 6010, and elongate strips 6006; however, here a simulated shape of a wound 6910 is also included for comparison.

Any of the stabilizing structures described herein this section or elsewhere in the specification may be constructed from any suitable means. For example, the stabilizing structures may be constructed via molding or may be printed directly using 3D printing technology. In certain embodiments, the stabilizing structures of FIGS. 2A-C may be constructed from a single polymer via 3D printing. In some embodiments, the stabilizing structures may be constructed from one polymer, two polymers, three polymers, or more than three polymers. The stabilizing structures may be constructed from any material disclosed herein this section or elsewhere in the specification. The stabilizing structure can be made by cutting the structure out of a solid block of material. Methods used for cutting can include, for example, water jet cutting, laser cutting, or die cutting. The stabilizing structures may be cut to size along the walls of the cells 6004. For example, the intervening members along the outside face of elongate strips 6006 can be cut off to appropriately size the stabilizing structure. The stabilizing structure may be cut along the walls, along any portions of the elongate strips, and/or along any portions of the intervening members.

In some embodiments, the stabilizing structure 6000 of FIGS. 2A-C can be configured to include perforations or detachable sections that allow portions of the device to separate from the remainder of the device. For example, perforations may be incorporated into the joints 6900 between various cells 6004 contained within the stabilizing structure 6000, allowing for the removal of individual rows or cells to alter the shape of the stabilizing structure 6000.

Applicable to all stabilizing structures or wound closure devices described in this section or elsewhere in the specification, the stabilizing structure or wound closure device may be tearable such that the stabilizing structure may be shaped into the shape of a wound. In some embodiments, the stabilizing structure may be torn at the intersections between intervening members and elongate strips, while in further embodiments, the elongate strips or intervening members may be torn at any suitable position.

Figure 3A:
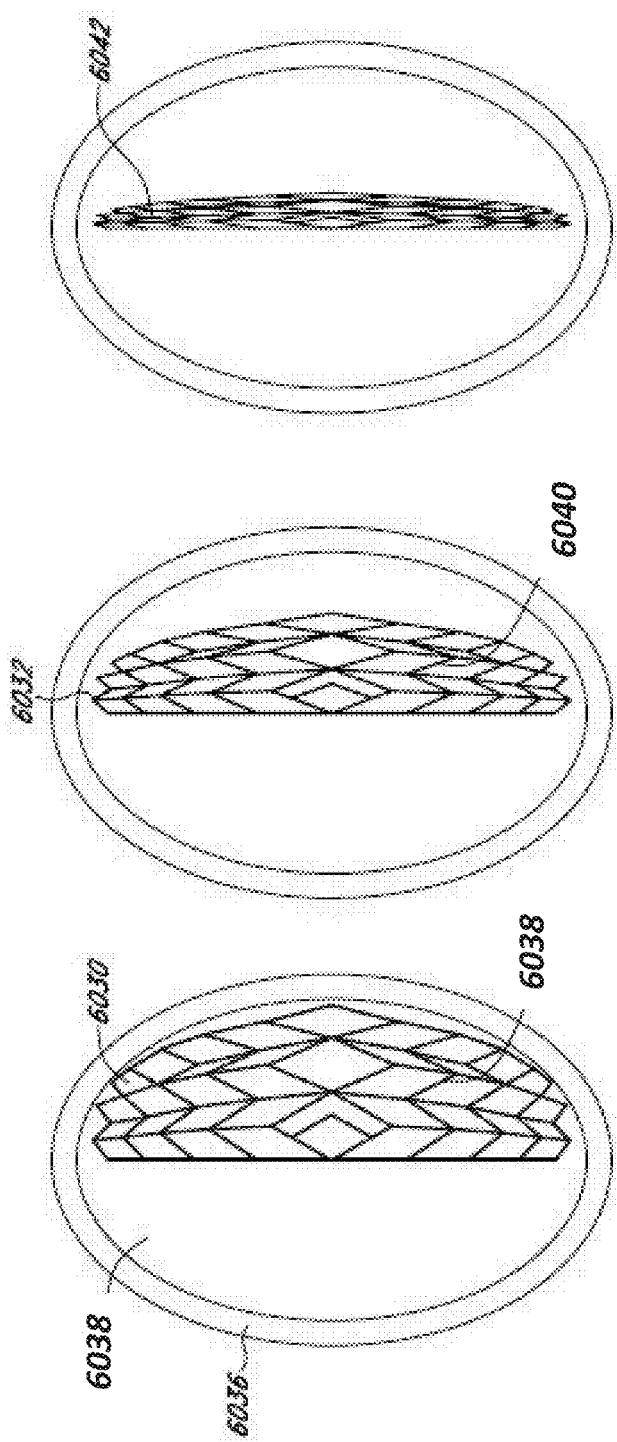
FIGS. 3A-E illustrate multiple views of another embodiment of a stabilizing structure and a method of creating the stabilizing structure.

FIGS. 3A-E depict methodologies for generating the design of a stabilizing structure, such as the stabilizing structures of FIGS. 2A-C. To facilitate various types of closure (for example, maximum closure) the shape, size, and location of the elongate strips, intervening members, and cells may be determined via various methods. For example, as depicted in FIG. 3A, each collapsible cell 6030 has four sides, and each intersection between an intervening member(s) and/or elongated strip(s) may be modeled via pin-joints 6032. Further, the entirety of stabilizing structure 6034 may be modeled inside of an oval wound model 6036. As depicted in FIG. 3A, the stabilizing structure 6034 may be modeled to collapse from an open state 6038 to a semi-collapsed state 6040, to a fully collapsed state 6042. In some clinical scenarios, maximum closure down to a completely flattened stabilizing structure may be desirable to maximize wound closure by drawing the edges of the wound as close together as possible.

Figure 3B:
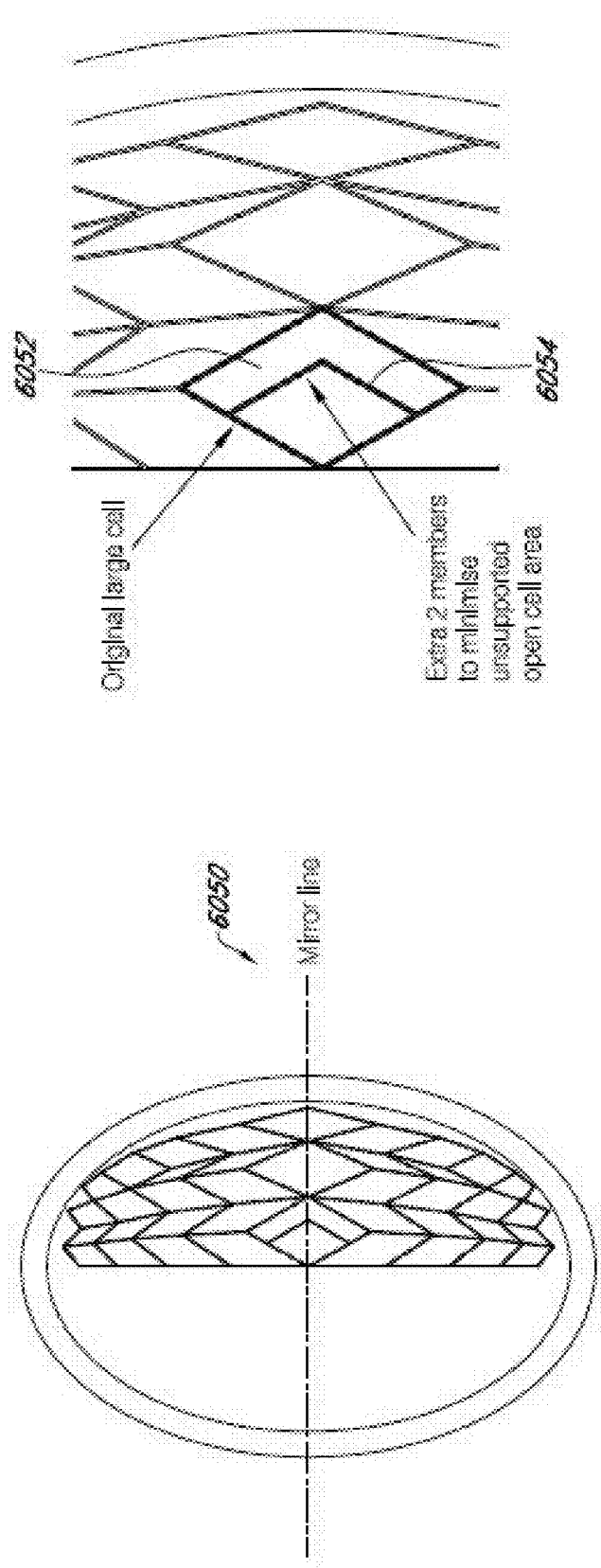

As illustrated in FIG. 3B, in certain embodiments, the process of determining the optimal shape, size, and location of the elongate strips, intervening members, and cells for wound closure may be facilitated by modeling the stabilizing structure as a mirrored pattern on opposite sides of a mirror line 6050 (which may also be referred to as the transverse axis, perpendicular to a longitudinal axis of the stabilizing structure), thereby making the curve and collapse of the stabilizing structure symmetrical. The mirror axis may be along the minor axis or it may be along the major axis of the stabilizing structure. Alternatively, the mirror line may be located in any suitable location within the stabilizing structure, such as diagonally across the stabilizing structure. In certain embodiments, this method may lead to large diamond-shaped cells near the center line. These large diamond-shaped structures 6052 may be further subdivided to further support the stabilizing structure by including smaller diamond shapes 6054 within larger shapes. In some embodiments, these smaller shapes 6054 within a larger shape 6052 may comprise any shape disclosed herein this section or elsewhere in the specification. The larger cells may be further subdivided by two smaller shapes, three smaller shapes, four smaller shapes, or more than four smaller shapes. It will be understood by one of skill in the art that the mirror line need not be confined to a line perpendicular to the longitudinal orientation of the wound. Instead, the mirror line may be located along the longitudinal axis of the wound or at an angle to the longitudinal axis of the wound. In some embodiments, the stabilizing structure may contain multiple mirror lines, thereby having multiple subsections that are symmetrical or different.

Figure 3C:
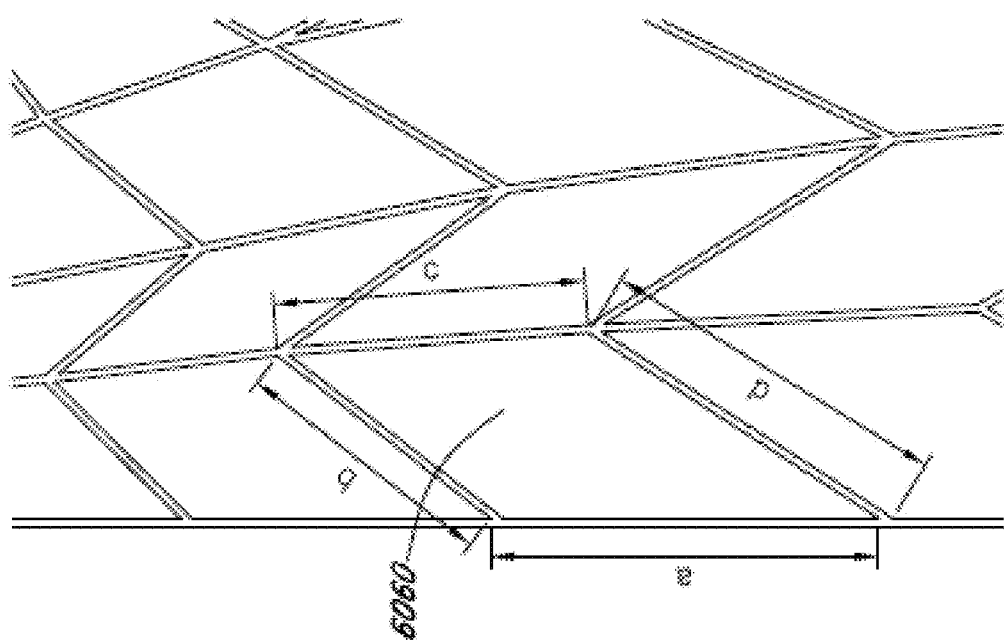

As illustrated in FIG. 3C, for a four-sided cell to collapse, it must follow a simple formula: $a+b=c+d$, where a, b, c, and d are the lengths of individual sides of a single cell within the stabilizing structure such as the cell 6060 of FIG. 3C. When members c and b collapse together, then d and a collapse together. Such a formula may be the basis for developing a pattern for a stabilizing structure that maximizes collapsibility.

Figure 3D:
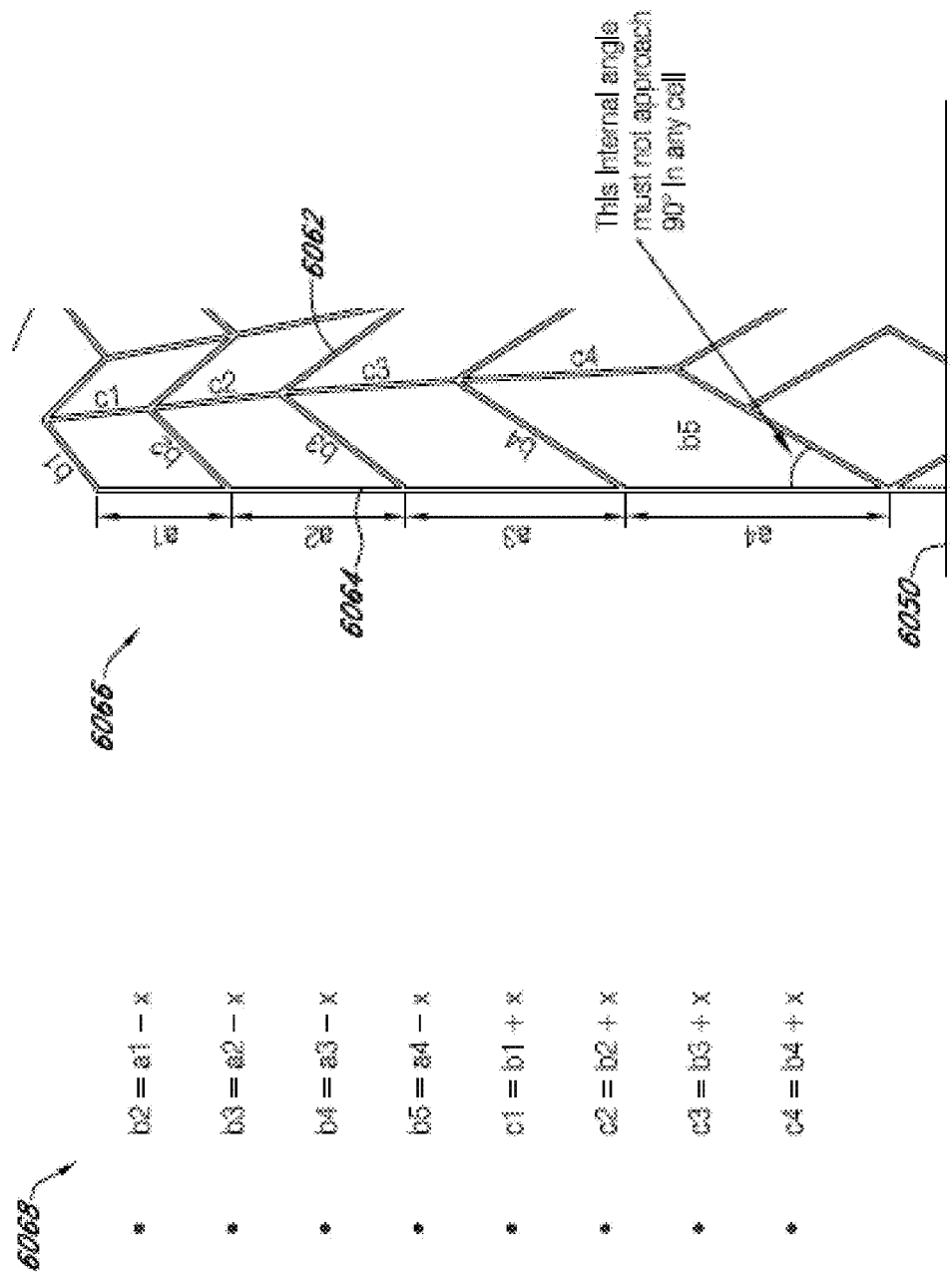
Figure 3E:
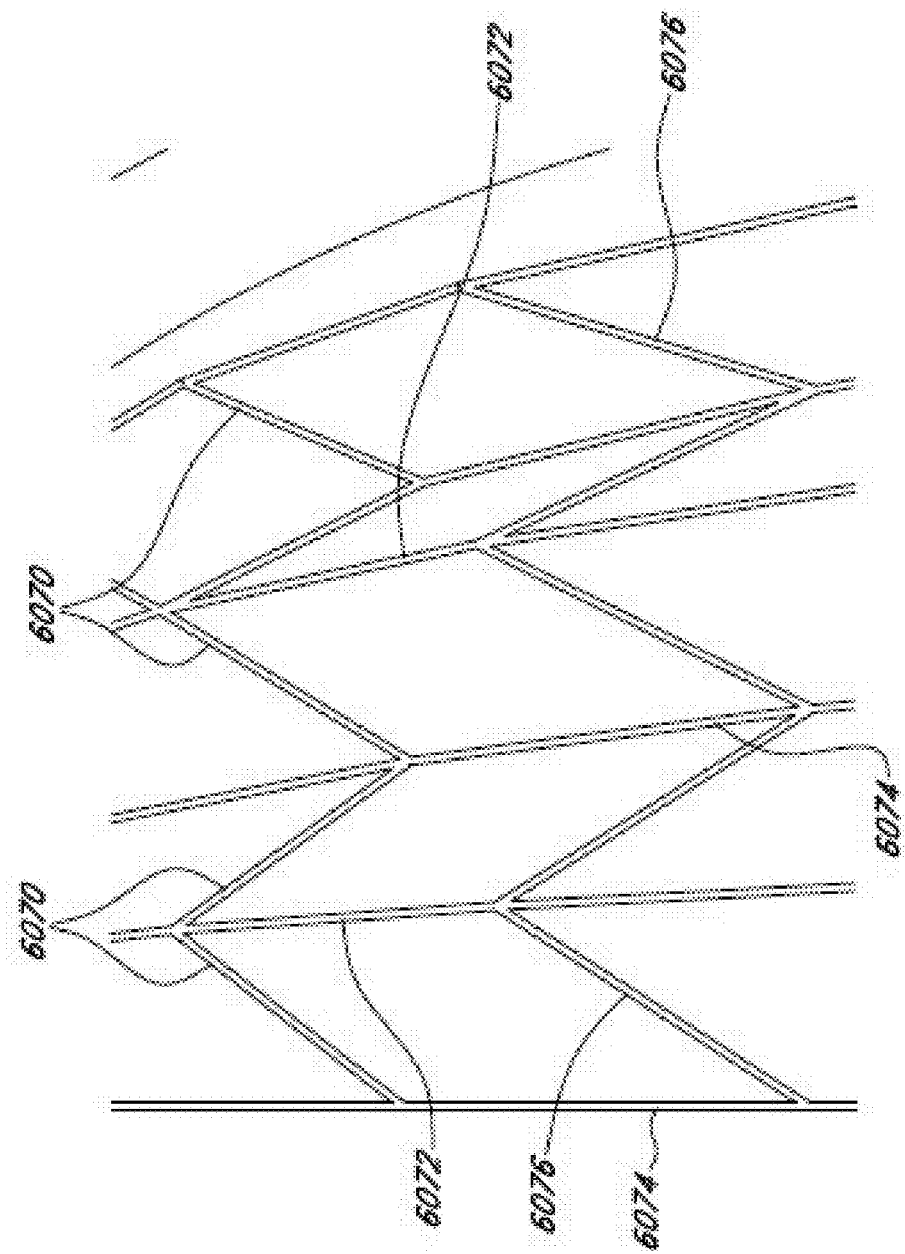

FIG. 3D illustrates an expansion of the concept described in FIG. 3C. By using the base formula $a+b=c+d$, the elongate strips were progressively lengthened ($a4>a3>a2>a1$) towards the horizontal mirror line 6050, thereby achieving a curve in the stabilizing structure while preventing any of the intervening members 6062 from becoming perpendicular to the elongate strips 6064 (i.e. having an internal angle of 90 degrees). As illustrated in FIG. 3D, a value for b1 may be chosen, at which point an arbitrary offset value x may also be chosen to ease the construction of the various cell geometries. Using the progressive values for a1 through a4, illustrated visually in FIG. 3D 6066, values for b1-b4 may be calculated 6068. Using calculated values derived from equations 6068 for the various walls of the individual cells allows for the design of a stabilizing structure that collapses completely, such as those depicted in FIGS. 3A-B.

In some embodiments, a method for generating a stabilizing structure design may include steps to speed up the initial geometry construction. For example if all members from left to right in a specific row, as visualized by intervening members 6036 in FIG. 3E, a pattern then emerges where alternating vertical members are also the same length.

Walls of the same length are indicated by their respective labels 6070, 6072, 6074, and 6076. Once the initial design is generated then individual cells may be modified by lengthening, shortening, removing or inserted according to the formulas of FIG. 3D to achieve the desired shape of the overall stabilizing structure.

The Anchoring Layers of FIGS. 4-6B

Figure 4:
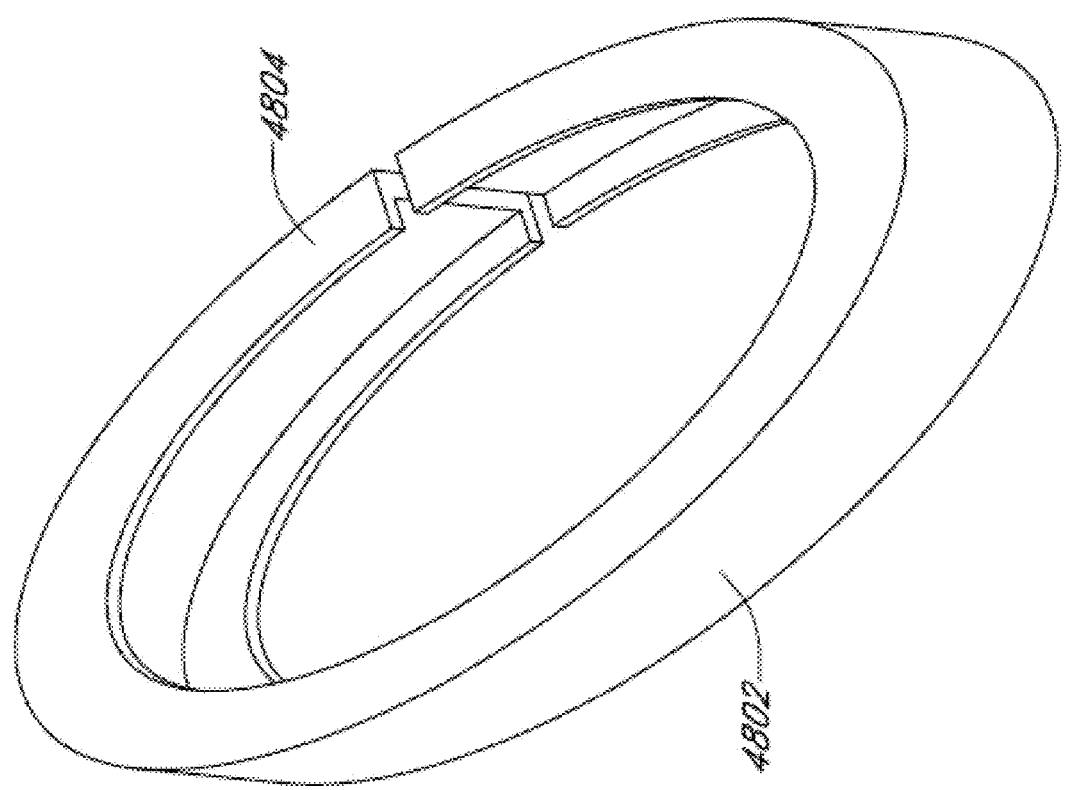
FIG. 4 illustrates an embodiment of a ring that can surround a stabilizing structure.

FIG. 4 illustrates an embodiment of an anchoring layer 4800 that may surround the stabilizing structures as described in this section or elsewhere in this specification. The ring 4800 can comprise a layer of tissue anchors 4802 configured to grip the surrounding edges of a wound. For example, the tissue anchors can be hooks, barbs, prongs, or other structures that serve to attach to the tissue of a wound. In certain embodiments, the tissue anchors comprise hook and loop fasteners such as those used in Velcro technologies. In certain embodiments, the ring 4800 can be comprised of foam, such as those described previously or the ring can be comprised of a combination of a foam layer and a tissue anchor layer 4802. A lip 4804 may extend inward from the ring 4800 and serve to overlap the top and/or the bottom of a stabilizing structure as described in this section or elsewhere in this specification, thereby securing the ring 4800 around the stabilizing structure.

FIGS. 5A-D are photographs of a wound closure device 5000 according to another embodiment. The wound closure device 5000 comprises a stabilizing structure 5002 which may be similar to the structures described in FIGS. 2A-3E, or may comprise any of the stabilizing structures described elsewhere in this specification. The stabilizing structure 5002 may optionally be surrounded by a porous layer 5004 such as a layer of foam, and the porous layer may be surrounded by an anchoring layer 5006 comprising tissue anchors such as those anchors produced by Velcro industries, various barbs and/or various hooks. In certain embodiments, the porous layer may be in the form of a ribbon. The stabilizing structure 5002, porous layer 5004 and anchoring layer 5006 may be provided as separate components to be attached by the practitioner in use, or they may be preattached to each other.

Similar to the embodiments illustrated in FIGS. 2A-3E, the stabilizing structure 5002 can collapse in any manner described elsewhere in this specification, for example, horizontally. When the wound closure device 5000 is implanted, the surrounding tissues can be pressed against the tissue anchors to embed them within the tissue and anchor the device. In some embodiments, the wound closure device 5000 may be placed in a wound and sealed with a drape. Although the embodiments further described in this section comprise an anchor layer that surrounds a porous layer, other embodiments may omit the porous layer, such that the anchoring layer directly surrounds or is attached to the stabilizing structure.

In some embodiments, the anchoring layer 5006 comprises an elongate strip of material comprising a plurality of tissue anchors extending from a base layer 5007, wherein the tissue anchors can have different shapes and sizes as described elsewhere in the specification. The tissue anchors may extend from a first planar side of the elongate strip, and the second planar side of the elongate strip may comprise an adhesive covered by an adhesive backing layer. The structure of the anchors can have various forms depending on the tissue they are intended to bind. Longer anchors can be used for loosely bound tissues such as fat or connective tissue, while shorter anchors can be used for denser tissues such as muscle. In other embodiments, depending upon the shape of the anchor, shorter anchors may be more desirable for softer, fatty tissue, while longer anchors are utilized for denser tissues. Anchors with more rigid stems can be utilized to penetrate denser tissues. In some embodiments, anchors can have bilateral prongs that tend to collapse upon insertion in tissue and yet expand when pulled in an opposite direction such that a certain pulling force can be applied to tissue. The characteristics of the anchors or attachment mechanisms, and their resulting force profiles, can vary by a number of parameters, such as the length of the anchor, the shape of the attachment mechanisms, the structure of grasping features, the material(s) used for the attachment mechanisms, the relative flexibility/rigidity of the attachment mechanisms, and the spacing/density of the attachment mechanisms.

The anchors may have various lengths for optimal penetration of the surrounding tissue. For example, the length of the anchors may be at most about 0.01 mm, at most about 0.1 mm, at most about 0.2 mm, at most about 0.5 mm, at most about 1 mm, at most about 2 mm, at most about 3 mm, at most about 5 mm, at most about 10 mm, at most about 20 mm, at most about 30 mm, at most about 40 mm, at most about 50 mm, at most about 75 mm, at most about 100 mm, or more than 100 mm.

Figure 5A:
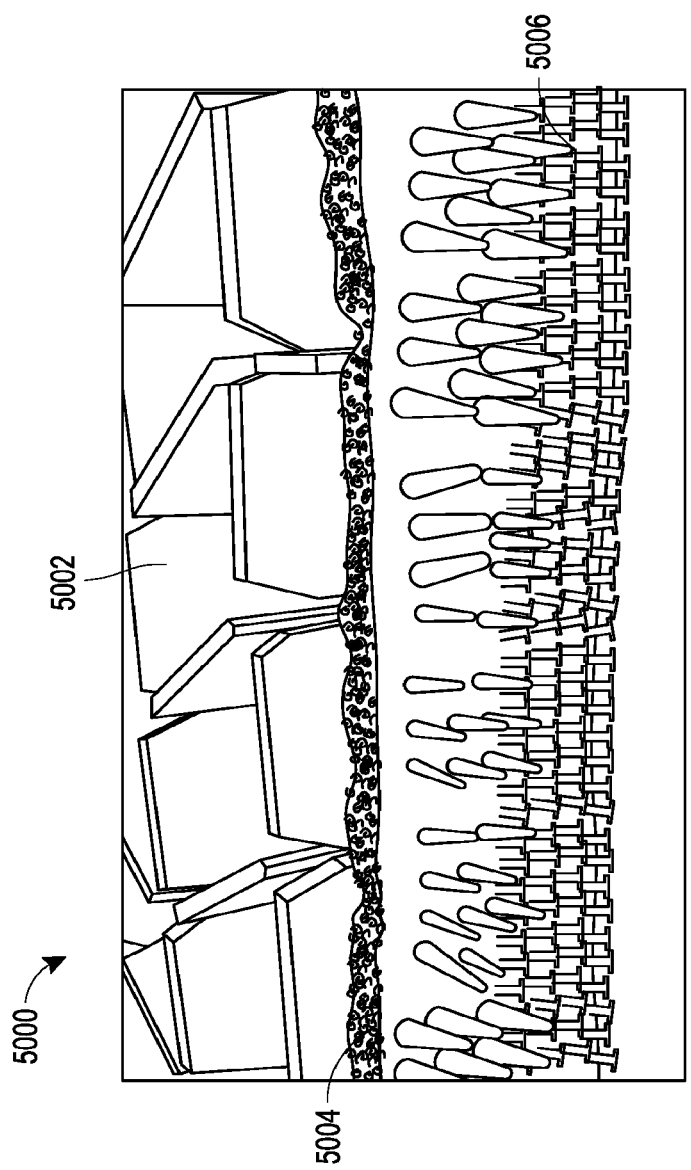
FIGS. 5A-D are photographs of embodiments of stabilizing structures with surrounding anchoring and foam layers.
Figure 5B:
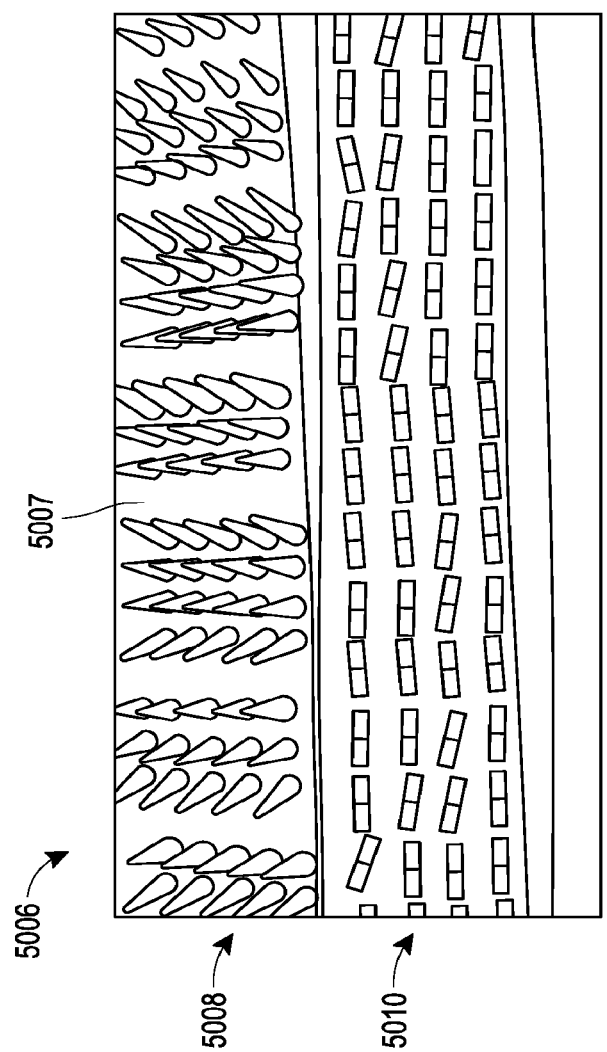

FIG. 5B is a photograph of a closer view of the anchoring layer 5006 of the wound closure device 5002 depicted in FIG. 5A. The anchoring layer may consist of a first band of longer anchors 5008 configured to surround the porous layer 5004 and stabilizing structure 5002, and a second band of shorter anchors 5010 configured to surround the porous layer 5004 and stabilizing structure 5002. As illustrated, the first band 5008 may be disposed above the second band 5010. In some embodiments, there may be additional alternating series of bands vertically relative to each other. In further embodiments, the different bands may have different anchor lengths and shapes, as disclosed herein this section and elsewhere in the specification. For example, instead of 2 types of bands with 2 types of anchors, there may be 3 types of band with 3 types of anchors or 4 types of bands with 4 types of anchors and so on. Preferably, the anchors are selected for the appropriate tissue types. For example, returning to FIG. 5B, the first band 5008 may comprise longer anchors, desirable for penetration into the denser fascia, and thus may be positioned towards the bottom of the device. Similarly, the second band 5010 comprises shorter double hooks, desirable for penetration into denser tissue. Other suitable tissue anchors, as described elsewhere in this specification, include the hook and loop configuration of Velcro, barbs, hooks, spikes, pegs, arrowheads, or any suitable shape. Further examples of surfaces include textured surfaces, such as roughened sandpaper-like surfaces, or nano-textured surfaces that may facilitate tissue adhesion.

In some embodiments, the use of surface anchors can be used in combination with a surgical adhesive, providing a much stronger bond between tissue layers than the adhesive alone, and providing temporary adhesion while the adhesive sets. In some embodiments, the surgical adhesive can be added to the anchors themselves. In certain embodiments, the surgical adhesive may simply be applied between the anchors to coat at least a portion of the anchoring layer. In further embodiments, the anchors may be replaced with a surgical adhesive, and the surgical adhesive may act to anchor the device to the surrounding wound.

In certain embodiments, the anchors may be constructed from a variety of materials, including any materials disclosed elsewhere in the specification, such as: synthetic or natural polymers, metals, ceramics, or other suitable materials. The anchors may be constructed from biodegradable materials such as biodegradable synthetic or natural polymers. Non-limiting examples of biodegradable synthetic polymers include: polyesters such as polylactic acid or polyglycolic acid, polyanhydrides, and linear polymers with biodegradable linkages. Further, the anchors may be constructed of biodegradable biological materials, such as autografts, allografts, and/or xenografts.

Figure 5C:
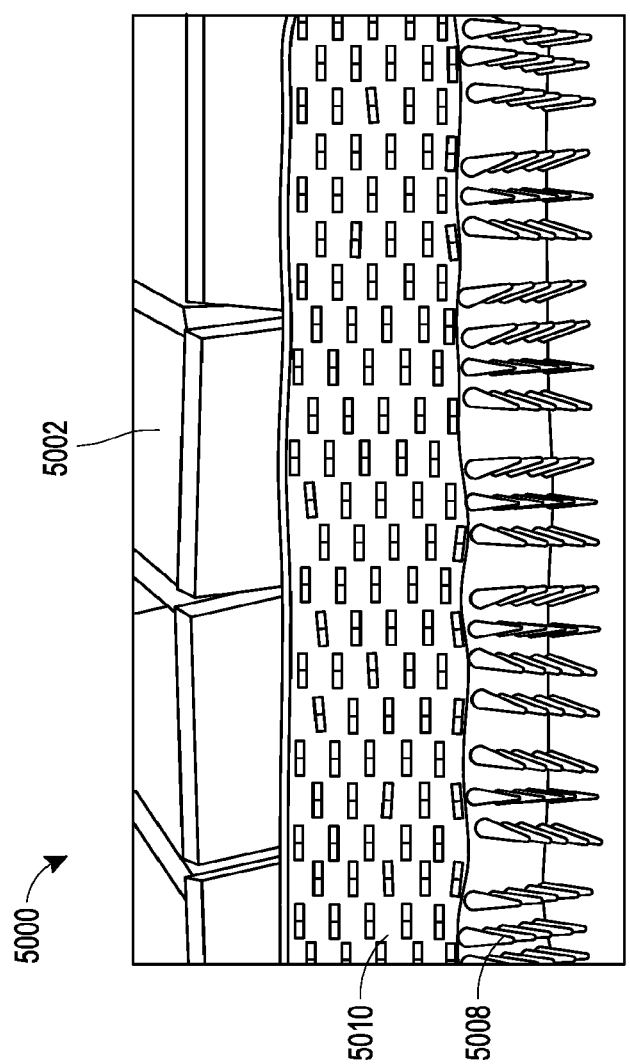
Figure 5D:
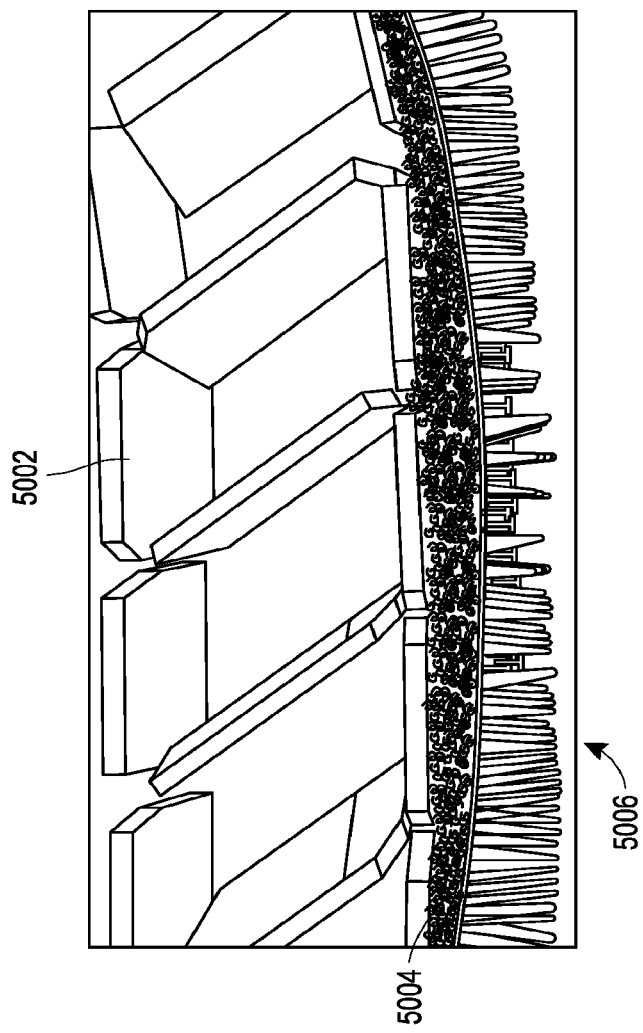

FIG. 5C is a photograph of an embodiment of a wound closure device 5000, similar to the wound closure devices of FIGS. 5A-B. However, in this orientation the first band 5008 of anchors is towards the bottom of the device, while the second band of anchors 5010 is towards the top. As described above, the bands of anchors may be arrayed in any desired manner. FIG. 5D is a top view of an embodiment of a wound closure device 5000, similar to the wound closure devices of FIGS. 5A-C.

Considering the anchoring layer of FIGS. 5A-D, the shape of the anchoring layer is not limited to the ring shape of FIG. 4. In some embodiments, the anchoring layer is wrapped around the entirety of the stabilizing device, i.e. the top, bottom, and sides. In other embodiments, the anchoring layer is only around a portion of the perimeter of the stabilizing structure. In certain embodiments, the anchoring layer is only attached to discrete portions of the stabilizing structure as needed. In some embodiments, the anchoring layer covers at most about 5%, at most about 10%, at most about 20%, at most about 30%, at most about 50%, at most about 75%, and at most about 100% of the outside of the stabilizing structure. In embodiments, the anchoring layers may be incorporated on any face of the stabilizing clips of FIGS. 23A-31H, discussed in greater detail below.

In some embodiments, the bands of different tissue anchors can be organized in a vertical direction, while in other embodiments, they may be organized in a horizontal direction. They may also be organized in either the horizontal and vertical directions when considered in the xy plane, i.e. facing downward into the wound.

In certain embodiments, the different types of anchors may be interspersed with one another, rather than organized into discrete bands of specific types of anchors. For example, the longer anchors may be surrounded by smaller anchors and vice-versa. In some embodiments, the anchors may be organized randomly across the anchoring layer or in other suitable patterns.

In particular embodiments, the anchoring layer may be disposed on the inner faces of the stabilizing structure. For example, the anchoring layer may cover at most about 5%, at most about 10%, at most about 20%, at most about 30%, at most about 50%, at most about 75%, and at most about 100% of the interior surfaces of the stabilizing structure.

In further embodiments, the entire anchoring layer may be comprised of only one type of anchor, for example the entirety of the anchoring layer may be comprised of the longer hooks 5008 or the shorter hooks 5010 as depicted in FIG. 5B. Some embodiments may call for the anchors to be color coded. For example, the anchors on the bottom may be made to be one color while the anchors on the top may be another so as to identify the proper orientation of the stabilizing structure in the wound.

Figure 6A:
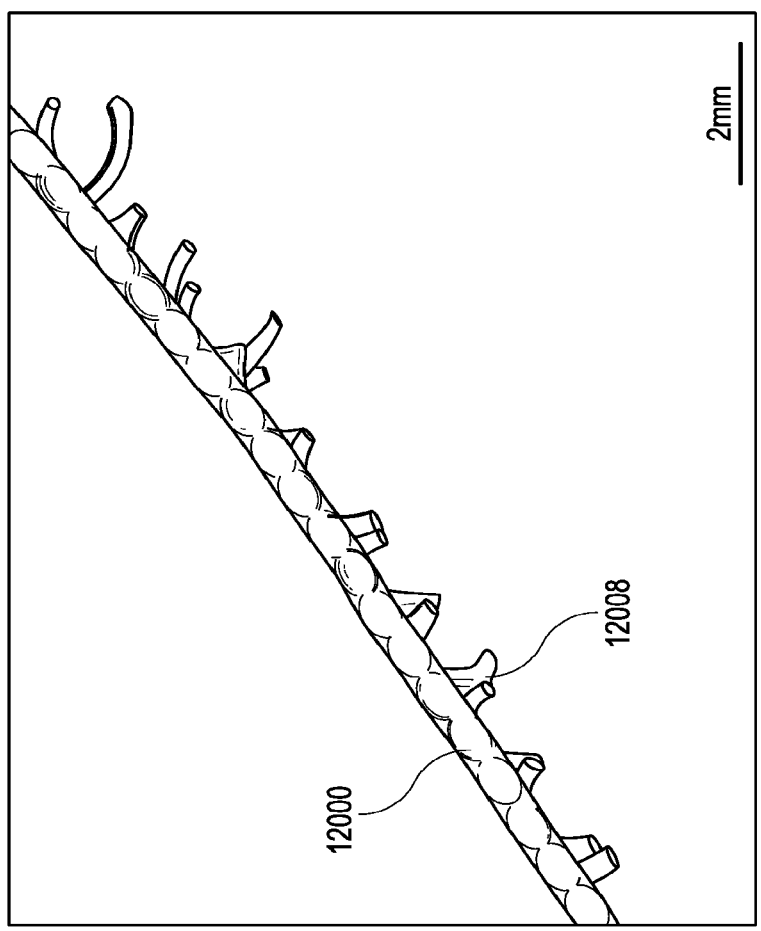
FIGS. 6A-B are photographs of an embodiment of an anchoring layer.
Figure 6B:
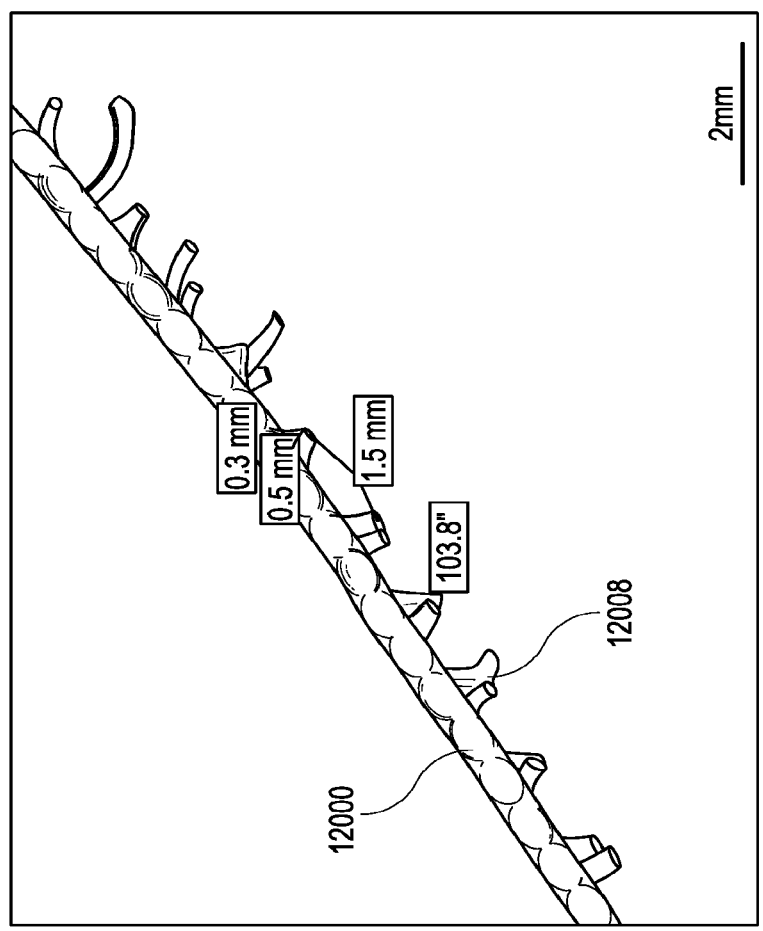

FIGS. 6A-B are pictures of embodiments of an anchoring layer 12000 with anchors 12008, similar to the anchors depicted in FIGS. 5A-D. Examples of such anchors may be available from Alfatex. In one embodiment, an anchoring layer may be provided comprising a 3D fabric material or portion thereof. For example, a 3D fabric may comprise a woven fabric layer provided along a first plane and a plurality of monofilaments extending perpendicularly from or at an angle relative to the woven fabric layer. The woven fabric layer may be configured to be attached to directly or indirectly to the outside of a stabilizing structure as described elsewhere in this specification and in the applications incorporated by reference. Monofilaments may have a mushroom-shaped head or other shapes configured to engage tissue surrounding the stabilizing structure. The head of the monofilaments may be similar to a peened rivet with a flatted head and extended edges that engage the surrounding tissues. If the monofilaments protrude at an angle then the material creates more grip in one direction of shear than another. This directionality means the anchoring layer and monofilaments can be positioned on a stabilizing structure so that the shear acts to stop the device being forced up or out of the wound by the viscera but can be easily released by pushing it down.

Wound Closure and Treatment Methods of FIGS. 7-15E

The stabilizing structures and/or wound closure devices described in this section or elsewhere in this specification may be used in conjunction with methods or systems for the closure of a wound. In some embodiments of methods of use for closure of a wound, one or more of the stabilizing structures or wound closure devices of any of the embodiments described in this section or elsewhere in this specification is placed into a wound. In some embodiments, an organ protection layer may be provided in the wound before placement of the stabilizing structure. In certain embodiments, foam or other porous material may be placed in the wound along with the stabilizing structure or wound closure device, either below, above, or surrounding the stabilizing structure or wound closure device. Foam or other porous material may also surround the perimeter of the stabilizing structure or wound closure device. The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement in the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

FIGS. 7-15E are photographs and illustrations depicting embodiments of methods for the treatment of a wound that utilize a wound closure device comprising a stabilizing structure as described herein this section and elsewhere in the specification. To better illustrate non-limiting embodiments of the methods, numbers have been added to the steps of FIG. 13 to allow the reader to more easily follow these steps of the method. However, the steps can be performed in any order, and any numbering system is for clarity only. Further, in some embodiments, different steps of these methods may be excluded. In other embodiments, additional steps may be added to the methods based on methods described herein this section and elsewhere in the specification. The porous layers and structures described in this section may be of any material or structure described elsewhere in the specification, such as foam.

Figure 7:
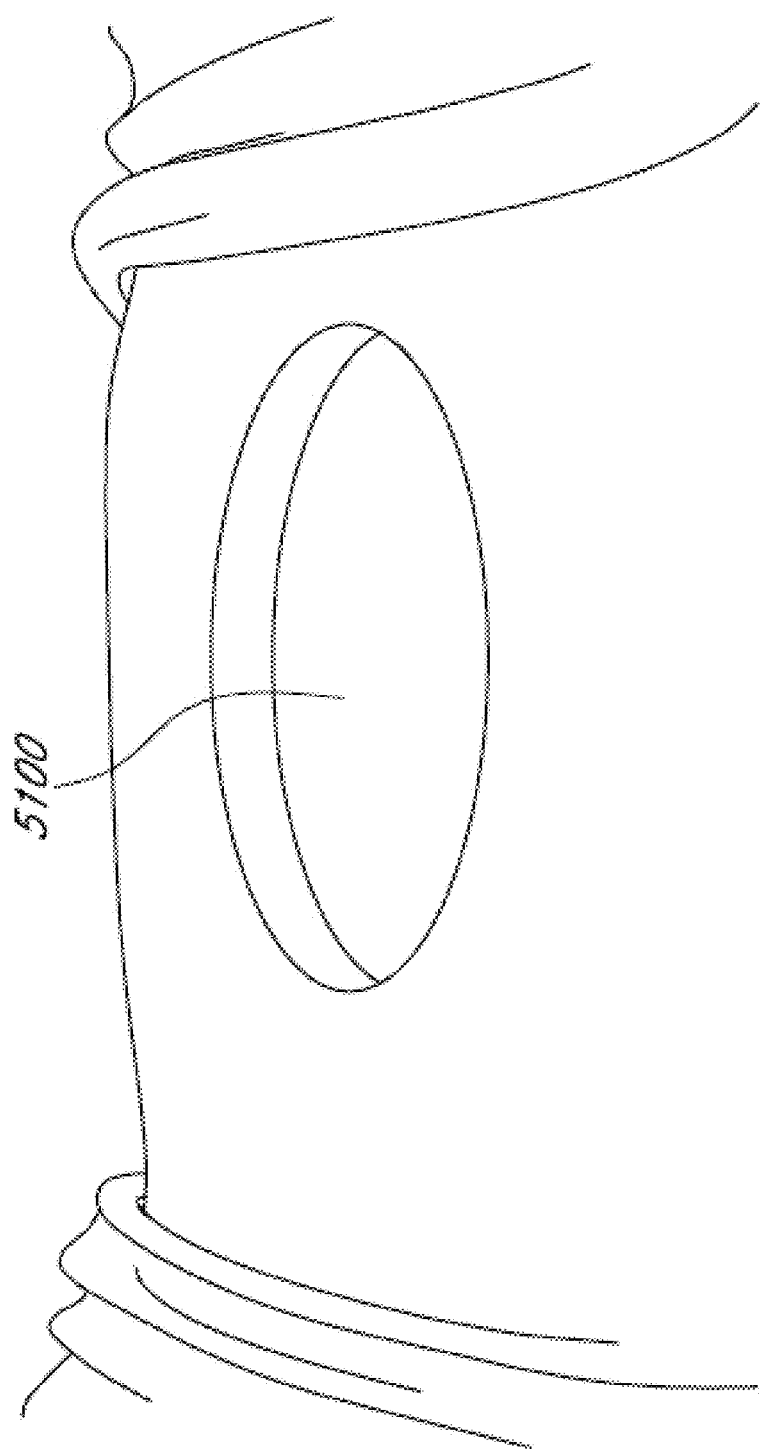
FIG. 7 illustrates an embodiment of an open abdominal wound.

FIG. 7 depicts an embodiment of an open wound 5100 prior to treatment with a wound closure device as will be described in much greater detail below. The open wound of FIG. 6 is similar to the wounds described elsewhere in the specification, particularly as relate to FIG. 1. In some instances, as described elsewhere in the specification, such a wound may be produced via a surgical incision or other means.

Figure 8:
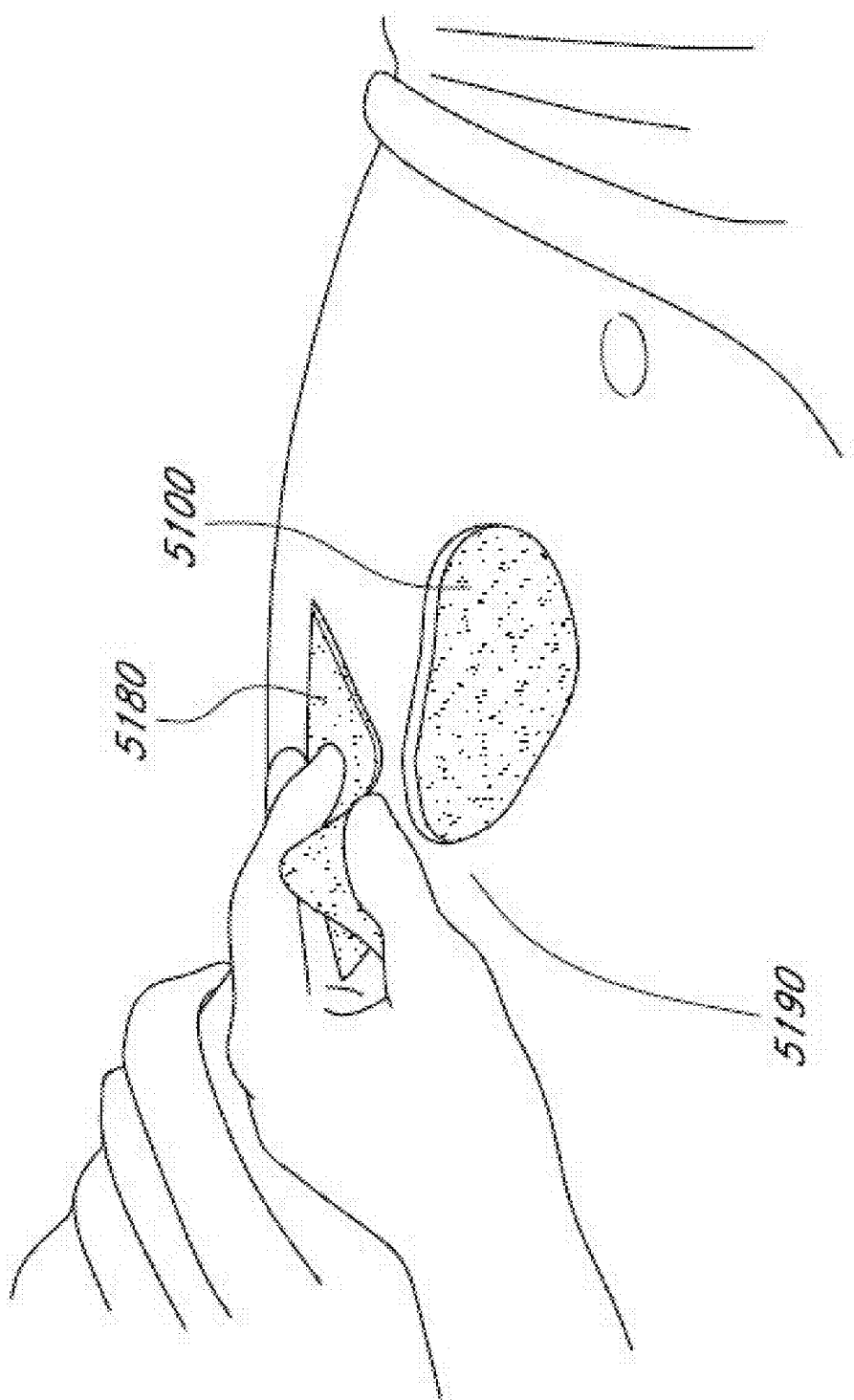
FIG. 8 illustrates an embodiment of a step in a method of treating a wound.

FIG. 8 depicts an embodiment of an initial step in a method for the treatment of an open wound 5100 with a wound closure device. Before treatment, the wound may be cleaned with a pad 5180 and the skin 5190 prepared for application of a wound closure device, such as those described in relation to FIGS. 2A-3E.

Figure 9:
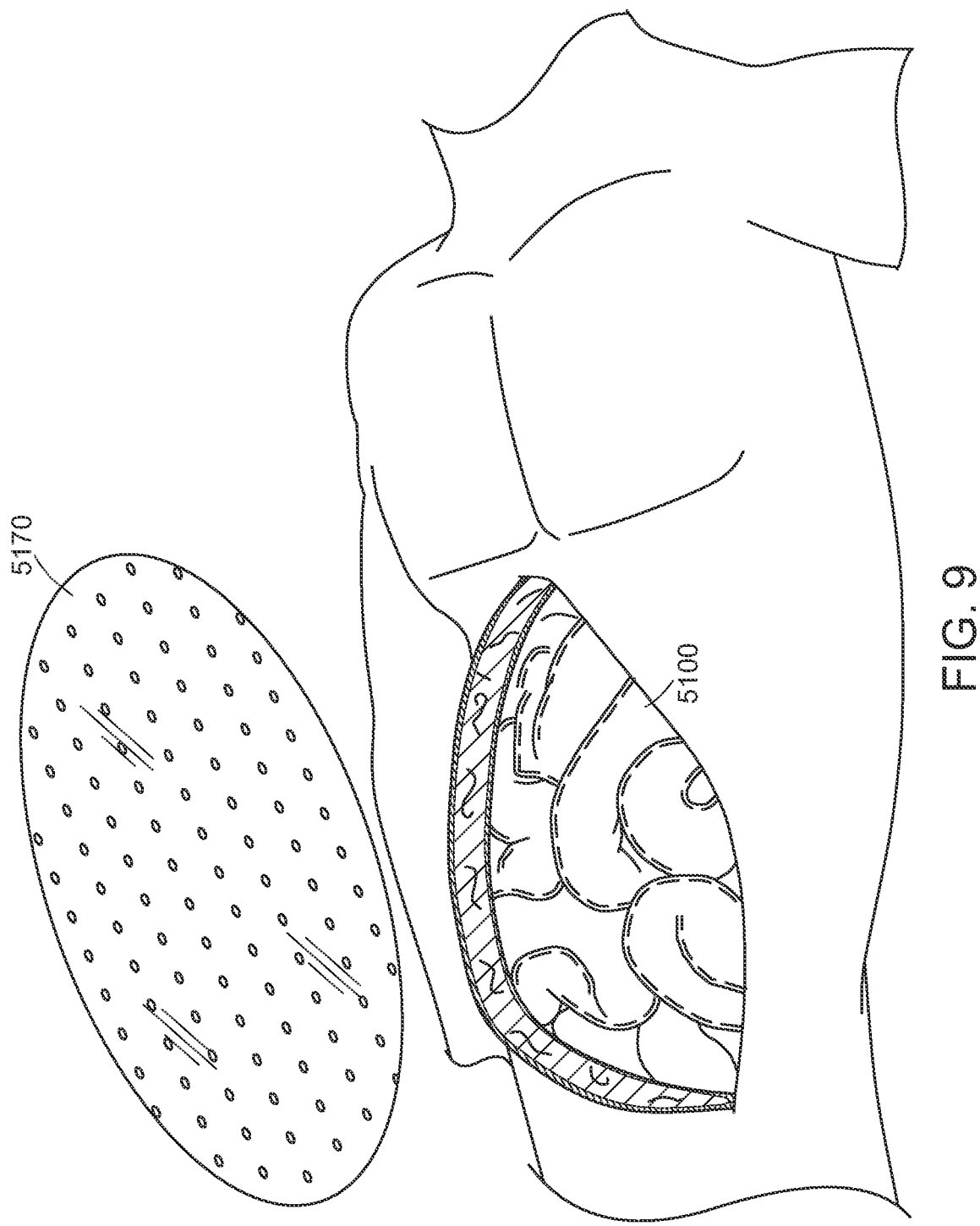
FIG. 9 illustrates an embodiment of a step in a method of treating a wound.

FIG. 9 depicts an embodiment of an early step in a method for the treatment of an open wound 5100. In some embodiments, a tissue protection layer 5170 may be placed over the wound to protect the underlying tissues from the rigors of negative pressure wound therapy or other potential harms. Accordingly, certain embodiments provide for a tissue protection layer 5170 which may be cut to size to be placed over the wound site 5100. The tissue protection layer 5170 can be a material which will not adhere to the wound site or to the exposed viscera in close proximity. Such a tissue protection layer may be constructed from any suitable material such as a biocompatible polymer. For example, organ protection layers manufactured by Smith & Nephew and sold under the brand RENASYS® may act as tissue protection layers and be placed over the abdominal cavity and/or wound bed 5100 and tucked over the peritoneal gutter. In further examples, materials such as the fluoropolymer polytetrafluoroethylene (PTFE) may be applicable as these materials are generally non-adherent and used in surgical grafts. In one embodiment, the tissue protection layer is permeable. For example, the tissue protection layer 5170 can be provided with openings, such as holes, slits, or channels, to allow the removal of fluids from the wound site 5100 or the transmittal of negative pressure to the wound site 5100. In further embodiments, the tissue protection layer may be used over non-abdominal wounds on other areas of the body, such as the leg, arm, shoulder, or back. In certain embodiments, the tissue protection layer may comprise a sensor configured to measure pressures in and around the wound. For example, the sensor may be used to measure the level of negative pressure applied to the wound or to measure the pressure on the underlying organs beneath the abdominal wound.

Figure 10B:
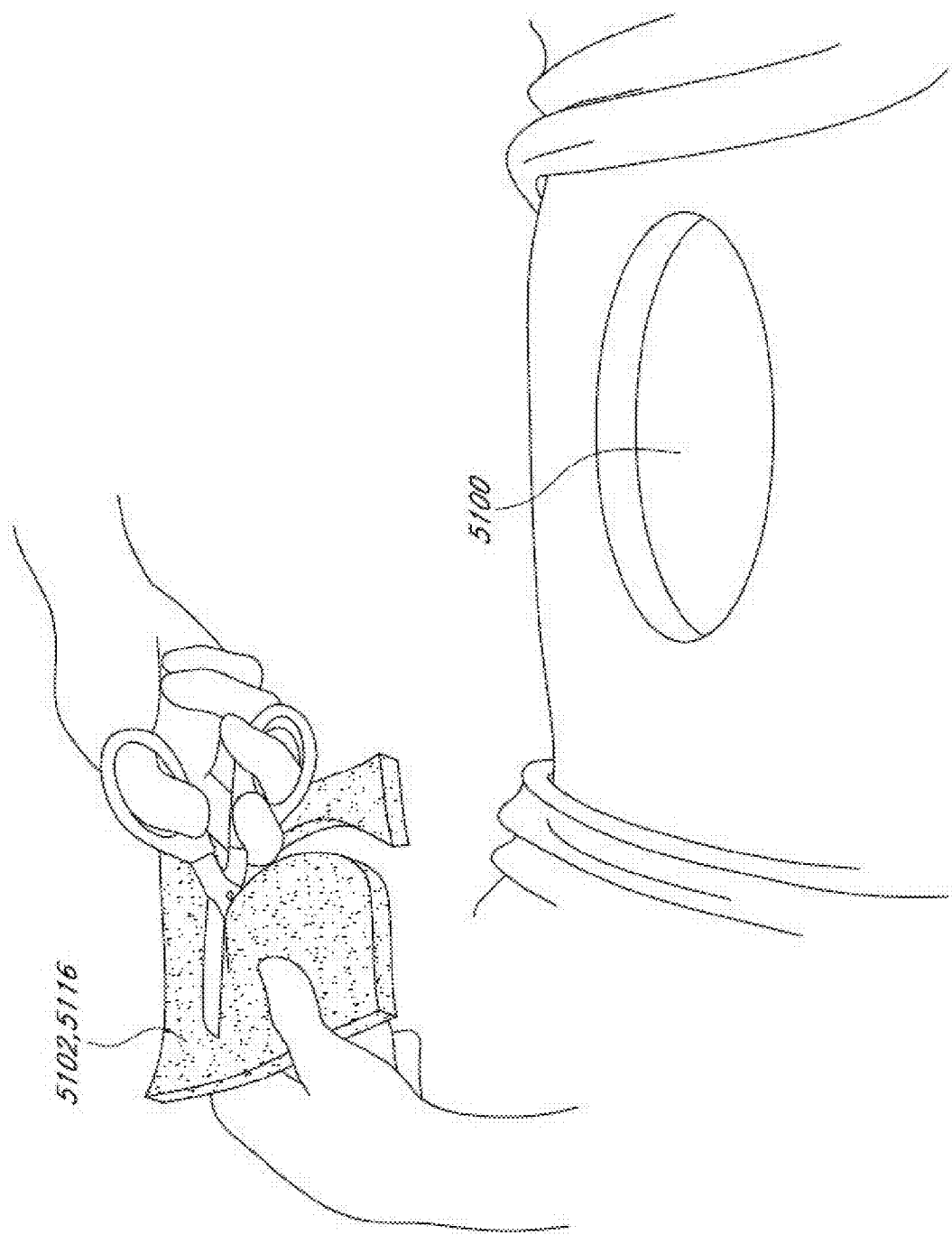

FIGS. 10A-C illustrate embodiments of possible initial steps in a method for the treatment of an open wound. However, as described above, the steps need not be performed in this order and may be performed in any order. In FIG. 10A, two pieces of a porous material such as foam, a bottom piece 5102 and a top piece 5116 are selected so as to approximate the size of the wound 5100. In some embodiments, the top piece and the bottom piece are of identical thickness. However, in certain embodiments, and vice-versa, top piece 5116 may be at least twice as thick, at least four times as thick, at least 10 times as thick or more than ten times as thick as bottom piece 5102. FIG. 10B illustrates an embodiment of additional steps in a method for the treatment of an open wound. Bottom piece 5102 may be shaped via cutting or other suitable means to the shape of the wound and subsequently placed into the wound 5100, as shown in FIG. 10C and depicted further below in FIG. 11A.

Figure 11A:
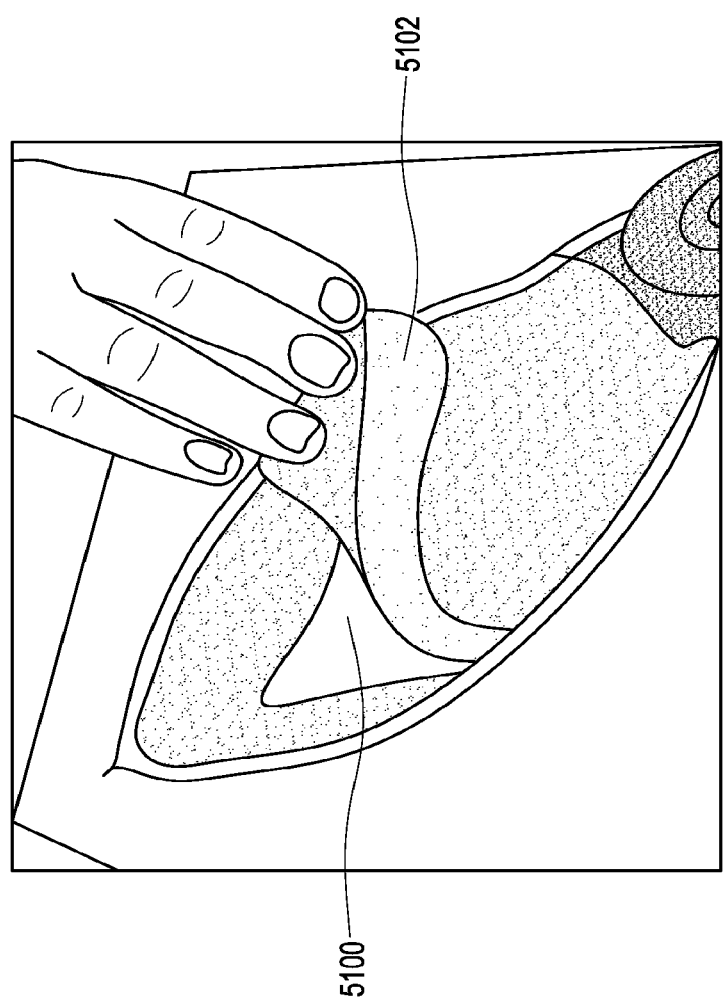
FIGS. 11A-B are photographs of steps of a method of treating a wound.
Figure 11B:
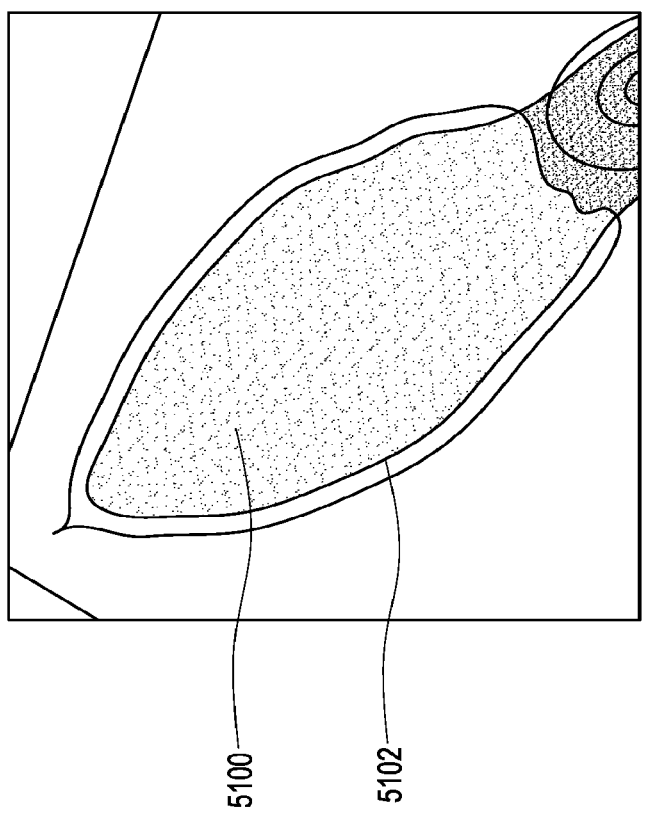
Figure 12A:
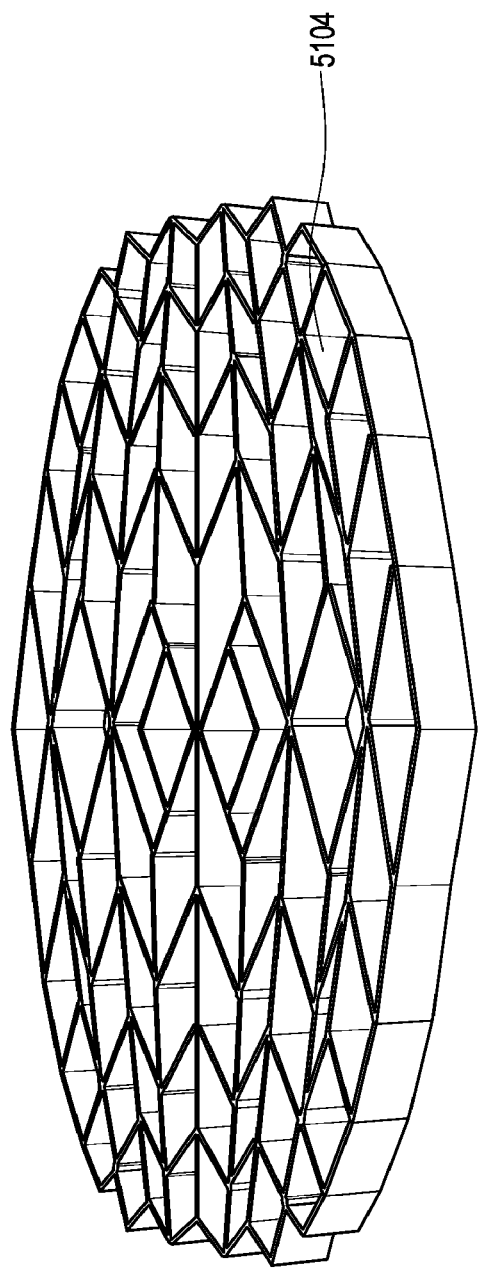
FIGS. 12A-C depict an embodiment of steps of a method of treating a wound.
Figure 12B:
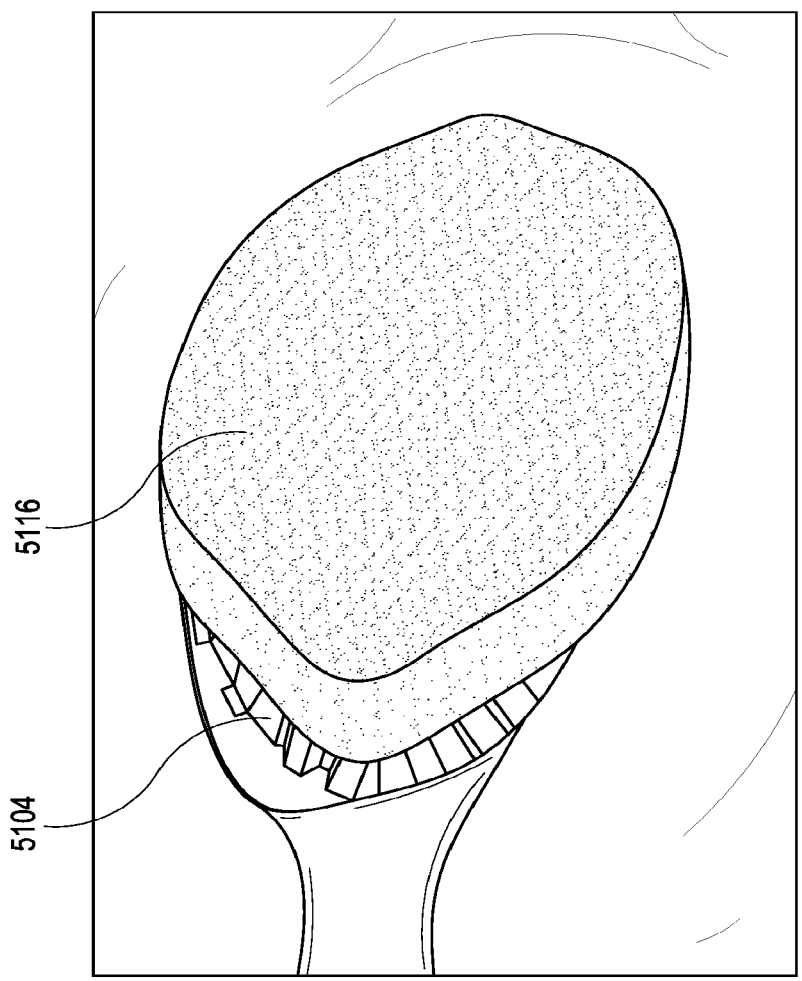
Figure 12C:
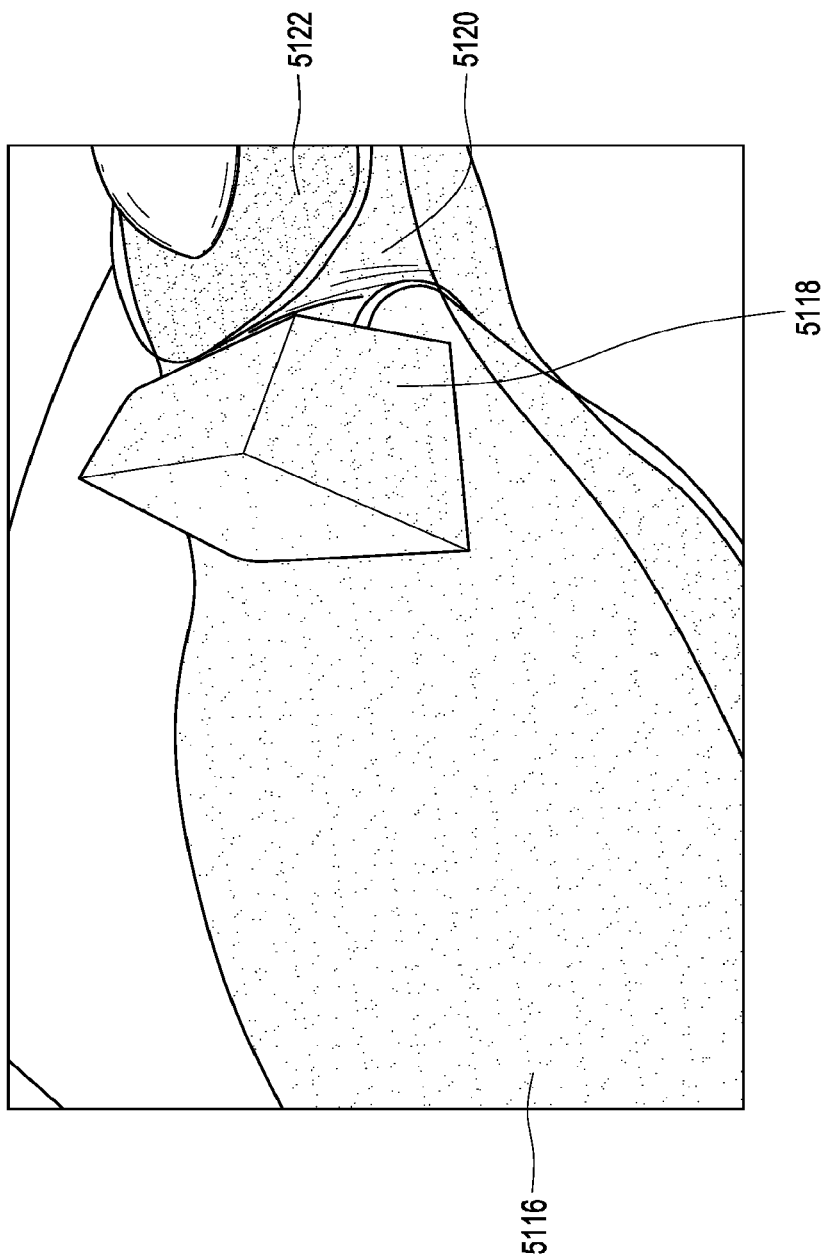

FIGS. 11A-B are photographs of a foam layer 5102 (for example, a 15 mm layer of foam), after shaping, placed into a wound bed 5100. In FIGS. 12A-C, a stabilizing structure 5104 similar to the stabilizing structures disclosed in FIGS. 2A-3E or any other stabilizing structure described elsewhere in the specification, is in the shape of the wound. The stabilizing structure may be shaped into the shape of the wound via cutting or other suitable means or the stabilizing structure may initially be of a size that is readily accommodated by the wound. As displayed in FIG. 12B, the stabilizing structure 5104 may be placed into the wound. To assist with the insertion of the device into the wound bed, the device can be deformed slightly inwardly or horizontally to facilitate entrance into the wound site. In some embodiments, the device may be squeezed slightly during insertion and then release upon contact with the walls of the wound. In certain embodiments, the wound closure device 5104 may be placed such that the longitudinal sides of the matrix align with the longitudinal axis of the wound 5100. Continuing with FIG. 12B, another foam layer 5116 (for example, a 10 mm layer of foam) is placed on top of the wound closure device 5104.

FIG. 12C is a photograph of application of a port 5122 to the stabilizing structure and foam of FIGS. 12A-B. A bridging portion of foam 5118 may be placed in intimate contact with the foam layer 5116 at the edge of the wound. The bridging portion of foam 5118 may extend over intact skin, with a piece of drape 5120 placed between it and the intact skin. Further, a suction port 5122 may be connected to the bridging portion 5118 with a section of drape 5120 between. In alternative embodiments, the bridging portion 5118 and suction port 5122 may be placed on the wound during a different step depicted in FIGS. 11A-12B.

Figure 13:
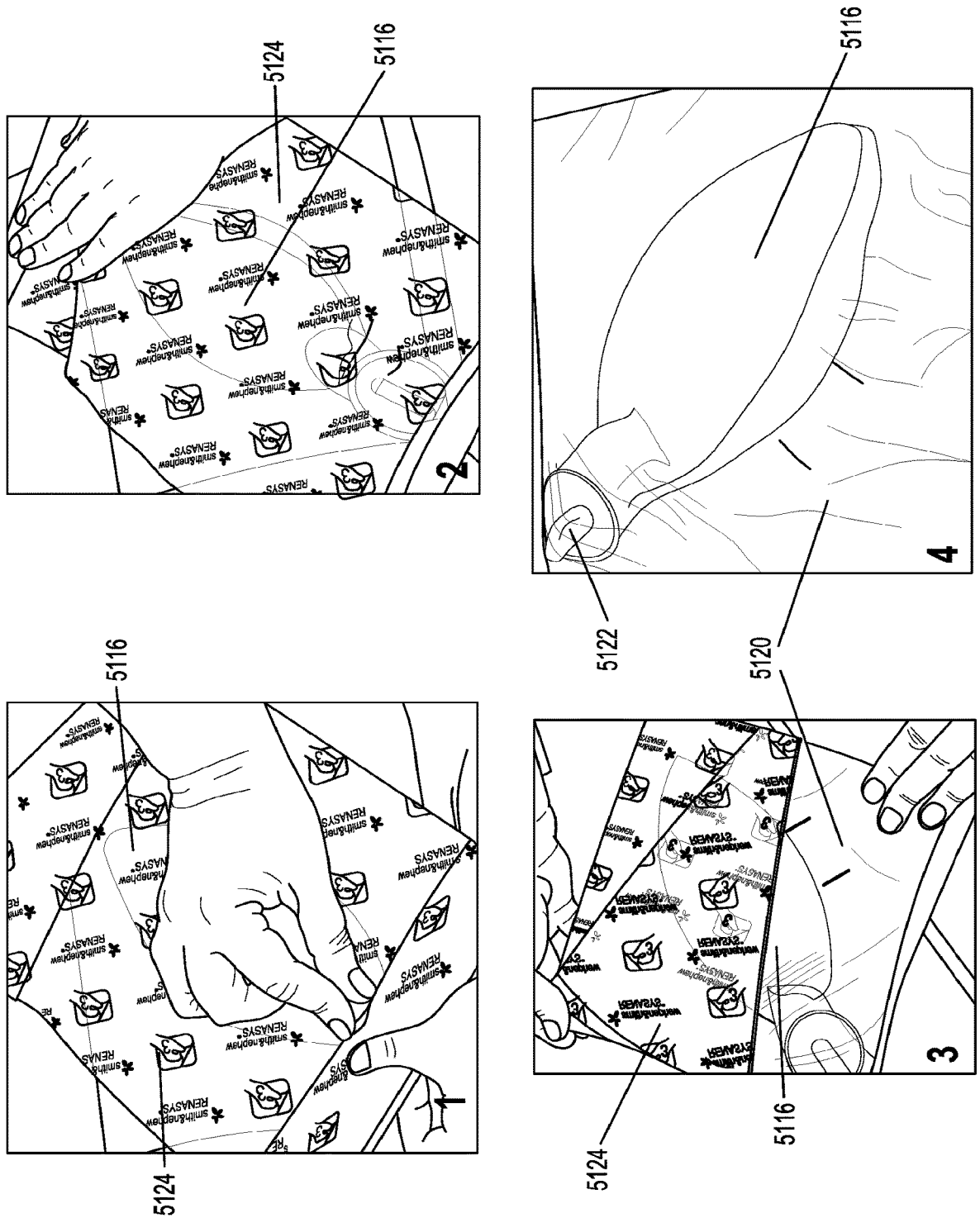
FIG. 13 contains photographs of embodiments of steps of a method of treating a wound.

In FIG. 13, as shown by steps 1-4, the device may be covered by one or more drapes 5120. A hole may be made in the drape covering the bridging portion of foam, and a suction port 5122 may be placed over the hole. A protective layer 5124 on the top surface of the one or more drapes may be removed after the drapes 5120 are applied. Once the drapes 5120 are applied and the port is in place, negative pressure may be applied to the wound through the drape from a vacuum source. The negative pressure can cause the stabilizing structure to collapse horizontally as described elsewhere in this specification. The tissue anchors adhered to the stabilizing structure through the porous layer engage tissue of the wound and may facilitate closure of the wound.

Figure 14A:
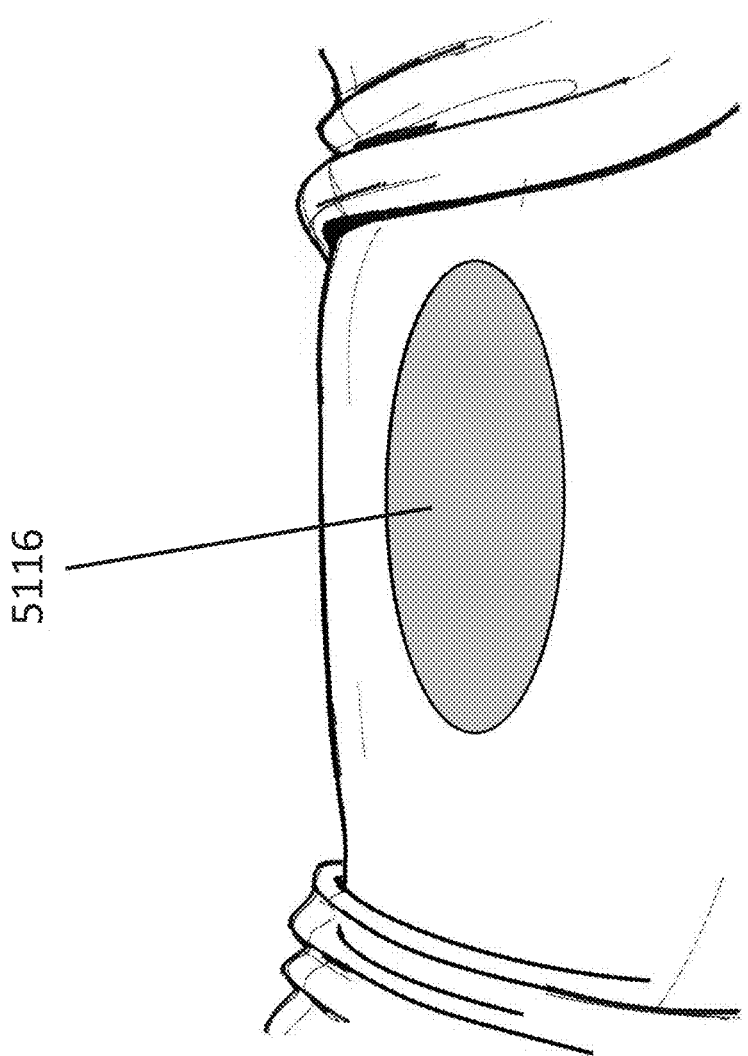
FIGS. 14A-G illustrate an embodiment of a method of treating a wound.
Figure 14B:
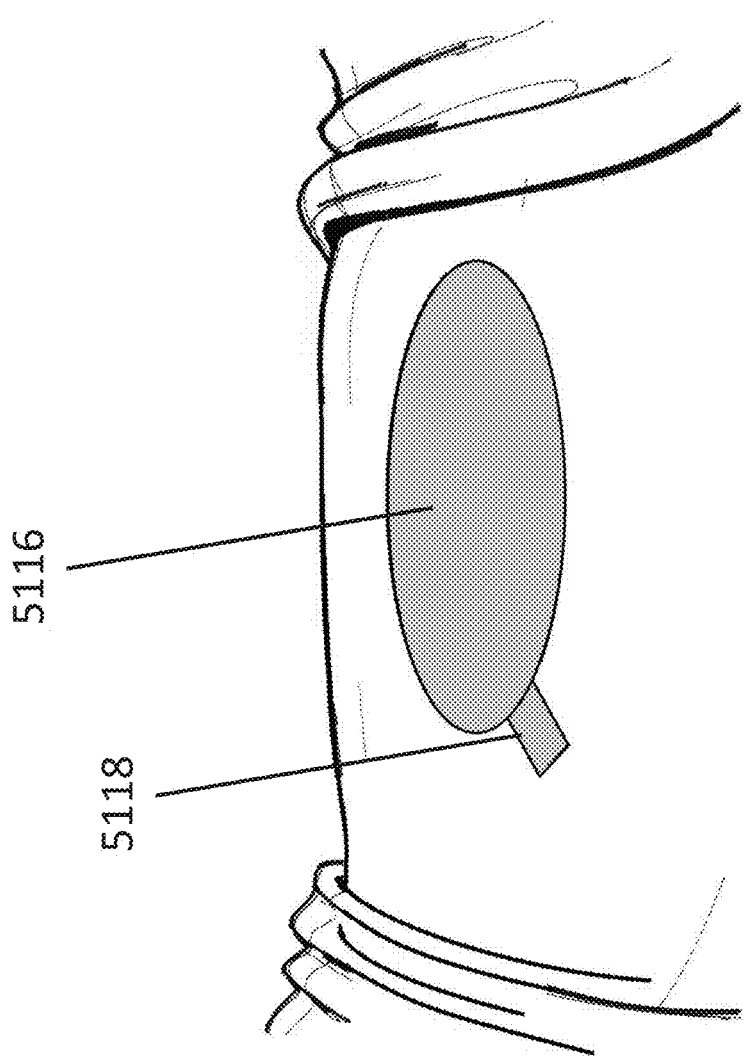
Figure 14C:
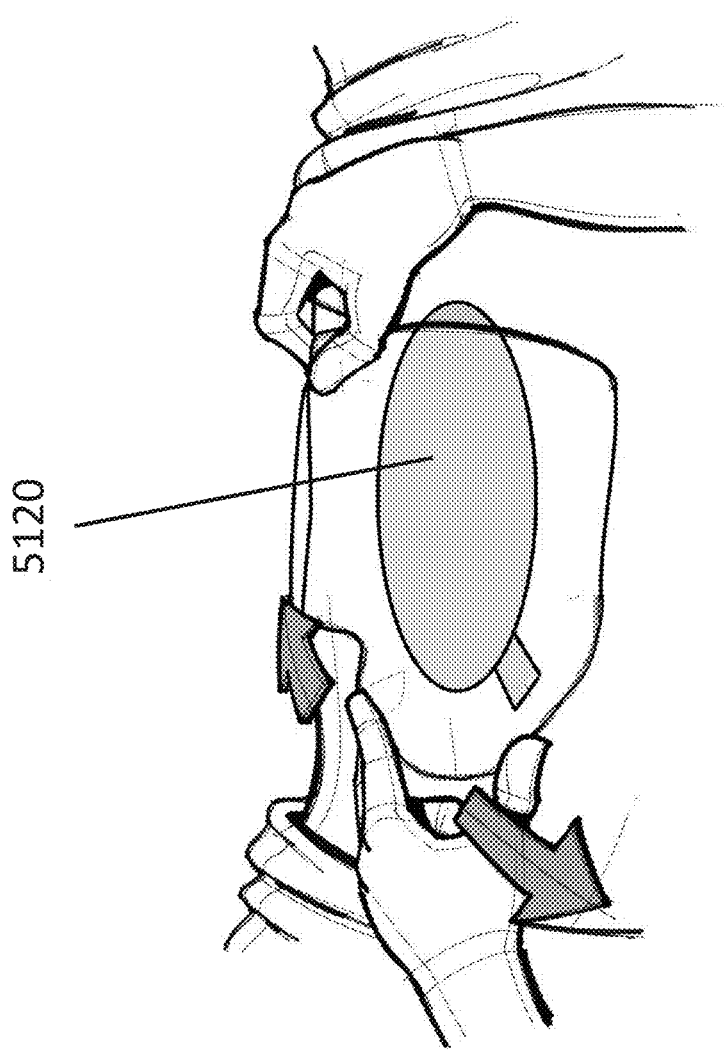
Figure 14D:
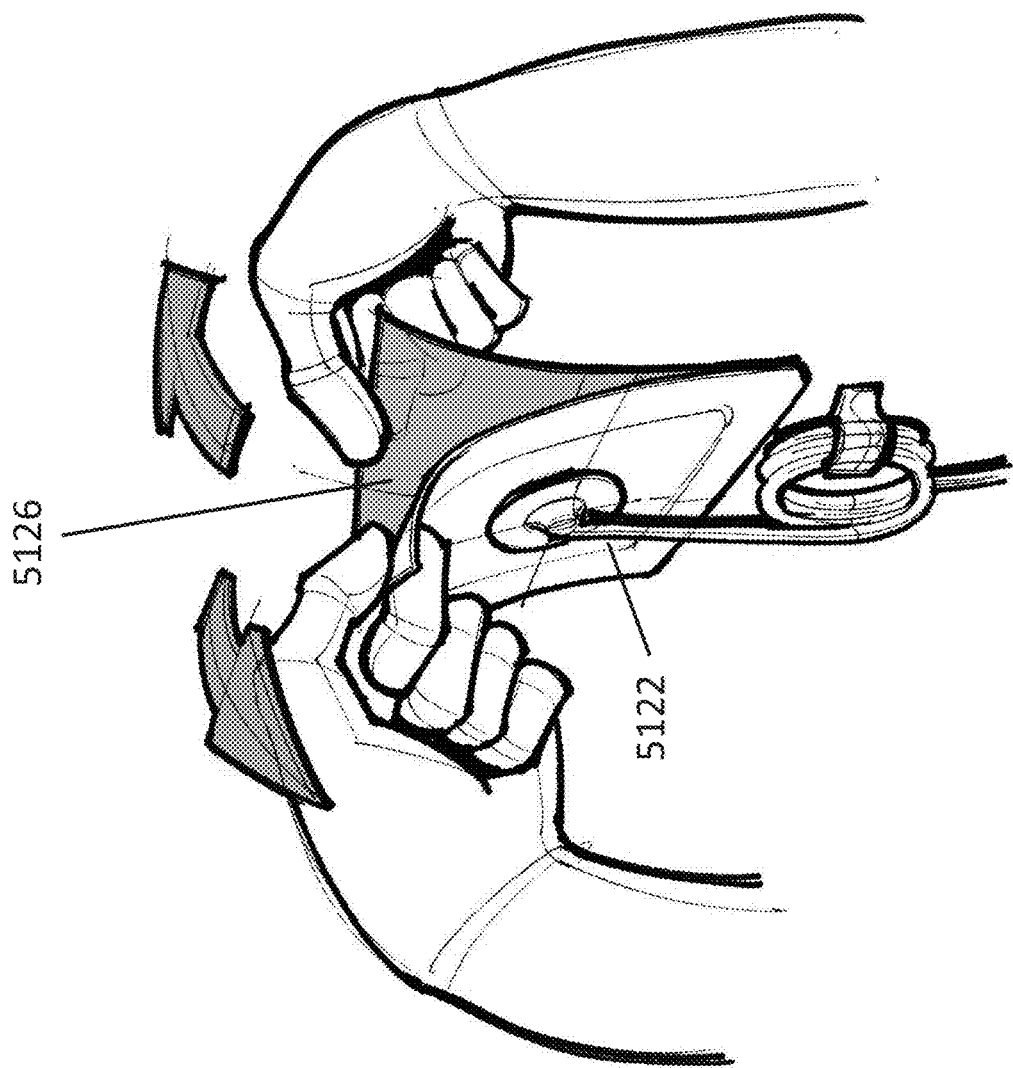
Figure 14E:
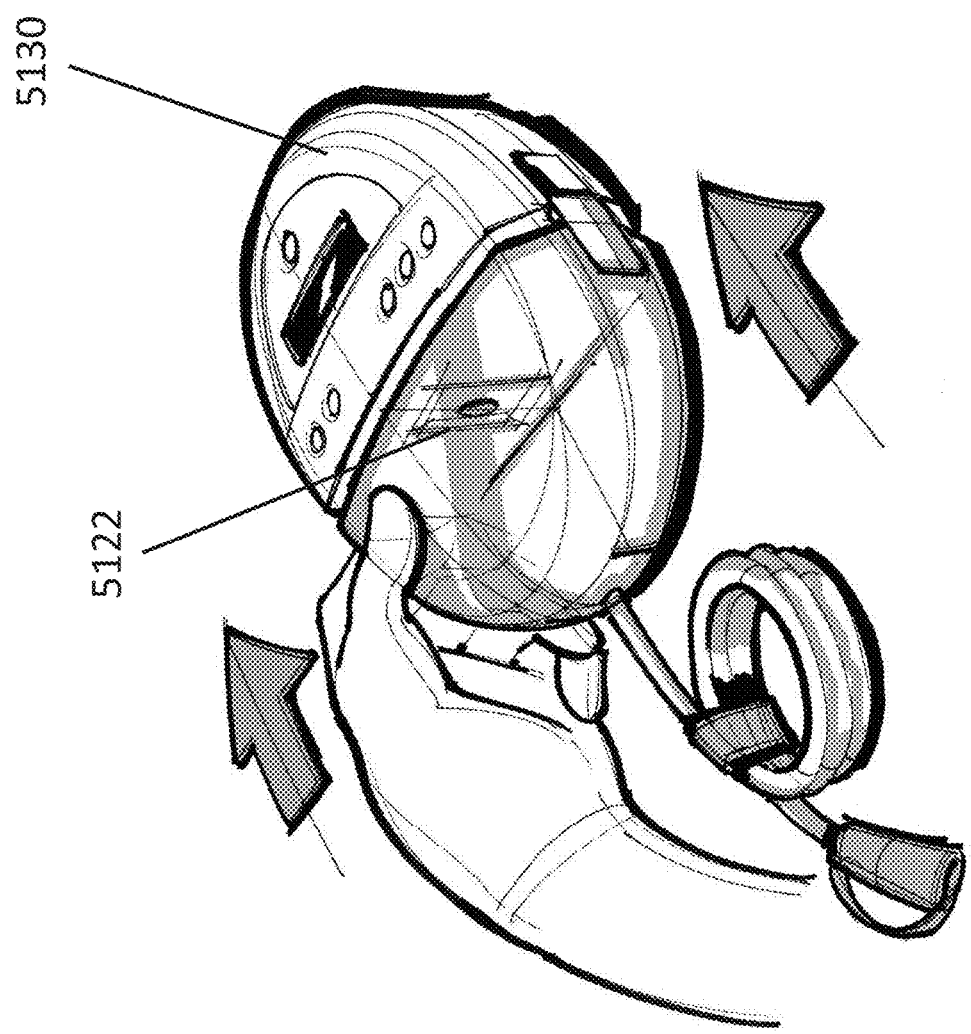
Figure 14F:
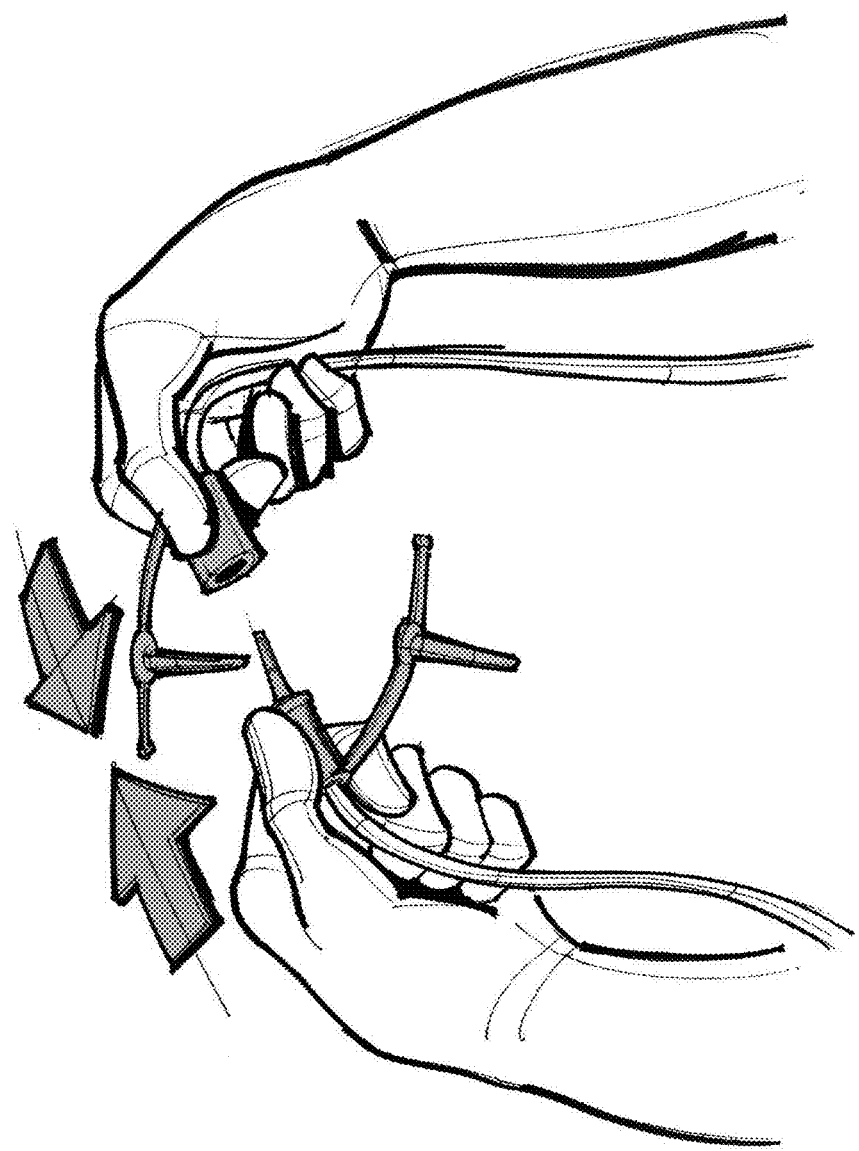
Figure 14G:
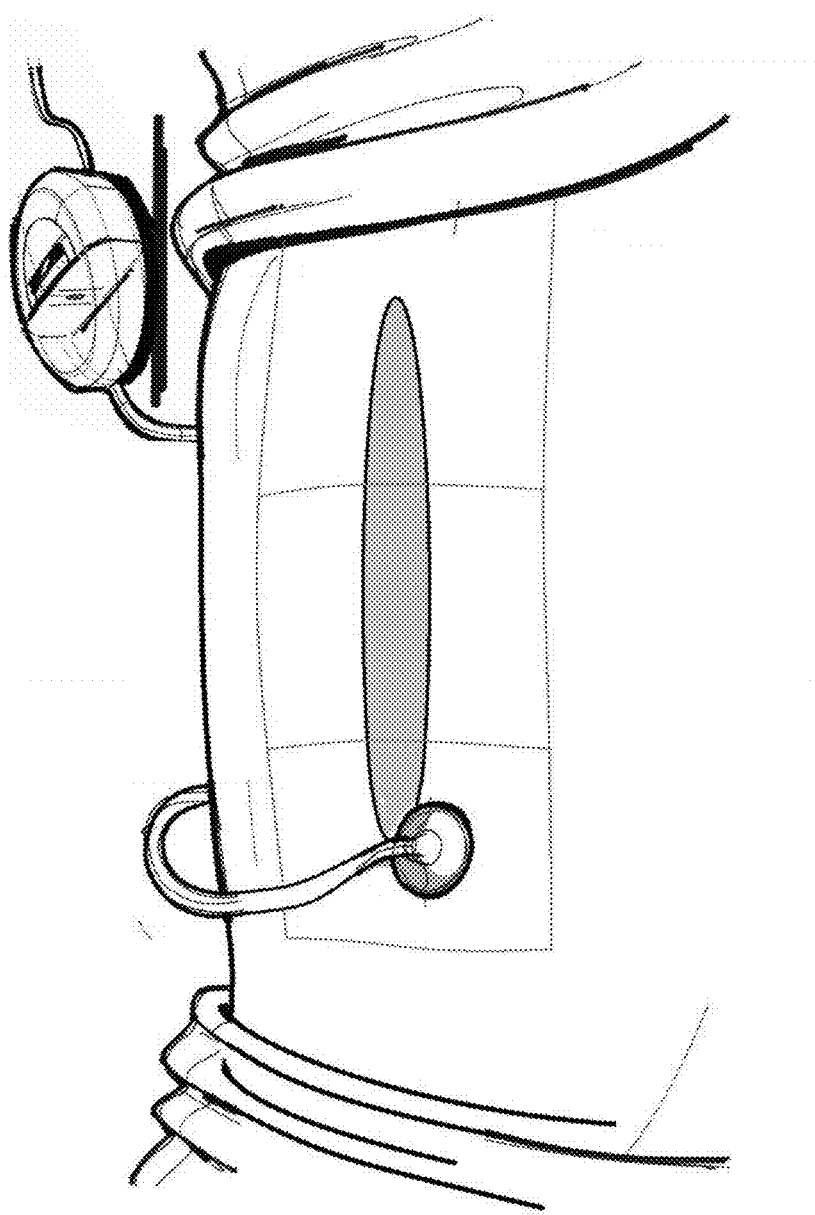

FIGS. 14A-14C provide further illustrations of an upper foam layer 5116 being placed in a wound, followed by placing a bridging portion 5118 and placing one or more drapes or wound covers 5120. FIGS. 14D-14G illustrate an embodiment of several steps in a method for the treatment and closure of a wound. As illustrated in FIG. 14D, a suction port 5122 is separated from a release liner 5126 and later applied to a wound as depicted in FIGS. 11A-13. FIG. 14E illustrates a canister 5128 being inserted into a negative pressure wound therapy device 5130 in preparation for the collection of wound exudate. FIG. 14F illustrates the snap connection between the tubing connected to the suction port and the tubing connected to the negative pressure wound therapy device 5130. Once the connection has been made, negative pressure wound treatment may begin as depicted in FIG. 14G.

Figure 15A:
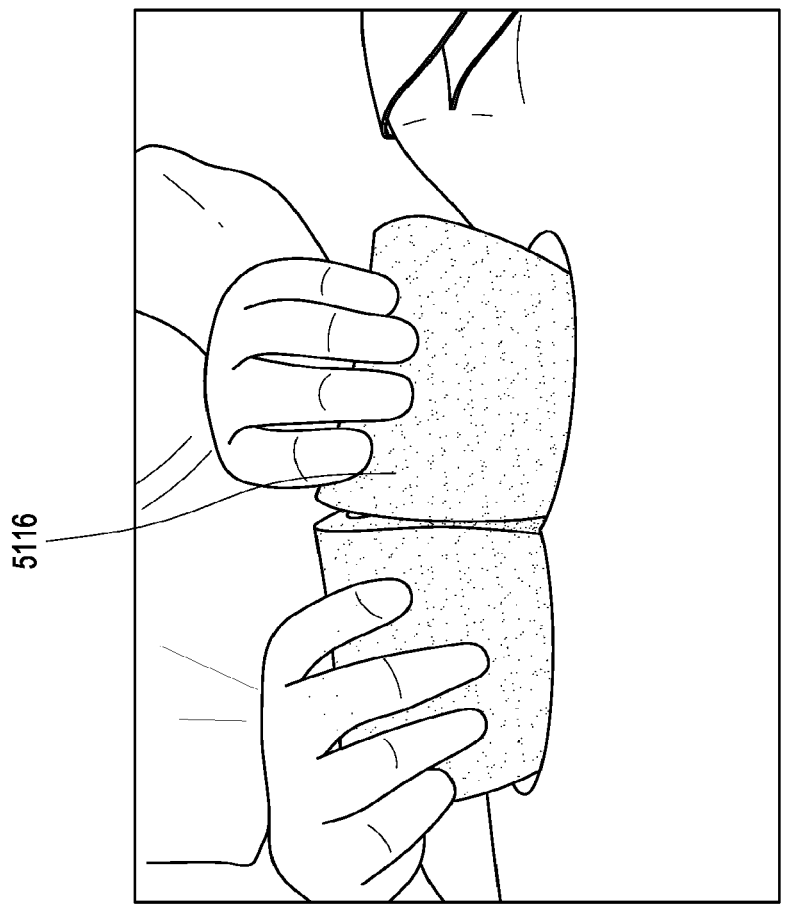
FIG. 15A-E are photographs of an embodiment of a method of treating a wound.
Figure 15B:
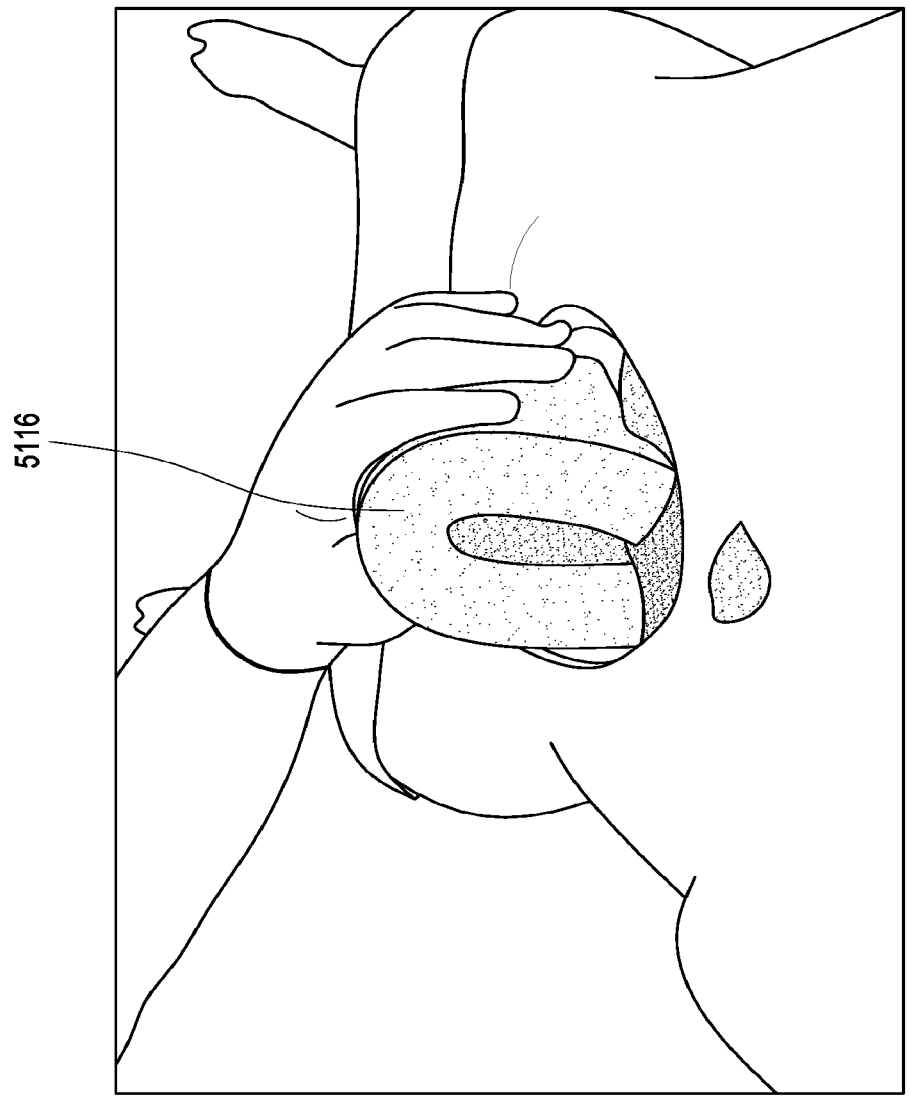
Figure 15C:
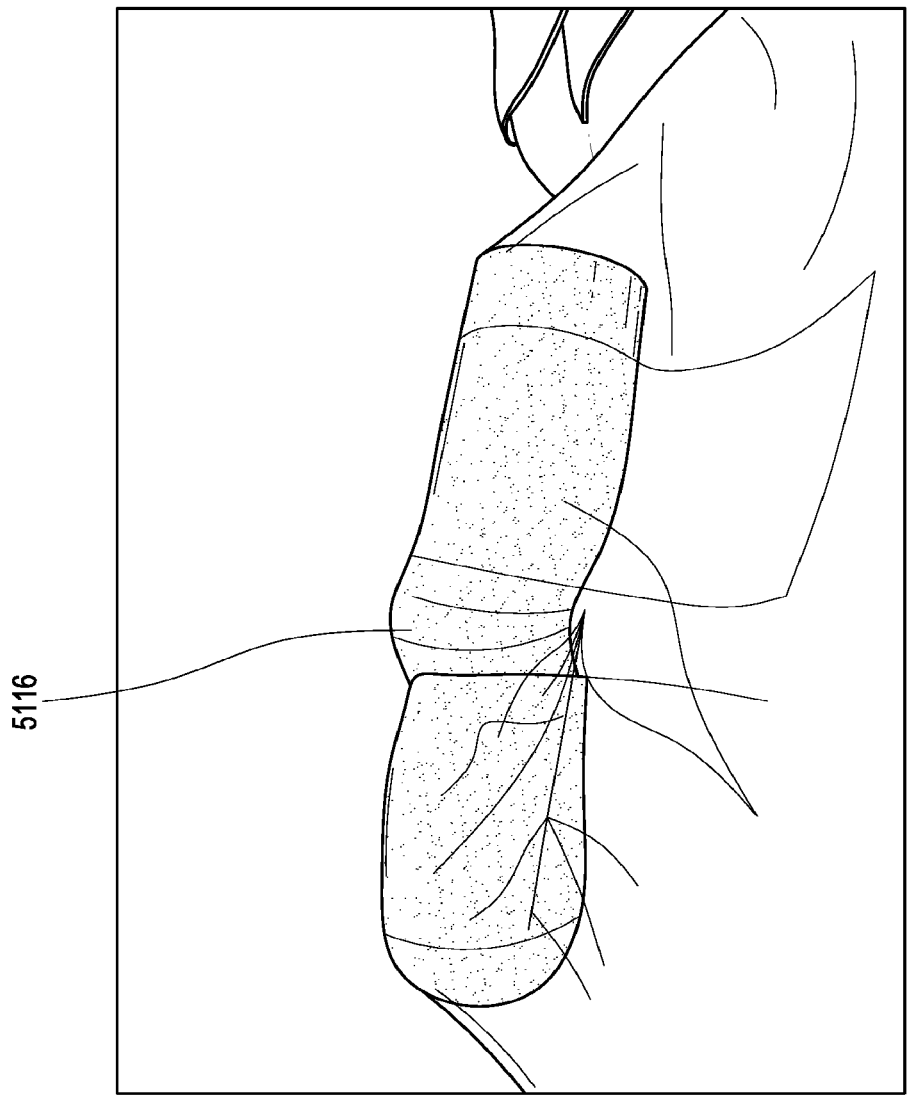
Figure 15D:
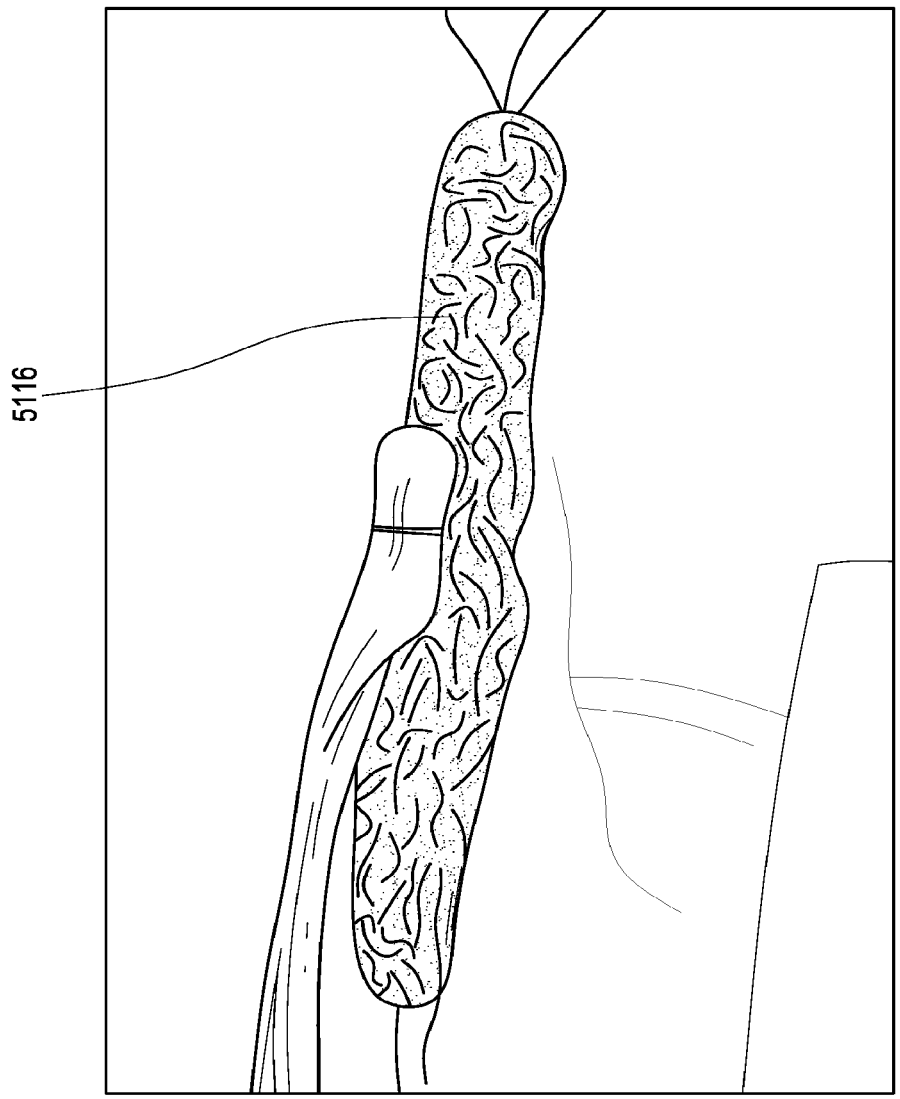
Figure 15E:
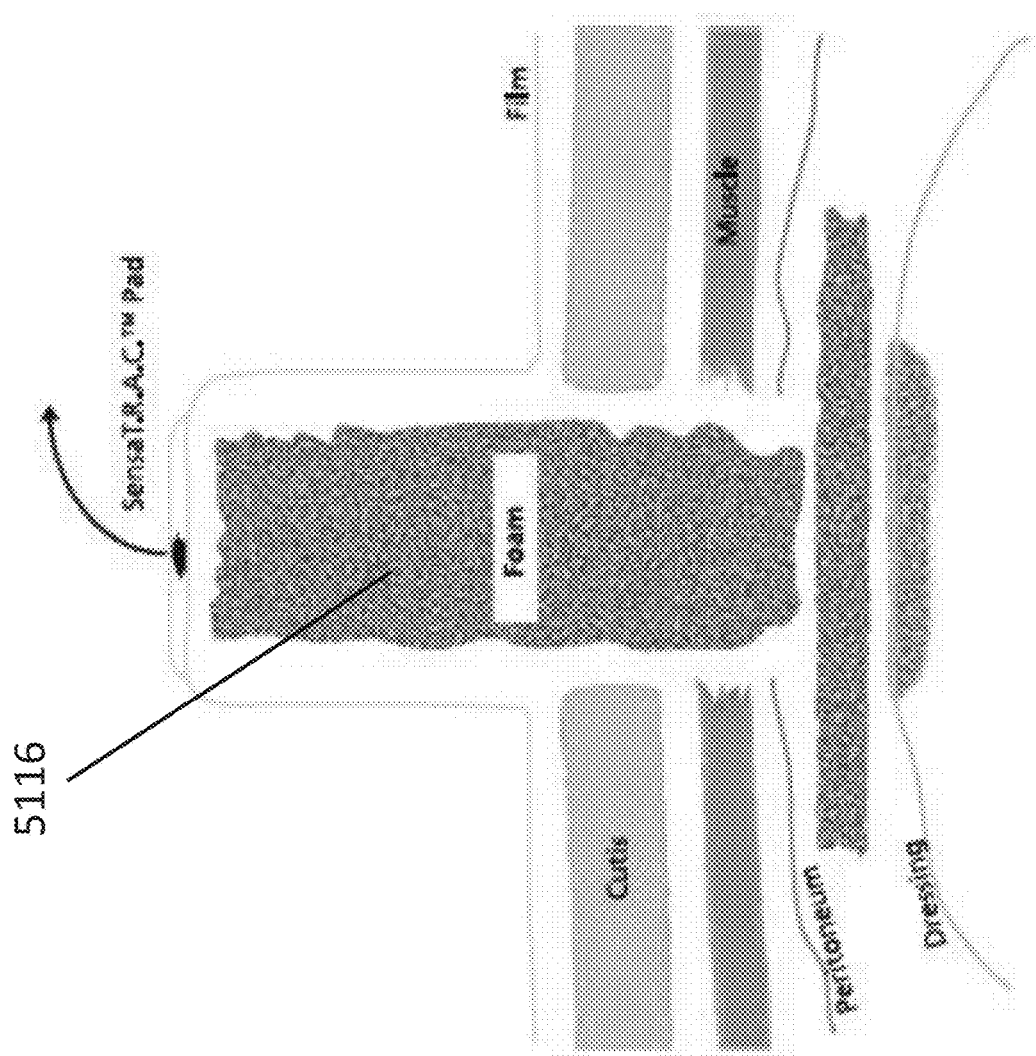

FIGS. 15A-E are photographs and a drawing of a prior art or alternative method for closing a wound, with some similarities to the methods of FIGS. 7-14G. Here, foam is placed under the muscle and fascia, followed by foam extending vertically out of the wound and folded over. Such a method may provide enhanced closure of the dermis but possibly not at the fascia level. In alternative embodiments, such a configuration may be combined with a stabilizing structure such as those disclosed herein this section and elsewhere in the specification, by providing a folded over foam layer 5116 that bulges out of the wound. FIG. 15E is a cross-sectional drawing of the prior art or alternative method.

Further details regarding the wound closure devices, stabilizing structures, related apparatuses and methods of use that may be combined with or incorporated into any of the embodiments described herein are found elsewhere throughout this specification and in International Application No. PCT/US2013/050698, filed Jul. 16, 2013, published as WO 2014/014922 A1, the entirety of which is hereby incorporated by reference.

The Stabilizing Structures of FIGS. 16-19D

Figure 16:
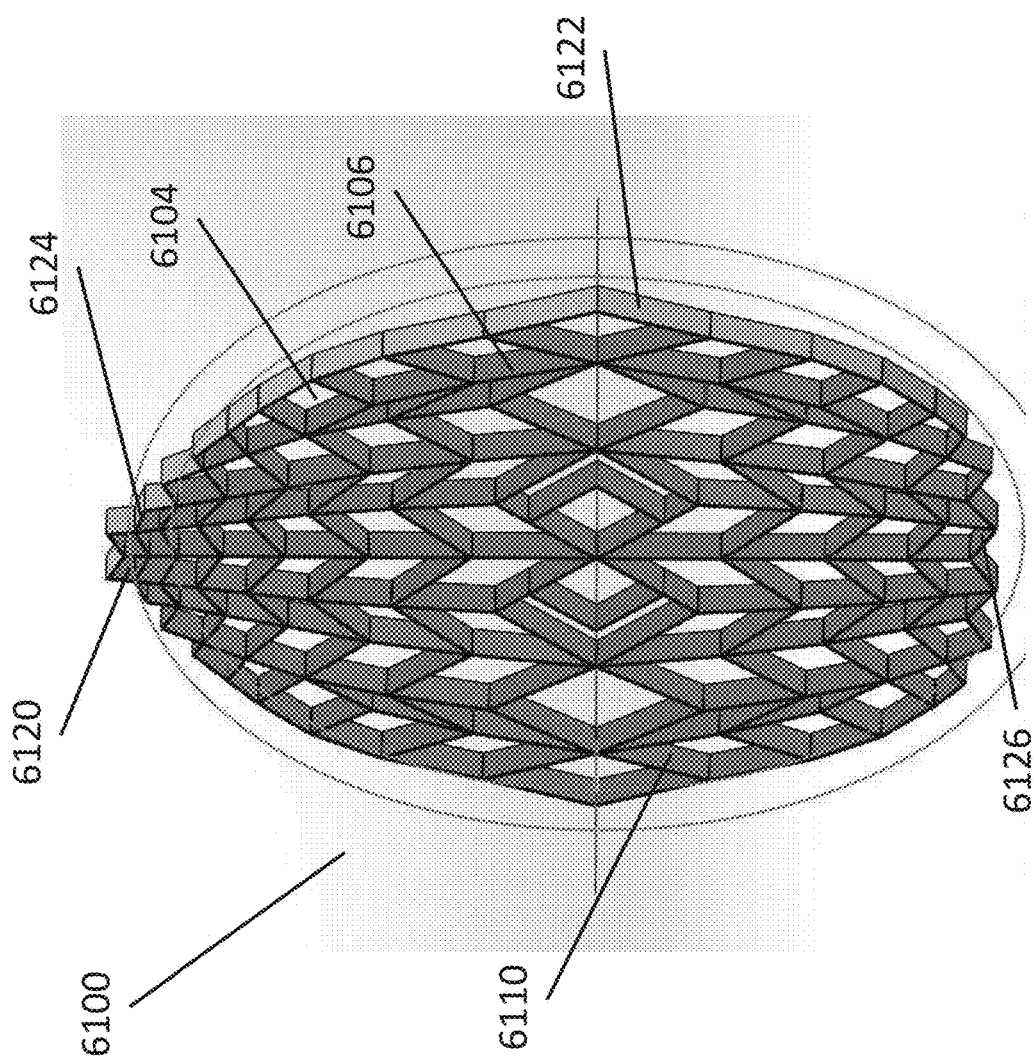
FIG. 16 illustrates an embodiment of a stabilizing structure.

FIG. 16 is a drawing of an embodiment of a stabilizing structure 6100, similar to the stabilizing structures of FIGS. 2A-3E. Stabilizing structure 6100 may be constructed via any means described herein this section or elsewhere in the specification, such as via 3D printing and via the calculation method described in FIGS. 3A-3E. Further, stabilizing structure 6100 may be constructed from any material described herein this section or elsewhere in this specification such as the materials described in relation to FIGS. 2A-3E. Similar to the stabilizing structures of FIGS. 2A-3E, stabilizing structure 6100 comprises a plurality of elongate strips 6106 arranged in parallel or semi-parallel, whose longitudinal length can be aligned with the longitudinal axis of a wound. In embodiments, the elongate strips 6106 may also be arranged in a non-parallel fashion. The various cells within this stabilizing structure 6100 may have a variety of shapes and sizes. As was described in greater detail above, the length and shape of the elongate strips 6106, intervening members 6110, and cells 6104 may be designed so as to facilitate greater closure of the stabilizing structure.

In embodiments, the stabilizing structure of FIG. 16 differs from the stabilizing structures of FIGS. 2A-3E, due to the inclusion of an extended section 6120. Extended section 6120 comprises one or more additional cells that extend outward along the longitudinal axis of the stabilizing structure 6100. Extended section 6120 may allow the stabilizing structure to better fit within a long incisional wound. Further, the addition of extended section 6120 may serve to prevent pinching of the surrounding tissue during collapse of the stabilizing structure 6100. Extended section may comprise about 6 additional cell, 12 additional cells, 16 additional cells, 20 additional cells, 30 additional cells, or more than 30 additional cells.

As depicted in FIG. 16, extended section 6120 may include additional rows having progressively fewer cells across its width. For example, extended section 6120 may comprise a row of four cells, then a row of two cells, followed by another row of two cells. In some embodiments, a row of six cells precedes the row of four cells. The extended section 6120 extends beyond the outer edge of a virtual ellipse formed by the majority of the perimeter of the stabilizing structure along the longitudinal axis of the stabilizing structure. In certain embodiments, the extended section may extend from both ends of the stabilizing structure along the longitudinal axis. The extended section 6120 in some embodiments provides a stepped outer perimeter to the outer wall of the stabilizing structure at the longitudinal edges of the stabilizing structure, in contrast to the continuous outer perimeter along the sides of the stabilizing structure 6122.

Absent the extended section 6120, the stabilizing structure comprises non-stepped side walls along substantially the entire length of the oval. However, with the extended section, the additional rows may provide a stepped outer perimeter 6124 based on the additional rows, in contrast to the flattened oval end of the stabilizing structure 6126. Further embodiments of the extended section will be described in more detail below in relation to FIGS. 17A-17E.

FIGS. 17A-17E are drawings and pictures of embodiments of stabilizing structure 6200, similar to the stabilizing structures of FIGS. 2A-3E and FIG. 16. Much like the stabilizing structures disclosed elsewhere in the specification, stabilizing structure 6200 comprises elongate strips 6206, cells 6204, and intervening members 6210. Stabilizing structure 6200 further comprises extended sections 6220 at both ends of the longitudinal axis of the stabilizing structure. As described above in relation to FIG. 16, extended sections 6220 may allow the stabilizing structure to better fit within the contours of a wound. Further, extended sections 6220 may prevent pinching of the surrounding tissue after collapse of the stabilizing structure. As described above, extended section may comprise multiple cells.

The stabilizing structures of FIGS. 17A-17E, and any of stabilizing structure disclosed herein this section or elsewhere in the specification may be produced in a variety of sizes. The possible size and shape of an actual wound may vary dramatically in size and shape, thus suitable stabilizing structures may also be prepared in a variety of sizes. For example, the length of an un-collapsed stabilizing structure may be approximately at least 25 mm, 50 mm, 75 mm, 100 mm, 125 mm, 150 mm, 175 mm, 200 mm, 250 mm, 300 mm, 350 mm, 400 mm, 450 mm, 500 mm, 750 mm, or greater than 750 mm. In certain embodiments, the width of an un-collapsed stabilizing structure may be at least 10 mm, 15 mm, 25 mm, 35 mm, 50 mm, 75 mm, 100 mm, 125 mm, 150 mm, 175 mm, 200 mm, 250 mm, 300 mm, 350 mm, 400 mm, 450 mm, 500 mm or greater than 500 mm.

Figure 17A:
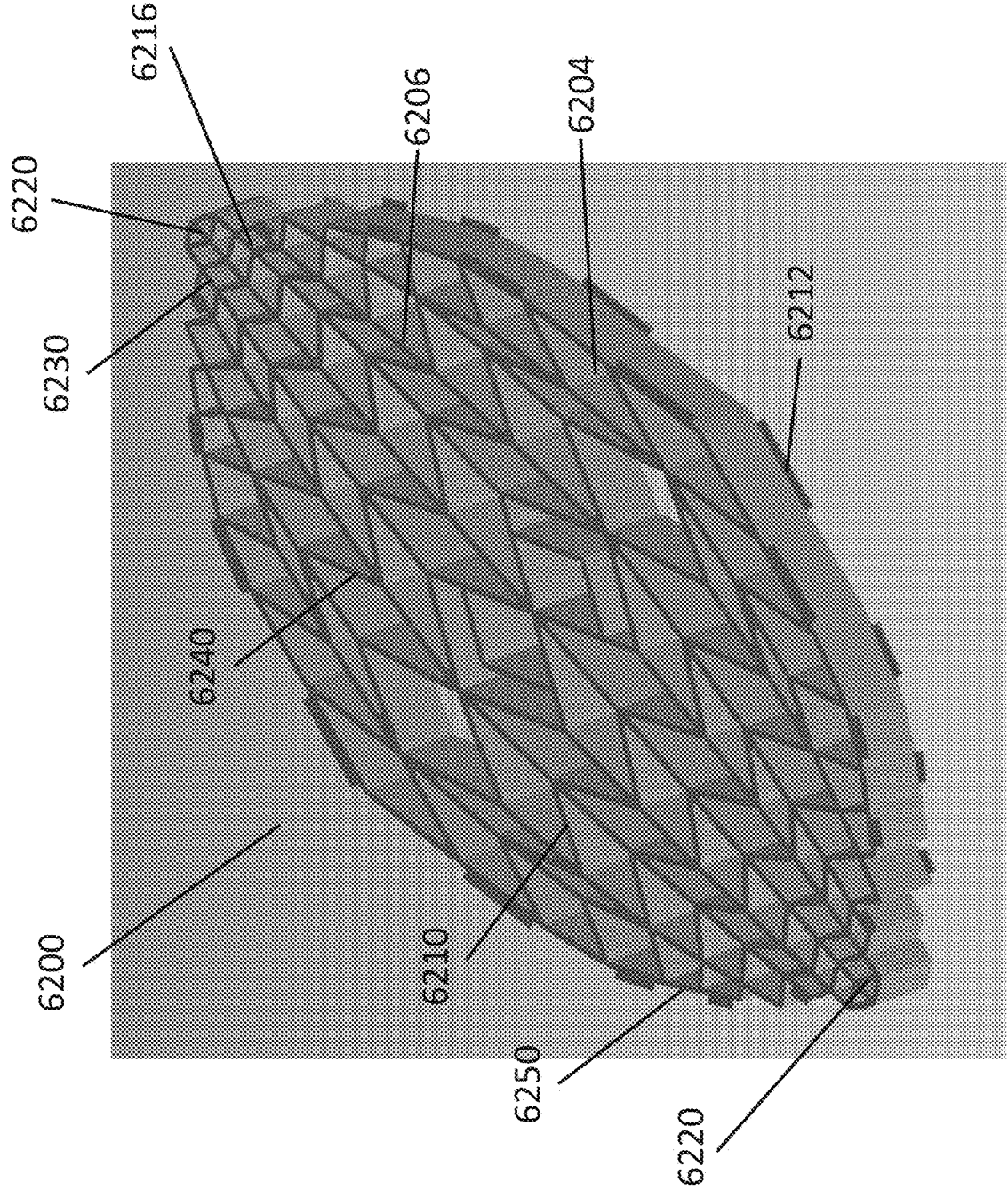
FIGS. 17A-E are drawings and photographs of an embodiment of a stabilizing structure.
Figure 17B:
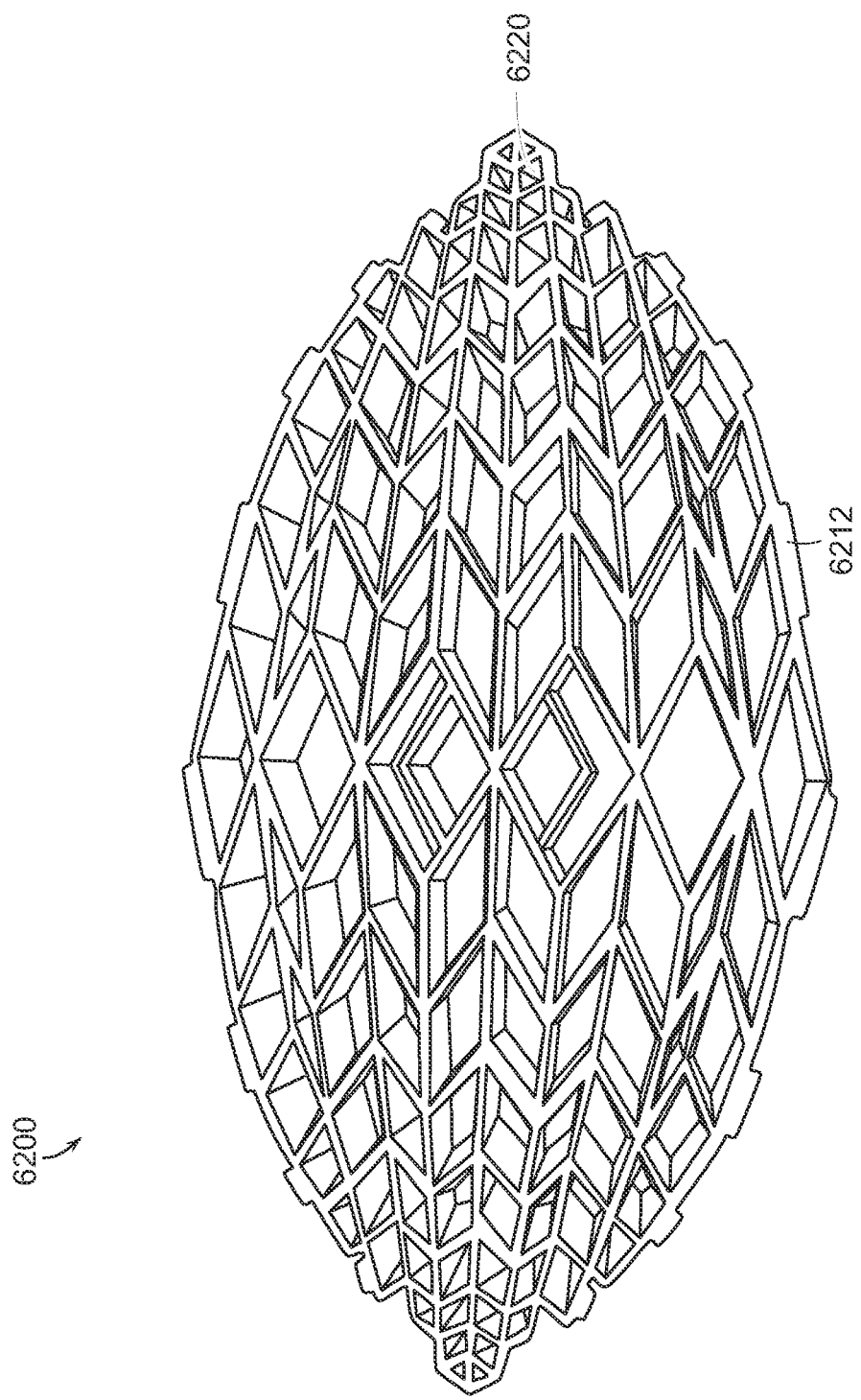
Figure 17C:
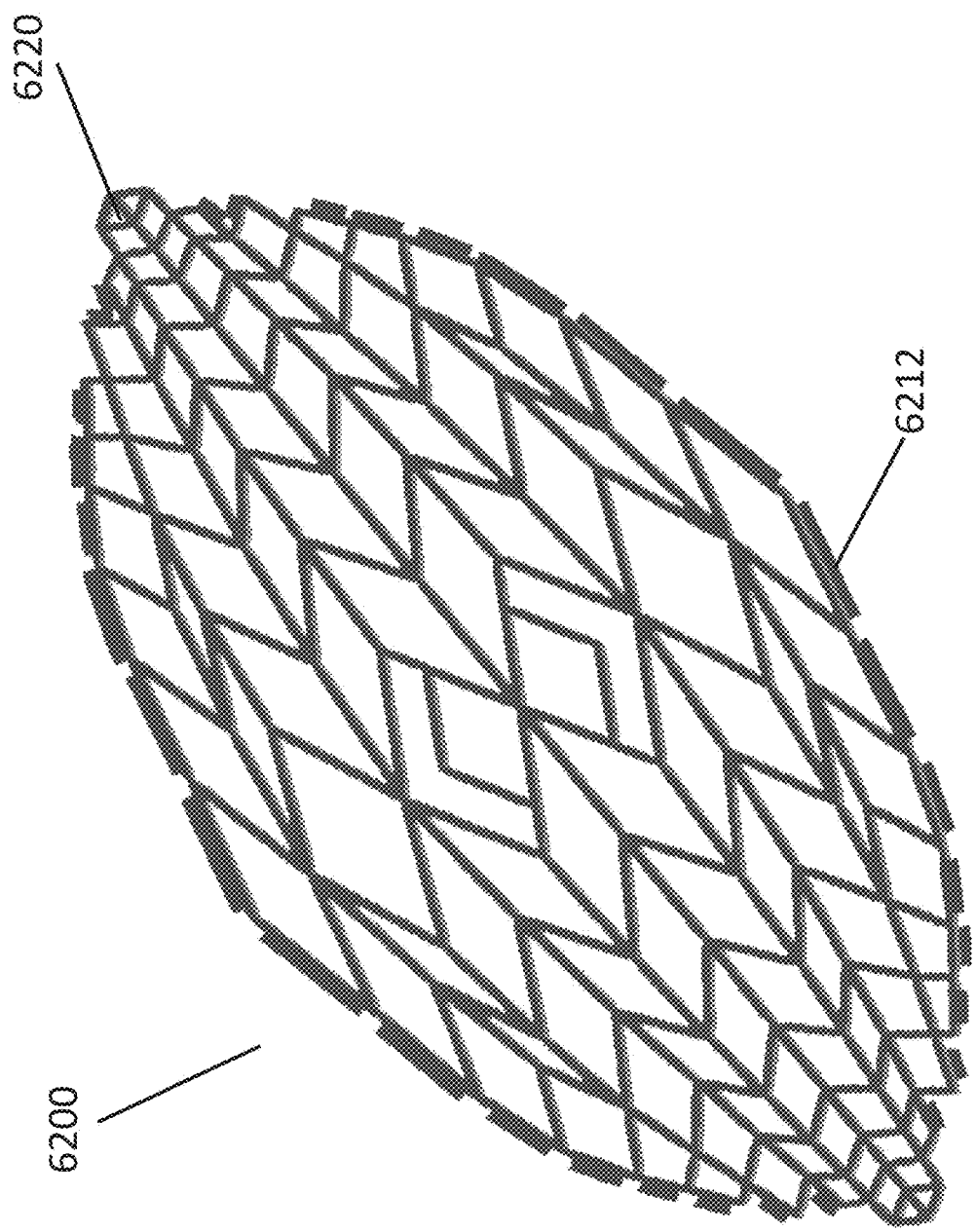
Figure 17D:
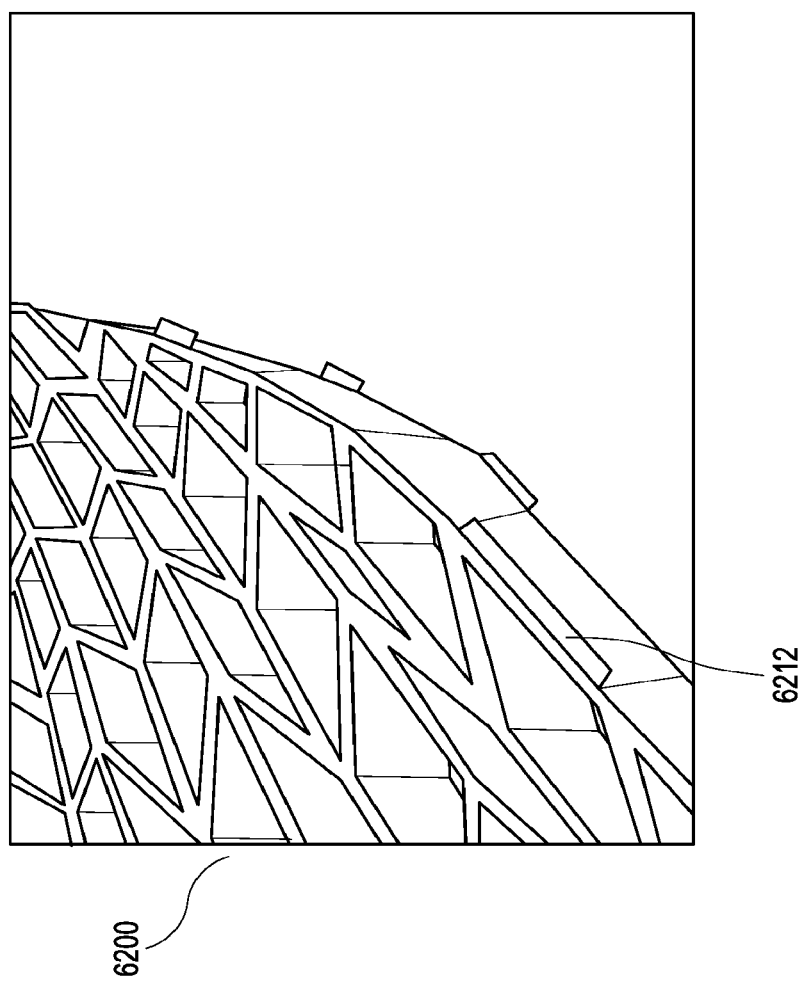
Figure 17E:
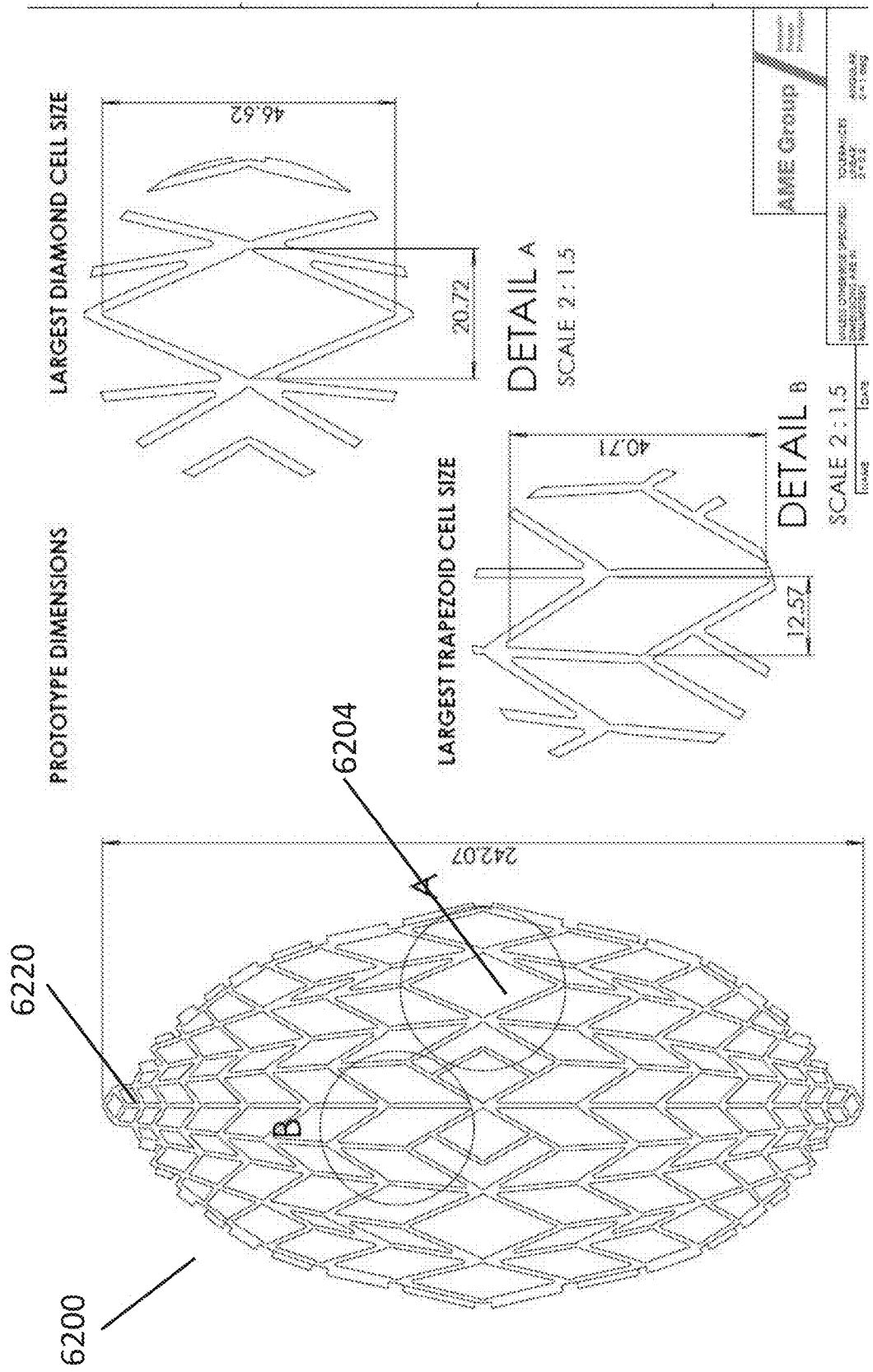

As depicted in FIG. 17E, in some embodiments the un-collapsed stabilizing structure may have a length of approximately 242 mm. However, the stabilizing structure may be of any size disclosed herein this section or elsewhere in the specification. The cells 6204 of the stabilizing structure may be of a variety of sizes, for example the width of a cell 6204 may be approximately at least 5 mm, 10 mm, 15 mm, 20 mm, 25 mm, 30 mm, 50 mm, or more than 50 mm. For example, the length of a cell may be approximately at least 5 mm, 10 mm, 15 mm, 20 mm, 25 mm, 30 mm, 50 mm, or more than 50 mm.

In some embodiments, extended sections 6220 may comprise a first row of four cells, followed by a row of two cells, followed by another row of two cells. The row of four cells may be preceded by a row of six cells. However, in further embodiments, the extended section may comprise various numbers of cells per row and different numbers of rows. For example, extended section may comprise 1 row, 2 rows, 3 rows, 4 rows, 5 rows, 6 rows, or more than 6 rows. In embodiments, the rows may comprise 1 cell, 2 cells, 3 cells, 4 cells, 5 cells, 6 cells, 8 cells, 10 cells, 16 cells, or more than 16 cells.

Returning to FIG. 17A, in certain embodiments, the extended section may comprise a series of cells 6104 comprising walls that are semi-parallel 6230 to the longitudinal axis of the stabilizing structure. These cell walls contrast with cell walls elsewhere in the stabilizing structure which comprise walls that run at an angle 6240 to the longitudinal axis of the stabilizing structure 6200.

In embodiments of the stabilizing structure comprising extended sections 6220, elongate members 6206 closest to the central longitudinal axis of the stabilizing structure extend further along the longitudinal axis than embodiments of the stabilizing structure that do not comprise an extended section. For example, the innermost elongate strips are the longest strips, while the next innermost strips are the second longest and so on. The presence of the extended sections causes the stabilizing structure when viewed from above to appear to be more eye-shaped rather than more oval-shaped.

As depicted in FIG. 17A-C, in embodiments, the stabilizing structure 6200 may be oculiform. An oculiform shape may appear to be shaped like a human eye, with curved upper and lower edges converging to points at either longitudinal pole in the corners of the eye. Here, the outer walls curve inward 6250 to converge at the extended sections 6220. This shape is in contrast to a more diamond shape (not shown) where the outer walls would converge in a straight line to extended section 6220. However, in some embodiments, the stabilizing structure may be in the form of a diamond, rather than an oculiform.

Stabilizing structure 6200 further comprises tabs 6212 extended outward from the outer wall of the stabilizing structure 6200. Such tabs may extend outward from the top or the bottom of the stabilizing structure or both. The tabs may extend out from all outer cells of the stabilizing structure as depicted by FIG. 17C or the tabs may alternate as depicted in FIG. 17A. FIG. 17D is a photograph of a close up view of a tab 6212. The tabs may be constructed from any material described herein this section or elsewhere in the specification, such as those materials used for construction of the stabilizing structures. In certain embodiments, the tabs may be 3D printed as part of the stabilizing structure.

The tabs 6212 may further comprise an anchoring layer, such as those described above in relation to FIGS. 4-6B. This anchoring layer may be used to adhere the tabs to a layer of foam. In embodiments, the tabs may be coated in a suitable adhesive, allowing the tabs to be adhered to a layer of foam. The attachment of foam to the upper and lower layers of the stabilizing structure will be described in greater detail below in relation to FIG. 20A-22E. The tabs may further serve to extend outward above or below tissues surrounding the stabilizing structure or around other structures such as foam, wrapped around the perimeter of the stabilizing structure.

The stabilizing structures of FIGS. 17A-17E may be provided in a variety of sizes such as those described above in relation to FIGS. 2A-3E. As described above, it may be advantageous in a clinical setting to minimize adjustments to the size of the stabilizing structure, therefore a kit may be provided that includes stabilizing structures of various sizes that may be fit to a wound of the appropriate size. For example, the kit may comprise only two sizes of matrices, a large size and a small size. The larger size stabilizing structure may be at least about 1.25×, 1.5×, 1.75×, 2×, 2.5×, 3×, 4×, 5×, 6× or greater than 6 times the size of the smaller stabilizing structure.

FIGS. 18A-D are photographs of multiple views of the stabilizing structure 6200 of FIG. 17B, in a collapsed state. During collapse, the length and height of the stabilizing structure remain approximately the same while the width decreases dramatically. As described above, the stabilizing structure may collapse in such a manner when subjected to negative pressure, thereby facilitating closure of the wound.

Figure 18A:
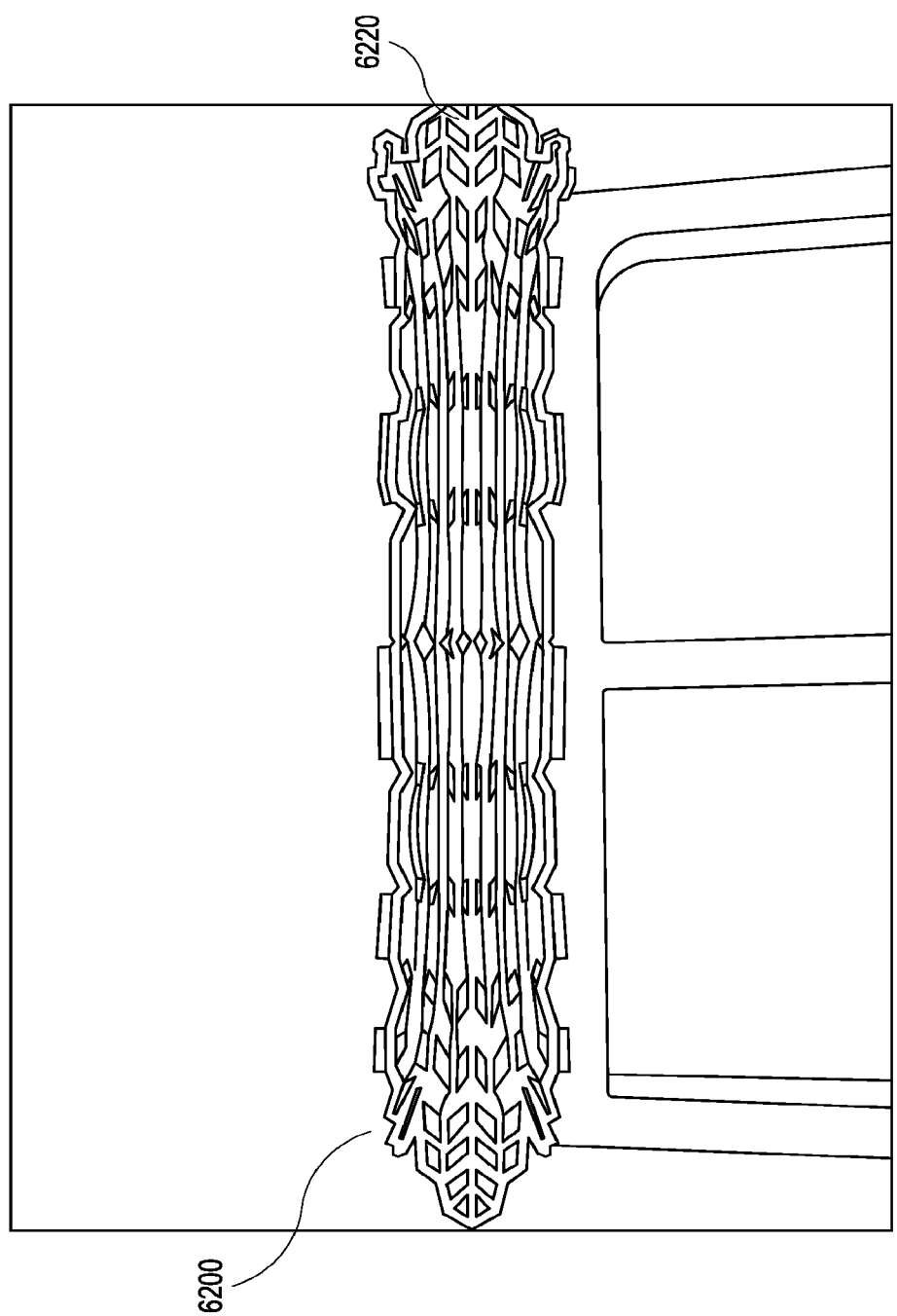
FIGS. 18A-D illustrate an embodiment of a collapsed stabilizing structure.
Figure 18B:
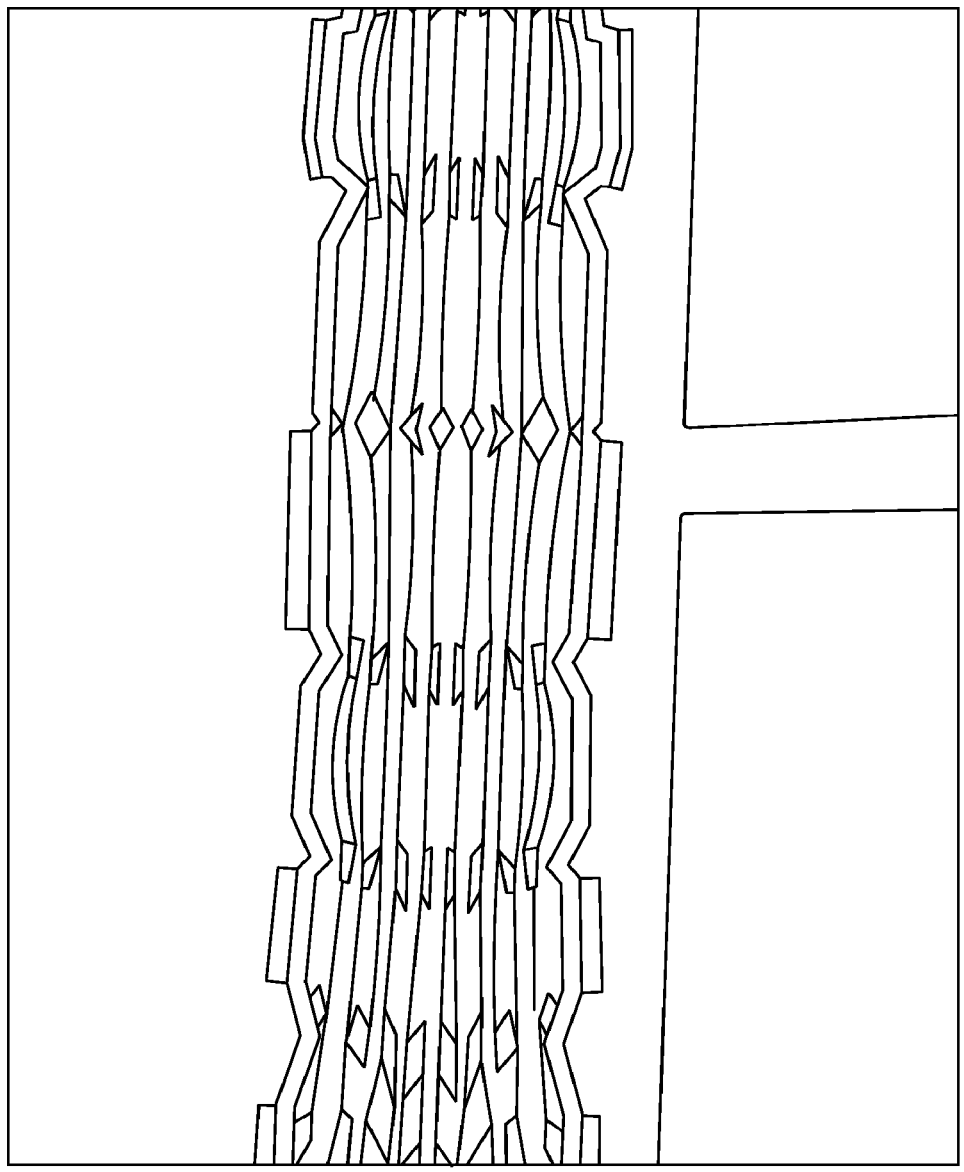
Figure 18C:
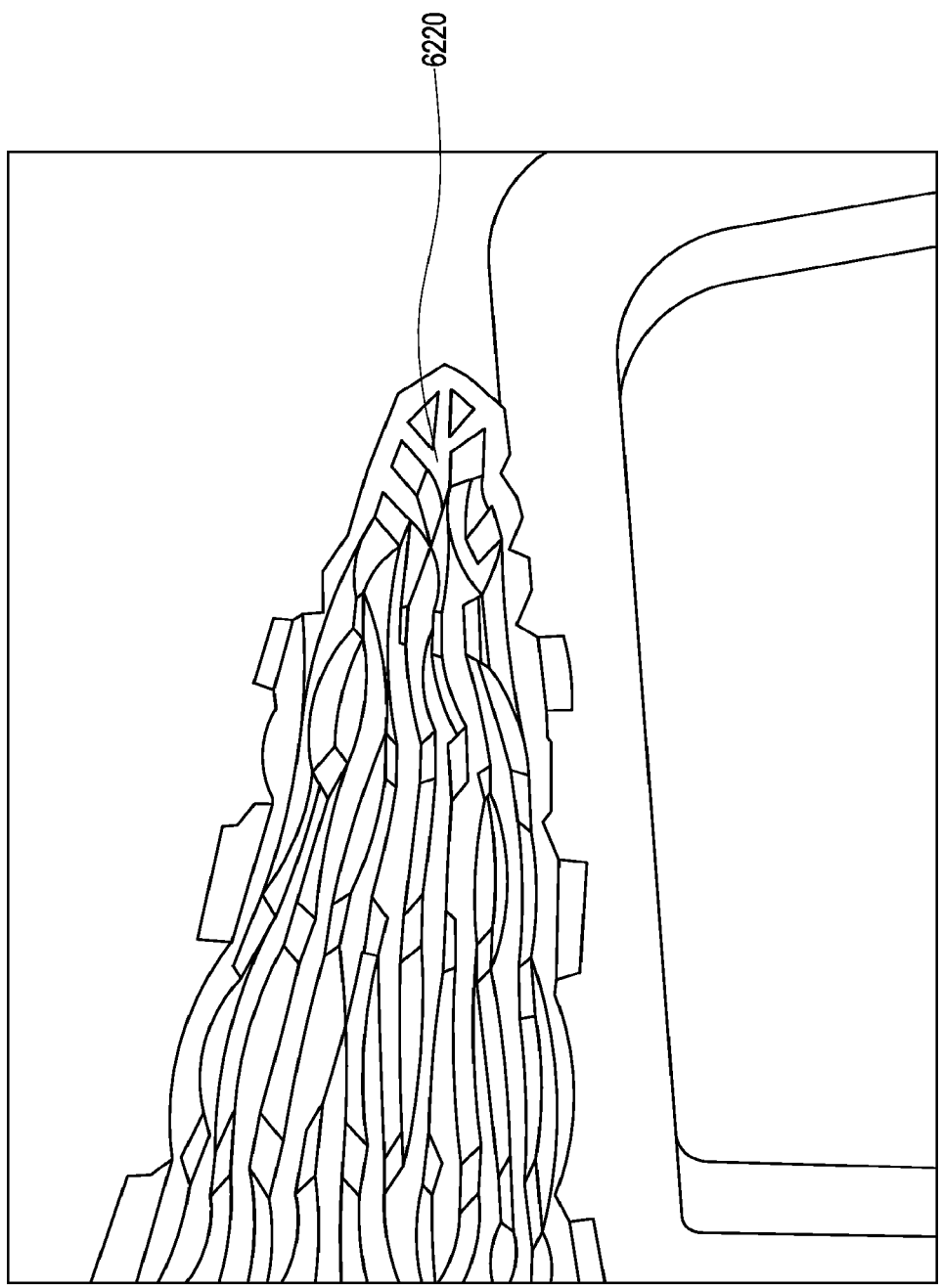
Figure 18D:
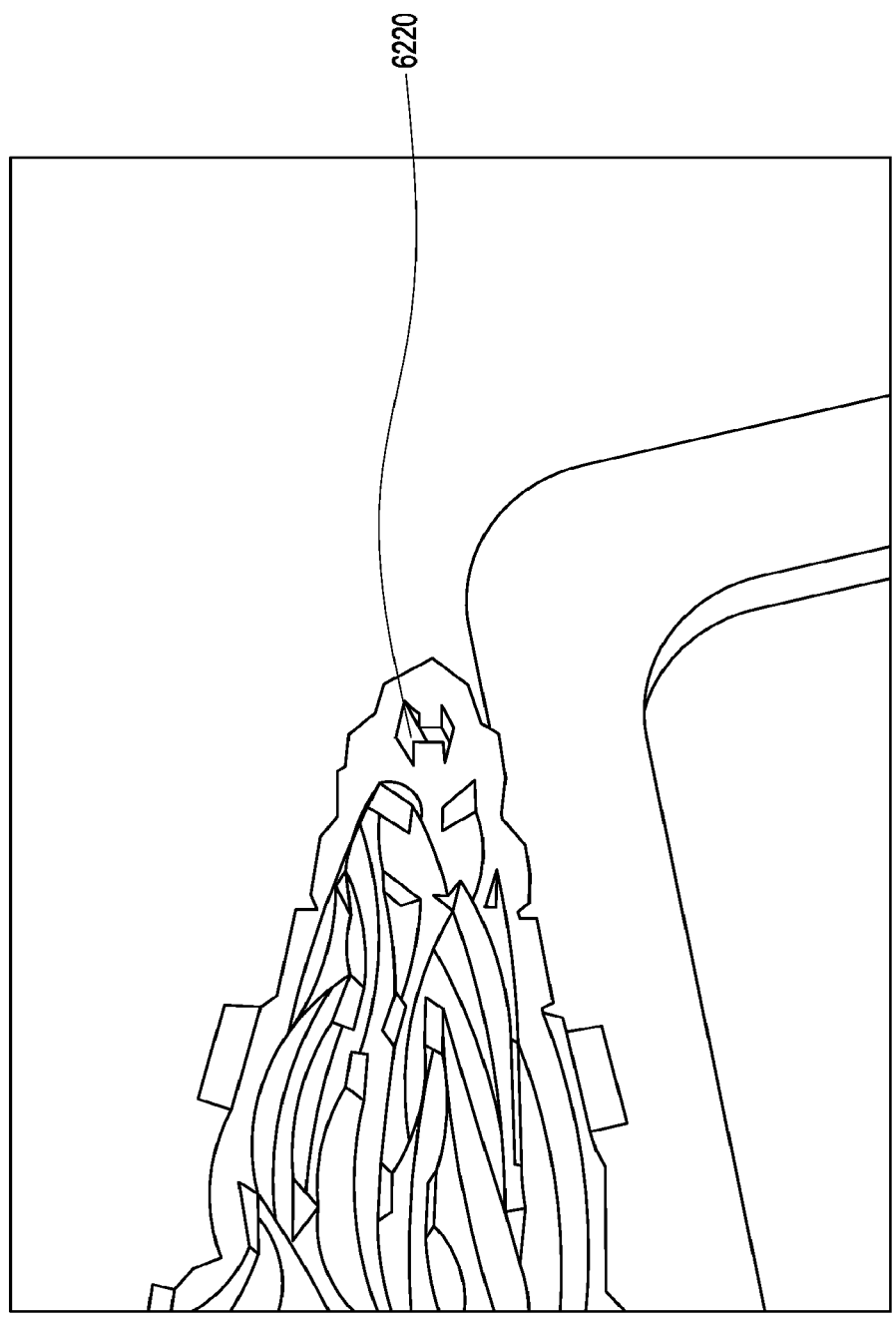

As shown in FIG. 18A, in some embodiments, the extended sections 6220 may avoid collapse, however as shown in FIGS. 18C-D, in embodiments the extended section will collapse along with the remainder of the stabilizing structure.

Figure 19A:
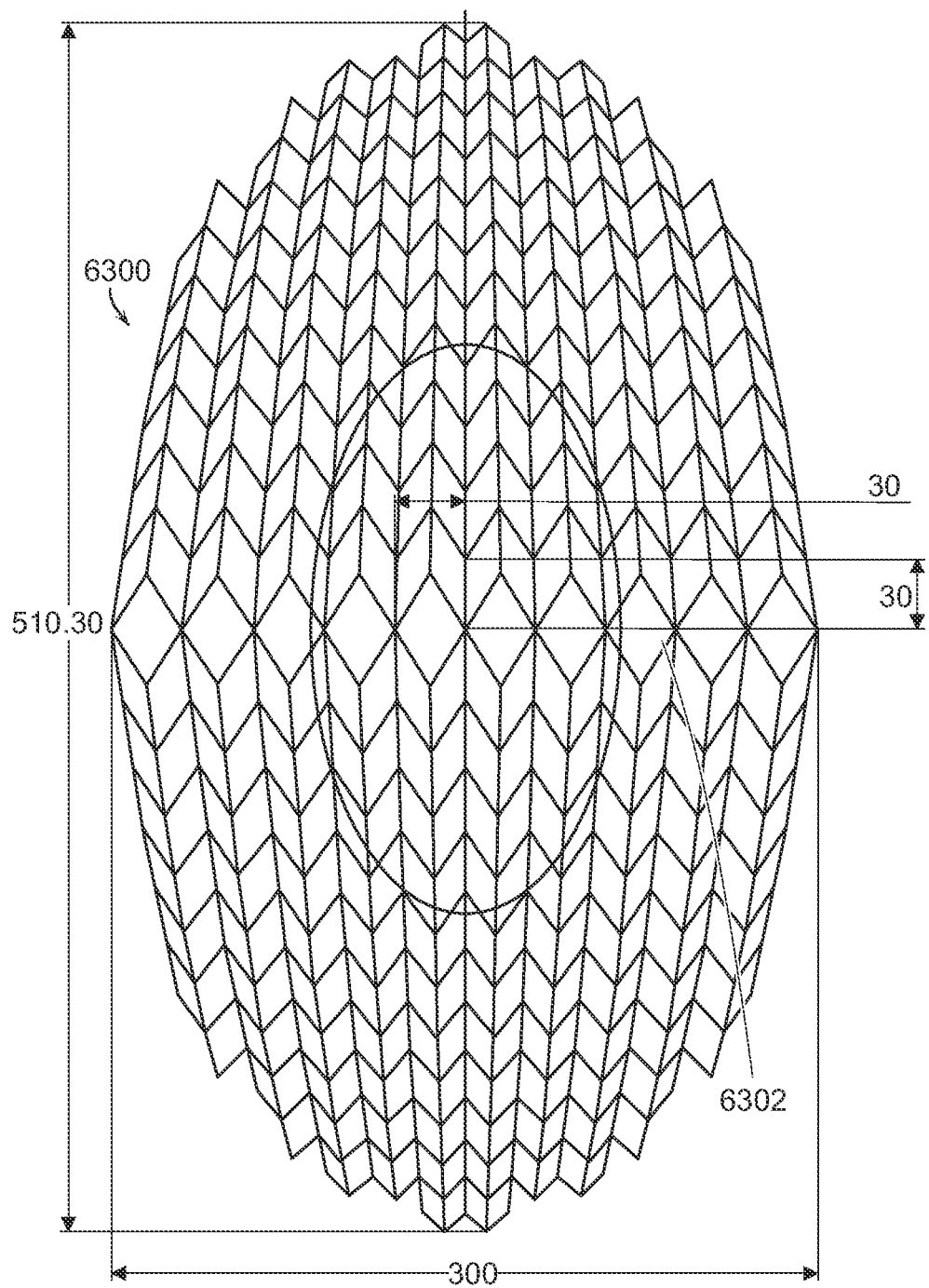
FIGS. 19A-B illustrate embodiments of stabilizing structures.
Figure 19B:
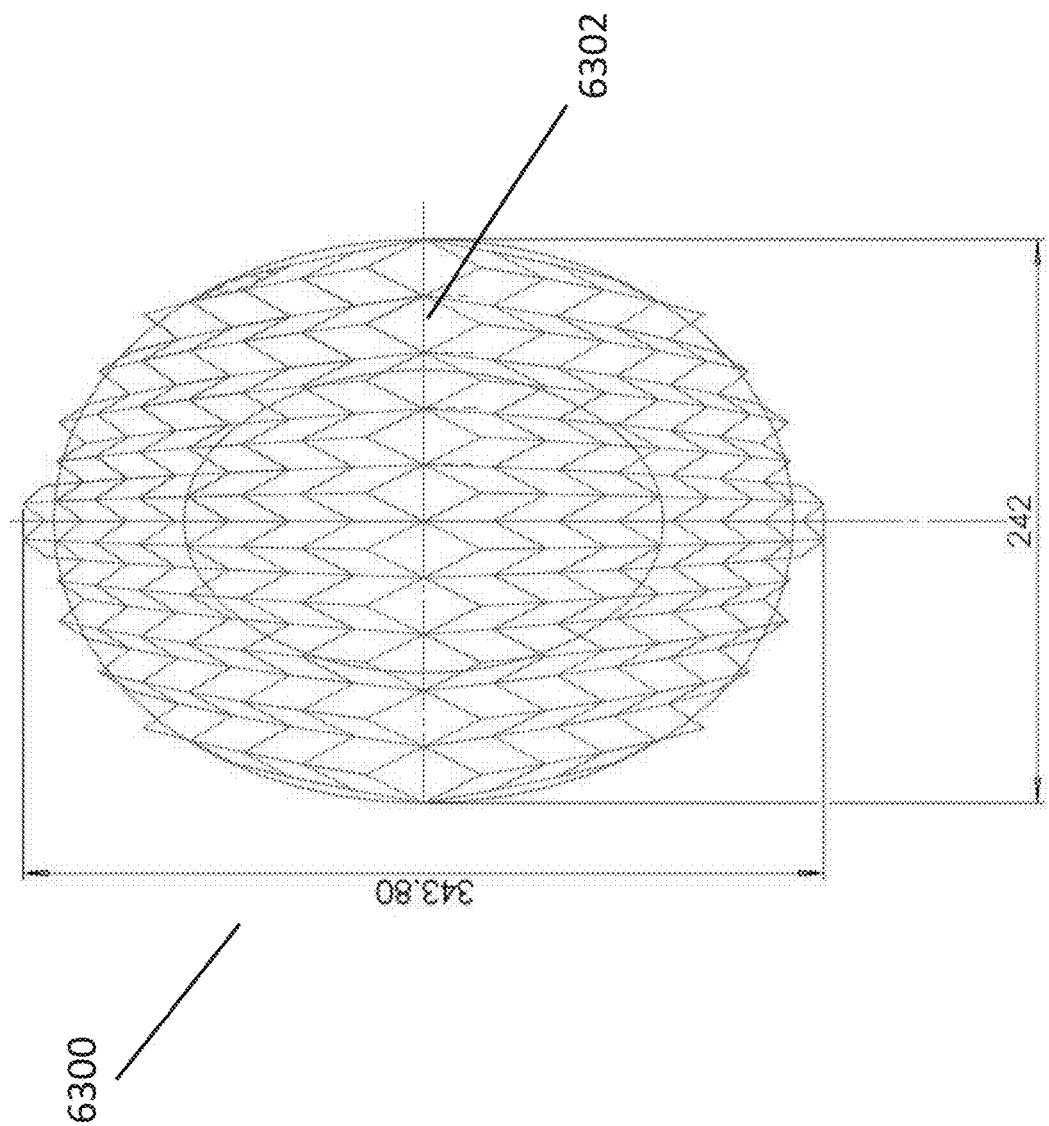

FIGS. 19A-B depict further embodiments of stabilizing structures 6300, similar to the stabilizing structures disclosed herein this section or elsewhere in the specification. The pattern of the stabilizing structures of FIGS. 19A-B comprises a series of cells symmetrically oriented around a mirror line 6302 along the minor axis of the stabilizing structure. In embodiments, the stabilizing structure of FIG. 19A has an un-collapsed width of 300 mm and a length of approximately 510 mm, while the stabilizing structure of FIG. 19B may have an un-collapsed width of 242 mm and length of 343 mm. The largest cells of the stabilizing structure of FIG. 19B may have a width of 30 mm. However, it will be understood by one of skill in the art that the stabilizing structures of FIGS. 19A-B may comprise any size and shape disclosed herein this section or elsewhere in the specification.

The Stabilizing Structures and Foam Layers of FIGS. 20A-22E

FIGS. 20A-22E are drawings and photographs of foam layers in combination with stabilizing structures such as those described above in relation to FIGS. 2A-3E and 16-19B. The foam layers described below may include any type of foam described herein this section or elsewhere in the specification. Possible foams may include open-celled and/or reticulated foams made from a polymer. Suitable foams include foams composed of, for example, polyurethane, silicone, hydrophobic materials, hydrophilic materials, open-celled materials, close-celled materials, mixed open and close-celled materials, reticulated materials, polyester, silicone, and/or polyvinyl alcohol. In embodiments, the foam layers described herein may include materials that change their properties over time. For example, a particular foam may be rigid initially but become more flexible when wet and/or lose rigidity over time due to degradation of the material.

The foam layers described in this section or elsewhere in the specification may have a variety of suitable thicknesses. For example, a foam layer may have a thickness of at least about 1 mm, 3 mm, 5 mm, 10 mm, 15 mm, 20 mm, 25 mm, 30 mm, 35 mm, 40 mm, 45 mm, 50 mm, or more than 50 mm thick. Single layers of foam may be laid atop one another to create a greater total thickness of foam, for example, a 15 mm thick layer of foam may be laid atop a 10 mm layer of foam to create a 25 mm total thickness of foam.

In certain embodiments, any of the foam layers described herein this section or elsewhere in the specification, may be pre-attached to an organ protection layer such as described above. For example, the lowest layer of foam, closest to the underlying organs, may be attached to an organ protection layer before placement within the wound, thereby saving the clinician the step of first placing an organ protection layer within the wound. In certain embodiments, the organ protection layer may be pre-attached to the underside of a stabilizing structure such as those described herein this section or elsewhere in the specification. In embodiments, the organ protection layer may be attached to the top of the bottom-most foam layer placed in the wound, thereby positioning the organ protection layer between the stabilizing structure and the bottom-most layer of foam. The organ protection layer may completely encase the bottommost layer of foam or stabilizing structure. The presence of a bottom layer of foam and/or organ protection layer may serve to protect the underlying bowel from damage due to direct interaction with the stabilizing structure.

FIGS. 20A-D are drawings and photographs of embodiments of a wound closure device 6350 comprising a stabilizing structure 6302 (similar to the stabilizing structures described above in relation to FIGS. 2A-3E and 16A-19D), a top porous foam layer 6352, and a bottom porous foam layer 6354. As will be described in greater detail below, top and bottom porous layers 6352 and 6354 may be shaped in any desired manner to conform to the shape of stabilizing structure 6302. In embodiments, the top and bottom layers of foam may be attached to the stabilizing structure 6302 before placement in the wound. Pre-attachment of the foam layers advantageously reduces the number of steps that need to be completed by the clinician As described elsewhere in the specification, stabilizing structure 6302 may comprise tabs 6304. These tabs advantageously provide a larger surface area for attachment of the foam layers to the stabilizing structure. Without the tabs, adhesive would necessarily need to be applied to the narrow upper edges of the stabilizing structure, potentially creating a weak or non-existent attachment. As described above, the tabs may be located on the top and bottom edges of the stabilizing structure. In embodiments, rather than adhesive, the tabs may be covered in anchors, such as those described above in relation to FIGS. 4-6B. The anchors act much like the adhesive, allowing the foam layers to be attached to the stabilizing structure prior to placement in the wound. The stabilizing structure may be pre-attached to the bottom layer of foam, top layer, or both. In certain embodiments, the adhesive may be applied to the central longitudinal elongate member of the stabilizing structure rather than to the tabs or other location. By applying adhesive only to the central elongate member, the stabilizing structure may collapse without resistance from the foam.

FIGS. 20A-D show embodiments of wound closure devices where the bottom foam is larger than the top foam, either by width, length, or both. Here, the foam extends outward from the stabilizing structure to create a lip, thereby allowing the lip of foam to extend above or below the surrounding tissue layers such as the fascia. The lip may serve to maintain the stabilizing structure in place by providing a downward force to resist the upward force applied by the expanding underlying viscera. In certain embodiments, the lip may need to be folded during placement within the wound bed so as to allow the closure device to be properly positioned. Thereafter the lip may unfold and extend into the surrounding tissues to aid in securing the device and applying negative pressure to the surrounding tissues.

The top layer may be sized to the top of the stabilizing structure, thereby facilitating closure of the wound to the size of the collapsed stabilizing structure. The lip extending outward from the matrix may be rounded so as to provide a better fit within the wound. In contrast, in the embodiment of FIG. 20E, the bottom layer may be smaller than the top layer. The top layer may advantageously prevent drawing of the drape down into the stabilizing structure or between the stabilizing structure and the edges of the wound.

Figure 20A:
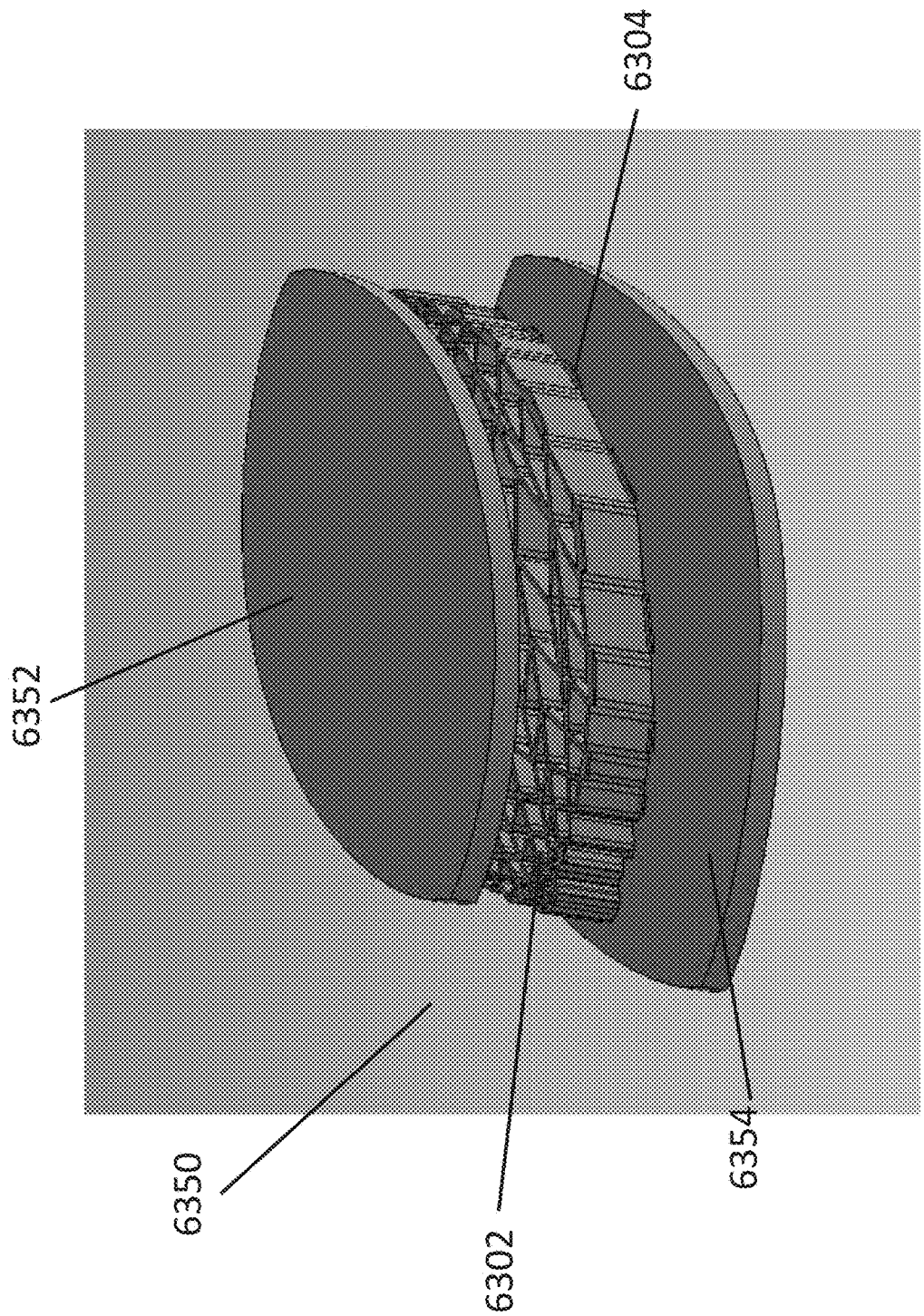
Figure 20B:
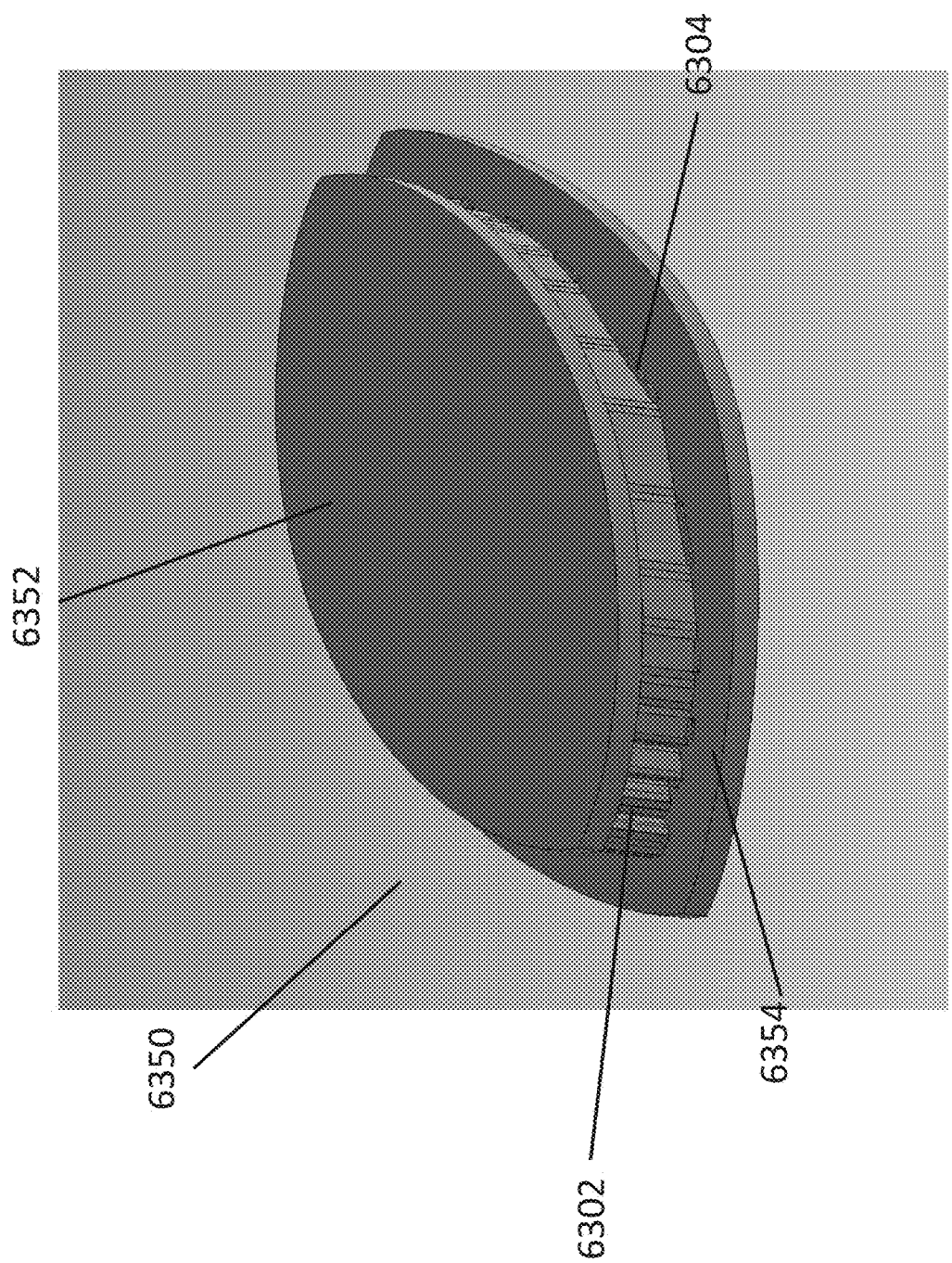
Figure 20C:
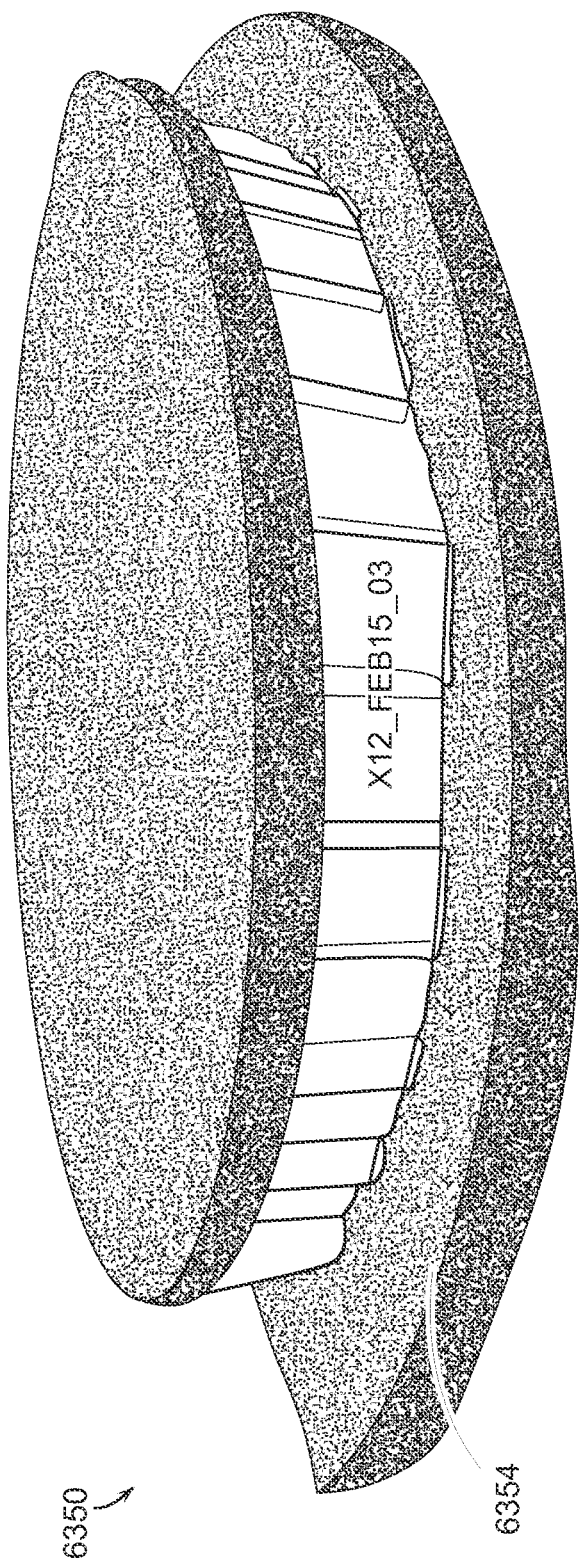
Figure 20D:
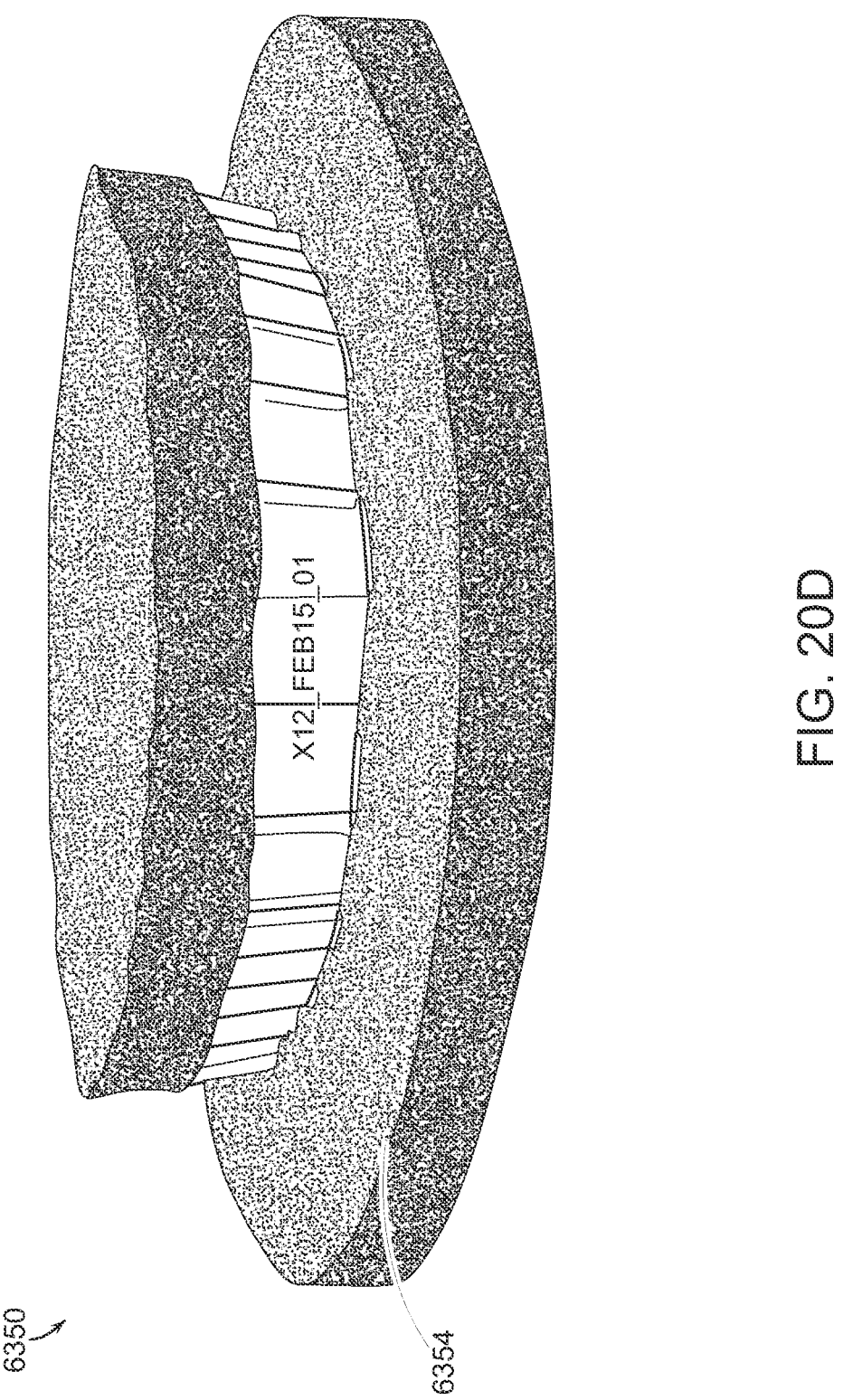

In certain embodiments, the foam layers may be of any thickness disclosed herein this section or elsewhere in the specification. The bottom layer of foam 6354 may be approximately 15 mm thick or approximately 10 mm thick. For example, the bottom foam 6354 of FIG. 20D is thicker than the bottom foam of FIG. 20C.

Figure 20E:
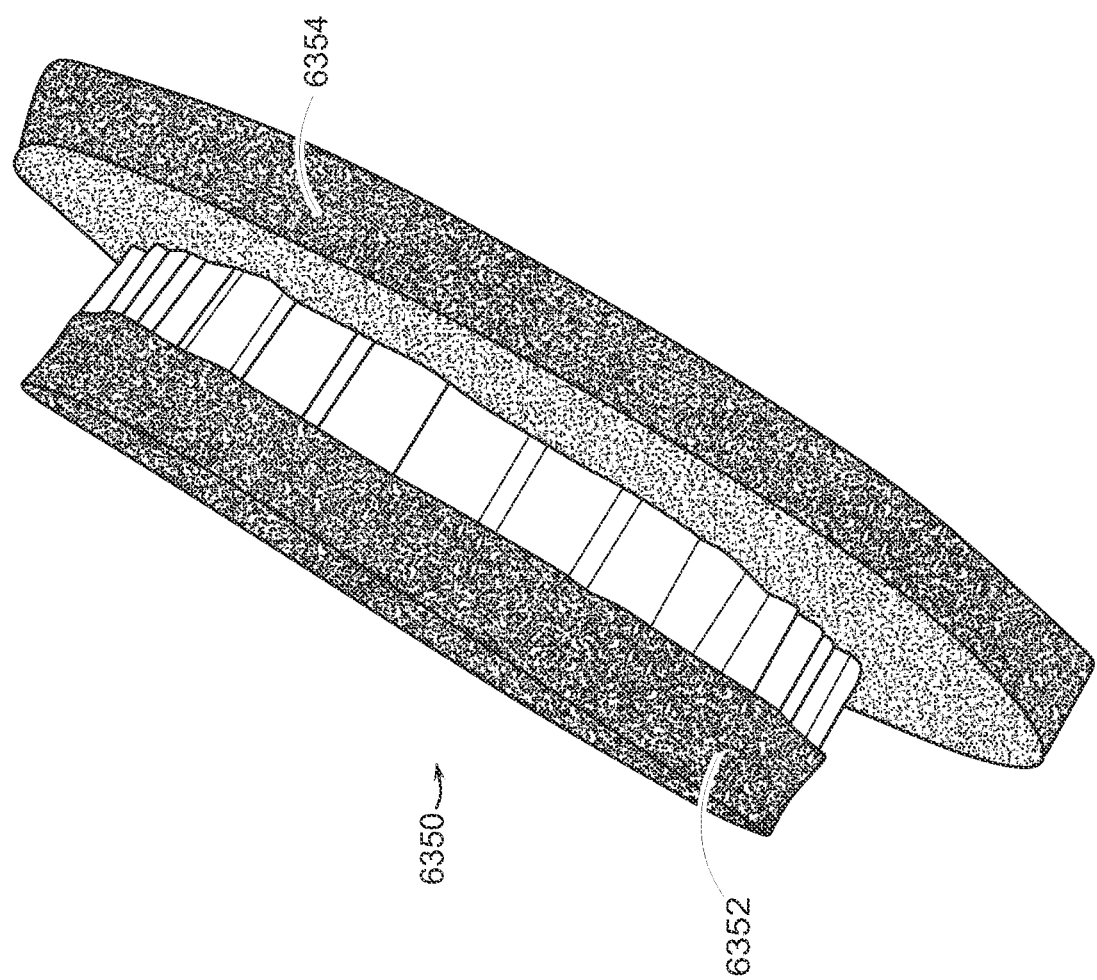
Figure 20G:
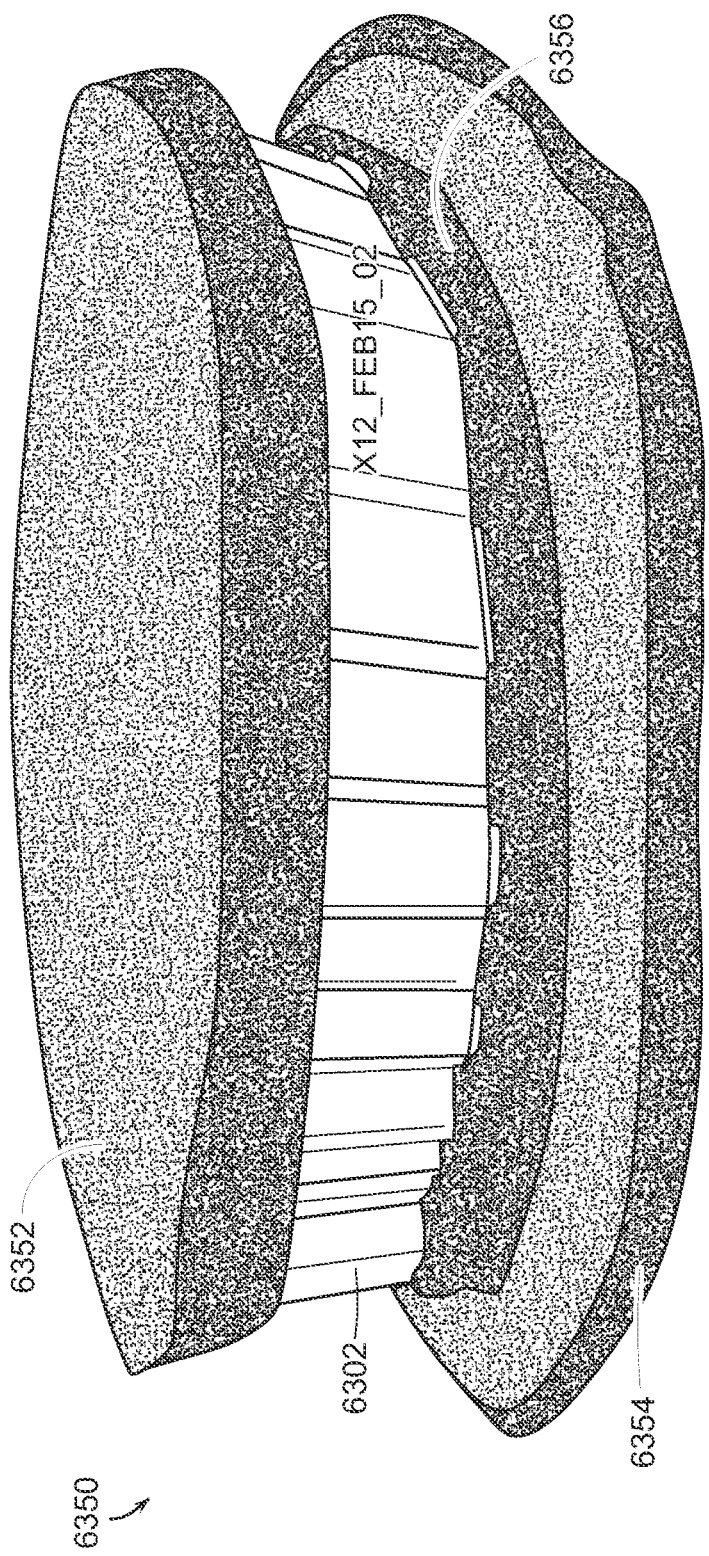

FIGS. 20E-20F depict an embodiment of a wound closure device involving a total of 3 layers of foam. Here, wound closure device 6350 comprises stabilizing structure 6302, top layer of foam 6352, bottom layer of foam 6354, and middle layer of foam 6356. The stabilizing structure may be pre-attached to the middle layer of foam, top layer of foam, or both. Further, the bottom layer of foam may be pre-attached to the middle layer of foam, or may be placed into the wound separately. In some embodiments, the top layer is 15 or 10 mm thick, the middle layer is 15 mm thick, and the bottom layer is 10 mm thick. Foam layers may be attached by any suitable means, such as via adhesive or anchors. As depicted in FIG. 20E, the bottommost layer of foam may comprise a lip that extends outward from the wound closure device into the surrounding tissue. As described above, such a lip may secure the device in place. The bottom layer of foam may be wider and/or longer than the middle and/or top layers of foam. In certain embodiments, in addition to the foam on the top and bottom of the stabilizing structure, foam may be attached to the entire outer perimeter of the stabilizing structure. Foam may be attached to the perimeter of the stabilizing structure via any suitable means, such as by adhesive or anchoring layer. Once foam has been applied to the perimeter of the stabilizing structure, the stabilizing structure will no longer be visible if there are also top and bottom layers of foam.

In embodiments of the foam layers of FIGS. 20A-20F, the layers of foam may comprise any type of suitable foam material described herein this section or elsewhere in the specification. For example, the foam may comprise "black foam" such as polyurethane and/or "white foam" comprising polyvinyl alcohol (PVA). In embodiments involving PVA foam, thinner foam layers may be needed as compared to other types of foam, because PVA foam is often more resilient and dense than other types of foam. Further, once PVA foam becomes wet it may also aid with lateral slip. In some embodiments, the foam layers may be combined with other fillers such as gauze, or other mesh/net products such as those on Fry and Kossel.

Figure 21:
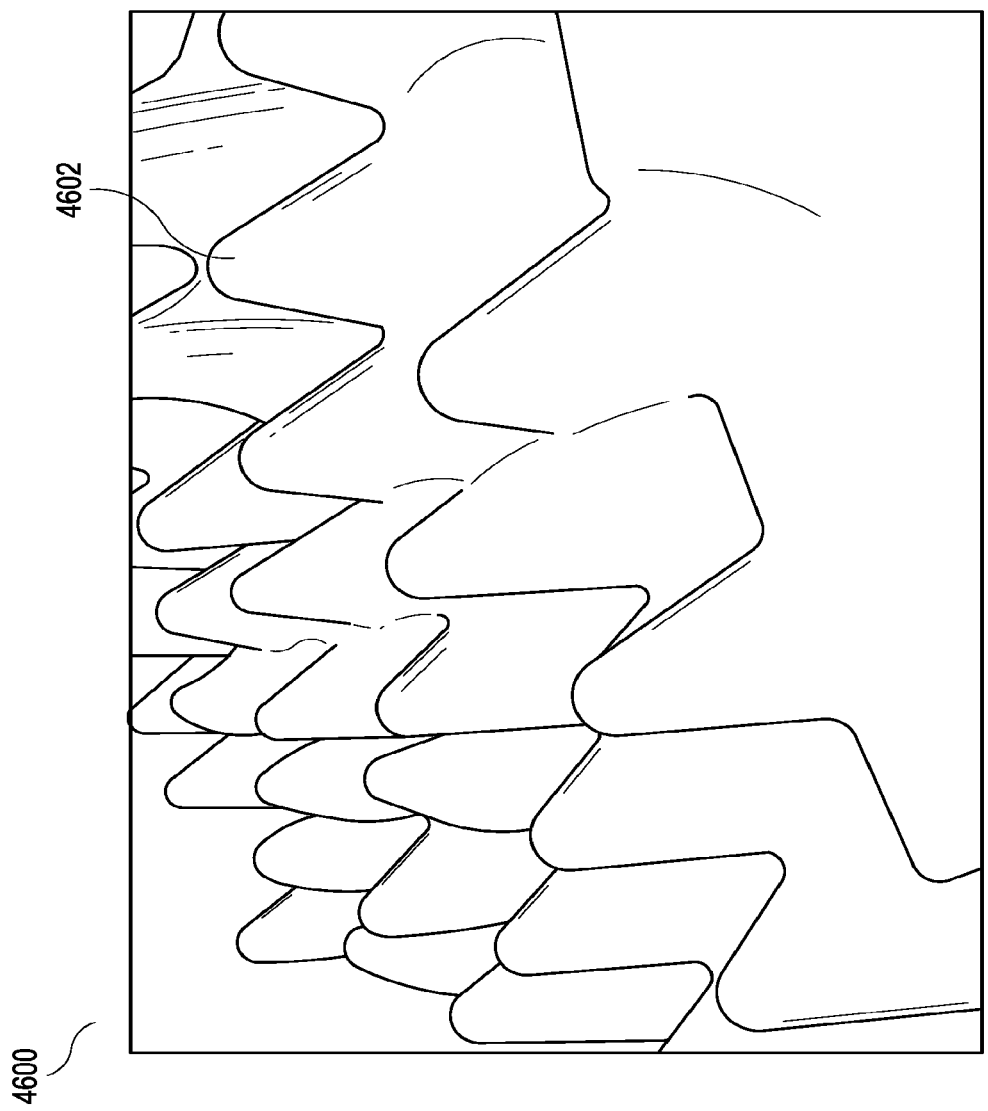
FIG. 21 illustrates an embodiment of a foam layer with fingers.

FIG. 21 is a photograph of an embodiment of a foam layer 4600 that may be used in combination with any of the stabilizing structures or wound closure devices described in this section or elsewhere in this specification. The foam layer of 4600 may be used in place of any foam layer described herein this section or elsewhere in the specification. As described in this section and elsewhere in the specification, the foam layer 4600 may be located above or below the stabilizing structure or wound closure device. In some embodiments, the foam layer 4600 is located both above and below the stabilizing structure or wound closure device. The foam layer 4600 can surround the perimeter of the stabilizing structure or wound closure device or completely surround the entirety of the stabilizing structure or wound closure device. The foam layer 4600 can be constructed from absorbent materials, materials configured to distribute fluid, or both.

The foam layer 4600 further comprises fingers 4602 that can extend from the foam layer into the stabilizing structure or closure device. For example, the fingers 4602 may extend into and around the gaps or cells depicted in the stabilizing structures described herein this section or elsewhere in the specification. The fingers 4602 may also extend around the outside of the perimeter of the stabilizing structure. In some embodiments, the fingers 4602 from one foam layer 4600 may extend through the interior or around the outside of the stabilizing structure to meet the fingers 4602 from a second foam layer 4600. Thus, one foam layer will be facing finger-side up, while a second foam layer may be facing finger-side down.

In some embodiments, the foam layer 4600 can have perforations or pre-cuts to allow portions of the foam layer 4600 to be easily torn away to shape the foam for a particular wound. In some embodiments, the fingers 4602 can extend at least about 1 mm from the surface of the foam layer, at least about 3 mm from the surface of the foam layer, at least about 5 mm from the surface of the foam layer, at least about 7.5 mm from the surface of the foam layer, at least about 10 mm from the surface of the foam layer, at least about 12.5 mm from the surface of the foam layer, at least about 25 mm from the surface of the foam layer, at least about 17.5 mm from the surface of the foam layer, at least about 20 mm from the surface of the foam layer, at least about 25 mm from the surface of the foam layer, or more than 25 mm.

In certain embodiments, the fingers 4602 can be varied so as to control the collapse of the stabilizing structure. For example, when a finger is extended into a particular cell of the stabilizing structure, the finger will prevent collapse of that particular cell. Therefore, a larger number of foam fingers extending into the stabilizing structure will reduce collapse more than a lesser number of foam fingers. For example, the fingers may extend into at least about: 10%, 20%, 30%, 50%, 75% or even 100% of the cells of the stabilizing structure, thereby further limiting collapse of the stabilizing structure.

FIGS. 22A-22E depict foams suitable for printing instructions. When placing a wound closure device such as those described herein this section or elsewhere in the specification, it may be difficult for the clinician to determine the proper orientation of the foam layer or other components of the wound closure device. Therefore, printing of symbols on the foam may make it easier for the clinician to properly orient the foam layer. Although not shown, any of the symbols or printing disclosed herein this section or elsewhere in the specification may be applied to different structures of the wound closure device, such as the stabilizing structure.

Figure 22A:
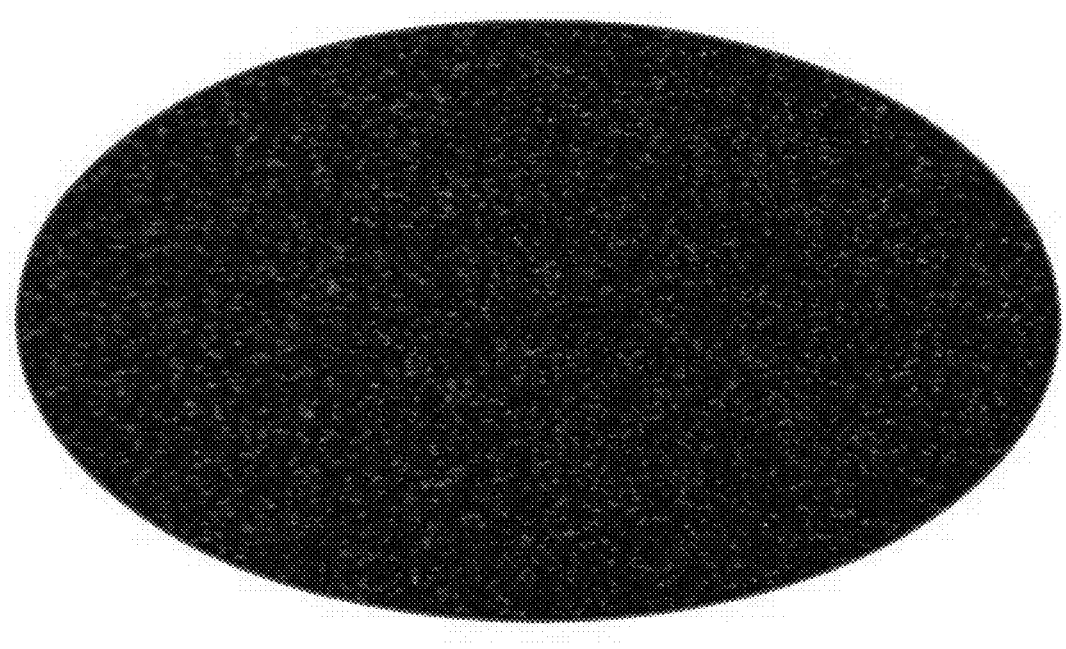
FIGS. 22A-E illustrate embodiments of a foam layer with printing.
Figure 22B:
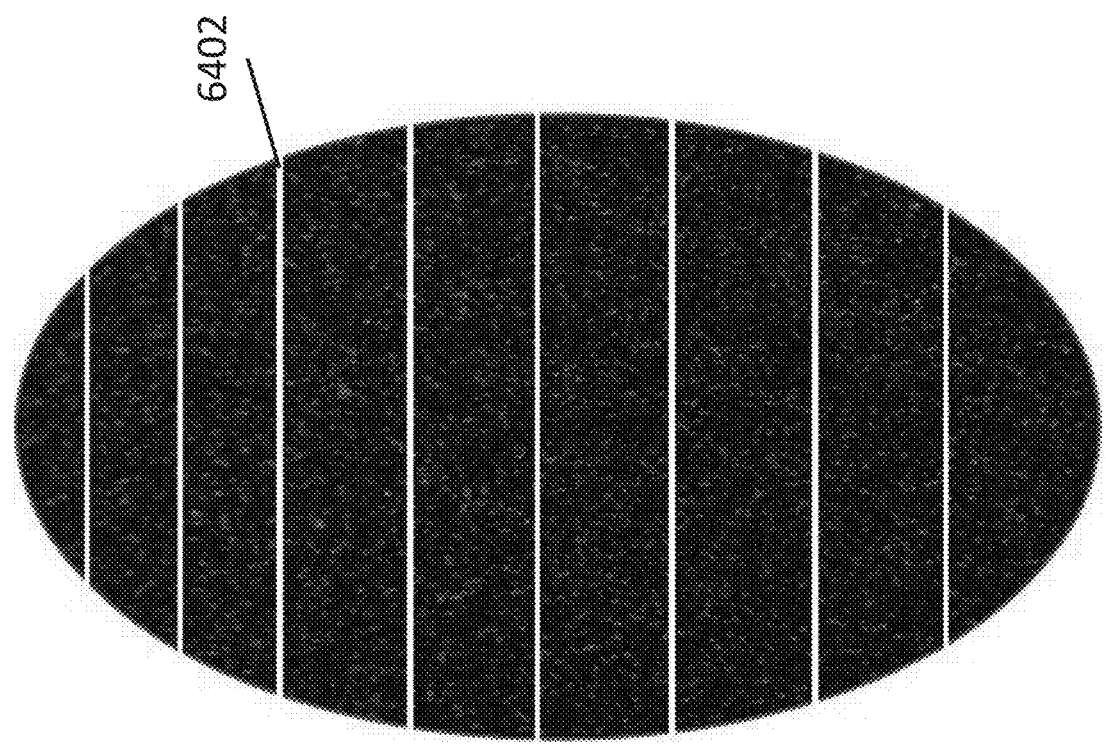
Figure 22C:
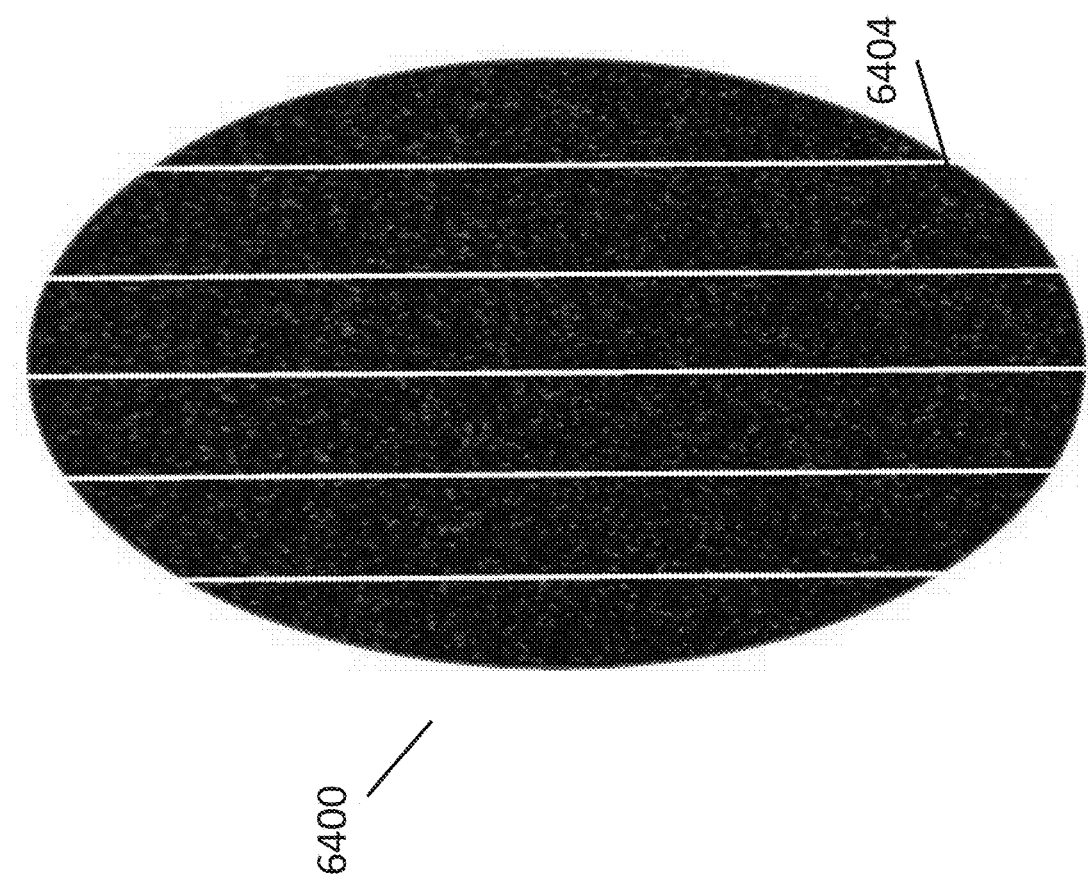
Figure 22D:
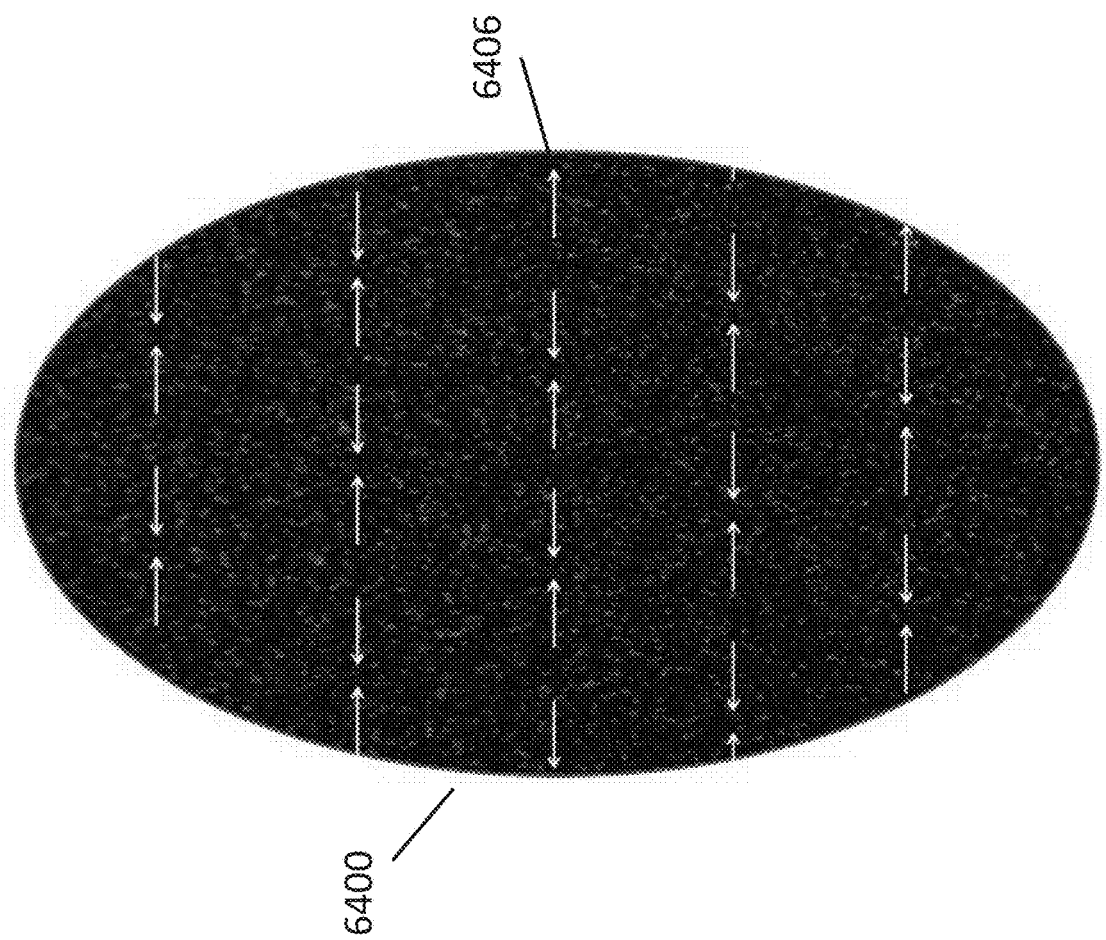
Figure 22E:
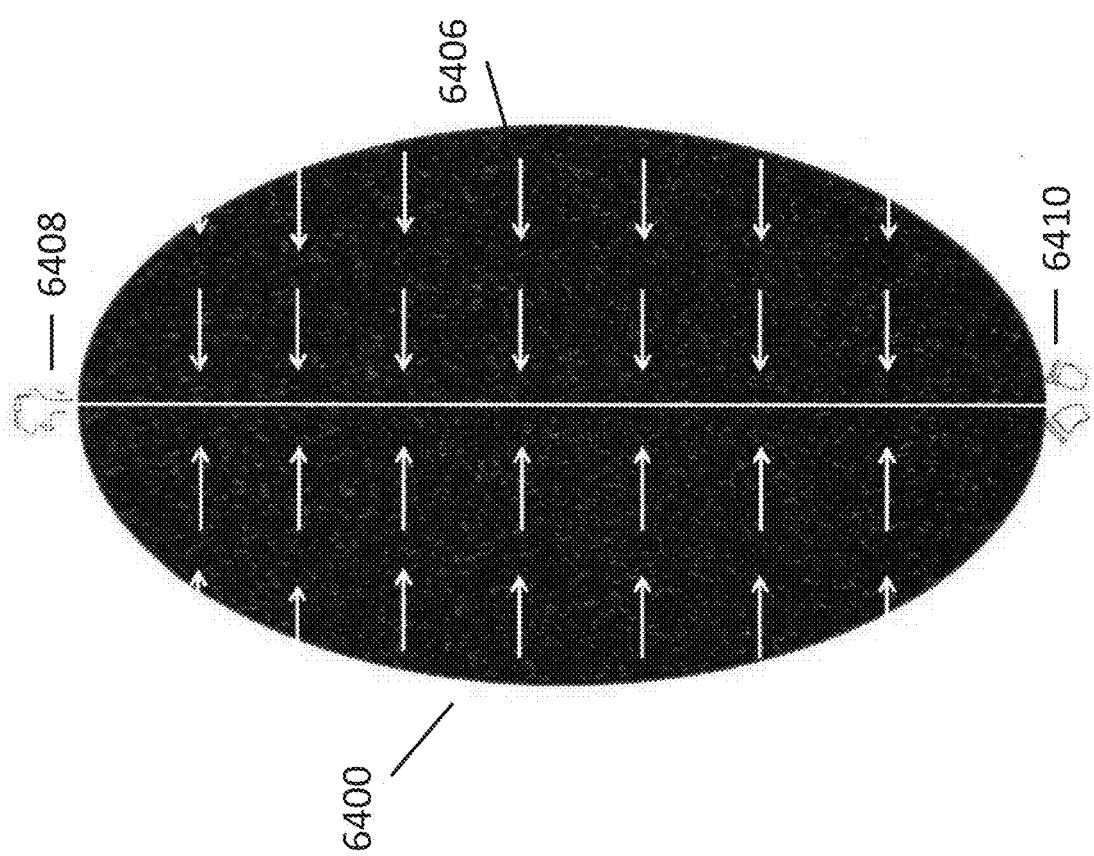

FIG. 22A depicts a simple unlabeled oval of foam 6400, such a layer provides little guidance for the proper orientation of the foam in the wound other than the general shape of the foam. FIG. 22B depicts an embodiment of a foam layer comprising horizontal stripes 6402. These horizontal stripes may be aligned along the shorter axis of a wound, thereby providing for ease of placement of the foam oval 6400. Similarly, FIG. 22C depicts an oval foam layer comprising longitudinal stripes 6404 which may be aligned with the longitudinal axis of the wound. FIG. 22D is similar to FIG. 22B, in that the horizontal arrows 6404 indicate alignment with the horizontal axis of the wound. Lastly, FIG. 22E combines the longitudinal stripes 6404 with the horizontal arrows 6404, but further includes "head" 6408 and "feet" 6410 symbols to direct the clinician to orient the head towards the head of the patient and the feet towards the feet of the patient.

In certain embodiments, foam layers similar to the foam layers of FIGS. 22B-E may include printing on one or both sides of the foam layer to indicate to the clinician which side of the foam or wound closure device is the top and which side is the bottom. Printing that precisely delineates the top, bottom, and orientation of the device may prevent a clinician from placing the wound closure device in a wound upside down or rotated in the wrong direction.

The Stabilizing Clips of FIGS. 23A-31H

Figure 23A:
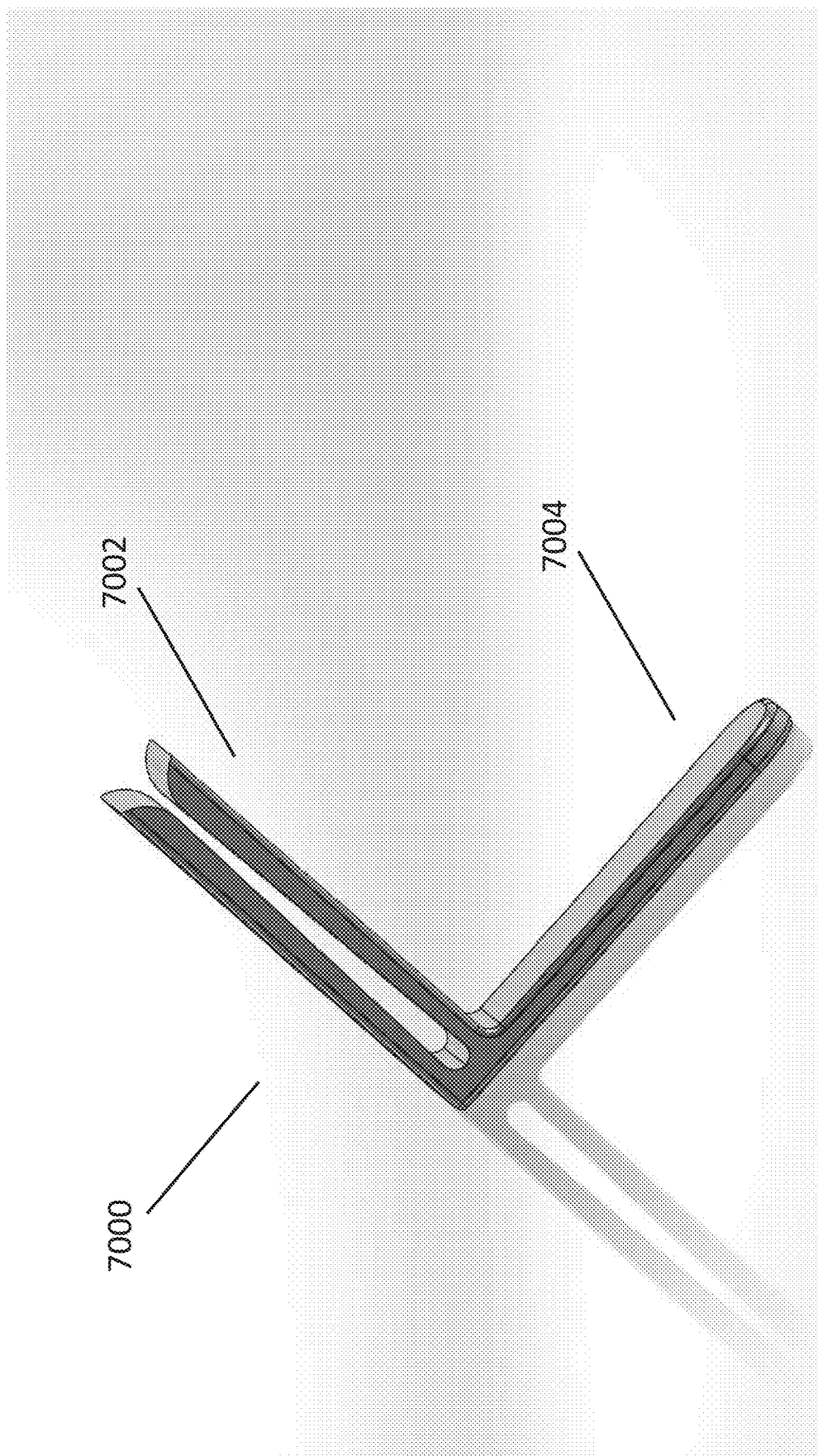
FIGS. 23A-F are drawings and photographs of stabilizing clips for attachment to a stabilizing structure.
Figure 23B:
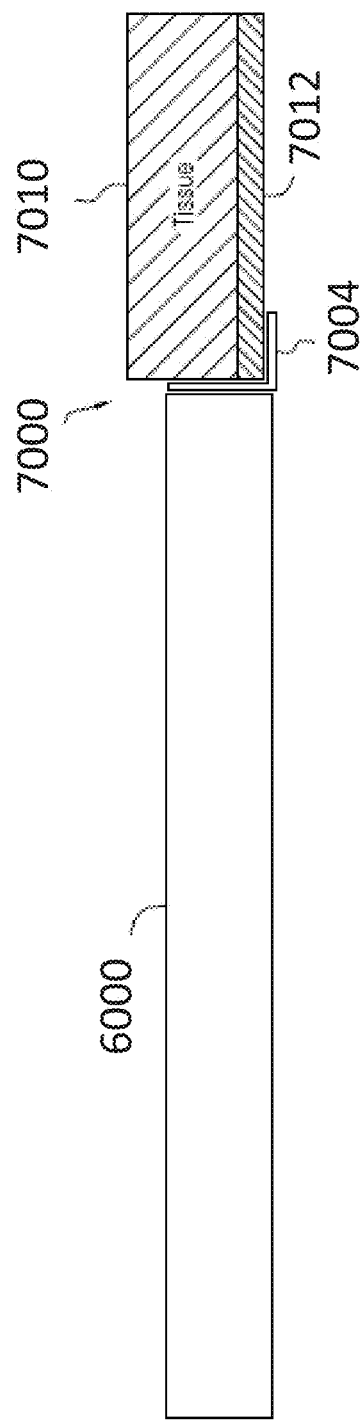

FIGS. 23A-23E illustrate multiple views of stabilizing clips that may be attached to the stabilizing structures of FIGS. 2A-3E and 16-20F. As illustrated in FIG. 23A, in some embodiments, stabilizing clip 7000 may comprise an attachment portion 7002 that allows it to "clip" onto a wall of a stabilizing structure, such as upon an elongate member or an intervening member. Stabilizing clip 7000 may also comprise a securing portion 7004 that can extend above or below tissue layers to aid in securing the stabilizing structure 6000 to the surrounding tissue. The securing portion 7004 may extend from a lower end of the attachment portion 7002, at the closed end of the attachment portion. For example, when a stabilizing structure, such as stabilizing structure 6000 of FIG. 2A, is placed into an abdominal wound, the underlying viscera may tend to expand and push the stabilizing structure upwards and out of the abdominal wound. Such an occurrence is undesirable because, as described above, the stabilizing structure is suited to be placed within an abdominal wound whereby the stabilizing structure can draw the edges of the wound together. To alleviate the outward pressure of the expanding viscera, in some embodiments as illustrated by FIG. 23B, before placing the stabilizing structure within the wound, the stabilizing clips 7000 may be attached to the underside of the stabilizing structure 6000. The securing portion 7004 of the stabilizing structure 6000 may then extend outward from the stabilizing structure and under the surrounding tissue 7010, for example the fascia 7012. This same rationale applies to the foam lip described above in relation to FIGS. 20A-F.

In some embodiments, the clips are rigid, therefore once the securing portion 7004 is extended below the fascia 7012, the securing portion can absorb upward force from the swelling viscera while maintaining the stabilizing structure 6000 in place within an abdominal wound. In further embodiments, the securing portion may be semi-rigid or soft. In some embodiments, the clip can be made from any suitable material including, for example, plastics, ABS, PU, PE, PP, PET, silicone, Nylon, or other suitable materials known in the art. Further, the clip can be made of metals including, for example, titanium, stainless steel, Inconel, or other suitable material known in the art. Additionally, the clip can be made of composites including, for example, carbon fiber, Kevlar, reinforced plastics, or other suitable material known in the art.

The stabilizing clip may be clipped to the top or the bottom of the stabilizing structure, thereby extending the securing portion over the top or below the surrounding tissue. In some embodiments, an anchoring layer such as those described elsewhere in the specification, particularly in FIGS. 4-6B, may be attached to the stabilizing clip. One of skill in the art with recognize that such an anchoring layer may be applied to the stabilizing clip in any suitable manner, such as around or under the stabilizing clip.

In some embodiments, the stabilizing clips are radiopaque, such that they are easily identifiable if lost within the body. To further make the stabilizing clips easier to find, the stabilizing clips may be attached or tied together in a suitable manner. In some embodiments two stabilizing clips are attached together, three stabilizing clips, four stabilizing clips, or more than four stabilizing clips attached together.

In embodiments, the stabilizing structure may have notches such that the stabilizing clips may be help more firmly over the notch. The stabilizing clip may further have an additional protrusion that serves to prop open the stabilizing structure such that the stabilizing structure cannot fully close. Instead of or in tandem with a protrusion, the stabilizing clip may have a loop that acts to prop open the stabilizing structure. In some embodiments, the stabilizing clip props open the stabilizing structure at least: 10%, 20%, 30%, 40%, 50%, or more than 50%.

Figure 23C:
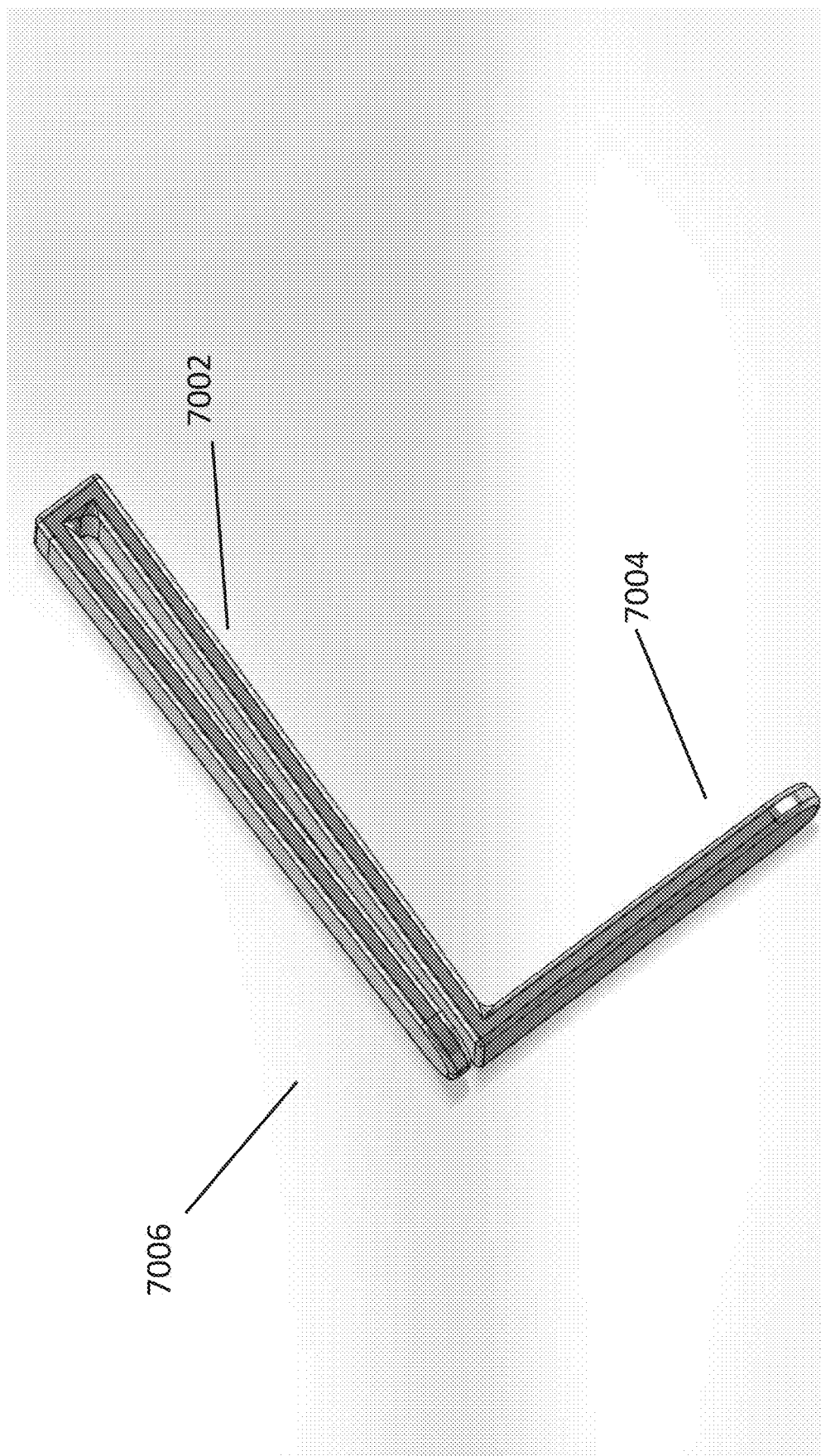

FIG. 23C illustrates an embodiment of stabilizing clip 7006, similar to the stabilizing clip of FIG. 23A. Stabilizing clip 7000 may comprise an attachment portion 7002 that loops over the top of a wall of a stabilizing structure. In this way, the stabilizing clip 7000 will be more difficult to dislodge from the stabilizing structure. As with the other stabilizing clip embodiments illustrated in FIG. 23A, the stabilizing clip of FIG. 23B may comprise a securing portion 7004 that extends below a layer of tissue such as the fascia, to maintain the stabilizing structure in place. The securing portion 7004 may extend from a lower end of the attachment portion 7002, however, in this instance the lower end of the attachment portion is the open end because the stabilizing clip "clips" onto the stabilizing structure from the top.

Figure 23D:
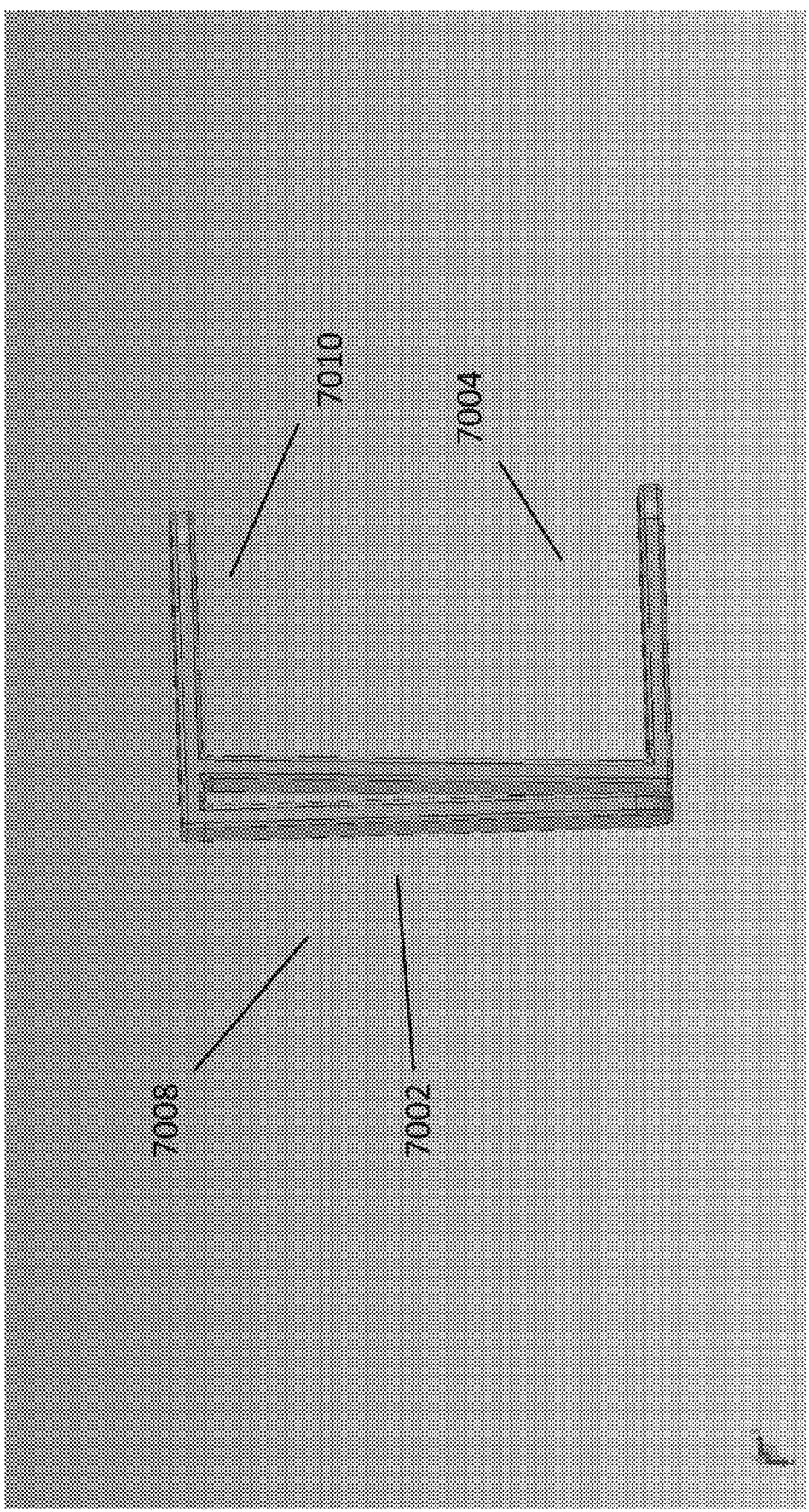
Figure 23E:
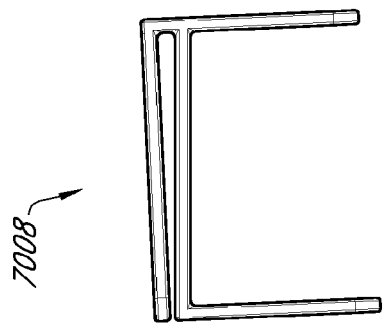
Figure 23E:
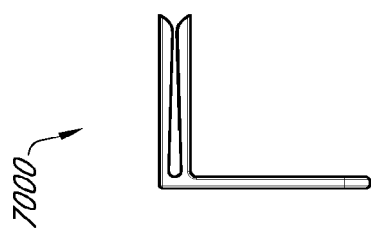
Figure 23E:
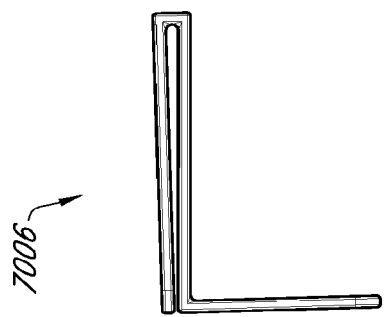
Figure 23F:
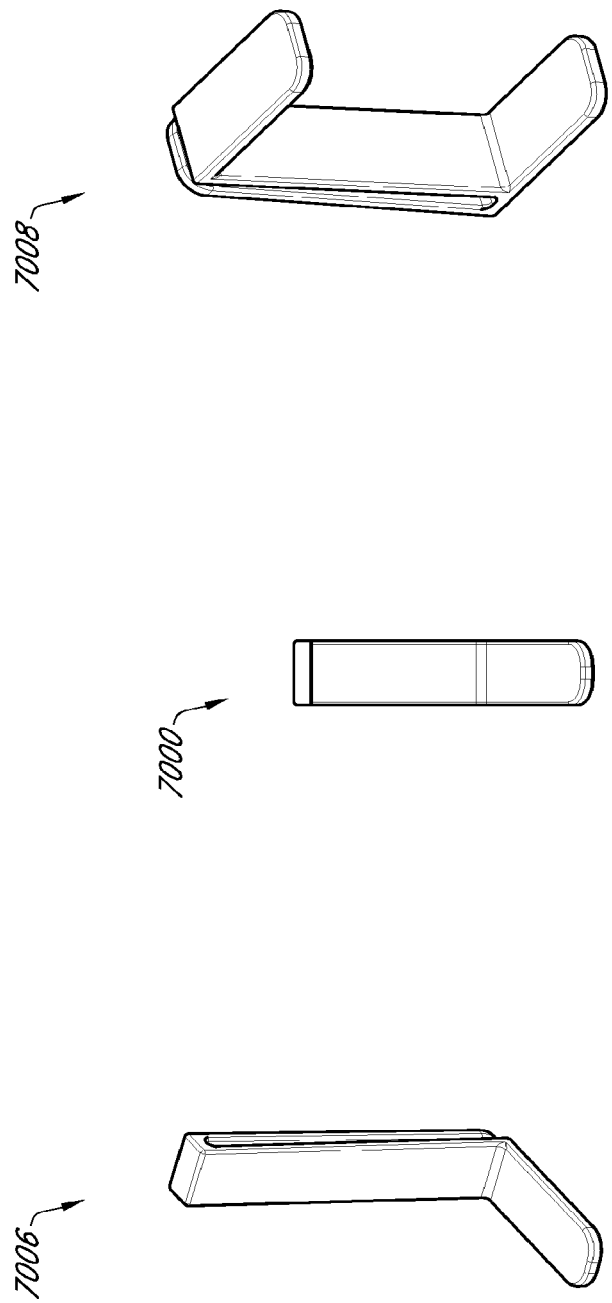

FIG. 23D depicts another embodiment of a stabilizing clip 7008, similar to the stabilizing clip embodiments of FIGS. 23A-B. Stabilizing clip 7008 has securing portions 7004, 7010 on both the upper and lower portions of the stabilizing clip. The stabilizing clip may have a first securing portion 7010 extending outward from an upper end of the attachment portion and a second securing portion 7004 extending outward from a lower end of the attachment portion. Therefore, once attached to a stabilizing structure, stabilizing clip 7008 may more tightly secure the stabilizing structure in place because the securing portions extend both above and below various tissue layers such as the fascia. FIG. 23E shows side views of stabilizing clips 7000, 7006, and 7008, while FIG. 23F shows a top front view of stabilizing clips 7000, 7006, and 7008.

FIGS. 24A-E are pictures of embodiments of stabilizing structures 8000 similar to the stabilizing structures of FIGS. 2A-3E and 16-20F. Stabilizing clips 8002 may be attached to the stabilizing structure to secure the stabilizing structure within the wound. As described herein this section and elsewhere in the specification, the stabilizing clips 8002 may extend outward from the stabilizing structure into the surrounding tissue and hold the stabilizing structure in place within the abdominal wound. In some embodiments, more than one stabilizing clip will be used. For example, a single stabilizing structure may contain 2 or more of one type of stabilizing clip on one side, three or more stabilizing clips, four or more stabilizing clips, five or more stabilizing clips, six or more stabilizing clips, or more than six stabilizing clips. Sometimes when using more than one clip, only one type of clip is used, however, at other times more than one type of clip may be used. In certain embodiments, there will only be one stabilizing clip per wall of the stabilizing structure; however, further embodiments may call for multiple stabilizing clips per wall of the stabilizing structure. FIGS. 24F-G are illustrations of the stabilizing structures with a larger number of stabilizing clips.

Figure 24A:
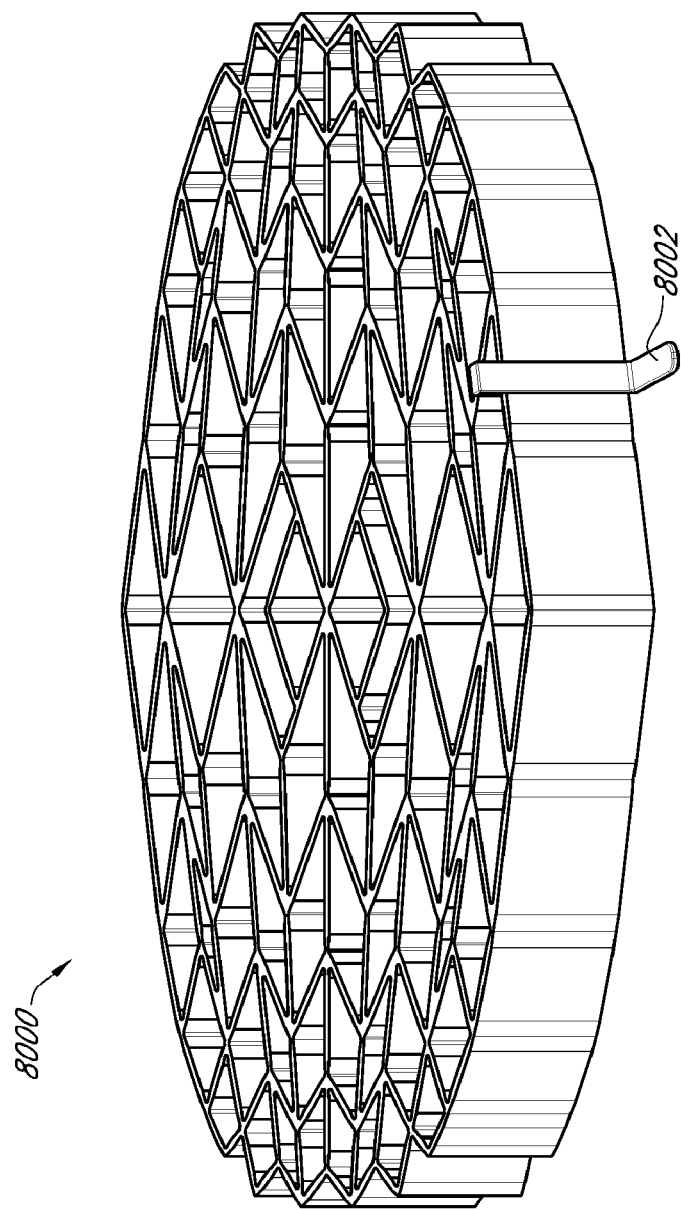
FIGS. 24A-G are photographs and illustrations of embodiments of an elliptical stabilizing structure with attached stabilizing clips.
Figure 24B:
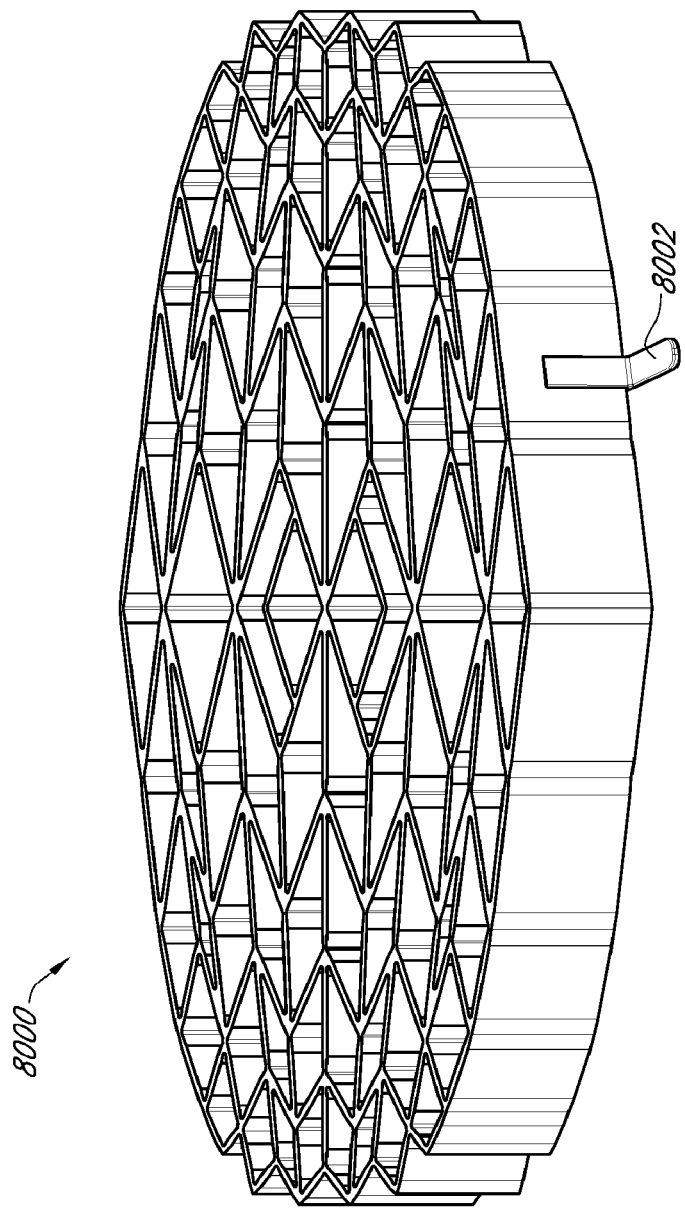
Figure 24C:
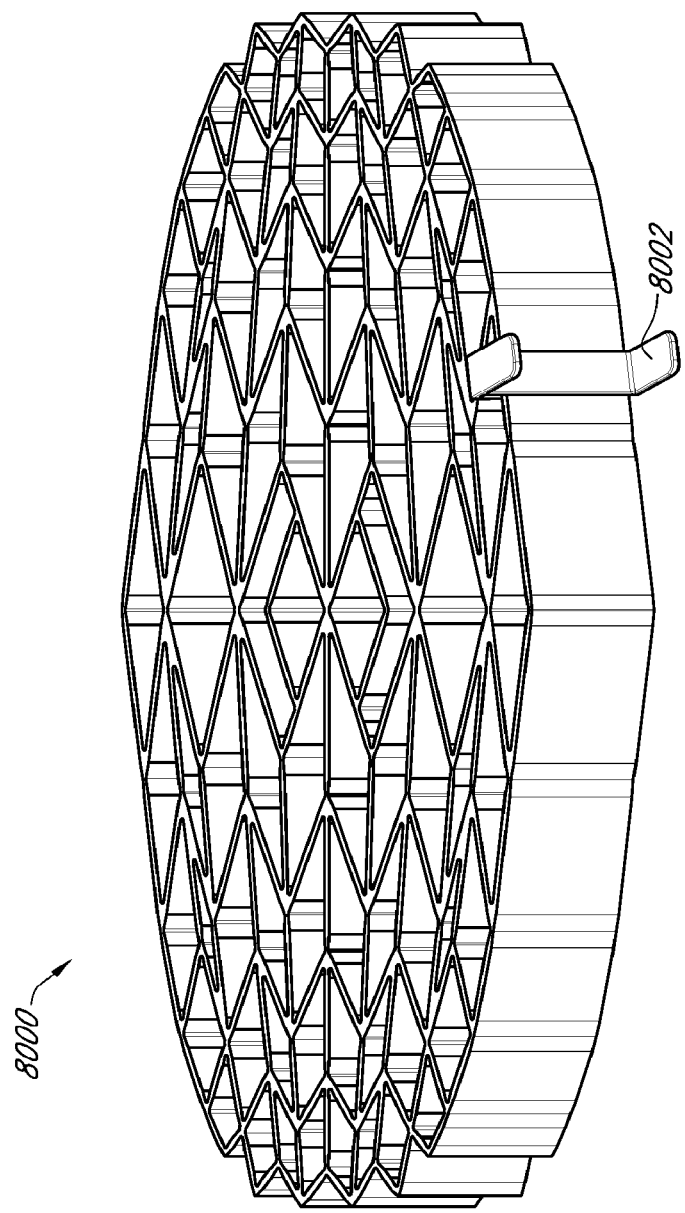
Figure 24D:
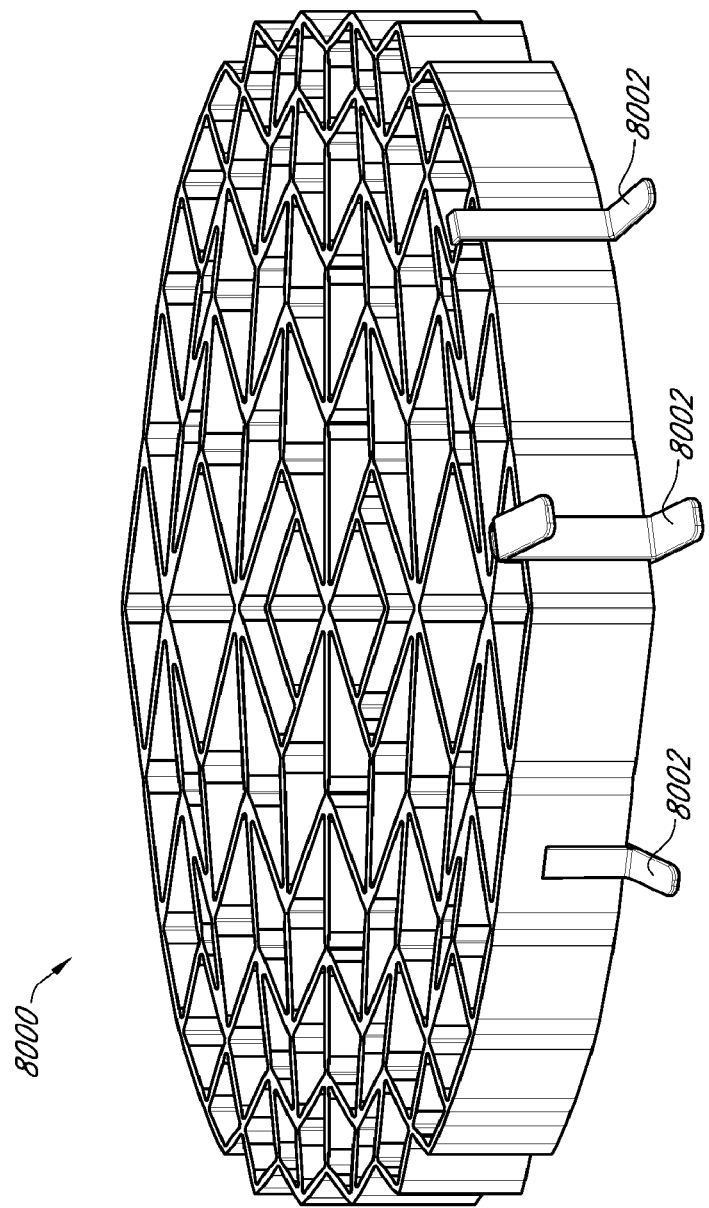
Figure 24E:
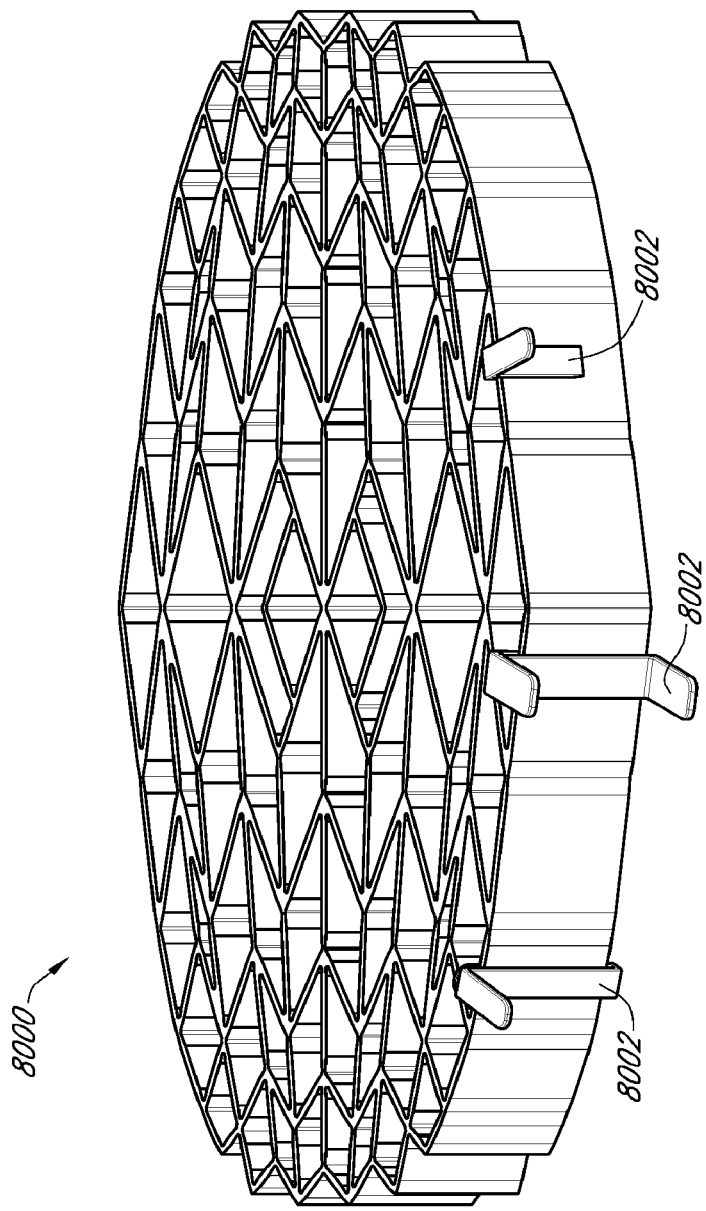
Figure 24F:
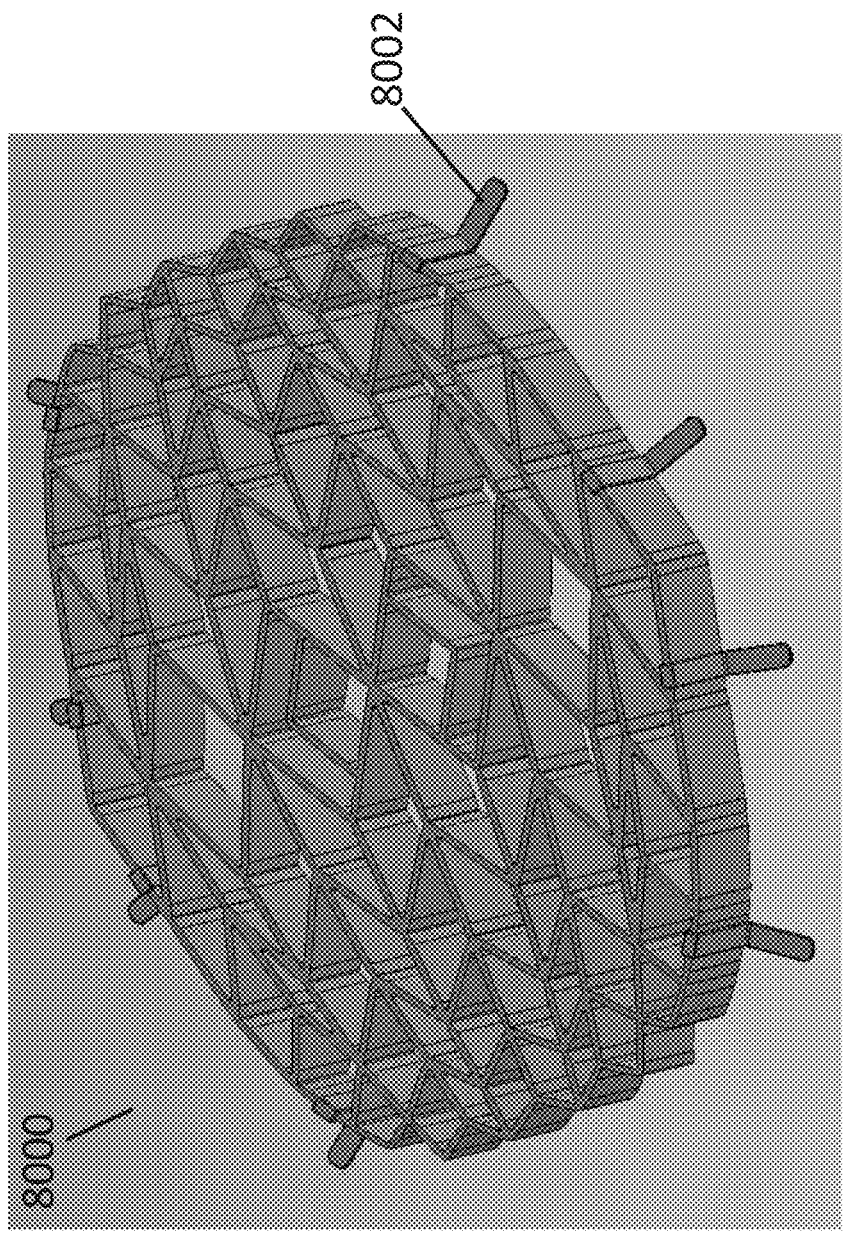
Figure 24G:
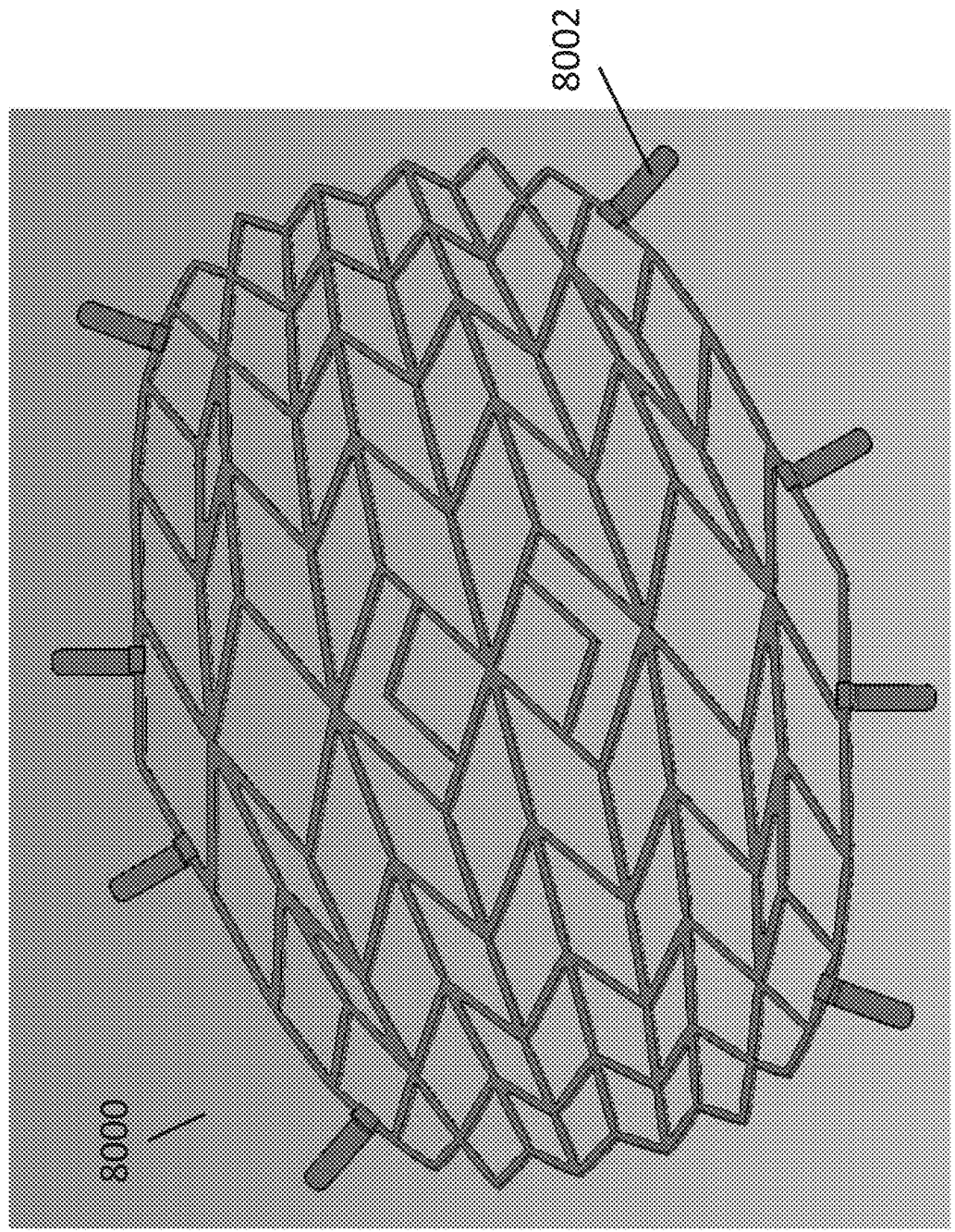
Figure 25A:
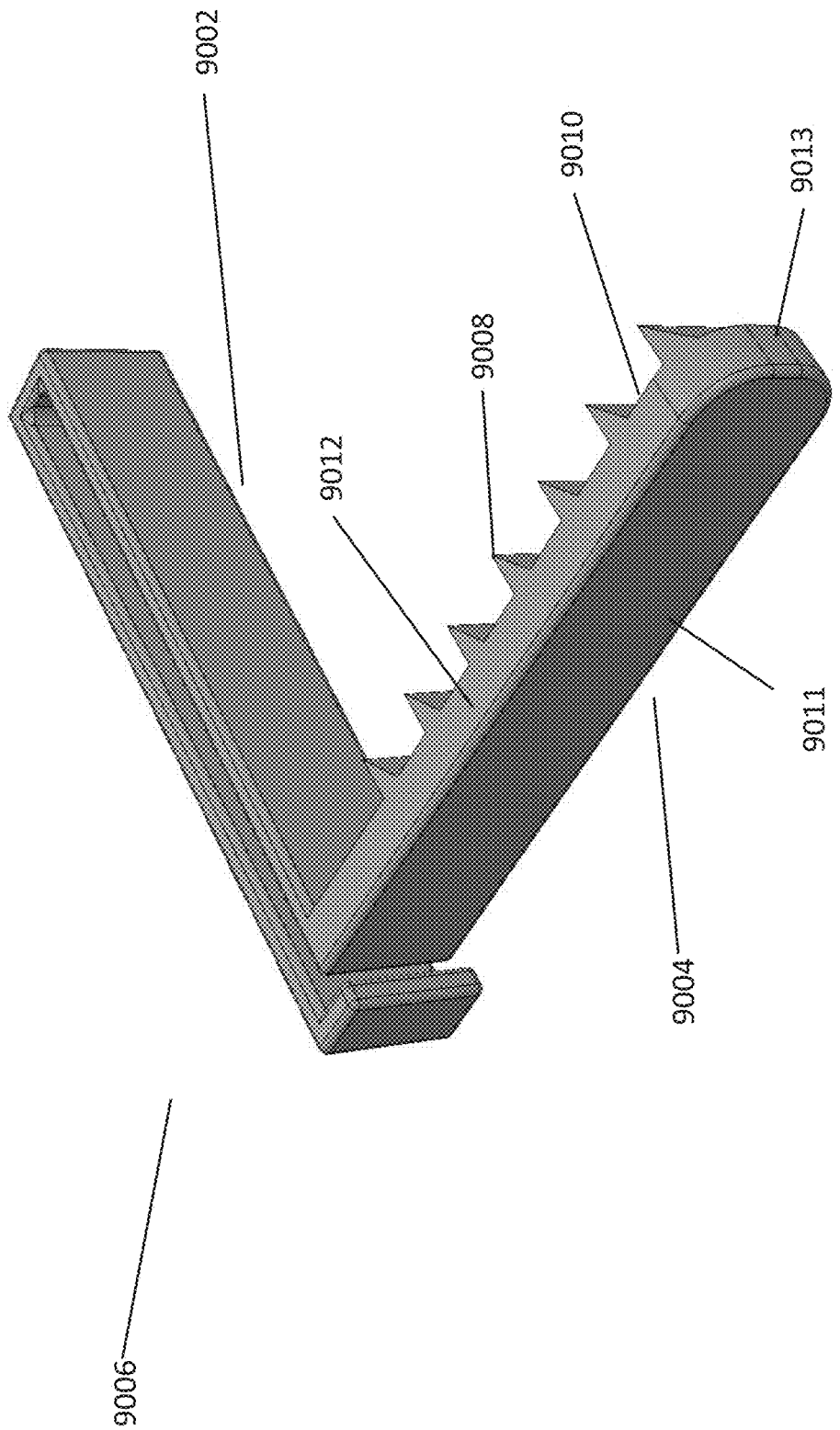
Figure 25B:
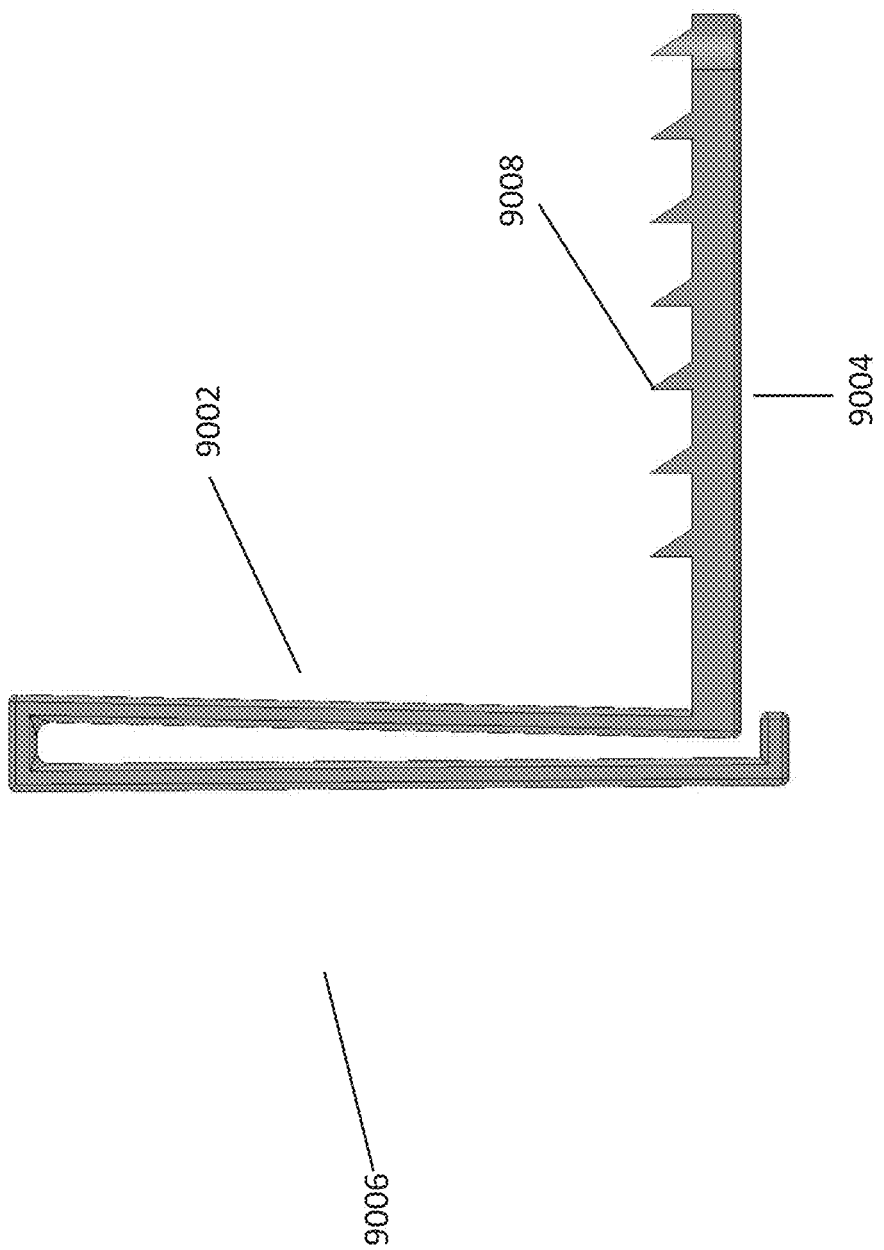
Figure 25D:
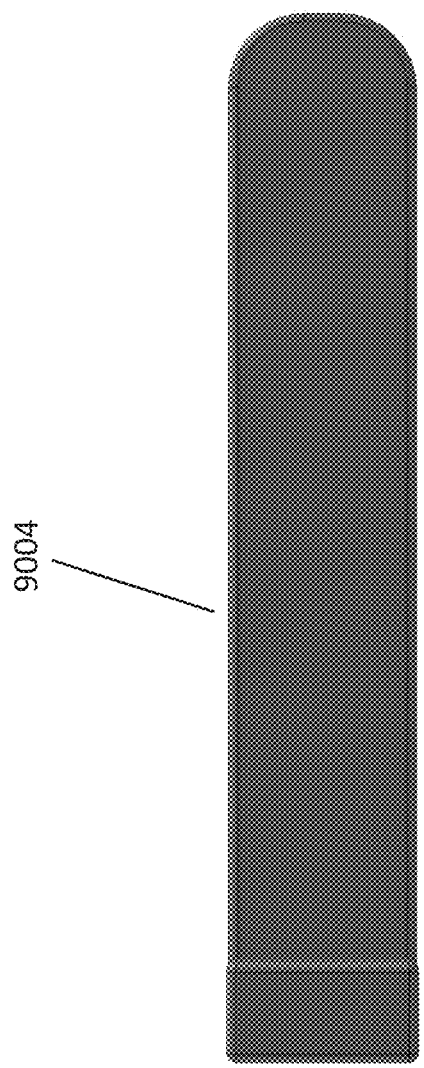
Figure 25E:
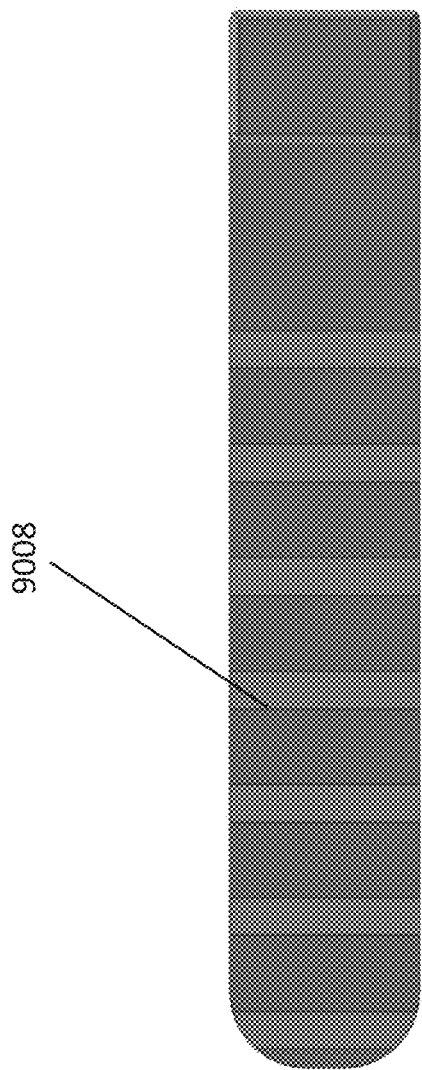
Figure 25F:
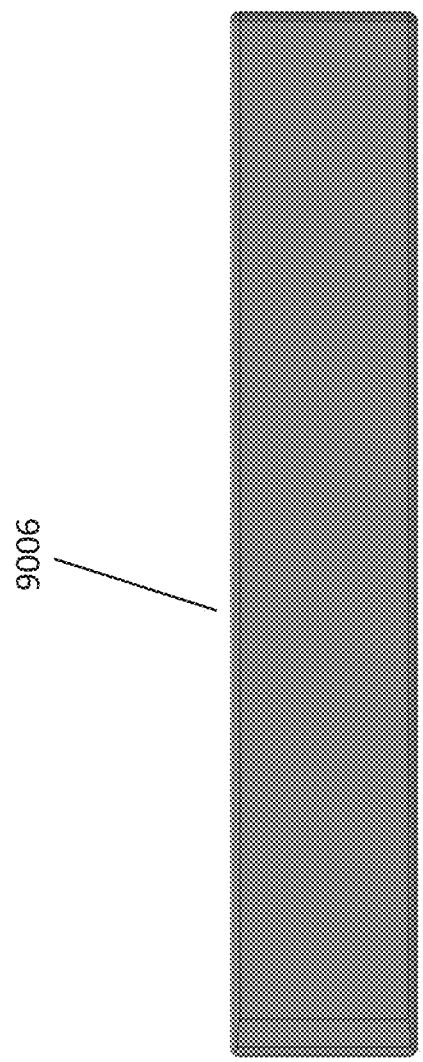
Figure 25G:
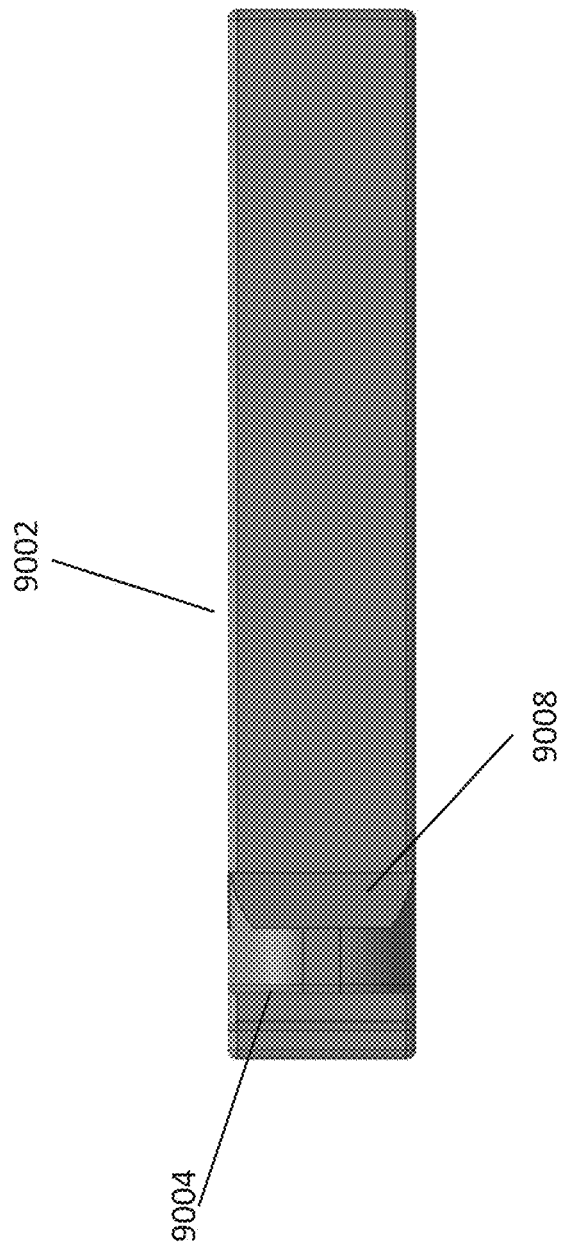

FIGS. 25A-G illustrate an embodiment of stabilizing clip 9006, similar to the stabilizing clip of FIG. 24C. Stabilizing clip 9006 may comprise an attachment portion 9002 that loops over the top of a wall of a stabilizing structure. As with the other stabilizing clip embodiments illustrated in FIG. 23C, the stabilizing clip of FIGS. 25A-G may comprise a securing portion 9004 that extends below a layer of tissue such as the fascia, to maintain the stabilizing structure in place. The securing portion 9004 may extend from a lower end of the attachment portion 9002. The securing portion 9004 can include grippers 9008. The grippers 9008 can assist in attaching the securing portion to the surrounding tissue. The securing portion 9004 and the grippers 9008 extend below a layer of tissue such as the fascia, to maintain the stabilizing structure in place. The tissue grippers 9008 can be similar to the tissue anchors described with reference to FIGS. 4-6B. The tissue grippers 9008 can be formed of the same material as the stabilizing clip. In some embodiments, the grippers 9008 can be formed of a different material than the material used for construction of the stabilizing clip. FIGS. 25A-G illustrate grippers 9008 on a top surface 9010 of the securing portion 9004. In some embodiments, the grippers 9008 may be provided on the bottom surface 9011, sides 9012, or front surface 9013 of the securing portion. Further, in some embodiments, the attachment portion of the stabilizing clips may include grippers that can assist in securing the stabilizing structure.

FIGS. 26A-J illustrate an embodiment of stabilizing clip 10006, similar to the stabilizing clip of FIGS. 25A-G. Stabilizing clip 10006 may comprise an attachment portion 10002 that loops over the top of a wall of a stabilizing structure. As with the other stabilizing clip embodiments illustrated in FIGS. 25A-G, the stabilizing clip of FIGS. 26A-J may comprise a securing portion 10004 that extends below a layer of tissue such as the fascia, to maintain the stabilizing structure in place. The securing portion 10004 may extend from a lower end of the attachment portion 10002. The stabilizing clip 10006 can include a step or recess 10010 at the intersection of the securing portion 10004 and the attachment portion 10002 or where the securing portion 10004 extends horizontally from the attachment portion 10002. In some embodiments, as depicted in FIGS. 26A-J, the securing portion 10004 may include grippers 10008 to assist in attaching the securing portion to the surrounding tissue. In other embodiments, the stabilizing clip 10006 with the step or recess 10010 may be used with a securing portion 10004 without grippers 10008 on the surface of the securing portion 10004. The step 10010 can provide a step or recess in the stabilizing clip to accommodate a foam and/or other material positioned below the matrix, similar to the foam layers described herein this section or elsewhere in the specification. The step 10010 allows the stabilizing clip 10006 attached to the matrix stabilizing structure 10013 to fit around a piece of foam that is placed below the stabilizing structure 10013 which may be slightly larger than the stabilizing structure 10013. In some embodiments, the size of the step can be changed to accommodate the various foam sizes.

Figure 26A:
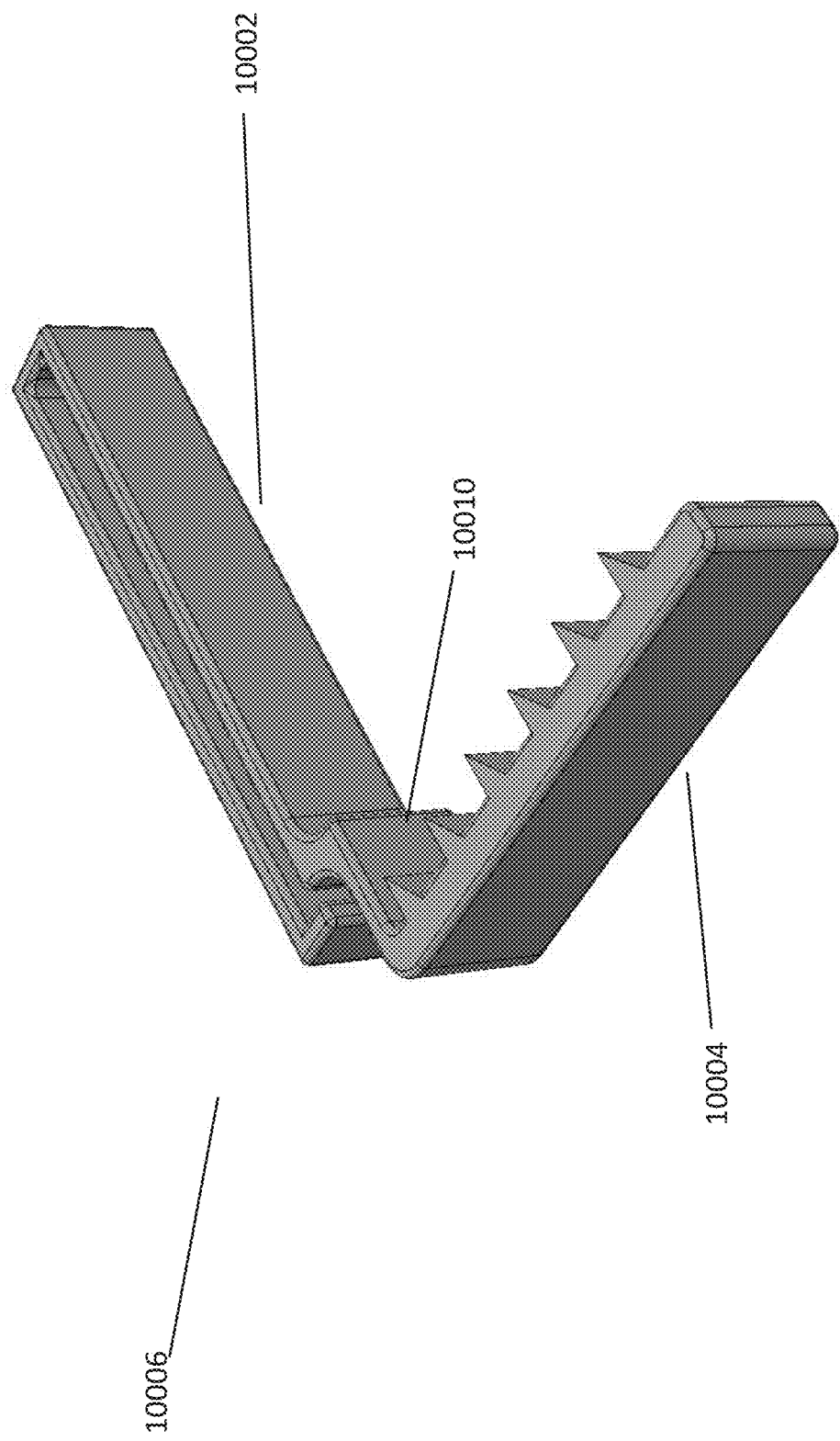
FIGS. 26A-J illustrate embodiments of stabilizing clips for attachment to a stabilizing structure with a step or recess at the intersection of the securing portion and the attachment portion.
Figure 26B:
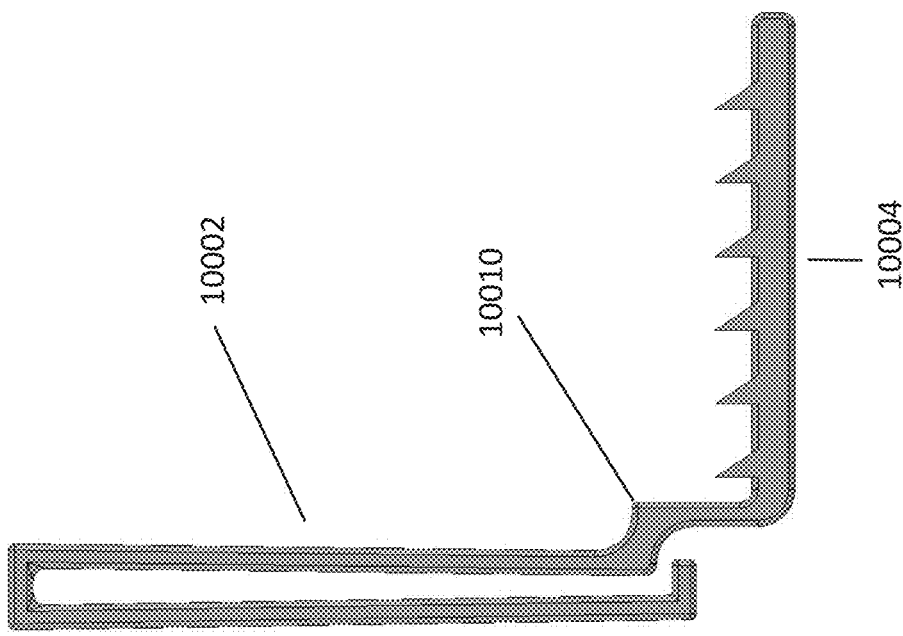
Figure 26C:
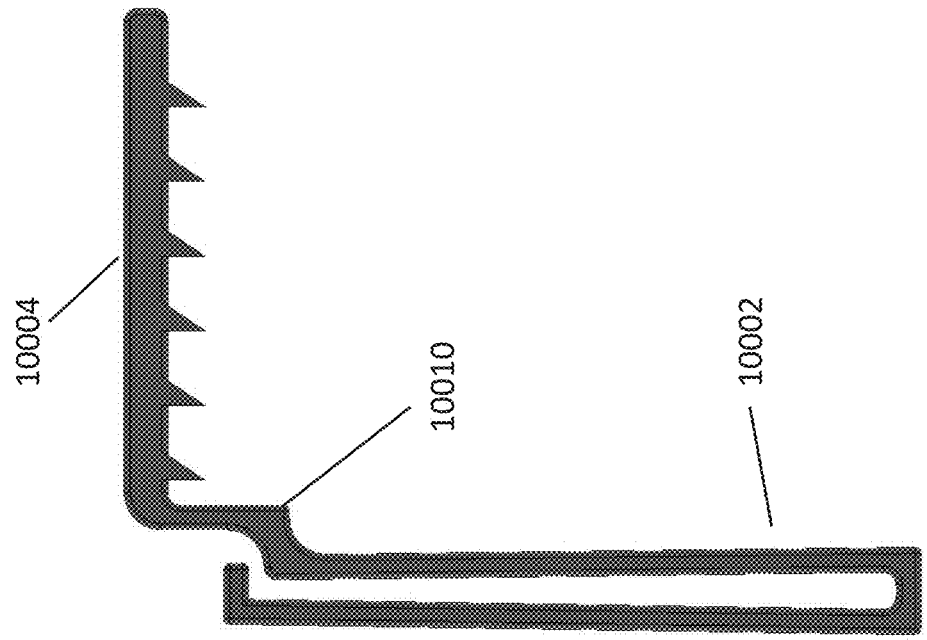
Figure 26D:
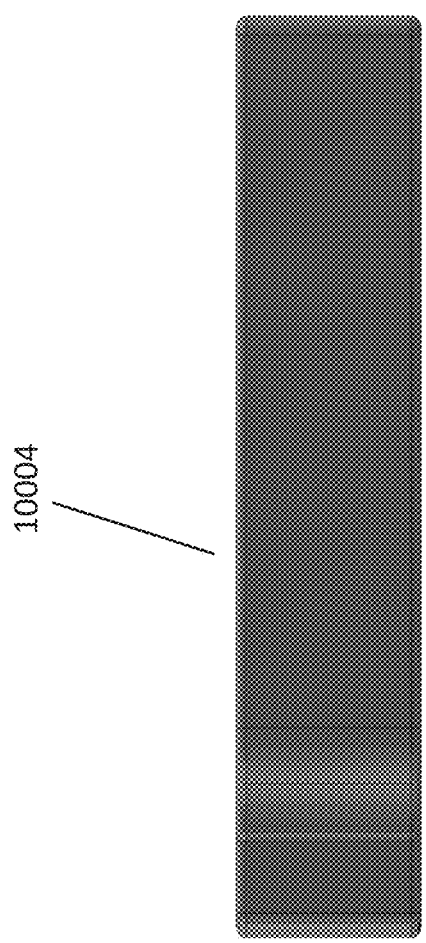
Figure 26E:
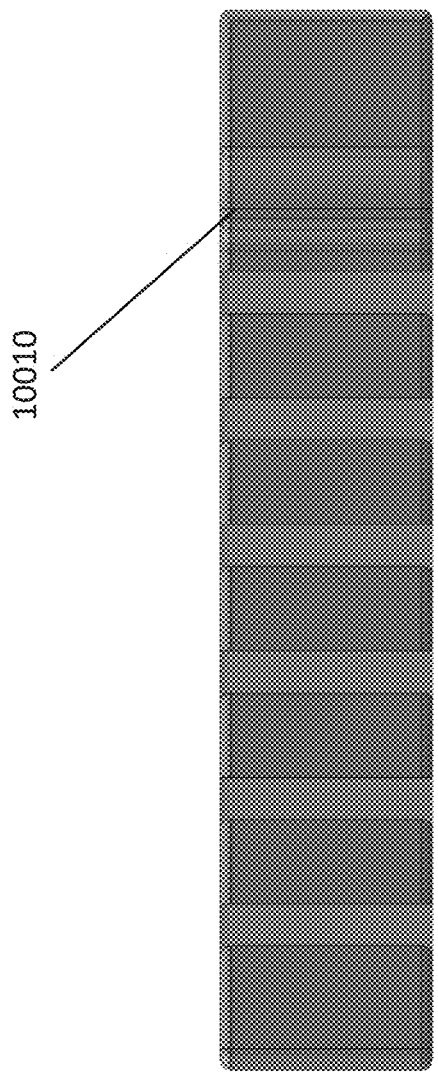
Figure 26F:
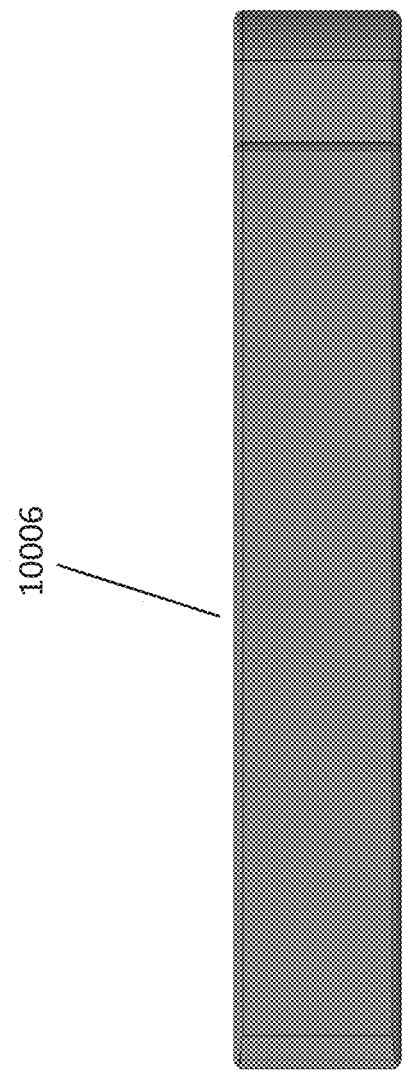
Figure 26G:
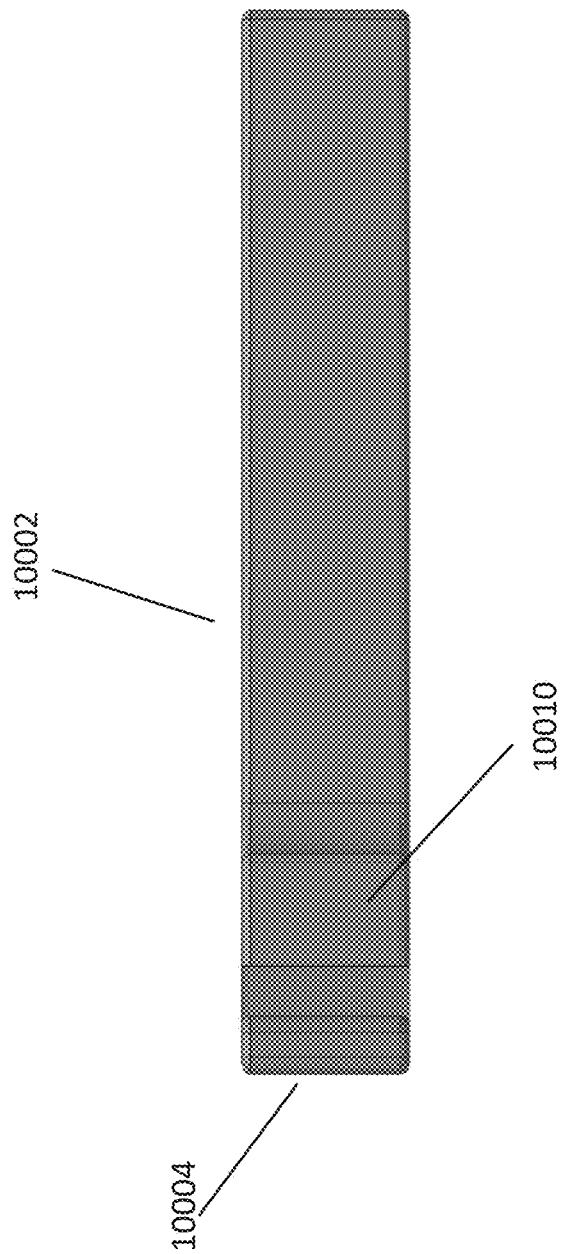
Figure 26H:
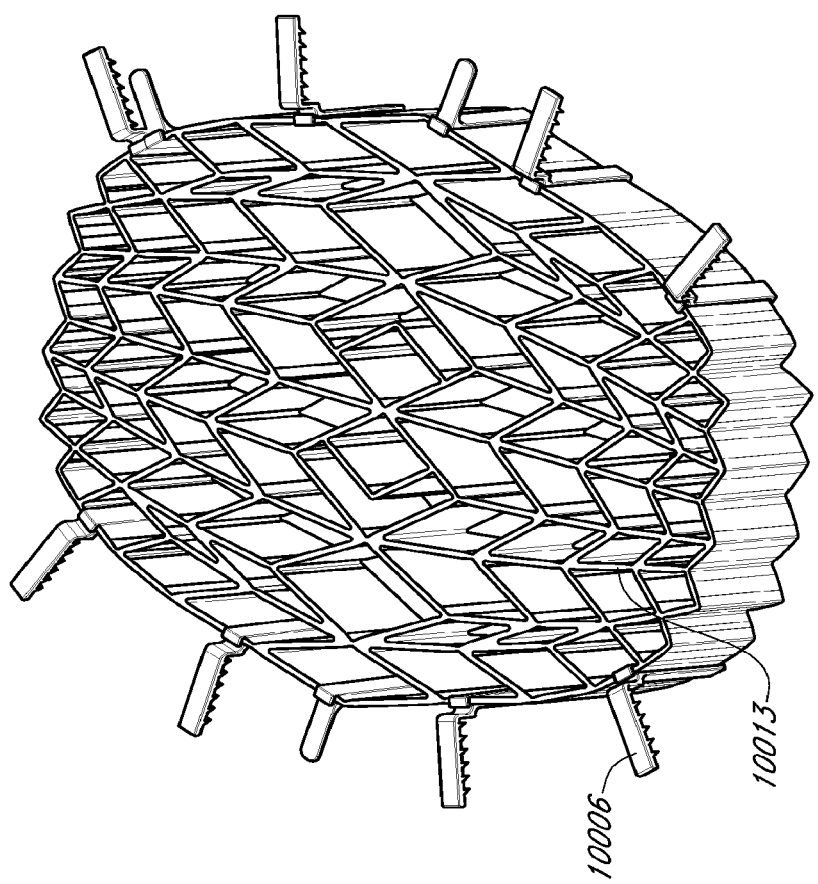
Figure 26I:
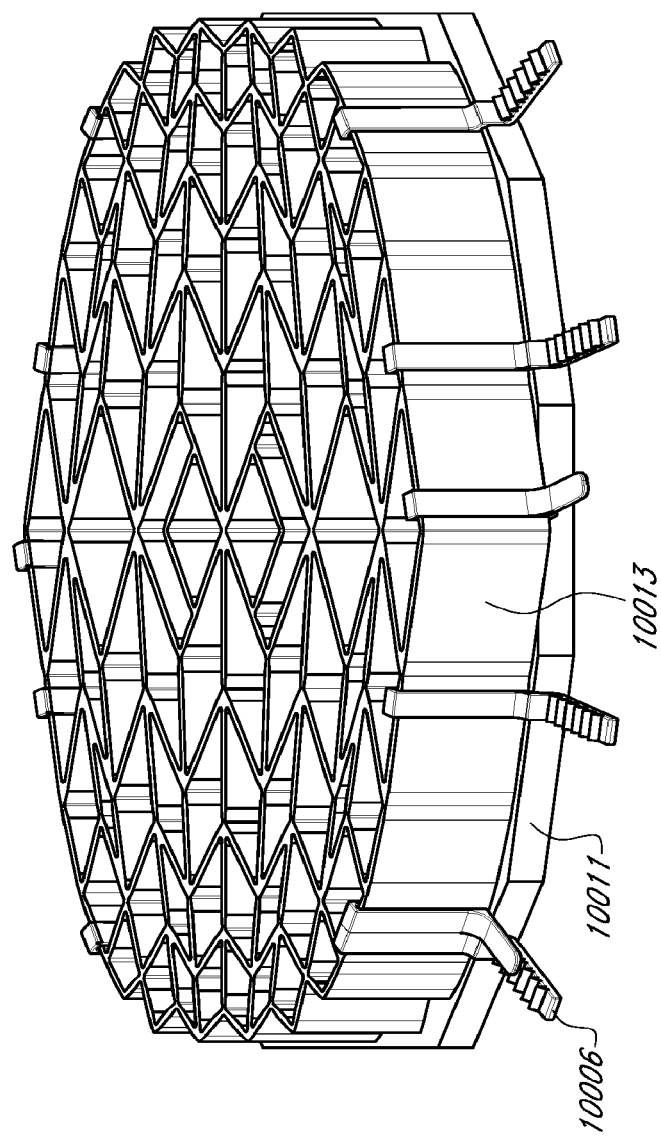
Figure 26J:
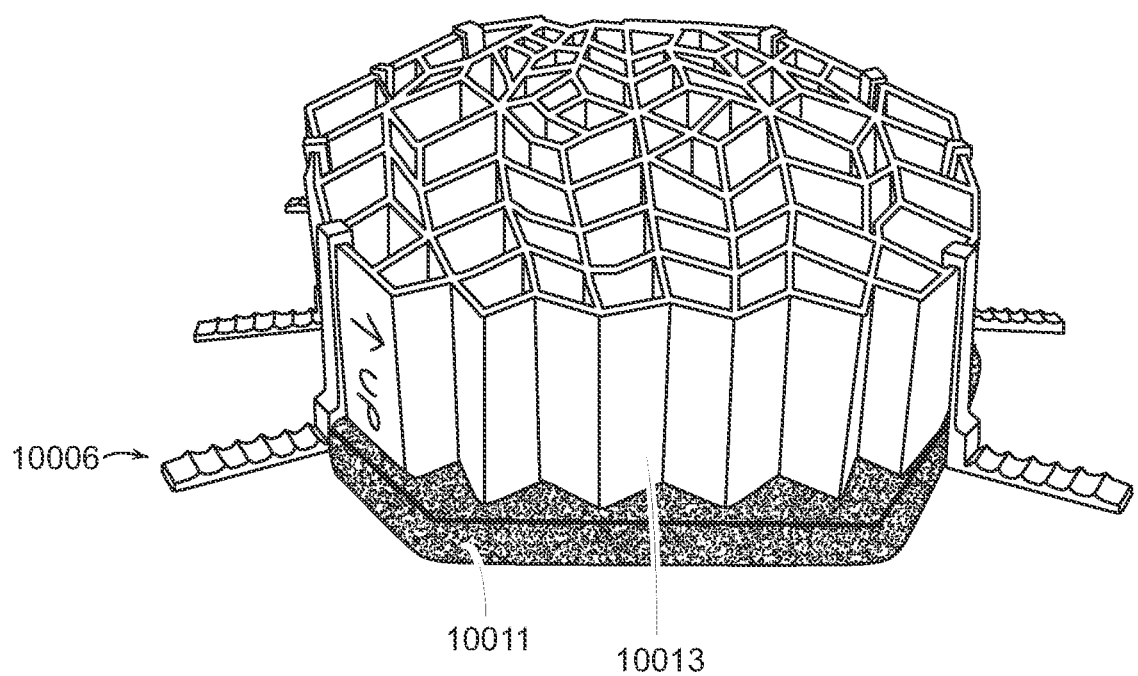

FIGS. 26H-J are pictures of the stabilizing clip 10006 attached to a stabilizing structure or matrix support 10013, similar to the stabilizing structures depicted in FIGS. 2A-3E and 16-19B. The stabilizing structure 10013 is positioned above a foam layer 10011. The foam layer 10011 is larger than the stabilizing structure 10013. The step or recess 10010 of the stabilizing clip fits around the larger foam layer 10011. The step or recess 10010 may allow the stabilizing clip to secure the stabilizing structure within the wound without applying excess pressure on the foam layer that is slightly larger than the stabilizing structure. The step or recess may be provided at any vertical position along the attachment portion of the stabilizing clip to accommodate various depths of foams, stabilizing structures, and/or stabilizing clips.

Figure 27A:
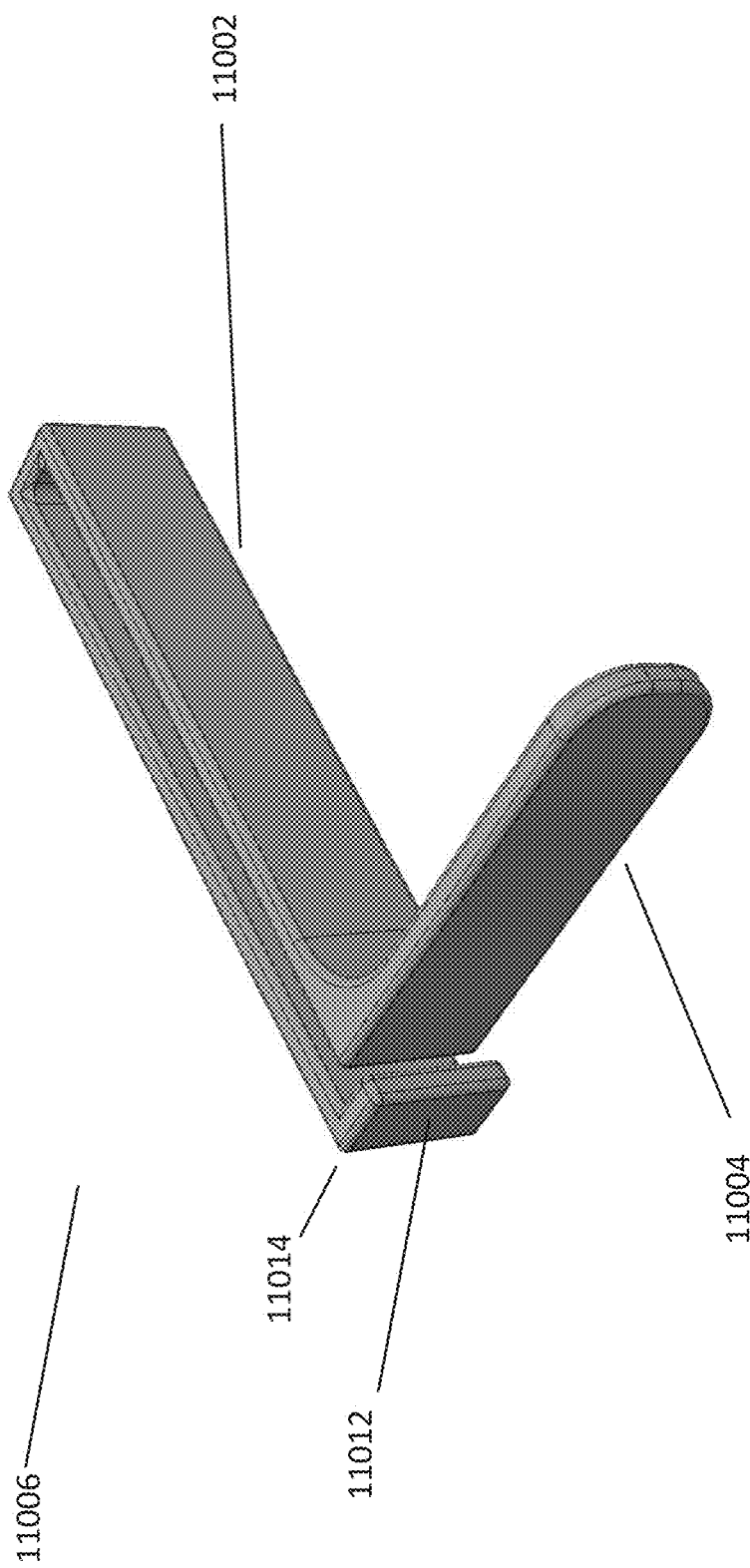
FIGS. 27A-J illustrate embodiments of stabilizing clips for attachment to a stabilizing structures with a foot.
Figure 27B:
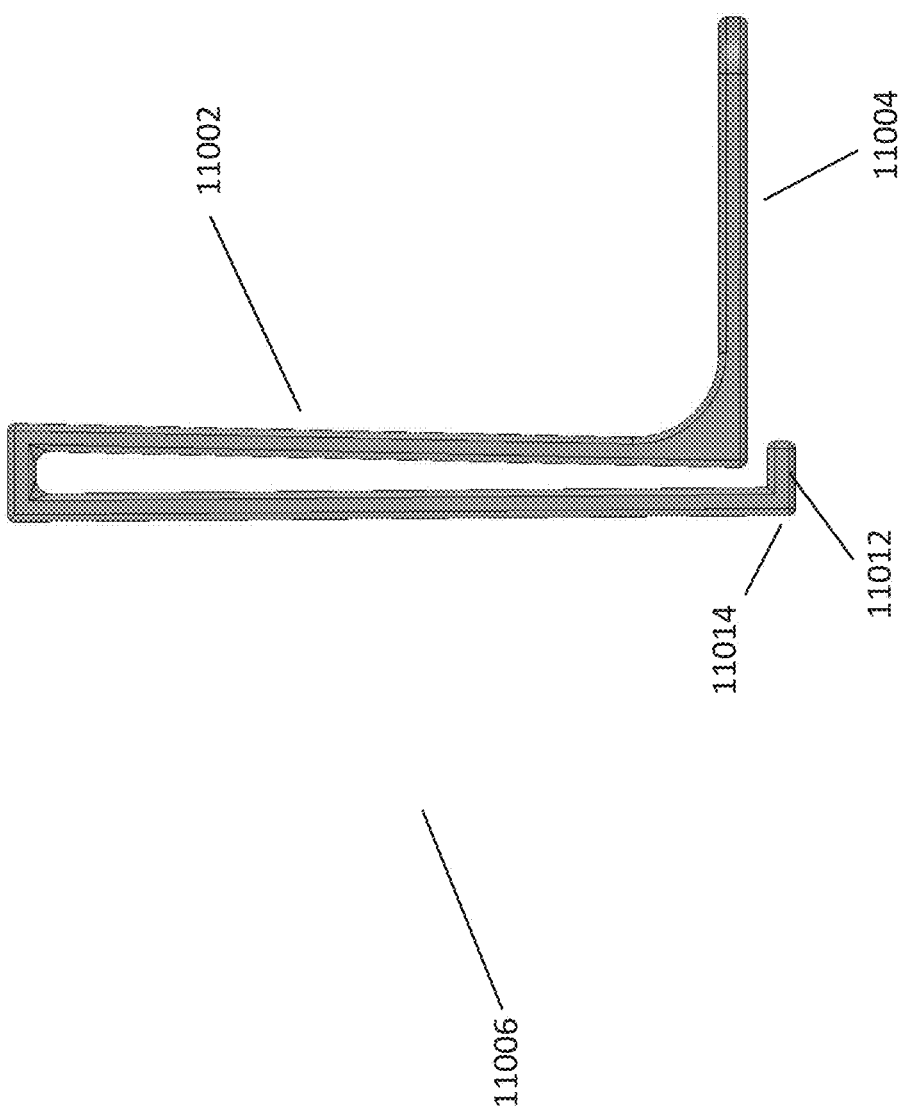
Figure 27C:
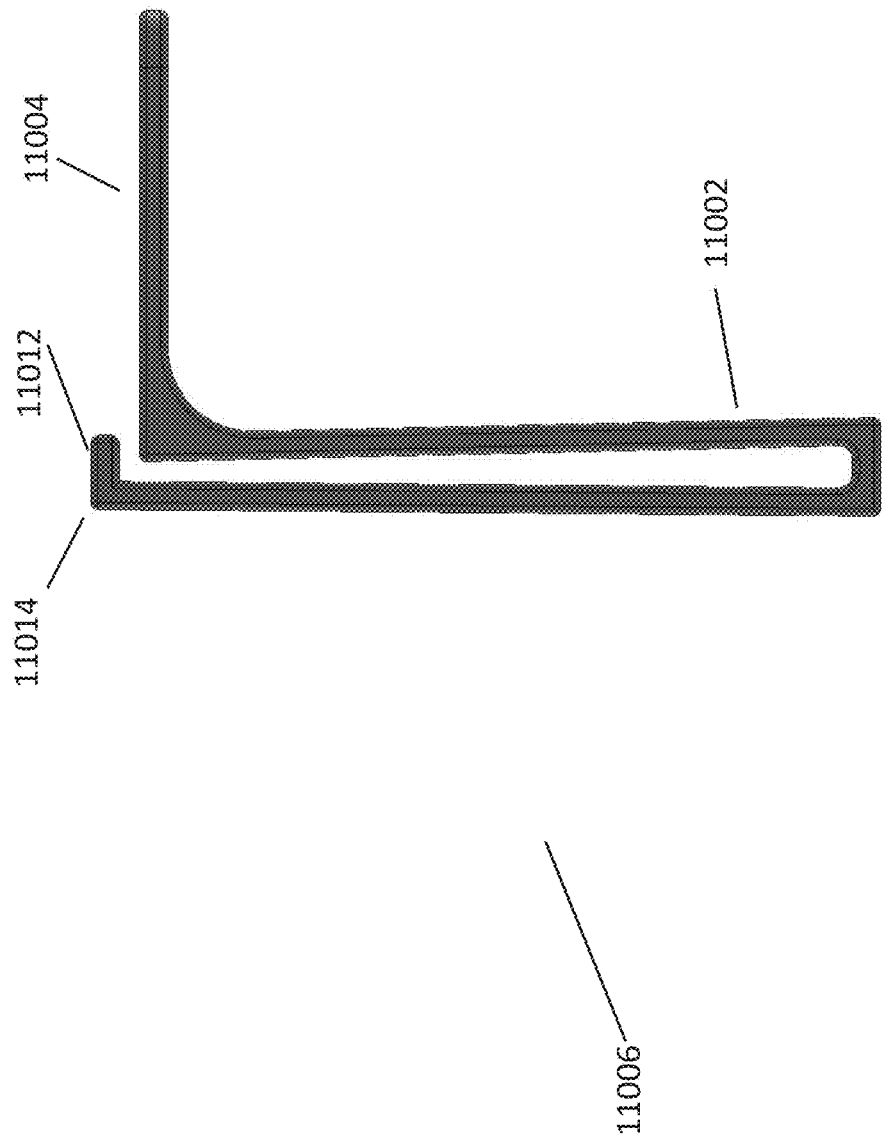
Figure 27D:
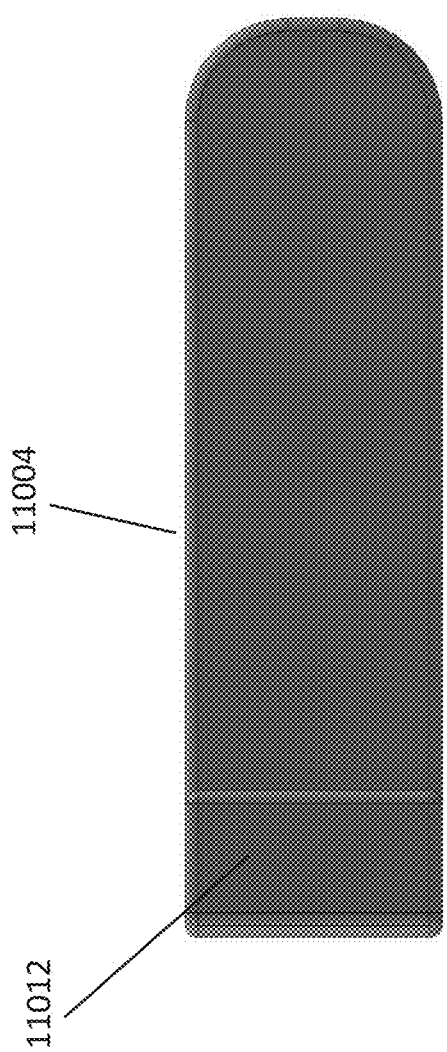
Figure 27E:
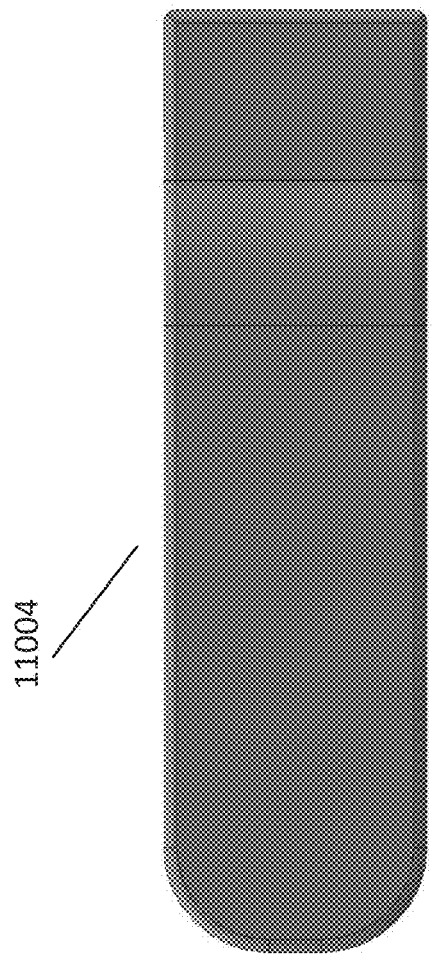
Figure 27F:
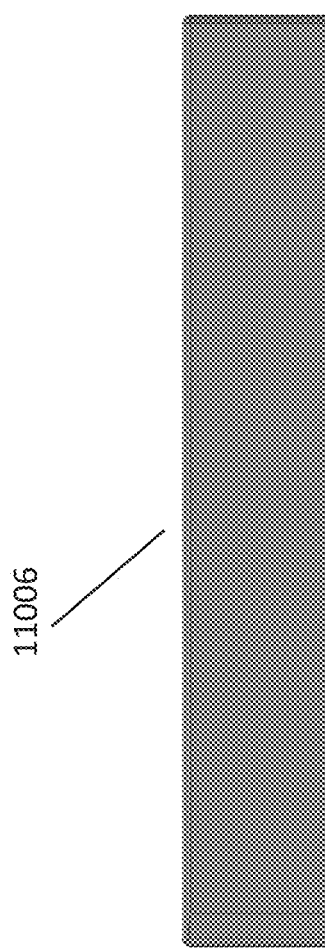
Figure 27G:
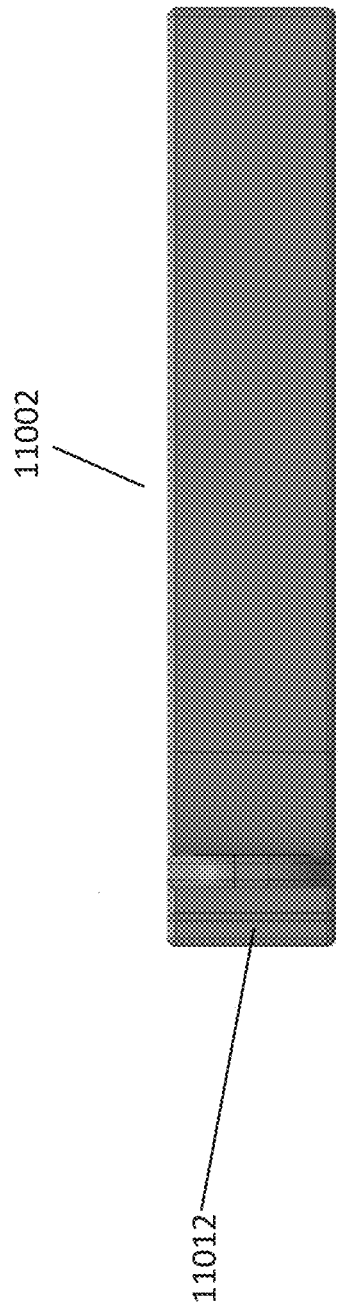
Figure 27H:
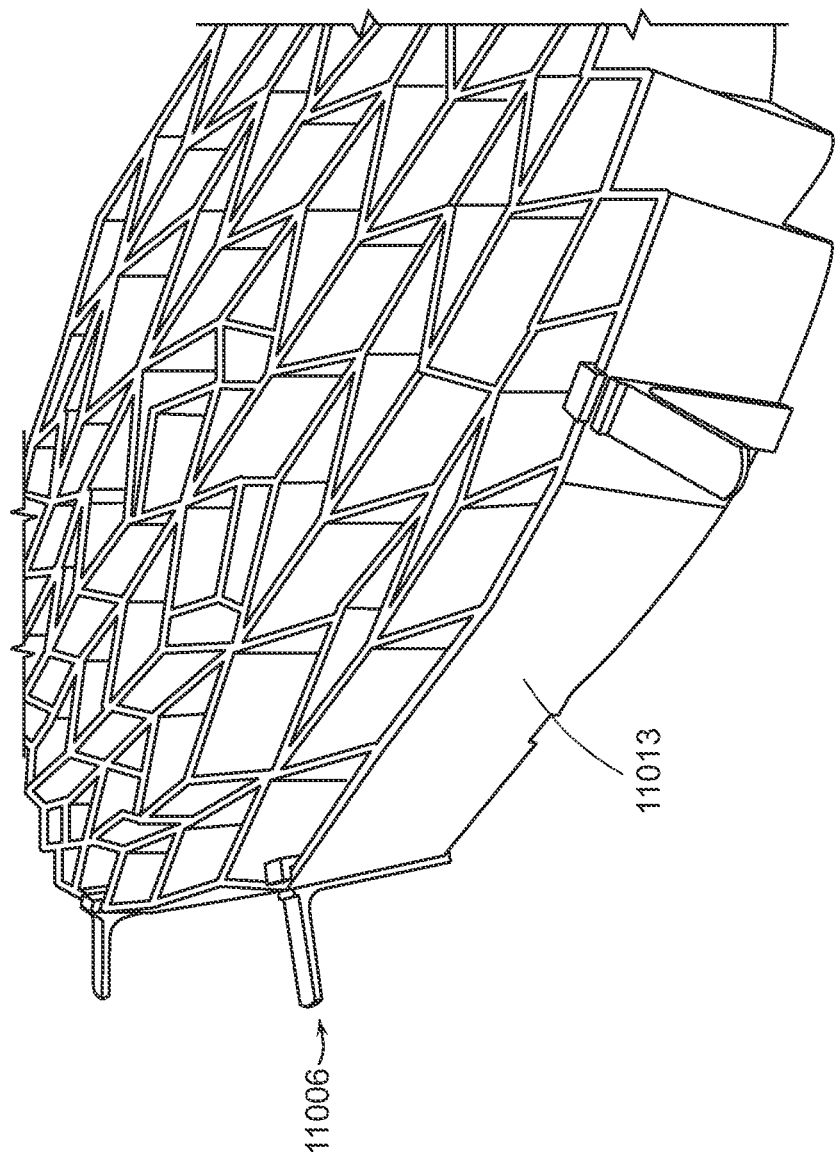
Figure 27I:
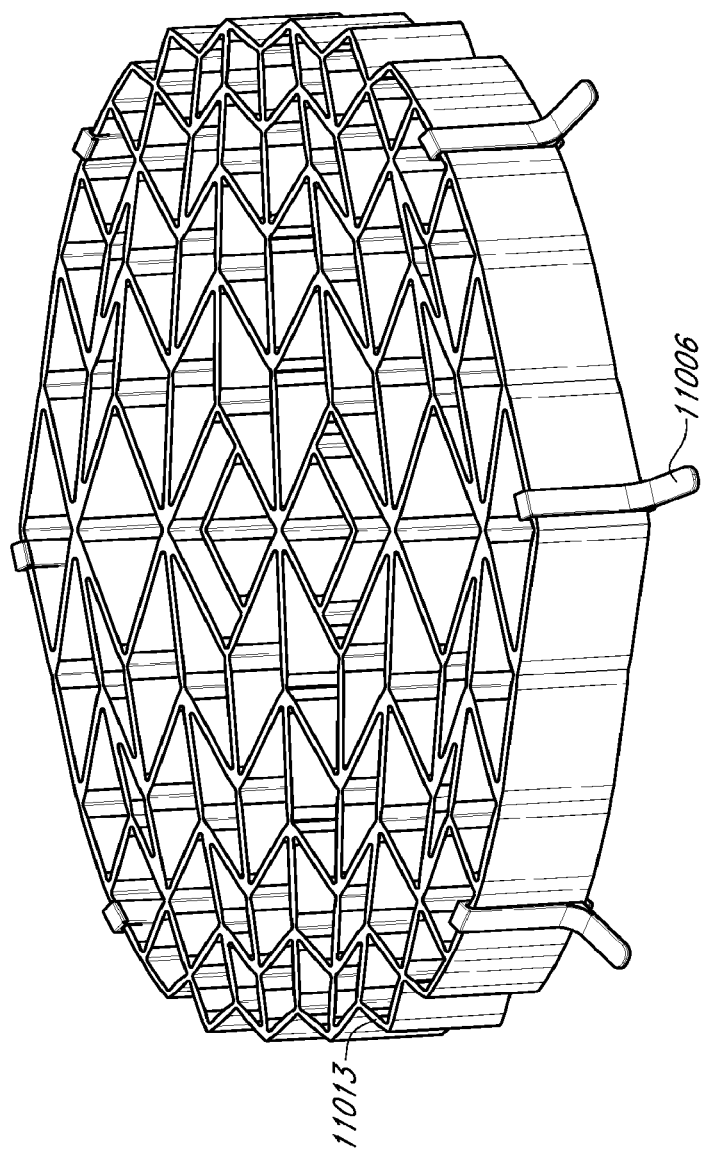
Figure 27J:
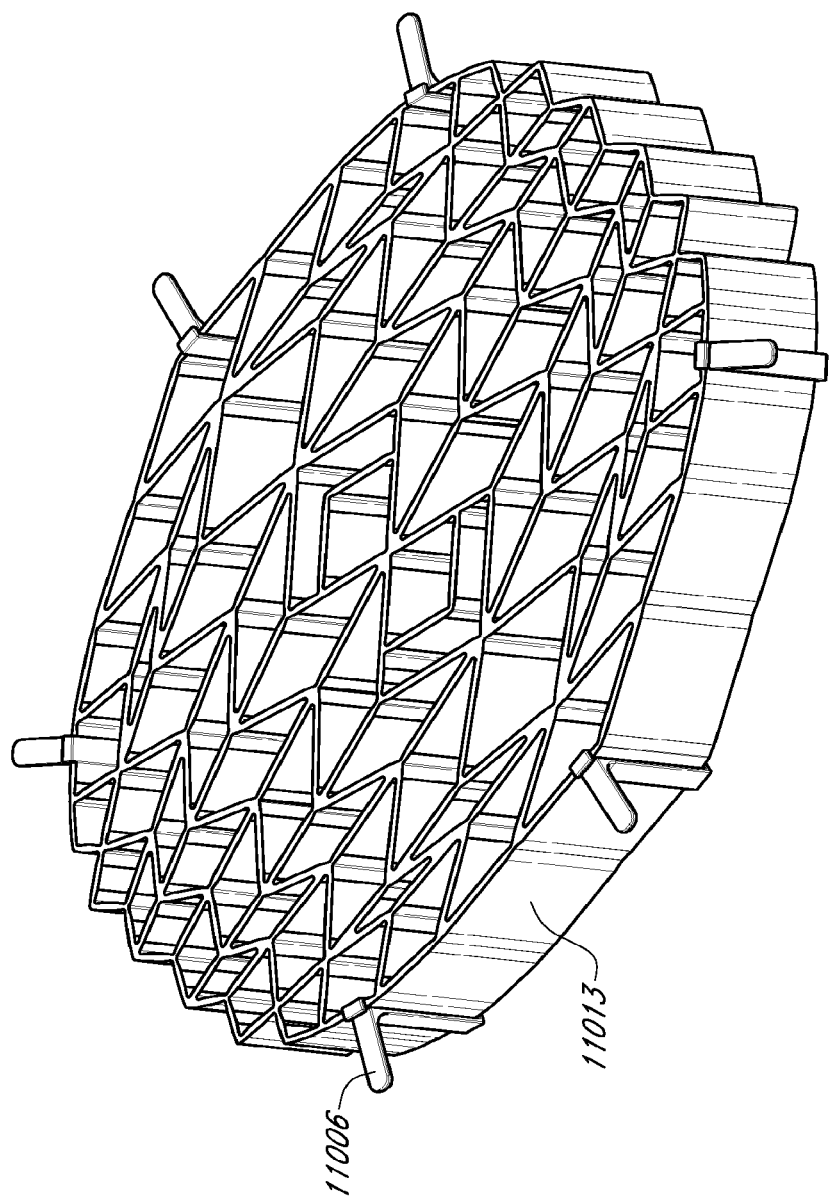

FIGS. 27A-J illustrate an embodiment of stabilizing clip 11006, similar to the stabilizing clip of FIG. 23C. As with the other stabilizing clip embodiments illustrated in FIG. 23C, stabilizing clip 11006 may comprise an attachment portion 11002 that loops over the top of a wall of a stabilizing structure and a securing portion 11004 that extends below a layer of tissue to maintain the stabilizing structure in place. The stabilizing clip 11006, as illustrated in FIGS. 27A-J, may include a foot 11012 to latch to the bottom of the stabilizing structure 11013. The foot 11012 may be provided at the end 11014 of the loop of the attachment portion 11002 that loops over the top of a wall of the stabilizing structure 11004. The foot 11012 can provide strengthening in the corner of the stabilizing clip 11006. The stabilizing clip 11006 with the foot 11012 improves the stability and strength of the stabilizing clip 11006. FIGS. 27H-27J are pictures of the stabilizing clip 10006 attached to the stabilizing structure 10013. The stabilizing clip 11006 can include a foot and grippers as illustrated in some embodiments in FIGS. 25A-G.

FIGS. 28A-D are illustrations of embodiments of stabilizing clips 13000 similar to the embodiments depicted in FIGS. 26A-26C. However, the stabilizing clips 13000 are wider than the clips depicted in FIGS. 26A-26C. Stabilizing clip 13000 may comprise an attachment portion 13002 that loops over the top of a wall of a stabilizing structure or may loop underneath the wall of the stabilizing structure. The stabilizing clip 13000 may also comprise a securing portion 13004 that extends below a layer of tissue such as the fascia, to maintain the stabilizing structure in place. The securing portion 13004 may extend from a lower end of the attachment portion 13002. The stabilizing clip 13000 can include a step or recess 13010 at the intersection of the securing portion 13004 and the attachment portion 13002 or where the securing portion 13004 extends horizontally from the attachment portion 13002. The securing portion 13004 may include grippers 13008 to assist in attaching the securing portion to the surrounding tissue. In other embodiments, the stabilizing clip 13006 with the step or recess 13010 may be used with a securing portion 13004 without grippers 13008 on the surface of the securing portion 13004. The step 13010 can provide a step or recess in the stabilizing clip to accommodate a foam and/or other material positioned below the matrix, similar to the foam layers described herein this section or elsewhere in the specification. The step 13010 allows the stabilizing clip 13006 attached to the matrix stabilizing structure to fit around a piece of foam that is placed below the stabilizing structure which may be slightly larger than the stabilizing structure. In some embodiments, the size of the step can be changed to accommodate the various foam sizes.

Figure 28B:
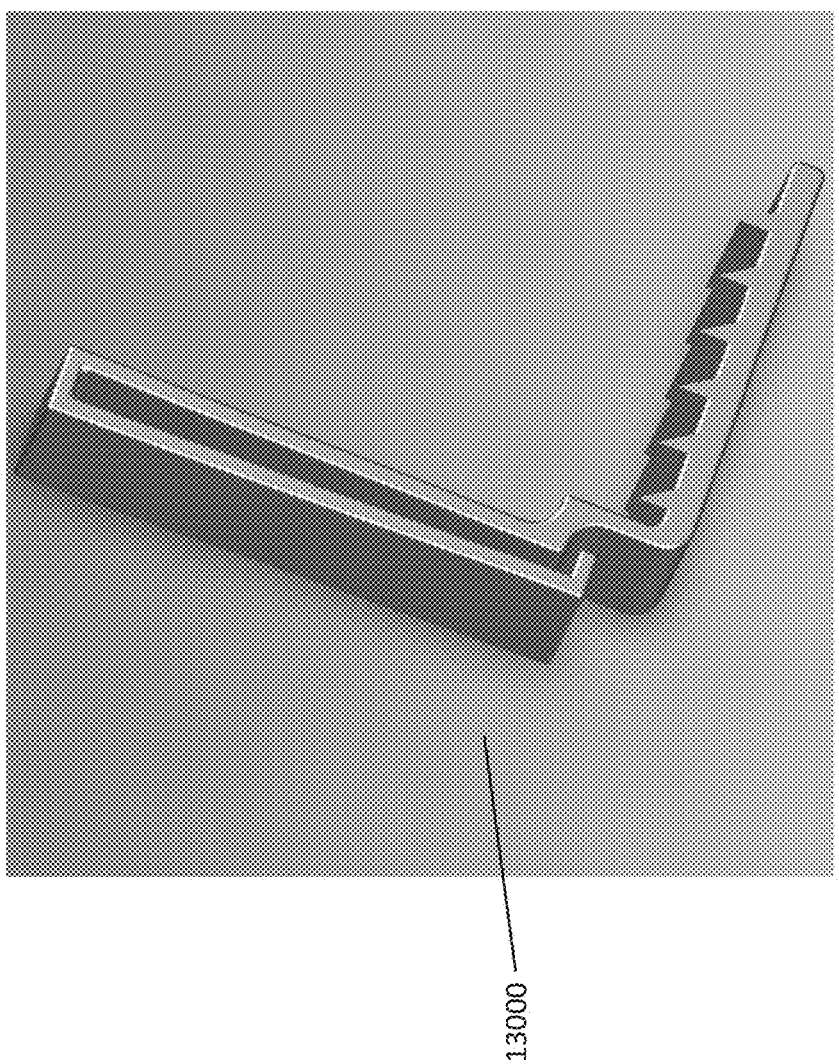
Figure 28C:
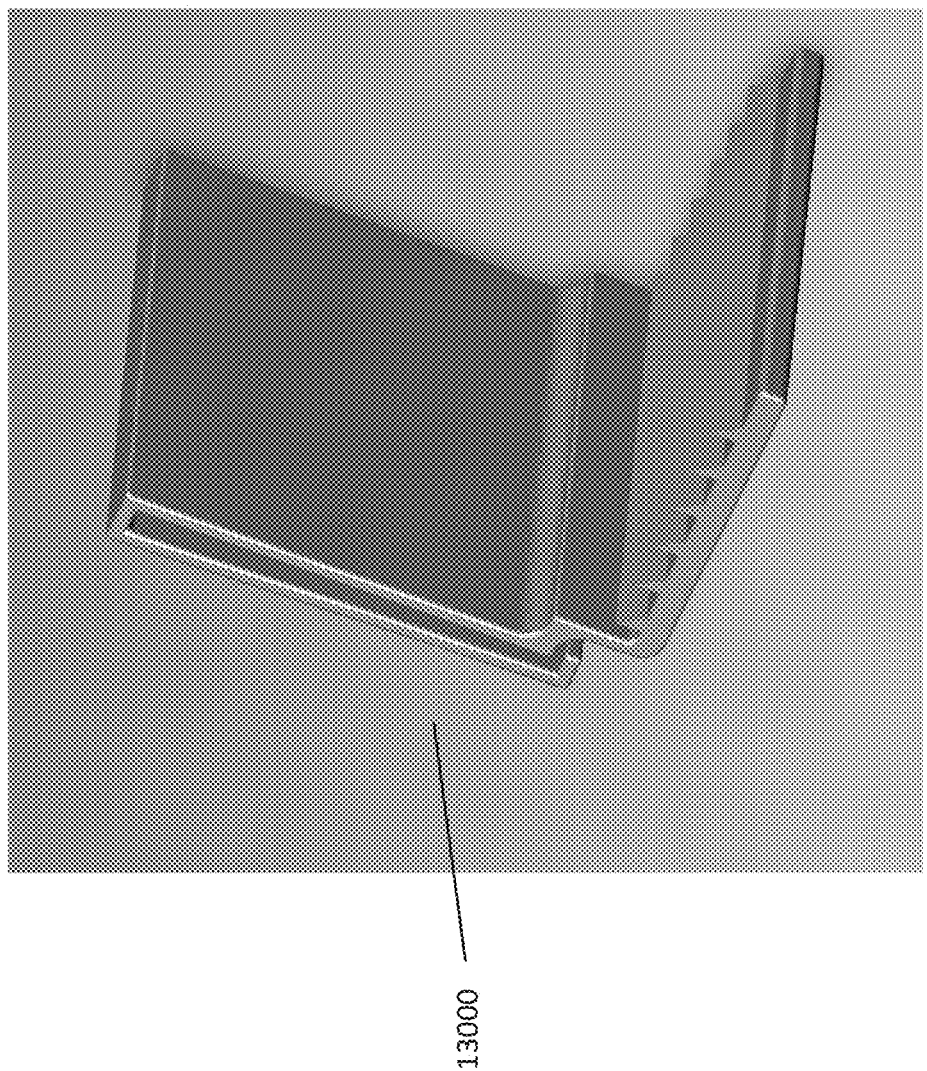
Figure 28D:
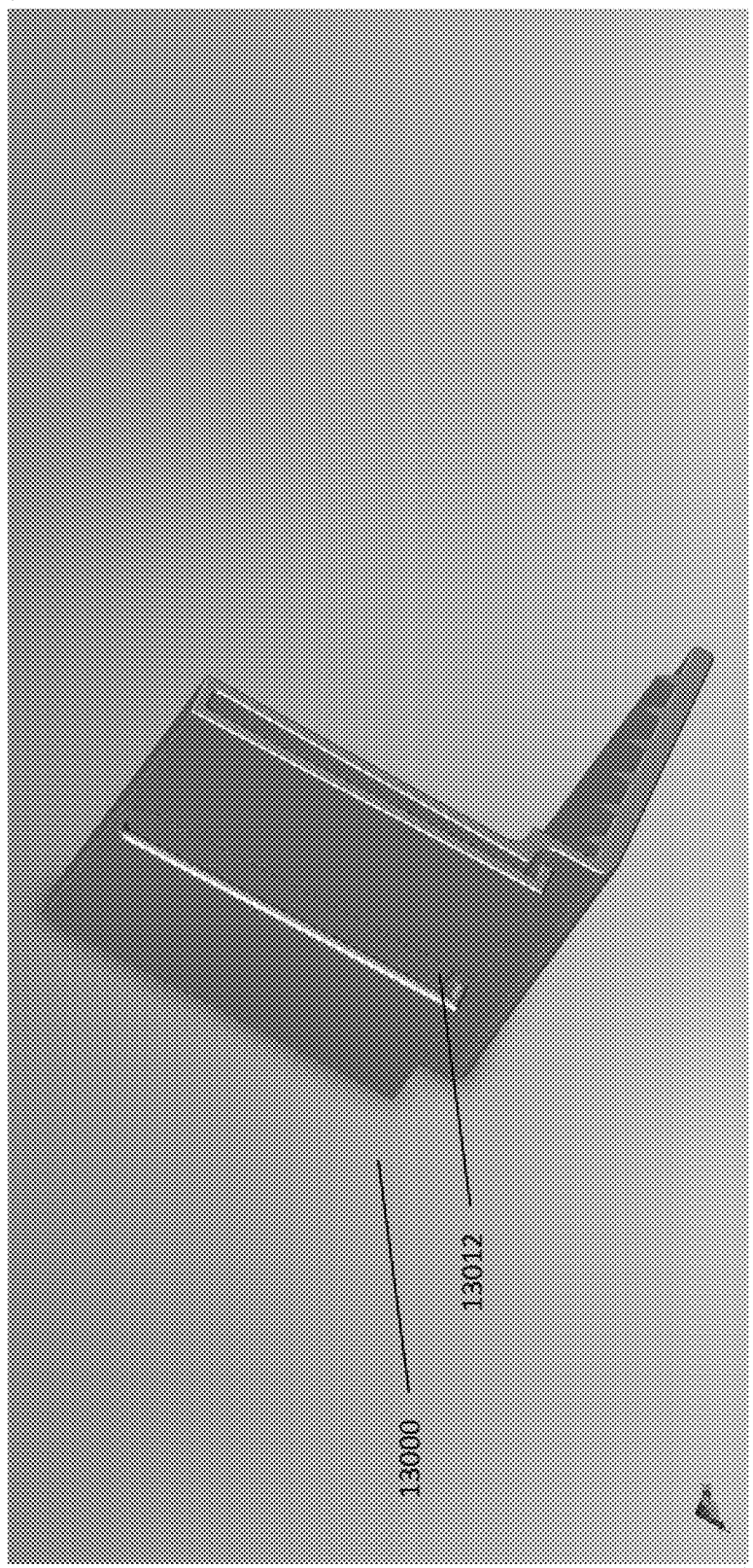

FIG. 28D depicts an embodiment of stabilizing clip 13000 which comprises a gap 13012 in the back of the stabilizing clip 13000. The gap allows the stabilizing clip 13000 to fit over an intersection or junction of the stabilizing structure, such as disclosed herein this section or elsewhere in the specification. By positioning the stabilizing clip over an intersection or junction within a stabilizing structure, the clip is more resistant to lateral and other forces that may dislodge the clip.

Figure 28E:
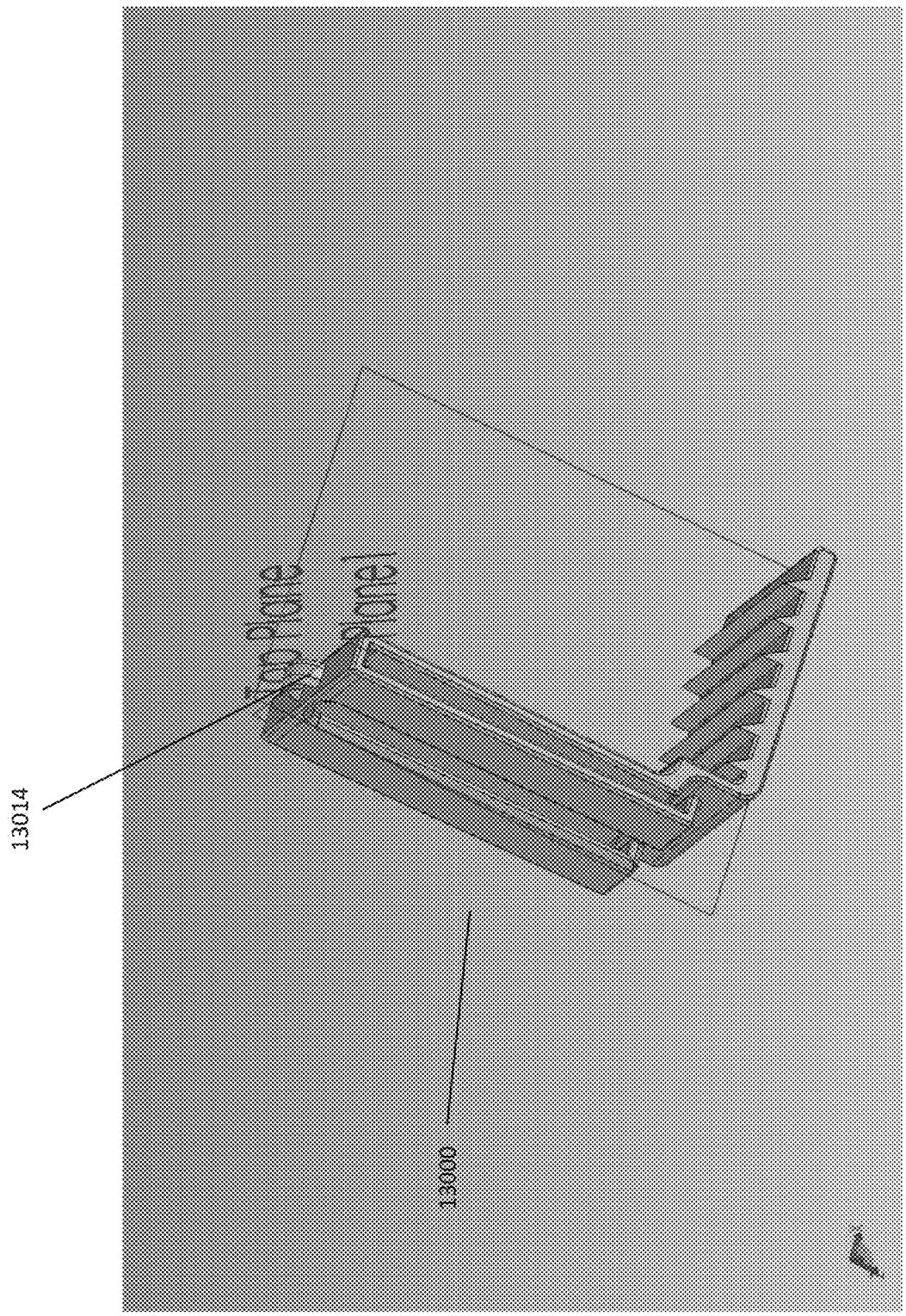

FIG. 28E depicts an embodiment of a stabilizing clip 13000, similar to the stabilizing clips of FIGS. 28A-D. Stabilizing clip 13000 of FIG. 28E further comprises a loop 13014 at the upper end of the stabilizing clip. This loop 13014 may be used to attach the clip to other components of the wound closure device, such as other clips via string or other means. Connecting clip 13000 to other clips may prevent the loss of clips within the wound.

Figure 29A:
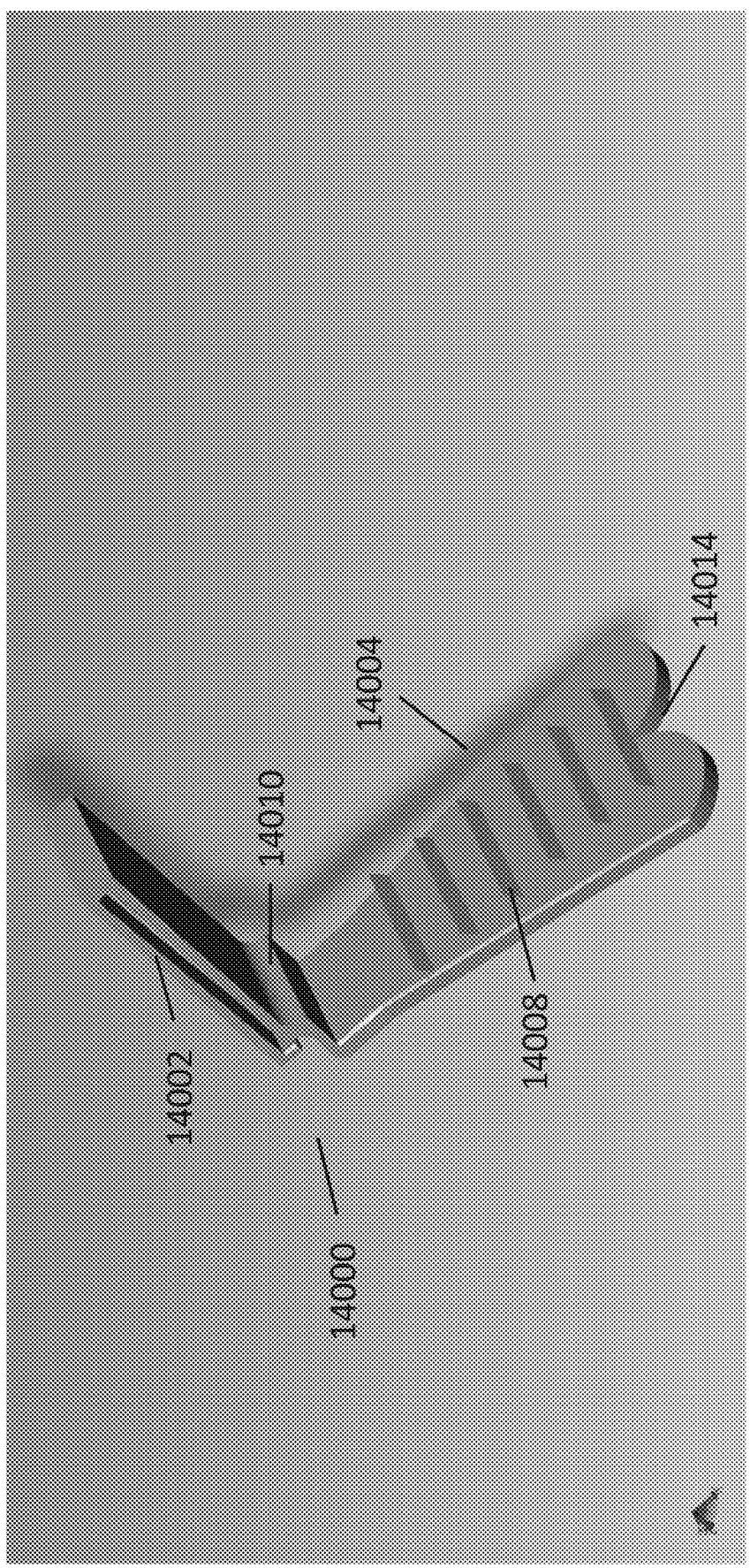
FIGS. 29A-E illustrate embodiments of stabilizing clips for attachment to a stabilizing structure.
Figure 29B:
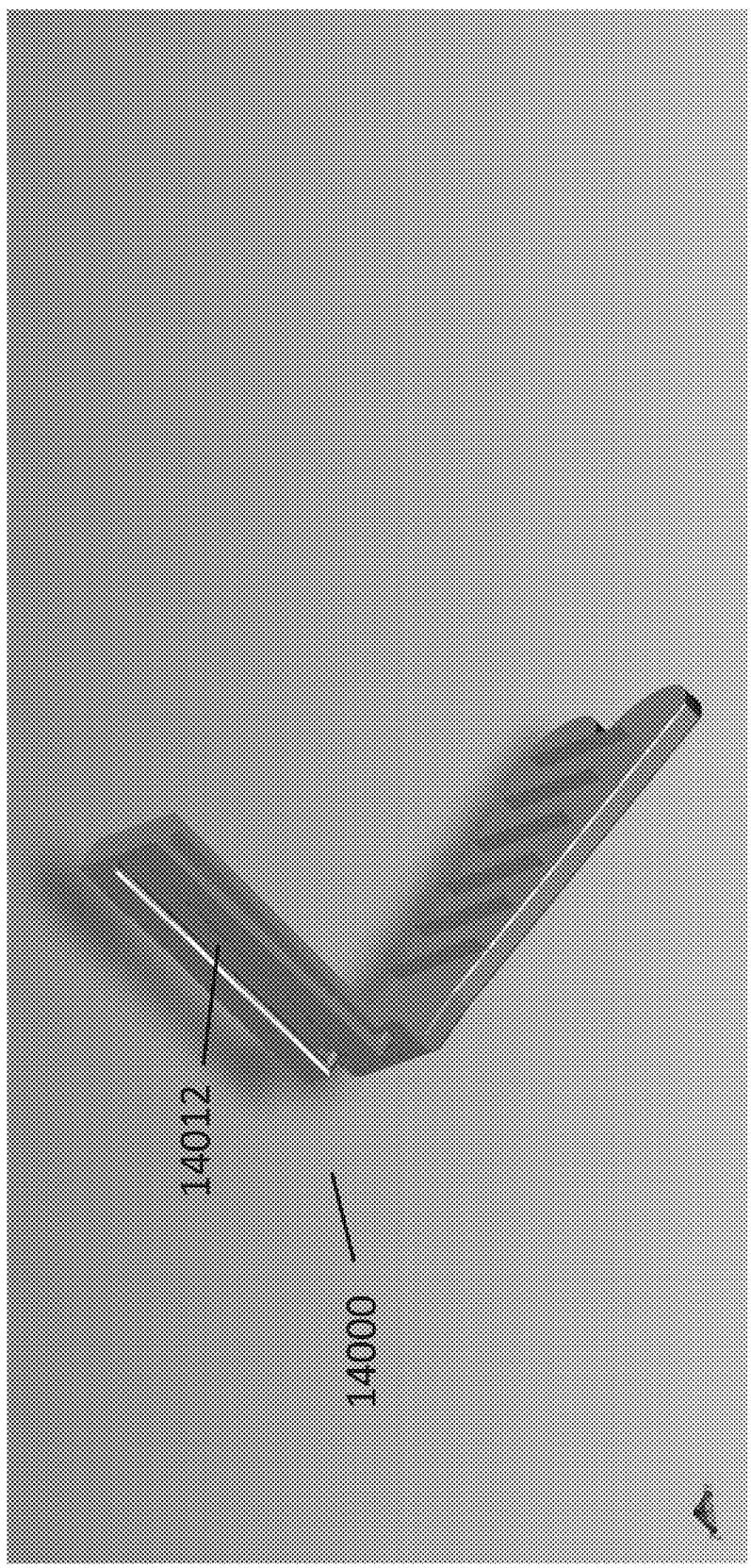
Figure 29C:
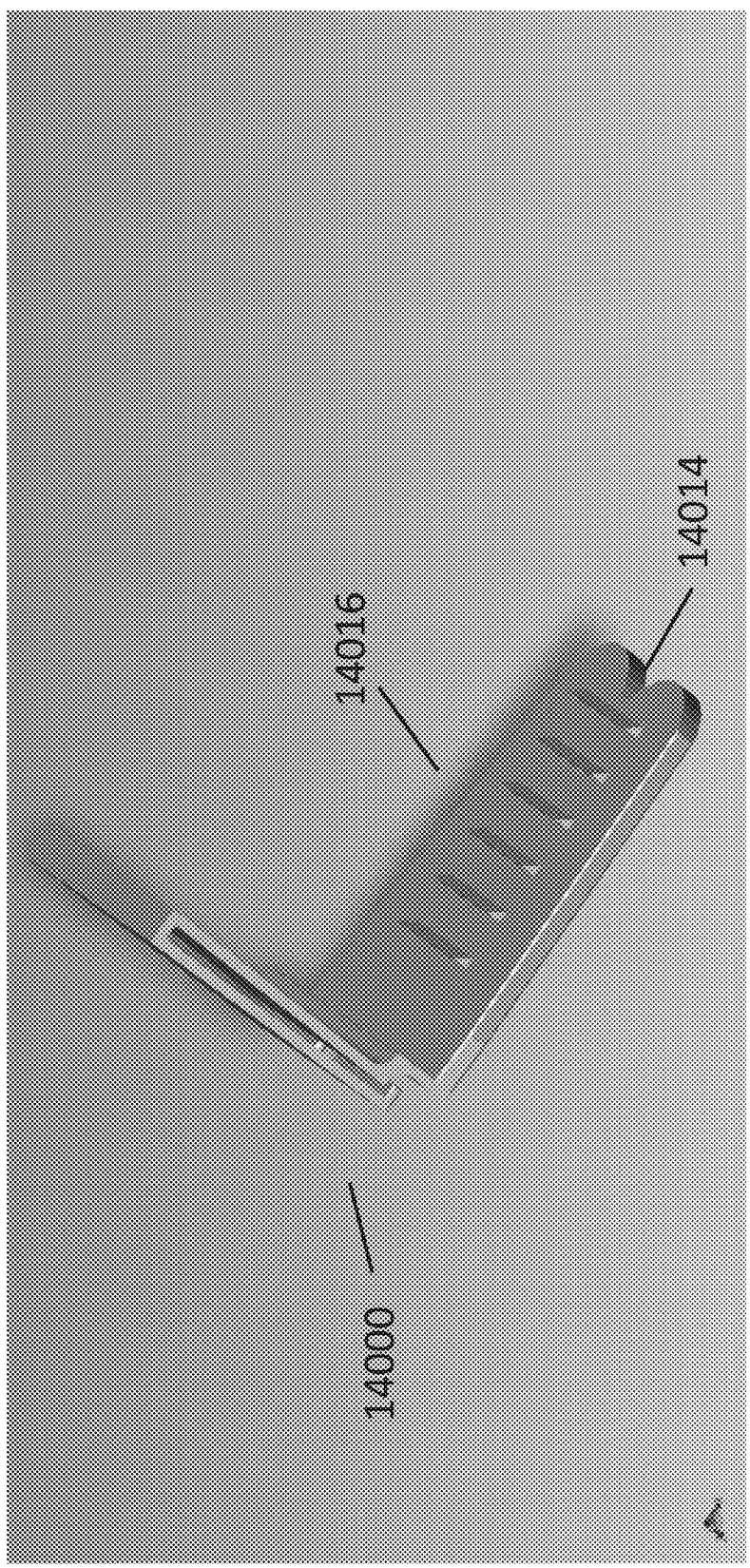
Figure 29D:
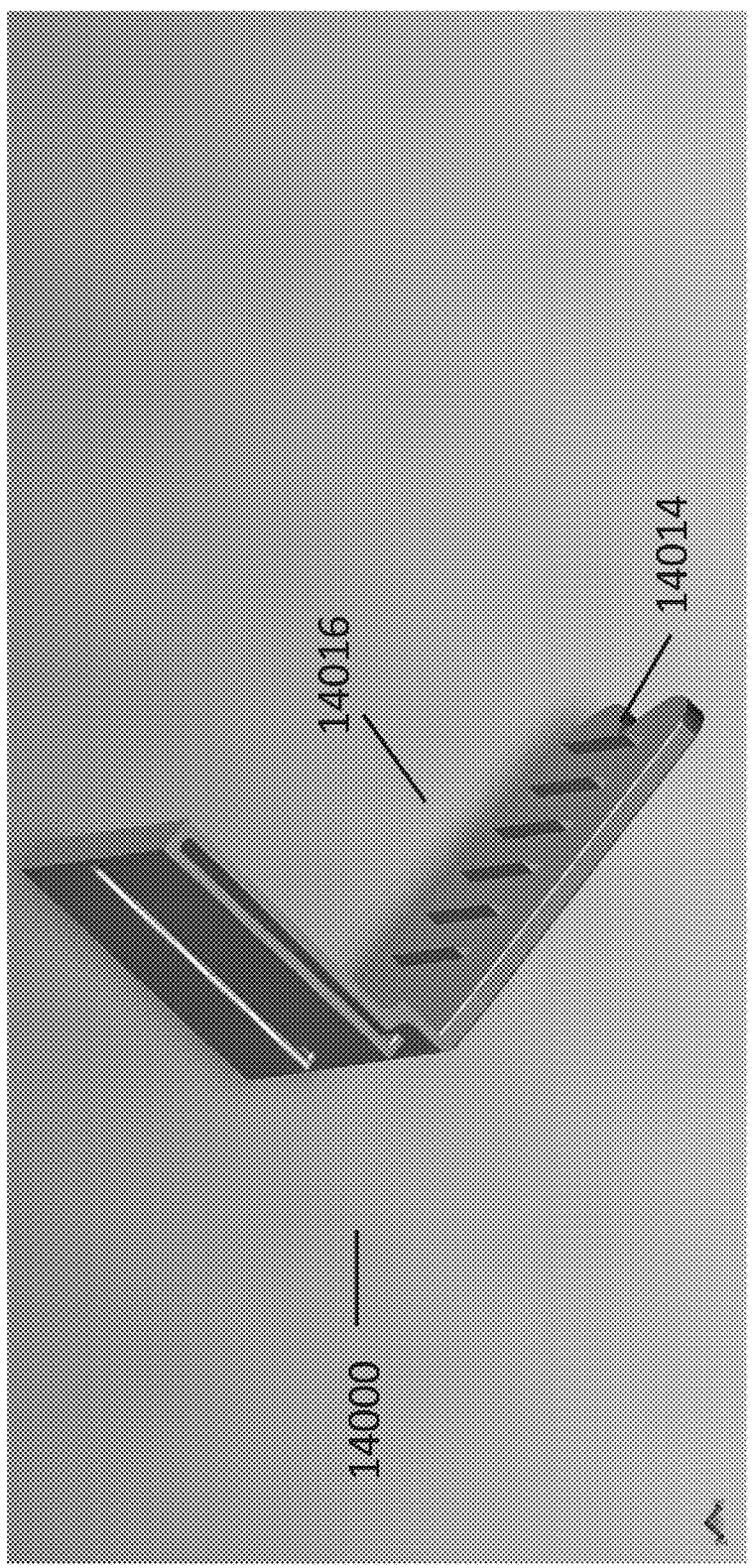
Figure 29E:
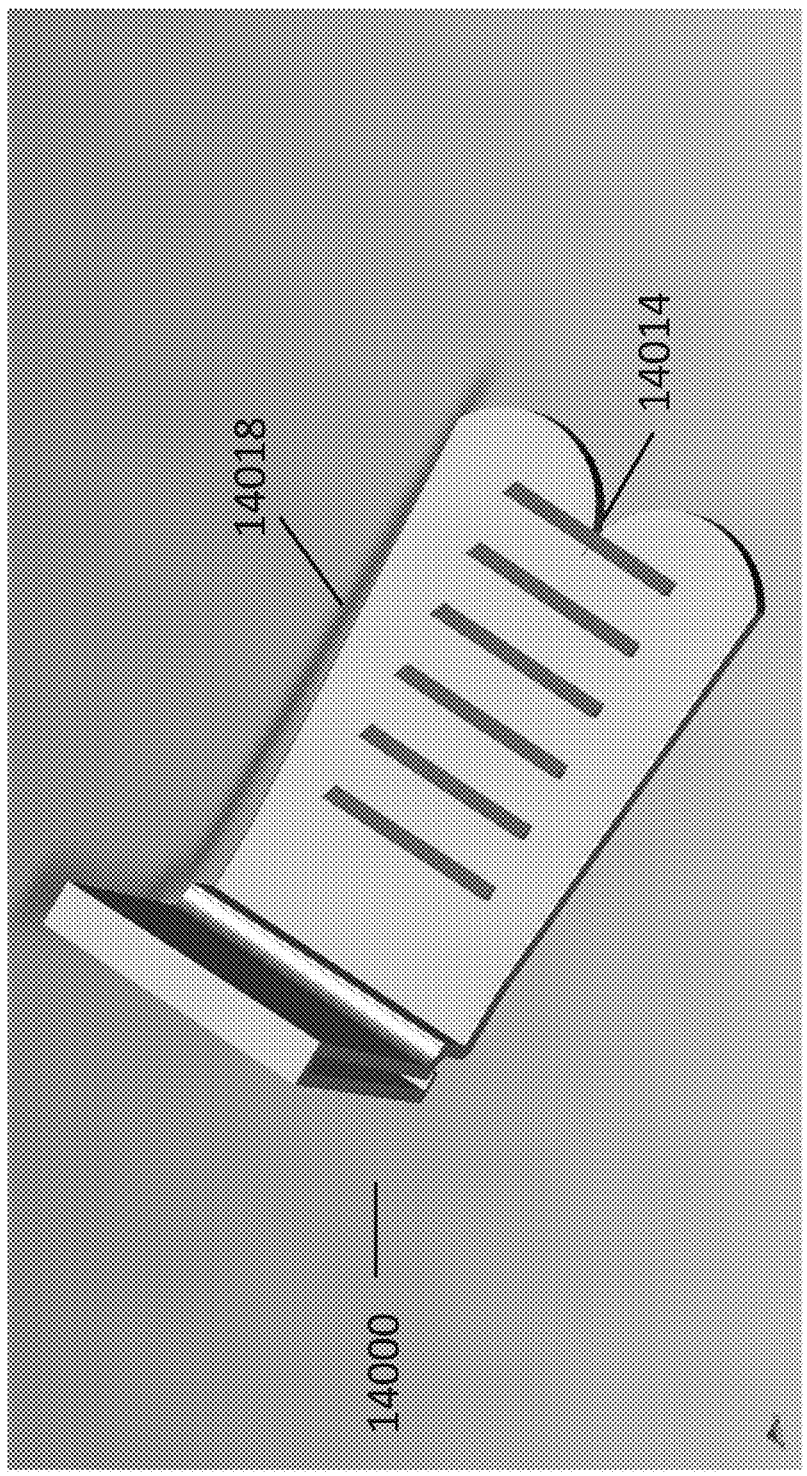

FIGS. 29A-E depict embodiments of stabilizing clip 14000, similar to the stabilizing clips of FIGS. 23-28D, particularly the clip of FIG. 28C-D. AS illustrated in FIGS. 29A-B, stabilizer clip 14000 comprises an attachment portion 14002, tapered securing portion 14004, step 14010, grippers 14008, and gap 14012. The tapered securing portion of 14004 comprises notch 14014. Similarly, the straight securing portion 14016 of the stabilizer clip 14000 of FIG. 29C-D comprises a notch 14014. FIG. 29E depicts a stabilizer clip 14000 with a wide securing portion 14018.

Figure 30A:
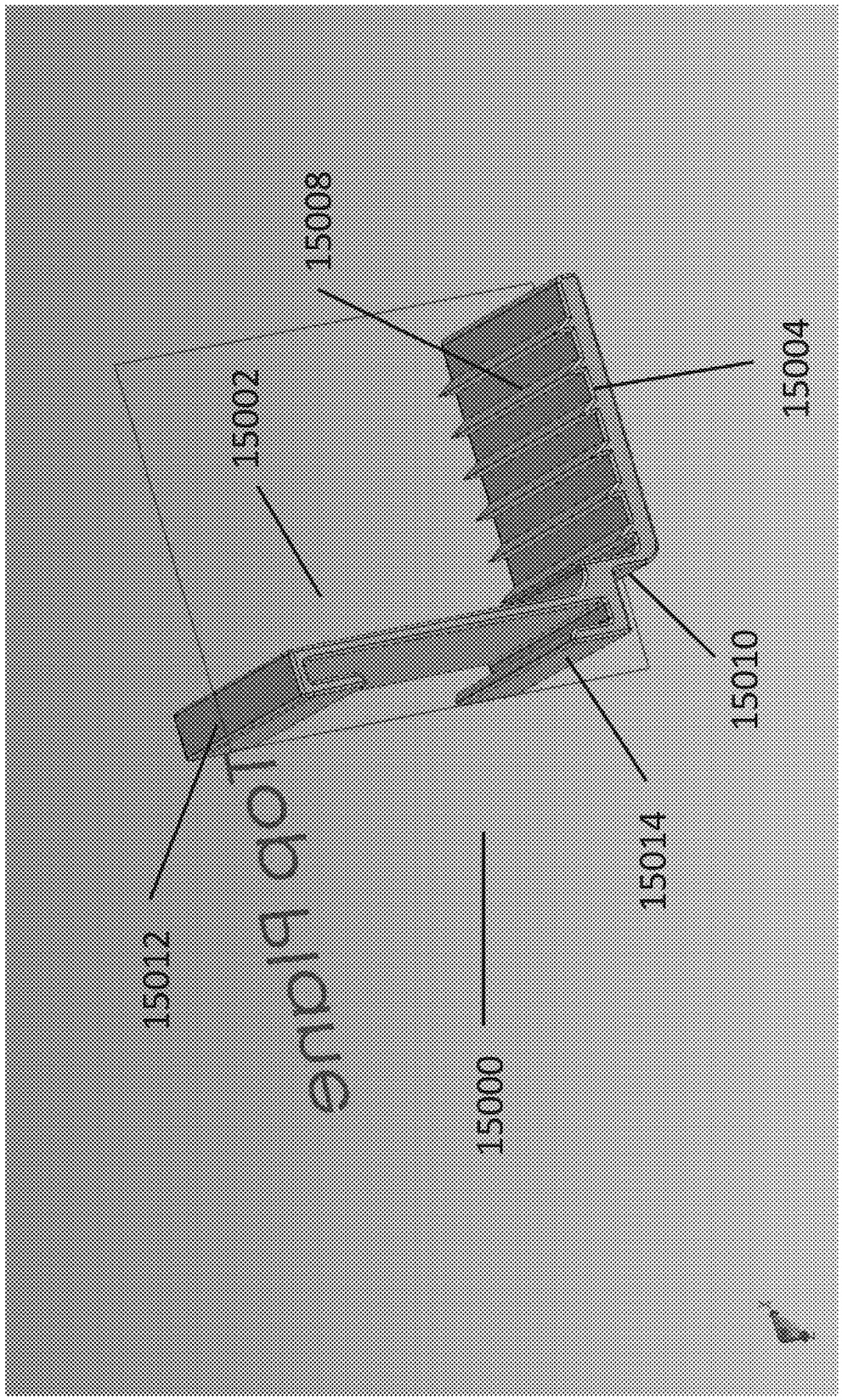
FIGS. 30A-B illustrate embodiments of stabilizing clips for attachment to a stabilizing structure.
Figure 30B:
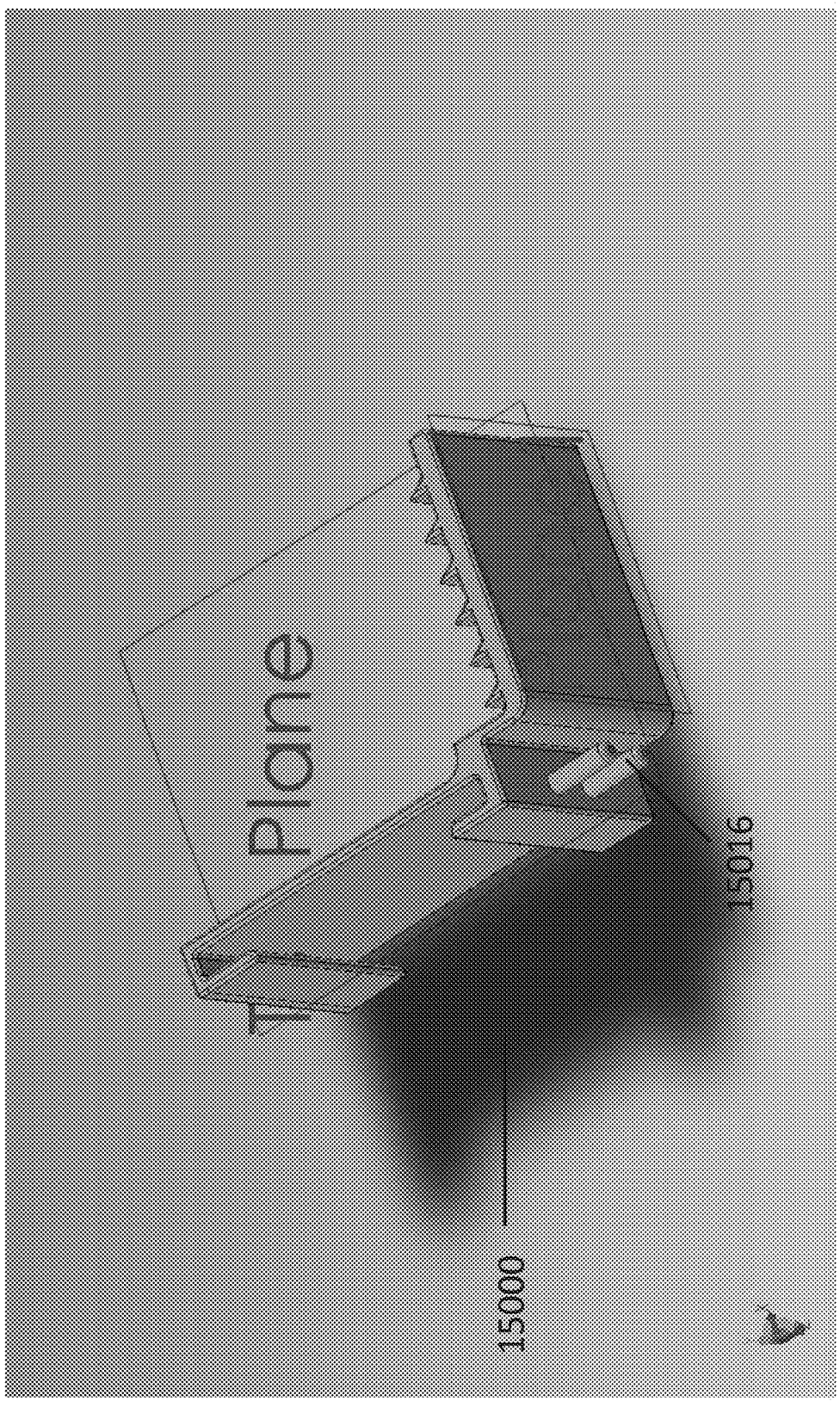

FIGS. 30A-B depict stabilizing clips 15000 similar to the stabilizing clips of FIGS. 23A-29E. Much like the embodiments of the stabilizing clips disclosed above, stabilizing clip 15000 comprises an attachment portion 15002, securing portion 15004, step 15010, and grippers 15008. However, stabilizing structure includes top hook 15012 and bottom hook 15014, allowing the clip to be securely fastened to a stabilizing structure such as those disclosed in FIGS. 2A-3E and 16-20F. Step 15010 allows the stabilizing clip to fit over a layer of foam positioned under the stabilizing structure.

FIG. 30B depicts an embodiment of a stabilizing clip 15000 further comprising pins 15016. These pins may be pressed securely into an underlying foam layer to maintain both the foam and the clip in position. In certain embodiments, the stabilizing clip may comprise, one, two, three, four, five or six individual pins. In some embodiments, the pin(s) may be located on other positions of the clip 15000, such as the underside of securing portion 15004 or the top of the clip near top hook 15012.

Figure 31A:
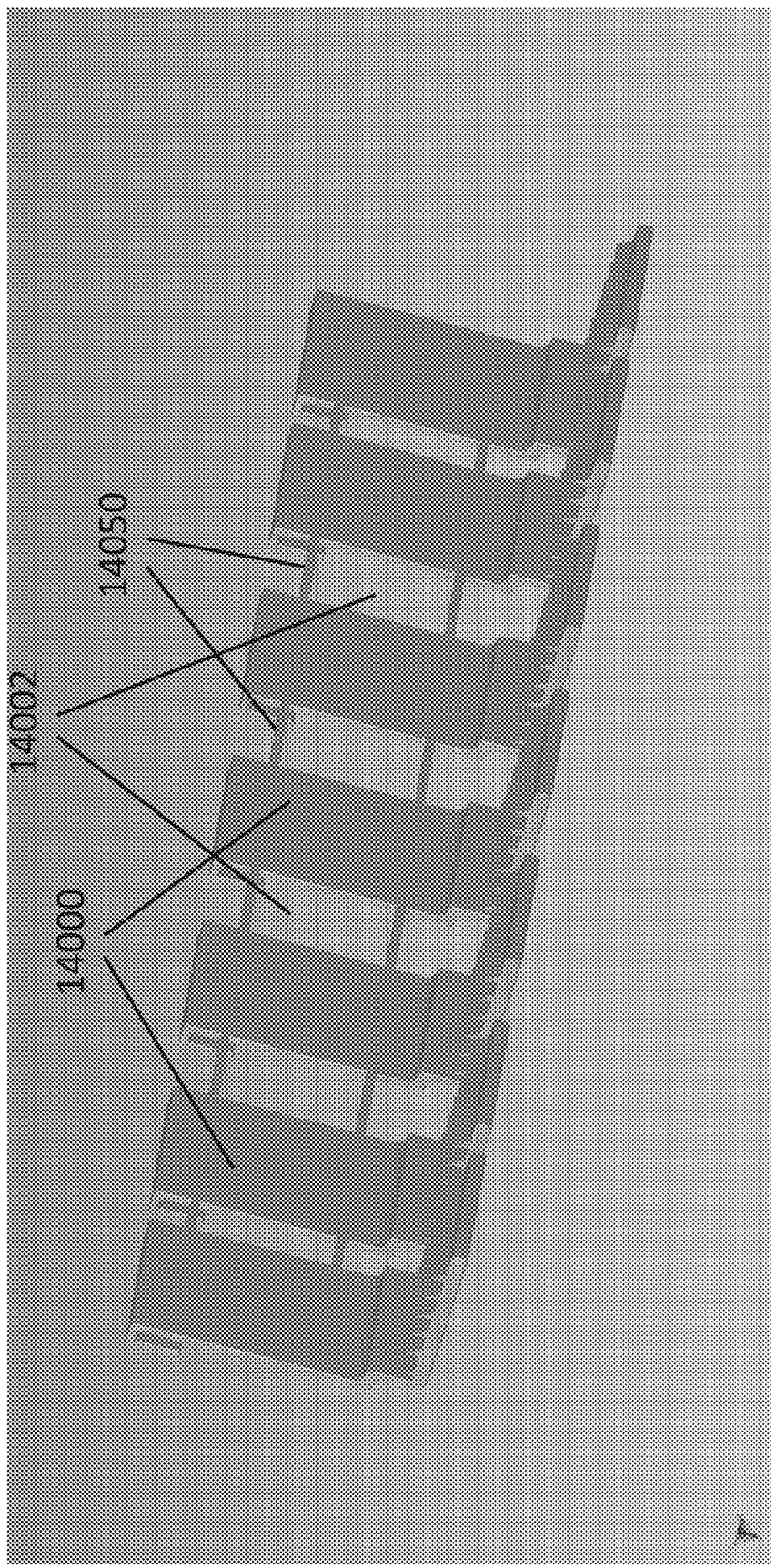
FIGS. 31A-H illustrate embodiments of stabilizing clips attached together by linkers.
Figure 31B:
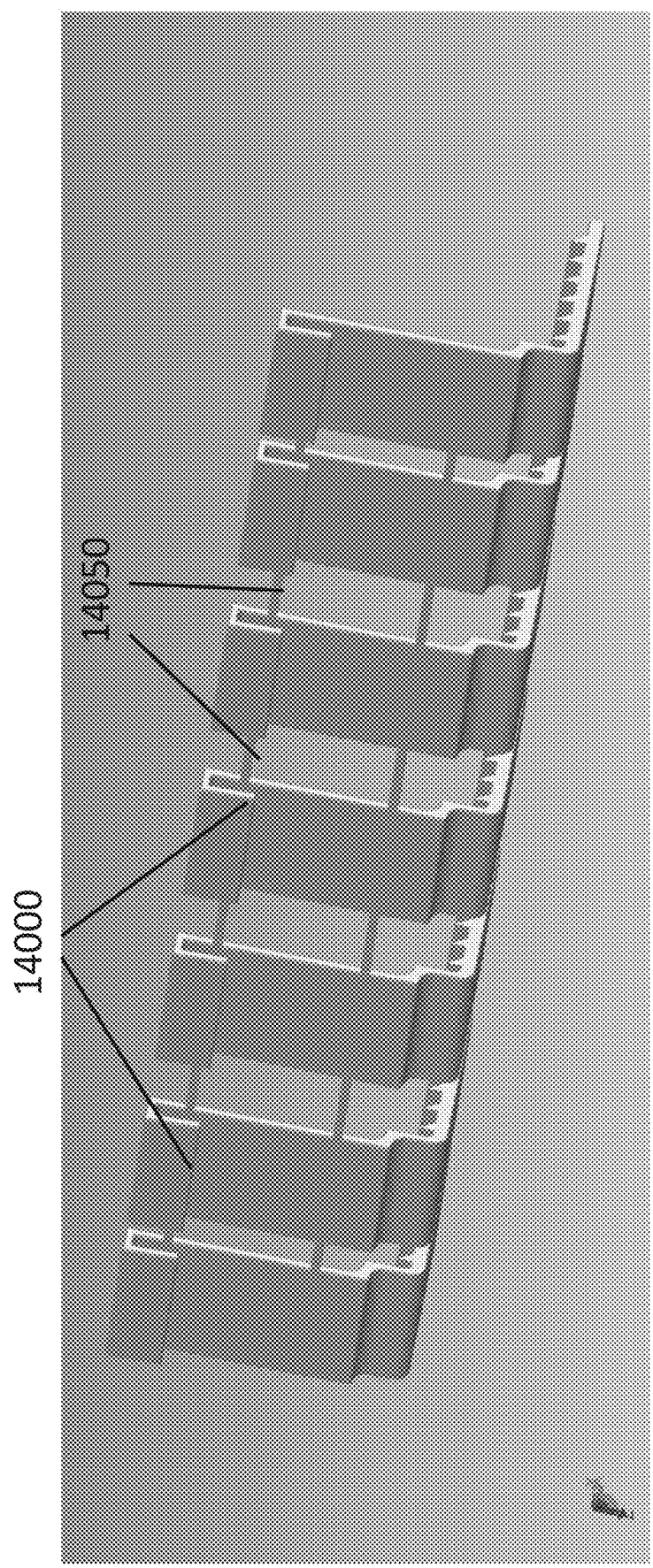
Figure 31C:
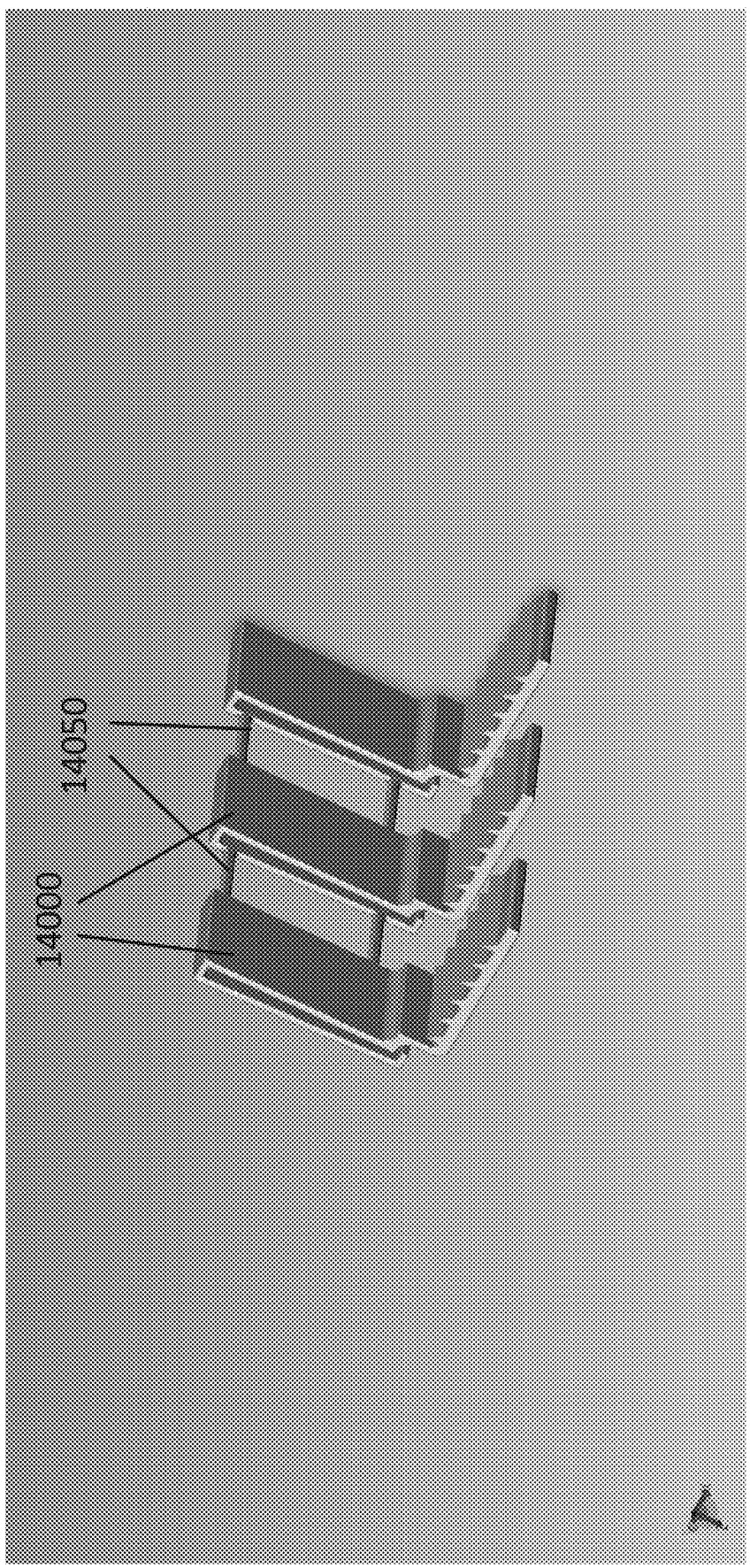
Figure 31D:
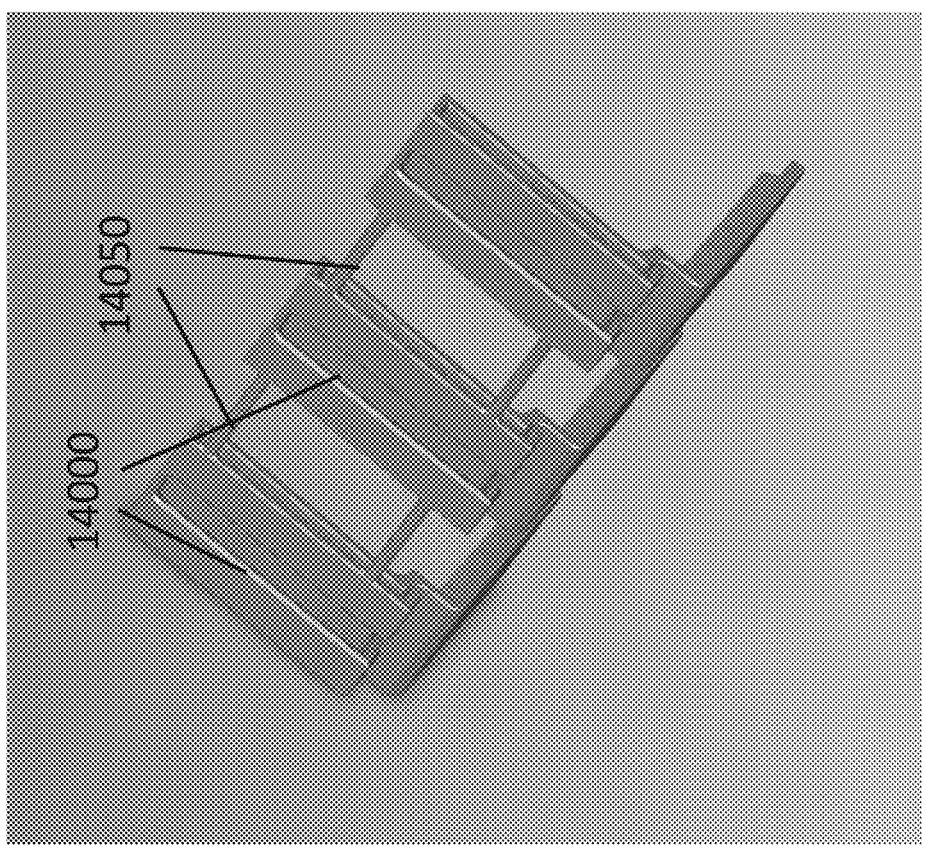
Figure 31E:
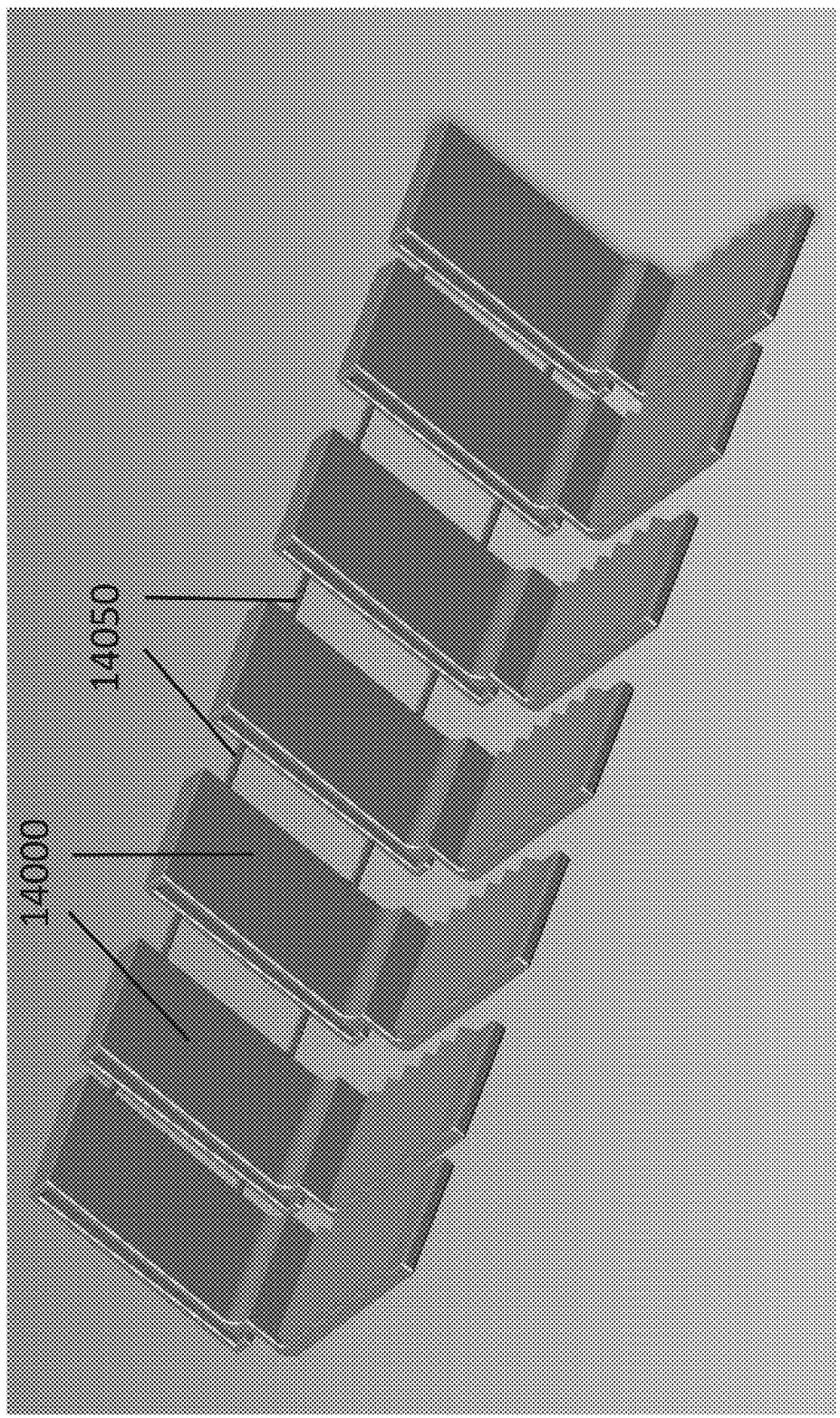
Figure 31F:
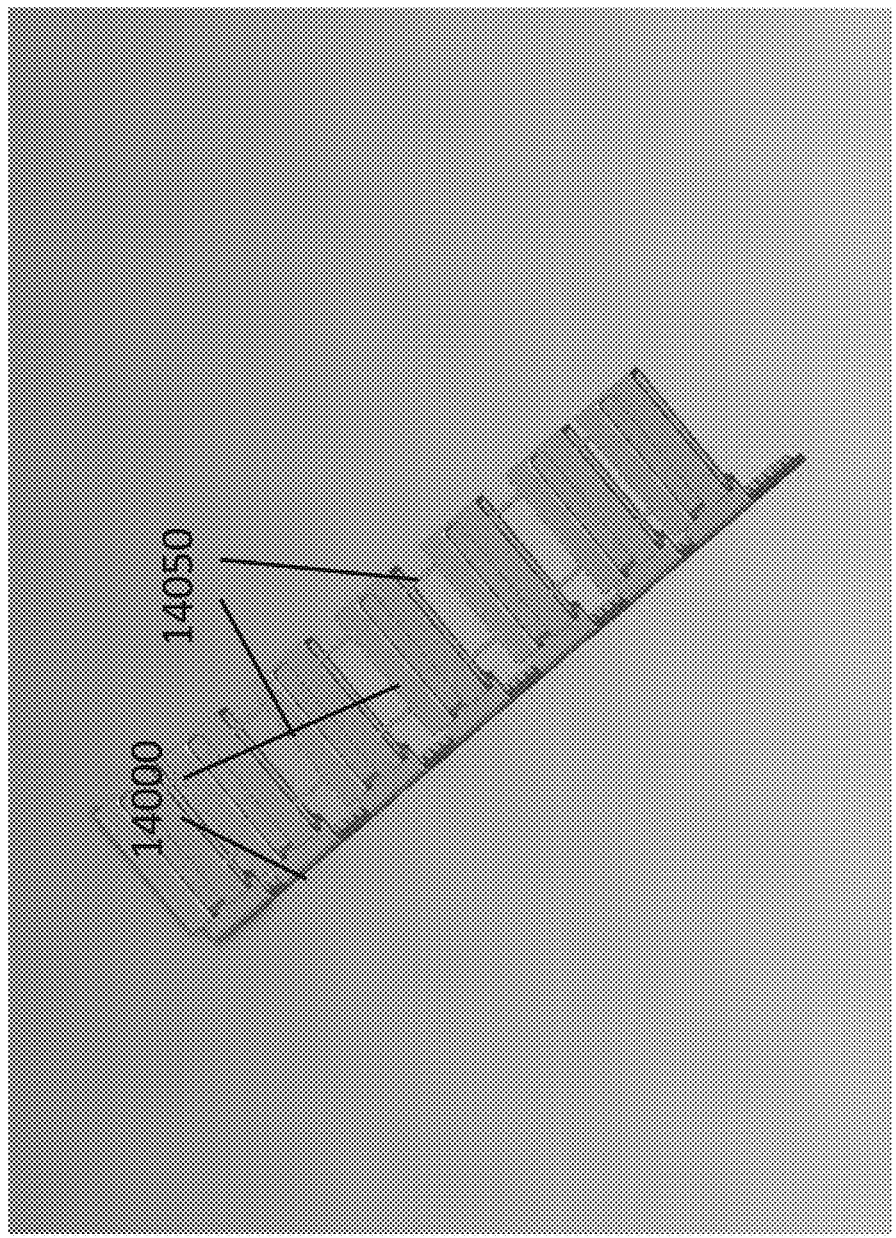

FIGS. 31A-31H depict stabilizing clips similar to the stabilizer clips of FIGS. 23A-30B, particularly the clip of FIGS. 28C-D. However, the stabilizing clips of FIGS. 31A-30H are linked together by linkers 14050. The linkers 14050 may be constructed from the same material as the stabilizing clips or any material disclosed herein this section or elsewhere in the specification. The linkers may be molded along with the stabilizer clips, 3D printed along with the stabilizer clips, or produced by any other suitable means. The linkers serve to keep the clips together, thereby reducing the likelihood that a clip will be lost within the wound. In certain embodiments, the linkers may take the form of string or an adhesive. The stabilizing clips may be linked within a long array including many stabilizing clips, which may be cut at the linker position to create smaller groups of stabilizing clips such as depicted in FIGS. 31C-D. In certain embodiments, and as depicted in FIG. 30A, the stabilizing clips may be grouped together such that 1, 2, 3, 4, 5 or more clips are closer together, followed by a wider gap 14002.

Figure 31G:
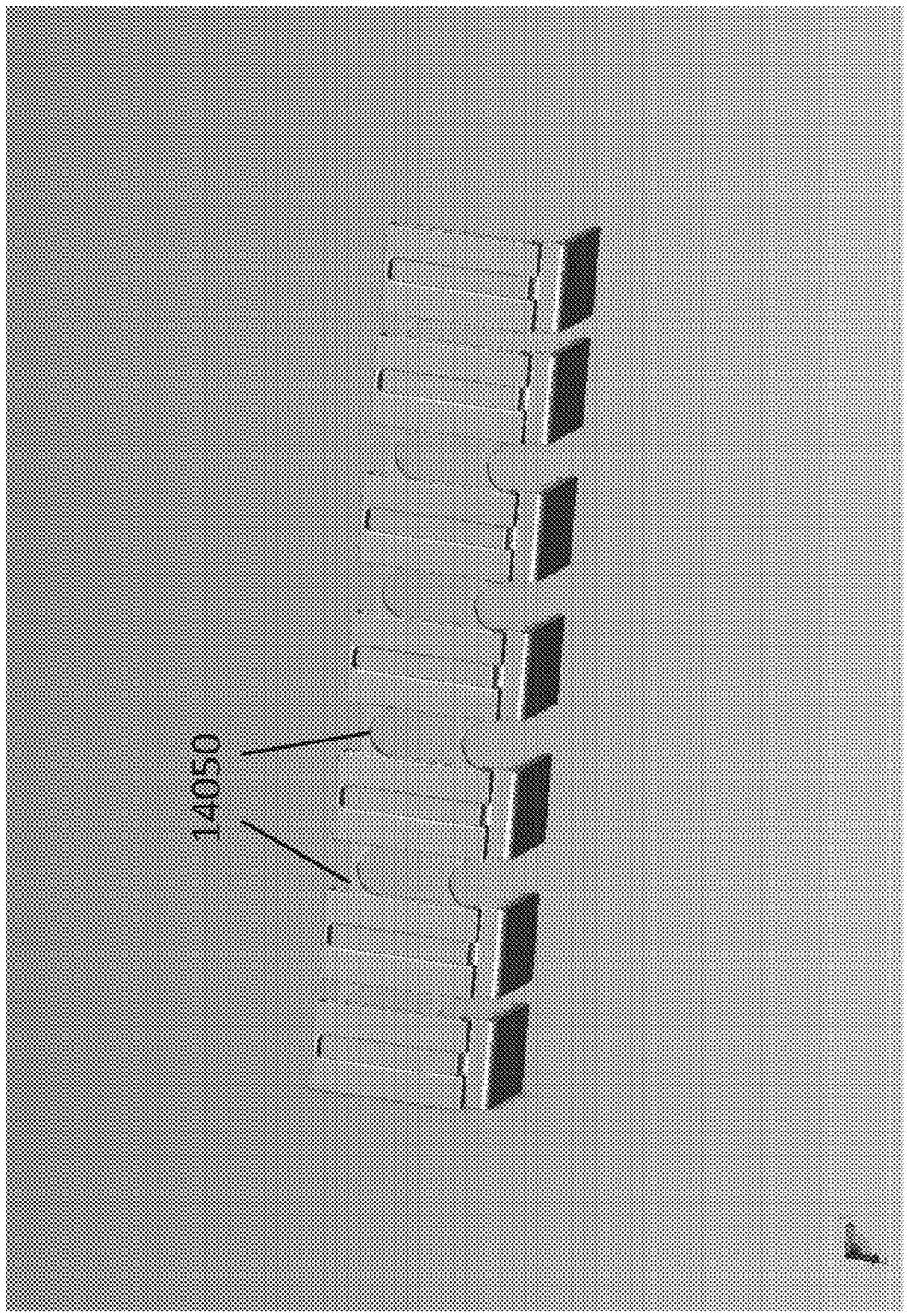
Figure 31H:
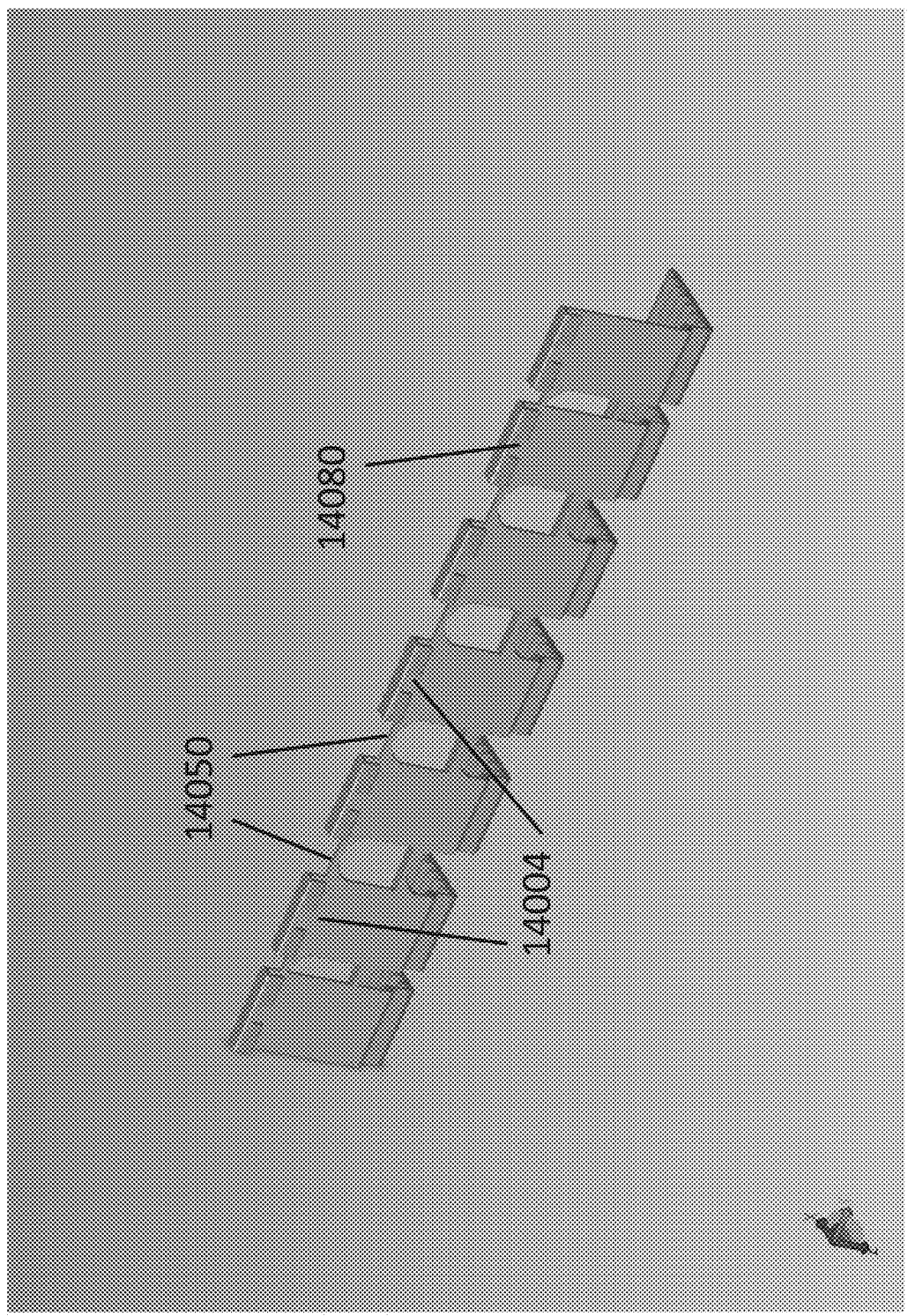

FIGS. 31G-31H depict embodiments of linked stabilizing clips linked by arches 14075. Further, FIG. 31H depicts stabilizing clips comprising an attachment portion 14004 with a short hook to loop over the top of a stabilizing structure, combined with a gap 14080 to allow the stabilizing clips to be attached to an intersection within a stabilizing structure.

Figure 32B:
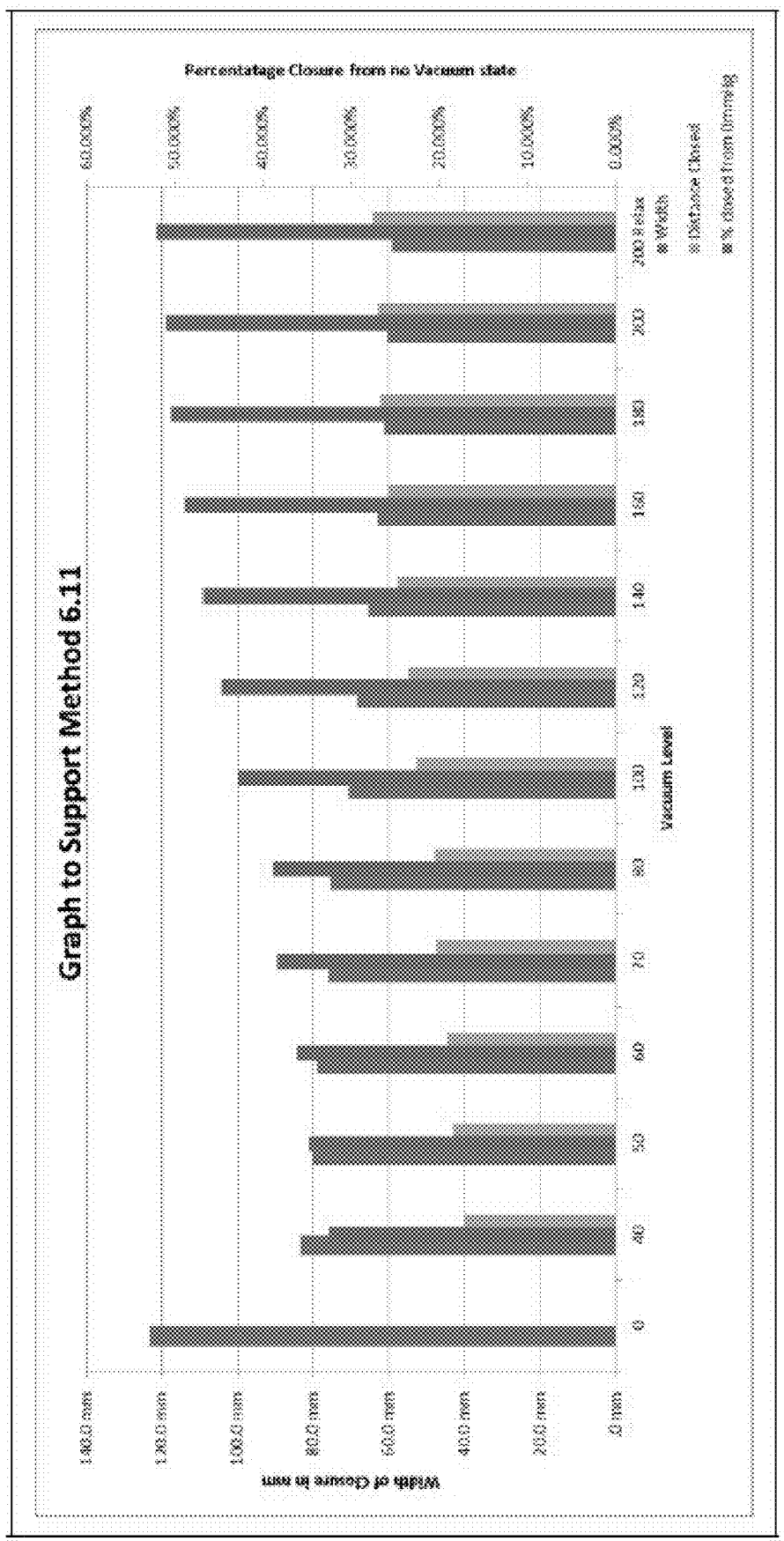

FIG. 32A is a data table that tracks the collapse (as measured by a decrease in width) of an embodiment of a wound closure device incorporating stabilizing structures similar to the structures of FIGS. 2A-3E and 16-20F, while the device is subjected to increasing levels of vacuum. Here, foam was attached to the top and the bottom of a stabilizing structure, similar to the embodiments of FIG. 20A-20F and entire device was placed within an animal model. The vacuum was increased from 40 mm Hg to 200 mm Hg. The pre vacuum width of the device was 123.4 mm, which decreased to 83.4 mm under vacuum. FIG. 32B displays the experimental data of FIG. 32A in the form of a bar graph.

As described above, a stabilizing structure such as those described herein this section or elsewhere in the specification may be securing within a wound through the use of any stabilizing clip described herein this section or elsewhere in the specification. The following steps need not be completed in any particularly order, but are provided in the following order as an example. As depicted above in relation to FIGS.

12A-C, the stabilizing structure may first be sized for a particular wound by trimming/removing portions of the stabilizing structure, or by providing a stabilizing structure pre-made at a size appropriate for the wound. Upon sizing the stabilizing structure to a particular wound shape, stabilizing clips and/or foam may then be attached to the stabilizing structure. Then, the stabilizing structure is partially closed so as to facilitate placing the stabilizing structure into an abdominal wound and securing the stabilizing clips and/or foam lip such that the clips and/or foam lip extend under the fascia layer. Since the fascia is a relative strong tissue, by securing the stabilizing clips underneath the fascia, the stabilizing structure cannot be pushed up in a direction out of the wound by the underlying viscera. As described above, any number of stabilizing clips may be used and they may extend above and/or below various layers of tissue. Also, as described above, the stabilizing structures may come pre-made as various sizes, thereby negating the need to further trim or re-size the stabilizing structure.

In certain embodiments any of the stabilizing clips disclosed herein may be combined with any of the anchoring layers or materials disclosed herein, such as those disclosed in FIGS. 4-6B. The anchoring material may be positioned on the face of the clip that faces the outside of the wound to provide additional attachment force to maintain the stabilizing structure within the wound bed. In some embodiments, the stabilizing clips may comprise a velcro or gripping sidewall or sidewalls to allow the clips to attach together to form a strip of clips. The anchoring layers can be placed at any suitable location of the clip, such as the top, bottom, front, back, or sides.

Various sensors may be placed within any of the stabilizing structures or foam layers described herein this section or elsewhere in the specification. For example, a pH, temperature, pressure sensor, or any other suitable sensor may be embedded within the stabilizing structure and/or within a foam layer. Such embodiments will advantageously allow a clinician to skip the step of removing a sensor within the wound bed, as the sensor simply be removed upon removal of the stabilizing structure or foam.

The stabilizer clips described herein this section or elsewhere in the specification may be constructed via any suitable means. For example, the stabilizer clips may be 3D printed or molded separately from the stabilizing structures disclosed herein this section or elsewhere in the specification. However, alternatively, the stabilizer clips may be 3D printed or molded directly attached to the stabilizing structure.

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (e.g., of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An apparatus for treating a wound with negative pressure wound therapy, comprising:
    a stabilizing structure having an oculiform shape for insertion into a wound and comprising a first plurality of cells along a central transverse axis, the stabilizing structure configured to collapse more in a horizontal plane parallel to a length and a width of the stabilizing structure than in a vertical plane perpendicular to the horizontal plane;
    wherein the stabilizing structure comprises two extended sections extending in opposite directions from the central transverse axis and along a longitudinal axis extending along opposite ends of the stabilizing structure, the extended sections each comprising a further plurality of cells in rows in a transverse direction wherein the rows in each extended section have fewer cells along a transverse direction than the first plurality of cells along the central transverse axis and wherein each extended section includes at least two cells that extend along the longitudinal axis at the opposite ends of the stabilizing structure; and
    wherein the stabilizing structure comprises curved outer walls on opposite sides of the longitudinal axis defining a perimeter, wherein the curved outer walls converge at the extended sections such that the extended sections extend beyond an outer edge of a virtual ellipse formed by a majority of the perimeter along the longitudinal axis of the stabilizing structure.

2. The apparatus of claim 1, wherein the extended sections comprise a stepped shaped.

3. The apparatus of claim 1, wherein the extended sections comprise a first row comprising four cells, a second row comprising two cells, and a third row comprising two cells.

4. The apparatus of claim 1, further comprising a plurality of tabs extending outward from the perimeter of the stabilizing structure.

5. The apparatus of claim 4, wherein the tabs comprise anchors configured to grip foam.

6. The apparatus of claim 1, further comprising a first bottom layer of foam attached to a bottom of the stabilizing structure.

7. The apparatus of claim 6, wherein the first bottom layer of foam comprises a lip that extends outward to extend into surrounding tissue.

8. The apparatus of claim 1, further comprising a top layer of foam attached to a top of the stabilizing structure.

9. The apparatus of claim 6, further comprising a second bottom layer of foam attached to the first bottom layer of foam.

10. The apparatus of claim 9, wherein the second bottom layer of foam comprises a lip that extends outward from the stabilizing structure for positioning beneath a fascia layer.

11. The apparatus of claim 6, wherein the first bottom layer of foam is attached to a plurality of tabs extending from the perimeter of the stabilizing structure.

12. The apparatus of claim 11, wherein the first bottom layer of foam comprises printed symbols, the symbols comprising arrows indicating the proper positioning of the foam layer within the wound.

13. The apparatus of claim 1, wherein each cell in the first plurality of cells comprises a length and a width, the lengths of at least some of the cells becoming progressively longer along the longitudinal axis of the stabilizing structure toward the central transverse axis of the stabilizing structure.

14. The apparatus of claim 1, wherein cells in the first plurality of cells along the central transverse axis of the stabilizing structure are larger than cells in the further plurality of cells near a longitudinal edge of the stabilizing structure.

15. The apparatus of claim 1, wherein cells in the first plurality of cells near the center of the stabilizing structure are larger than cells in the further plurality of cells near a longitudinal edge of the stabilizing structure.

16. The apparatus of claim 1, wherein the first plurality of cells along the central transverse axis and the further plurality of cells in the extended sections have different sizes.

17. The apparatus of claim 1, wherein the cells of the extended sections are configured to avoid collapse upon application of negative pressure to the stabilizing structure.

* * * * *